United States Patent
Pandey et al.

(10) Patent No.: US 12,122,785 B2
(45) Date of Patent: *Oct. 22, 2024

(54) SUBSTITUTED PYRIDINES, PYRIDAZINES, PYRIMIDINES, AND 1,2,4-TRIAZINES AS TYK2 INHIBITORS

(71) Applicant: Sudo Biosciences Limited, Altrincham (GB)

(72) Inventors: Anjali Pandey, Fremont, CA (US); Gregory Dietsch, Snohomish, WA (US); Bhaskar Chaudhuri, San Jose, CA (US); Seetharaman Manojveer, Bangalore (IN); Mahesh Thakkar, Bangalore (IN); Athisayamani Jeyaraj Duraiswamy, Bangalore (IN); Sukesh Kalva, Bangalore (IN)

(73) Assignee: SUDO BIOSCIENCES LIMITED, Altrincham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 18/160,479

(22) Filed: Jan. 27, 2023

(65) Prior Publication Data
US 2023/0242546 A1    Aug. 3, 2023

Related U.S. Application Data

(63) Continuation of application No. 17/737,872, filed on May 5, 2022, now Pat. No. 11,613,548, which is a continuation of application No. PCT/IB2022/000086, filed on Feb. 16, 2022.

(60) Provisional application No. 63/291,222, filed on Dec. 17, 2021, provisional application No. 63/234,934, filed on Aug. 19, 2021, provisional application No. 63/193,511, filed on May 26, 2021, provisional application No. 63/151,287, filed on Feb. 19, 2021.

(51) Int. Cl.
| | | |
|---|---|---|
| A61K 31/4162 | (2006.01) | |
| C07D 231/54 | (2006.01) | |
| C07D 471/04 | (2006.01) | |
| C07D 471/14 | (2006.01) | |
| C07D 487/04 | (2006.01) | |
| C07D 491/052 | (2006.01) | |

(52) U.S. Cl.
CPC ....... C07D 491/052 (2013.01); C07D 471/04 (2013.01); C07D 471/14 (2013.01); C07D 487/04 (2013.01)

(58) Field of Classification Search
CPC .......................... A61K 31/4162; C07D 231/54
USPC ...................... 514/403; 548/359.1
See application file for complete search history.

(56) References Cited

U.S. PATENT DOCUMENTS

| | | |
|---|---|---|
| 36,256 A | 8/1862 | McCurdy |
| 37,650 A | 2/1863 | Wanat |
| 47,929 A | 5/1865 | Manovill |
| 5,132,301 A | 7/1992 | Doherty et al. |
| 5,364,848 A | 11/1994 | Doherty et al. |
| 5,409,930 A | 4/1995 | Spada et al. |
| 5,656,643 A | 8/1997 | Spada et al. |
| RE36,256 E | 7/1999 | Spada et al. |
| RE37,650 E | 4/2002 | Myers et al. |
| 6,391,891 B1 | 5/2002 | Gaster et al. |
| 6,645,969 B1 | 11/2003 | Myers et al. |
| 7,078,409 B2 | 7/2006 | Zhang et al. |
| 7,115,746 B2 | 10/2006 | Snoonian et al. |
| 7,312,225 B2 | 12/2007 | Luecking et al. |
| 7,335,792 B2 | 2/2008 | Mortimore et al. |

(Continued)

FOREIGN PATENT DOCUMENTS

| | | |
|---|---|---|
| CN | 1761653 A | 4/2006 |
| CN | 100579965 C | 1/2010 |

(Continued)

OTHER PUBLICATIONS

Dorwald, F. Zaragoza. Side Reactions in Organic Synthesis: A Guide to Successful Synthesis Design, Weinheim: WILEY-VCH Verlag Gmbh & Co. KGaA, 2005, Preface.*

Berge et al. Pharmaceutical Salts. Journal of Pharmaceutical Sciences 66(1):1-19 (Jan. 1977).

(Continued)

*Primary Examiner* — Douglas M Willis
(74) *Attorney, Agent, or Firm* — WILSON SONSINI GOODRICH & ROSATI

(57) ABSTRACT

Described herein are compounds of Formula (I) that are TYK2 inhibitors, methods of making such compounds, pharmaceutical compositions and medicaments comprising such compounds, and methods of using such compounds in the treatment of conditions, diseases, or disorders that would benefit from modulation of TYK2 activity.

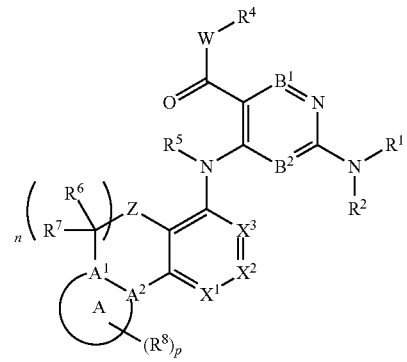

Formula (I)

20 Claims, No Drawings

(56) References Cited

U.S. PATENT DOCUMENTS

| | | |
|---|---|---|
| 7,507,485 B2 | 3/2009 | Oh et al. |
| 7,541,485 B2 | 6/2009 | Michalak et al. |
| 7,910,595 B2 | 3/2011 | Betebenner et al. |
| 8,034,950 B2 | 10/2011 | Snoonian et al. |
| 8,450,348 B2 | 5/2013 | Murthi et al. |
| 8,530,653 B2 | 9/2013 | Roberts |
| 8,546,565 B2 | 10/2013 | Eggenweiler et al. |
| 8,586,732 B2 | 11/2013 | Corkey et al. |
| 8,686,157 B2 | 4/2014 | Snoonian et al. |
| 8,697,863 B2 | 4/2014 | Elzein et al. |
| 8,734,962 B2 | 5/2014 | Adler et al. |
| 8,796,280 B2 | 8/2014 | Page et al. |
| 8,940,742 B2 | 1/2015 | Castro et al. |
| 9,012,462 B2 | 4/2015 | Wang et al. |
| 9,139,764 B2 | 9/2015 | Schmid |
| 9,145,387 B2 | 9/2015 | Haq et al. |
| 9,173,886 B2 | 11/2015 | Guenther et al. |
| 9,193,694 B2 | 11/2015 | Corkey et al. |
| 9,273,077 B2 | 3/2016 | Wang et al. |
| 9,340,528 B2 | 5/2016 | Bader et al. |
| 9,371,320 B2 | 6/2016 | Nara et al. |
| 9,464,052 B2 | 10/2016 | Edwards et al. |
| 9,504,686 B2 | 11/2016 | Haq et al. |
| 9,505,748 B2 | 11/2016 | Moslin et al. |
| 9,540,333 B2 | 1/2017 | Santella et al. |
| 9,561,228 B2 | 2/2017 | Haq et al. |
| 9,598,435 B2 | 3/2017 | Corkey et al. |
| 9,675,567 B2 | 6/2017 | Edwards et al. |
| 9,676,760 B2 | 6/2017 | Corkey et al. |
| 9,701,635 B2 | 7/2017 | Hartwig et al. |
| 9,796,700 B2 | 10/2017 | Haq et al. |
| 9,951,024 B2 | 4/2018 | Zheng et al. |
| 9,963,452 B2 | 5/2018 | Grueneberg et al. |
| 9,966,544 B2 | 5/2018 | Adler et al. |
| 9,980,964 B2 | 5/2018 | Haq et al. |
| 9,981,957 B2 | 5/2018 | Xiao et al. |
| 10,000,480 B2 | 6/2018 | Moslin et al. |
| 10,098,887 B2 | 10/2018 | Guenther et al. |
| 10,526,321 B2 | 1/2020 | Wrobleski et al. |
| 10,570,157 B2 | 2/2020 | Brough et al. |
| RE47,929 E | 4/2020 | Moslin et al. |
| 10,722,513 B2 | 7/2020 | Stewart et al. |
| 10,723,839 B2 | 7/2020 | Tonelli et al. |
| 10,781,218 B2 | 9/2020 | Wu et al. |
| 10,793,574 B2 | 10/2020 | Greenwood et al. |
| 11,001,559 B2 | 5/2021 | Sintim |
| 11,021,475 B2 | 6/2021 | Moslin et al. |
| 11,053,219 B2 | 7/2021 | Jin et al. |
| 11,163,230 B2 | 11/2021 | Verschuuren |
| 11,220,508 B2 | 1/2022 | Greenwood et al. |
| 11,485,713 B2 | 11/2022 | Zhou et al. |
| 11,485,731 B2 | 11/2022 | Morley et al. |
| 11,495,758 B2 | 11/2022 | Kim et al. |
| 11,613,548 B2 | 3/2023 | Pandey et al. |
| 11,866,414 B2 | 1/2024 | Spergel et al. |
| 2003/0118866 A1 | 6/2003 | Oh et al. |
| 2003/0162993 A1 | 8/2003 | Mortimore et al. |
| 2004/0014774 A1 | 1/2004 | Myers et al. |
| 2004/0048883 A1 | 3/2004 | Zhang et al. |
| 2004/0209895 A1 | 10/2004 | Luecking et al. |
| 2004/0230058 A1 | 11/2004 | Snoonian et al. |
| 2004/0235849 A1 | 11/2004 | Beyreuther et al. |
| 2007/0088172 A1 | 4/2007 | Michalak et al. |
| 2007/0142440 A1 | 6/2007 | Burgdorf et al. |
| 2007/0173649 A1 | 7/2007 | Snoonian et al. |
| 2007/0232627 A1 | 10/2007 | Betebenner et al. |
| 2008/0200523 A1 | 8/2008 | Murthi et al. |
| 2008/0227976 A1 | 9/2008 | Mortimore et al. |
| 2009/0054447 A1 | 2/2009 | Page et al. |
| 2010/0029598 A1 | 2/2010 | Kopitz et al. |
| 2010/0213824 A1 | 8/2010 | Adler et al. |
| 2010/0267709 A1 | 10/2010 | Young et al. |
| 2010/0320449 A1 | 12/2010 | Schmid |
| 2011/0112126 A1 | 5/2011 | Roberts |
| 2011/0245225 A1 | 10/2011 | Eggenweiler et al. |
| 2011/0245250 A1 | 10/2011 | Edwards et al. |
| 2012/0157684 A1 | 6/2012 | Snoonian et al. |
| 2012/0202776 A1 | 8/2012 | Wang et al. |
| 2012/0263708 A1 | 10/2012 | Bader et al. |
| 2013/0012492 A1 | 1/2013 | Corkey et al. |
| 2013/0071353 A1 | 3/2013 | Guenther et al. |
| 2013/0184255 A1 | 7/2013 | Corkey et al. |
| 2013/0225527 A1 | 8/2013 | Wang et al. |
| 2013/0225528 A1 | 8/2013 | Wang et al. |
| 2013/0267521 A1 | 10/2013 | Castro et al. |
| 2014/0031547 A1 | 1/2014 | Sheridan et al. |
| 2014/0066406 A1 | 3/2014 | Wang et al. |
| 2014/0135317 A1 | 5/2014 | Corkey et al. |
| 2014/0210339 A1 | 7/2014 | Adler et al. |
| 2014/0228322 A1 | 8/2014 | Haq et al. |
| 2015/0225436 A1 | 8/2015 | Wang et al. |
| 2015/0299139 A1 | 10/2015 | Santella et al. |
| 2015/0299183 A1 | 10/2015 | Moslin et al. |
| 2016/0002176 A1 | 1/2016 | Haq et al. |
| 2016/0031890 A1 | 2/2016 | Grueneberg et al. |
| 2016/0082008 A1 | 3/2016 | Haq et al. |
| 2016/0083353 A1 | 3/2016 | Zheng et al. |
| 2016/0096846 A1 | 4/2016 | Corkey et al. |
| 2016/0129006 A1 | 5/2016 | Guenther et al. |
| 2016/0185723 A1 | 6/2016 | Hartwig et al. |
| 2016/0347744 A1 | 12/2016 | Corkey et al. |
| 2016/0354375 A1 | 12/2016 | Sheridan et al. |
| 2016/0374969 A1 | 12/2016 | Edwards et al. |
| 2016/0376297 A1 | 12/2016 | Wang et al. |
| 2017/0008888 A1 | 1/2017 | Hu et al. |
| 2017/0022192 A1 | 1/2017 | Moslin et al. |
| 2017/0107208 A1 | 4/2017 | Xiao et al. |
| 2017/0137406 A1 | 5/2017 | Haq et al. |
| 2017/0210729 A1 | 7/2017 | Haq et al. |
| 2017/0218000 A1 | 8/2017 | Wang et al. |
| 2017/0342025 A1 | 11/2017 | Potter et al. |
| 2017/0349553 A1 | 12/2017 | Zheng et al. |
| 2017/0355712 A1 | 12/2017 | Campbell et al. |
| 2018/0071291 A1 | 3/2018 | Stewart et al. |
| 2018/0179209 A1 | 6/2018 | Wu et al. |
| 2018/0215772 A1 | 8/2018 | Brough et al. |
| 2018/0265504 A1 | 9/2018 | Moslin et al. |
| 2019/0022100 A1 | 1/2019 | Guenther et al. |
| 2019/0025313 A1 | 1/2019 | Si et al. |
| 2019/0092784 A1 | 3/2019 | Wu et al. |
| 2019/0100619 A1 | 4/2019 | Tonelli et al. |
| 2019/0106427 A1 | 4/2019 | Chakravarty et al. |
| 2019/0177278 A1 | 6/2019 | Sintim |
| 2019/0248810 A1 | 8/2019 | Dahlgren et al. |
| 2020/0048288 A1 | 2/2020 | Wang et al. |
| 2020/0054635 A1 | 2/2020 | Campbell et al. |
| 2020/0071315 A1 | 3/2020 | Moslin et al. |
| 2020/0113901 A1 | 4/2020 | Campbell et al. |
| 2020/0317705 A1 | 10/2020 | Wang et al. |
| 2020/0325128 A1 | 10/2020 | Morley et al. |
| 2020/0345740 A1 | 11/2020 | Stewart et al. |
| 2020/0354338 A1 | 11/2020 | Jin et al. |
| 2020/0407372 A1 | 12/2020 | Koltun et al. |
| 2021/0009616 A1 | 1/2021 | Kim et al. |
| 2021/0079167 A1 | 3/2021 | Verschuuren |
| 2021/0088520 A1 | 3/2021 | Si et al. |
| 2021/0101908 A1 | 4/2021 | Wu et al. |
| 2021/0147340 A1 | 5/2021 | Hinks et al. |
| 2021/0198208 A1 | 7/2021 | Sintim |
| 2021/0198213 A1 | 7/2021 | Zhou et al. |
| 2021/0198277 A1 | 7/2021 | Campbell et al. |
| 2021/0213014 A1 | 7/2021 | Cosmopoulos et al. |
| 2021/0220408 A1 | 7/2021 | Boitano et al. |
| 2021/0230163 A1 | 7/2021 | Greenwood et al. |
| 2021/0260040 A1 | 8/2021 | Penebre et al. |
| 2021/0261532 A1 | 8/2021 | Lennek et al. |
| 2022/0043341 A1 | 2/2022 | Verschuuren |
| 2022/0106265 A1 | 4/2022 | Thiele et al. |
| 2022/0144842 A1 | 5/2022 | Li et al. |
| 2022/0177459 A1 | 6/2022 | Du et al. |
| 2022/0181580 A1 | 6/2022 | Godding et al. |
| 2022/0289719 A1 | 9/2022 | Kong et al. |
| 2022/0315614 A1 | 10/2022 | Graham et al. |
| 2022/0356180 A1 | 11/2022 | Moslin et al. |

(56) References Cited

U.S. PATENT DOCUMENTS

| | | | |
|---|---|---|---|
| 2022/0380378 A1 | 12/2022 | Zhou et al. | |
| 2022/0388987 A1 | 12/2022 | Spergel et al. | |
| 2022/0411384 A1 | 12/2022 | Spergel et al. | |
| 2023/0174553 A1 | 6/2023 | Pandey et al. | |
| 2023/0183264 A1 | 6/2023 | Pandey et al. | |
| 2024/0124440 A1 | 4/2024 | Pandey et al. | |

FOREIGN PATENT DOCUMENTS

| | | | |
|---|---|---|---|
| CN | 102159535 A | 8/2011 | |
| CN | 102596932 A | 7/2012 | |
| CN | 103249719 A | 8/2013 | |
| CN | 105820175 A | 8/2016 | |
| CN | 105920010 A | 9/2016 | |
| CN | 106995415 A | 8/2017 | |
| CN | 107325111 A | 11/2017 | |
| CN | 107880038 A | 4/2018 | |
| CN | 105820175 B | 9/2019 | |
| CN | 111484480 A | 8/2020 | |
| CN | 111757878 A | 10/2020 | |
| CN | 112079830 A | 12/2020 | |
| CN | 112409331 A | 2/2021 | |
| CN | 112851579 A | 5/2021 | |
| CN | 107880038 B | 9/2021 | |
| CN | 113968846 A | 1/2022 | |
| EA | 035312 B1 | 5/2020 | |
| EA | 036058 B1 | 9/2020 | |
| EP | 0124081 A2 | 11/1984 | |
| EP | 0541042 A1 | 5/1993 | |
| EP | 0584222 B1 | 10/1997 | |
| EP | 2206712 A1 | 7/2010 | |
| EP | 1317005 B1 | 12/2012 | |
| EP | 2376489 B1 | 4/2015 | |
| EP | 2726469 B1 | 8/2015 | |
| EP | 2726466 B1 | 5/2016 | |
| EP | 3110819 A1 | 1/2017 | |
| EP | 3210609 A1 | 8/2017 | |
| EP | 2300013 B1 | 9/2017 | |
| EP | 2835131 B1 | 9/2017 | |
| EP | 2966067 B1 | 10/2017 | |
| EP | 2836487 B1 | 10/2018 | |
| EP | 2922846 B1 | 10/2018 | |
| EP | 3320021 B1 | 5/2019 | |
| EP | 2310357 B1 | 9/2019 | |
| EP | 3600318 A1 | 2/2020 | |
| EP | 3612181 A1 | 2/2020 | |
| EP | 3085694 B1 | 3/2020 | |
| EP | 3085696 B1 | 3/2020 | |
| EP | 3088395 B1 | 3/2020 | |
| EP | 3098218 B1 | 3/2020 | |
| EP | 3673920 A1 | 7/2020 | |
| EP | 3697400 A1 | 8/2020 | |
| EP | 3697420 A1 | 8/2020 | |
| EP | 3101013 B1 | 10/2020 | |
| EP | 3761385 A1 | 1/2021 | |
| EP | 3894392 A1 | 10/2021 | |
| EP | 3950678 A1 | 2/2022 | |
| EP | 3495358 B8 | 6/2022 | |
| EP | 4011882 A1 | 6/2022 | |
| EP | 4064376 A1 | 9/2022 | |
| EP | 4071144 A1 | 10/2022 | |
| EP | 3429591 B1 | 3/2023 | |
| EP | 3724189 B1 | 10/2023 | |
| KR | 101726059 B1 | 4/2017 | |
| KR | 101766961 B1 | 8/2017 | |
| WO | WO-9220642 A1 | 11/1992 | |
| WO | WO-9639145 A1 | 12/1996 | |
| WO | WO-9907700 A1 | 2/1999 | |
| WO | WO-03007958 A1 | 1/2003 | |
| WO | WO-03042169 A2 | 5/2003 | |
| WO | WO-03082830 A1 | 10/2003 | |
| WO | WO-2004026881 A1 | 4/2004 | |
| WO | WO-2004072038 A1 | 8/2004 | |
| WO | WO-2005085202 A1 | 9/2005 | |
| WO | WO-2006111560 A2 | 10/2006 | |
| WO | WO-2007044100 A1 | 4/2007 | |
| WO | WO-2007076034 A2 | 7/2007 | |
| WO | WO-2008141637 A2 | 11/2008 | |
| WO | WO-2009039845 A1 | 4/2009 | |
| WO | WO-2009069132 A2 | 6/2009 | |
| WO | WO-2009136995 A2 | 11/2009 | |
| WO | WO-2009143389 A1 | 11/2009 | |
| WO | WO-2010010380 A1 | 1/2010 | |
| WO | WO-2010012397 A1 | 2/2010 | |
| WO | WO-2010048149 A2 | 4/2010 | |
| WO | WO-2010066324 A1 | 6/2010 | |
| WO | WO-2010072338 A1 | 7/2010 | |
| WO | WO-2010100144 A1 | 9/2010 | |
| WO | WO-2011026579 A1 | 3/2011 | |
| WO | WO-2011056957 A2 | 5/2011 | |
| WO | WO-2011113060 A2 | 9/2011 | |
| WO | WO-2012038944 A1 | 3/2012 | |
| WO | WO-2012079032 A2 | 6/2012 | |
| WO | WO-2012080729 A2 | 6/2012 | |
| WO | WO-2012146936 A1 | 11/2012 | |
| WO | WO-2012172043 A1 | 12/2012 | |
| WO | WO-2013004984 A1 | 1/2013 | |
| WO | WO-2013005041 A1 | 1/2013 | |
| WO | WO-2013005057 A1 | 1/2013 | |
| WO | WO-2013006463 A1 | 1/2013 | |
| WO | WO-2013006485 A1 | 1/2013 | |
| WO | WO-2013154878 A1 | 10/2013 | |
| WO | WO-2013180265 A1 | 12/2013 | |
| WO | WO-2014074660 A1 | 5/2014 | |
| WO | WO-2014074661 A1 | 5/2014 | |
| WO | WO-2014074669 A1 | 5/2014 | |
| WO | WO-2014074670 A1 | 5/2014 | |
| WO | WO-2014120683 A1 | 8/2014 | |
| WO | WO-2014124230 A2 | 8/2014 | |
| WO | WO-2014141129 A2 | 9/2014 | |
| WO | WO-2015013715 A2 | 1/2015 | |
| WO | WO-2015129927 A1 | 9/2015 | |
| WO | WO-2015145143 A1 | 10/2015 | |
| WO | WO-2016108045 A2 | 7/2016 | |
| WO | WO-2016149756 A1 | 9/2016 | |
| WO | WO-2016198663 A1 | 12/2016 | |
| WO | WO-2016207345 A1 | 12/2016 | |
| WO | WO-2017005832 A1 | 1/2017 | |
| WO | WO-2017017469 A1 | 2/2017 | |
| WO | WO-2017117372 A1 | 7/2017 | |
| WO | WO-2017161028 A1 | 9/2017 | |
| WO | WO-2017174755 A1 | 10/2017 | |
| WO | WO-2017181177 A1 | 10/2017 | |
| WO | WO-2018035072 A1 | 2/2018 | |
| WO | WO-2018071794 A1 | 4/2018 | |
| WO | WO-2018167269 A1 | 9/2018 | |
| WO | WO-2018183923 A1 | 10/2018 | |
| WO | WO-2018195450 A1 | 10/2018 | |
| WO | WO-2018228275 A1 | 12/2018 | |
| WO | WO-2019076716 A1 | 4/2019 | |
| WO | WO-2019079596 A1 | 4/2019 | |
| WO | WO-2019079607 A1 | 4/2019 | |
| WO | WO-2019103952 A1 | 5/2019 | |
| WO | WO-2019118909 A1 | 6/2019 | |
| WO | WO-2019165204 A1 | 8/2019 | |
| WO | WO-2019209182 A1 | 10/2019 | |
| WO | WO-2019226991 A1 | 11/2019 | |
| WO | WO-2020033413 A2 | 2/2020 | |
| WO | WO-2020051207 A2 | 3/2020 | |
| WO | WO-2020076723 A1 | 4/2020 | |
| WO | WO-2020123675 A1 | 6/2020 | |
| WO | WO-2020136240 A1 | 7/2020 | |
| WO | WO-2020156311 A1 | 8/2020 | |
| WO | WO-2020178602 A1 | 9/2020 | |
| WO | WO-2020200209 A1 | 10/2020 | |
| WO | WO-2020222773 A1 | 11/2020 | |
| WO | WO-2020223431 A1 | 11/2020 | |
| WO | WO-2021001739 A1 | 1/2021 | |
| WO | WO-2021014453 A1 | 1/2021 | |
| WO | WO-2021055651 A1 | 3/2021 | |
| WO | WO-2021055652 A1 | 3/2021 | |
| WO | WO-2021133917 A1 | 7/2021 | |
| WO | WO-2021155253 A1 | 8/2021 | |
| WO | WO-2021180072 A1 | 9/2021 | |

(56) References Cited

FOREIGN PATENT DOCUMENTS

| WO | WO-2021222153 A1 | 11/2021 |
| WO | WO-2021249463 A1 | 12/2021 |
| WO | WO-2022017494 A1 | 1/2022 |
| WO | WO-2022098809 A1 | 5/2022 |
| WO | WO-2022136914 A1 | 6/2022 |
| WO | WO-2022175745 A1 | 8/2022 |
| WO | WO-2022175746 A1 | 8/2022 |
| WO | WO-2022175747 A1 | 8/2022 |
| WO | WO-2022175752 A1 | 8/2022 |
| WO | WO-2022226349 A1 | 10/2022 |
| WO | WO-2022232630 A1 | 11/2022 |
| WO | WO-2022241171 A1 | 11/2022 |
| WO | WO-2022241172 A1 | 11/2022 |
| WO | WO-2022241173 A1 | 11/2022 |
| WO | WO-2022241174 A1 | 11/2022 |
| WO | WO-2022241175 A1 | 11/2022 |
| WO | WO-2023227946 A1 | 11/2023 |

OTHER PUBLICATIONS

Bundgaard. Means to Enhance Penetration: Prodrugs as a Means to Improve the Delivery of Peptide Drugs. Advanced Drug Delivery Review 8:1-38 (1992).

Celsa et al. Making a Prima Facie Case (e.g. in Polymorph Cases). U.S. Patent & Trademark Office Powerpoint presentation dated Jun. 12, 2013 (47 pgs).

Fensome et al., Dual inhibition of TYK2 and JAK1 for the treatment of autoimmune diseases: discovery of ((S)-2,2-difluorocyclopropyl)((1 R,5 S)-3-(2-((1-methyl-1 H-pyrazol-4-yl)amino)pyrimidin-4-yl)-3,8-diazabicyclo[3.2.1]octan-8-yl)methanone (PF-06700841). J Med Chem. 61(19):8597-8612 (2018).

Gerstenberger et al., Discovery of tyrosine kinase 2 (TYK2) inhibitor (PF-06826647) for the treatment of autoimmune diseases. J Med Chem. 63(22):13561-13577 (2020).

*GlaxoSmithKline LLC* v. *Banner Pharmacaps, Inc.* 2013-1593 U.S. Court of Appeals Fed Circuit decided Feb. 24, 2014.

Jordan. Tamoxifen: A Most unlikely pioneering medicine. Nature Reviews: Drug Discovery 2:205-213 (2003).

PCT/IB2022/000061 International Search Report and Written Opinion dated May 6, 2022.

PCT/IB2022/000062 International Search Report and Written Opinion dated May 6, 2022.

PCT/IB2022/000065 International Search Report and Written Opinion dated May 10, 2022.

PCT/IB2022/000086 International Search Report and Written Opinion dated May 6, 2022.

Vippagunta et al. Crystalline Solids, Advanced Drug Delivery Reviews, 48:3-26 (2001).

Widder et al. Section III: Prodrugs Kinetics. Method in Enzymology. 112:309-396 (1985).

Dorwald. Chapter 1 and Chapter 8. Side Reactions in Organic Synthesis, Wiley:VCH, Weinheim p. IX of Preface, Wiley-VCH Verlag GmbH & Co. KGaA (37 pgs.) (2005).

PCT/IB2021/000877 International Search Report and Written Opinion dated Mar. 28, 2022.

PCT/IB2023/000306 International Search Report and Written Opinion dated Oct. 27, 2023.

Co-pending U.S. Appl. No. 18/546,941, inventors Pandey; Anjali et al., filed Aug. 17, 2023.

Co-pending U.S. Appl. No. 18/546,943, inventors Pandey; Anjali et al., filed Aug. 17, 2023.

* cited by examiner

SUBSTITUTED PYRIDINES, PYRIDAZINES, PYRIMIDINES, AND 1,2,4-TRIAZINES AS TYK2 INHIBITORS

CROSS-REFERENCE TO RELATED APPLICATIONS

This application is a continuation of U.S. application Ser. No. 17/737,872, filed May 5, 2022, now U.S. Pat. No. 11,613,548, issued Mar. 28, 2023, which is a continuation of International Application PCT/IB2022/000086, filed Feb. 16, 2022, which claims the benefit of U.S. Provisional Application No. 63/151,287 filed on Feb. 19, 2021, U.S. Provisional Application No. 63/193,511 filed on May 26, 2021, U.S. Provisional Application No. 63/234,934 filed on Aug. 19, 2021, and U.S. Provisional Application No. 63/291,222 filed on Dec. 17, 2021, each of which is incorporated herein by reference in its entirety.

BACKGROUND OF THE INVENTION

The present invention relates to compounds that bind to the pseudokinase domain (JH2) of the non-receptor tyrosine-protein kinase 2 (TYK2). Compounds of the present disclosure may inhibit certain cytokine signaling, for example IL-12, IL-23, and IFNα signaling. Additional aspects of the invention include pharmaceutical compositions comprising the compounds described herein, methods of using the compounds to treat certain diseases, and intermediates and processes useful in the synthesis of the compounds.

TYK2 is a non-receptor tyrosine kinase member of the Janus kinase (JAKs) family of protein kinases. The mammalian JAK family consists of four members, TYK2, JAK1, JAK2, and JAK3. JAK proteins, including TYK2, are integral to cytokine signaling. TYK2 associates with the cytoplasmic domain of type I and type II cytokine receptors, as well as interferon types I and III receptors, and is activated by those receptors upon cytokine binding. Cytokines implicated in TYK2 activation include interferons (e.g. IFN-α, IFN-β, IFN-K, IFN-δ, IFN-ε, IFN-τ, IFN-co, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF). The activated TYK2 then goes on to phosphorylate further signaling proteins such as members of the STAT family, including STAT1, STAT2, STAT3, STAT4, and STAT6.

BRIEF SUMMARY OF THE INVENTION

Compounds described herein are modulators of the JAK family of kinases. More specifically, the compounds of the present disclosure are inhibitors of TYK2. In some embodiments, compounds are selective for TYK2 over other JAKs. For example, compounds may bind specifically to the pseudokinase domain (JH2) of TYK2 thereby enhancing selectivity over JAK family members. In some embodiments, a compound of the present disclosure may be an allosteric modulator or noncompetitive inhibitor of TYK2. In additional embodiments, a compound described herein may be useful in the treatment of TYK2 mediated diseases or disorders.

In one aspect, described herein is a compound of Formula (I):

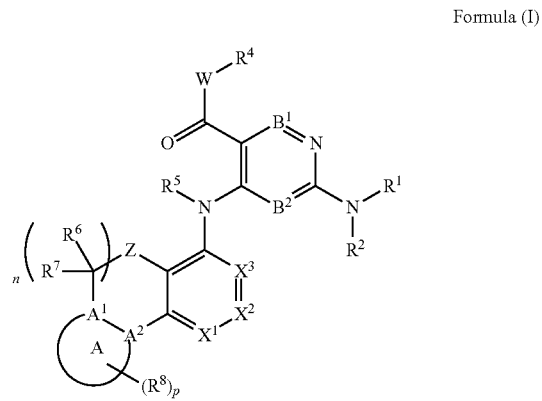

Formula (I)

or a pharmaceutically acceptable salt, tautomer, or solvate thereof, wherein:

Ring A is an unsubstituted or substituted pyrazole wherein $A^1$ and $A^2$ are independently N or C, wherein if Ring A is substituted then Ring A is substituted with p instances of $R^8$;

each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —C(=O)R$^{16}$, —CO$_2$R$^{16}$, —C(=O)N(R$^{16}$)$_2$, —S(=O)R$^{17}$, —SO$_2$R$^{17}$, or —SO$_2$N(R$^{16}$)$_2$;

Z is —NR$^{10}$—, —O—, —S—, —S(=O)—, or —SO$_2$—;

$R^{10}$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

$X^1$, $X^2$, and $X^3$ are each independently CR$^{11}$ or N;

each $R^{11}$ is independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

$B^1$ is N or CR$^{12a}$;

$B^2$ is N or CR$^{12b}$;

$R^{12a}$ and $R^{12b}$ are each independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

$R^1$ is hydrogen, $C_1$-$C_6$ alkyl, or $C_1$-$C_6$ fluoroalkyl;

$R^2$ is a Ring B that is an unsubstituted or substituted heterocycle or unsubstituted or substituted carbocycle, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

or two $R^{13}$ groups on adjacent atoms of Ring B are taken together with the intervening atoms to which they are attached to form an unsubstituted or substituted 5- or 6-membered monocyclic carbocycle or an unsubstituted or substituted 5- or 6-membered monocyclic heterocycle;

or $R^2$ is —C(=O)R$^{14}$, —C(=O)NR$^{14}$R$^{15}$, or —C(=O)OR$^{14}$;

$R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle;

$R^{15}$ is hydrogen, $C_1$-$C_6$ alkyl, or $C_1$-$C_6$ fluoroalkyl;

or $R^{14}$ and $R^{15}$ are taken together with the intervening atoms to which they are attached to form an unsubstituted or substituted 5- or 6-membered monocyclic heterocycle;

or $R^1$ and $R^{15}$ are taken together with the intervening atoms to which they are attached to form an unsubstituted or substituted 5- or 6-membered monocyclic heterocycle;

W is —NR$^3$— or —O—;

$R^3$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle $R^4$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

or $R^3$ and $R^4$ are taken together with the N atom to which they are attached to form a substituted or unsubstituted N-containing heterocycle;

or $R^3$ and $R^{12a}$ are taken together with the intervening atoms to which they are attached to form a substituted or unsubstituted 5- or 6-membered heterocycle;

$R^5$ is hydrogen, $C_1$-$C_6$ alkyl, $C_1$-$C_6$ fluoroalkyl, $C_3$-$C_6$ cycloalkyl, or monocyclic heterocycle;

each $R^6$ and $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

or attached to the same carbon atom are taken together with the carbon atom to which they are attached to form C=O or $C_3$-$C_4$ cycloalkyl;

each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

or two $R^{16}$ on the same N atom are taken together with the N atom to which they are attached to form a substituted or unsubstituted N-containing heterocycle; and each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

wherein each substituted alkyl, substituted fluoroalkyl, substituted deuteroalkyl, substituted alkoxy, substituted fluoroalkoxy, substituted heteroalkyl, substituted carbocycle, and substituted heterocycle is substituted with one or more $R^s$ groups independently selected from the group consisting of deuterium, halogen, $C_1$-$C_6$ alkyl, monocyclic carbocycle, monocyclic heterocycle, —CN, —CH$_2$CN, —OR$^{18}$, —CH$_2$OR$^{18}$, —CO$_2$R$^{18}$, —CH$_2$CO$_2$R$^{18}$, —C(=O)N(R$^{18}$)$_2$, —CH$_2$C(=O)N(R$^{18}$)$_2$, —N(R$^{18}$)$_2$, —CH$_2$N(R$^{18}$)$_2$, —NR$^{18}$C(=O)R$^{18}$, —CH$_2$NR$^{18}$C(=O)R$^{18}$, —NR$^{18}$SO$_2$R$^{19}$, —CH$_2$NR$^{18}$SO$_2$R$^{19}$, —SR$^{18}$, —CH$_2$SR$^{18}$, —S(=O)R$^{19}$, —CH$_2$S(=O)R$^{19}$, —SO$_2$R$^{19}$, —CH$_2$SO$_2$R$^{19}$, —SO$_2$N(R$^{18}$)$_2$, or —CH$_2$SO$_2$N(R$^{18}$)$_2$;

each $R^{18}$ is independently selected from hydrogen, $C_1$-$C_6$ alkyl, $C_1$-$C_6$ fluoroalkyl, $C_1$-$C_6$ heteroalkyl, $C_3$-$C_6$ cycloalkyl, $C_2$-$C_6$ heterocycloalkyl, phenyl, benzyl, 5-membered heteroaryl and 6-membered heteroaryl;

or two $R^{18}$ groups are taken together with the N atom to which they are attached to form a N-containing heterocycle;

each $R^{19}$ is independently selected from $C_1$-$C_6$ alkyl, $C_1$-$C_6$ heteroalkyl, $C_3$-$C_6$ cycloalkyl, $C_2$-$C_6$ heterocycloalkyl, phenyl, benzyl, 5-membered heteroaryl, and 6-membered heteroaryl;

n is 1, 2, or 3;

p is 1 or 2; and q is 1, 2, 3, or 4;

and wherein the compound is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide, nor 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, $R^1$ is hydrogen or $C_1$-$C_4$ alkyl.

In some embodiments, $R^5$ is hydrogen or $C_1$-$C_4$ alkyl. In some embodiments, $R^5$ is hydrogen.

In some embodiments, W is —NR$^3$—. In some embodiments, R$^3$ is hydrogen, C$_1$-C$_4$ alkyl, or C$_1$-C$_4$ deuteroalkyl. In some embodiments, R$^3$ is hydrogen.

In some embodiments, R$^4$ is hydrogen, C$_1$-C$_4$ alkyl, or C$_1$-C$_4$ deuteroalkyl.

In some embodiments, the compound has a structure of Formula (II):

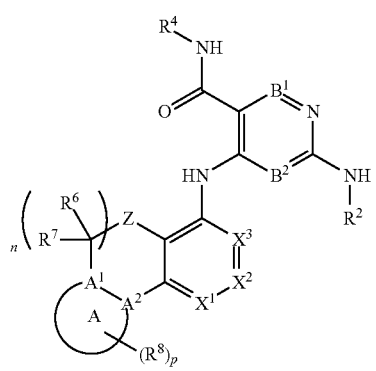

Formula (II)

or a pharmaceutically acceptable salt, tautomer, or solvate thereof.

In some embodiments, X$^1$ is CR$^{11}$, X$^2$ is CR$^{11}$, and X$^3$ is CR$^{11}$; or X$^1$ is CR$^{11}$, X$^2$ is CR$^{11}$ and X$^3$ is N; or X$^1$ is CR$^{11}$, X$^2$ is N, and X$^3$ is CR$^{11}$; or X$^1$ is CR$^{11}$, X$^2$ is N, and X$^3$ is N; or X$^1$ is N, X$^2$ is CR$^{11}$, and X$^3$ is CR$^{11}$; or X$^1$ is N, X$^2$ is CR$^{11}$, and X$^3$ is N; or X$^1$ is N, X$^2$ is N, and X$^3$ is CR$^{11}$. In some embodiments, X$^1$ is CR$^{11}$, X$^2$ is CR$^{11}$, and X$^3$ is CR$^{11}$; or X$^1$ is CR$^{11}$, X$^2$ is CR$^{11}$, and X$^3$ is N; or X$^1$ is CR$^{11}$, X$^2$ is N, and X$^3$ is CR$^{11}$; or X$^1$ is N, X$^2$ is CR$^{11}$, and X$^3$ is CR$^{11}$. In some embodiments, X$^1$ is CR$^{11}$, X$^2$ is CR$^{11}$, and X$^3$ is CR$^{11}$. In some embodiments, each R$^{11}$ is independently hydrogen, halogen, C$_1$-C$_6$ alkyl, C$_1$-C$_6$ fluoroalkyl, —CN, —OH, —OR$^{17}$, or —N(R$^{16}$)$_2$. In some embodiments, each R$^{11}$ is independently hydrogen or fluoro.

In some embodiments, the compound has a structure of Formula (IV):

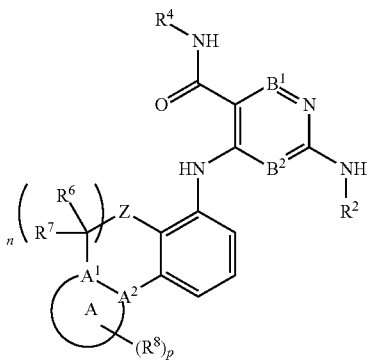

Formula (IV)

or a pharmaceutically acceptable salt, tautomer, or solvate thereof.

In some embodiments, the compound has a structure of Formula (VI):

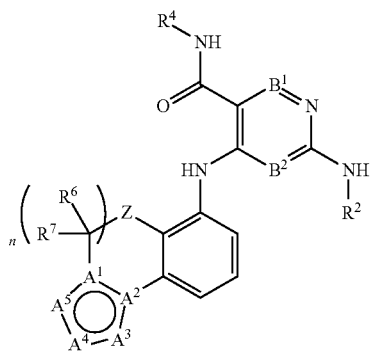

Formula (VI)

or a pharmaceutically acceptable salt, tautomer, or solvate thereof, wherein: A$^1$ and A$^2$ are each independently N or C; and A$^3$, A$^4$, and A$^5$ are each independently N, NR$^8$, or CR$^8$; wherein two adjacent ring atoms selected from A$^1$, A$^2$, A$^3$, A$^4$, and A$^5$ are N or NR$^8$; and the remaining atoms are C or CR$^8$.

In some embodiments, A$^1$ is C; A$^2$ is C; A$^3$ is N; A$^4$ is NR$^8$; and A$^5$ is CR$^8$; or A$^1$ is C; A$^2$ is C; A$^3$ is NR$^8$; A$^4$ is N; and A$^5$ is CR$^8$; or A$^1$ is C; A$^2$ is N; A$^3$ is N; A$^4$ is CR$^8$; and A$^5$ is CR$^8$.

In some embodiments, the compound has a structure of Formula (VIa-1):

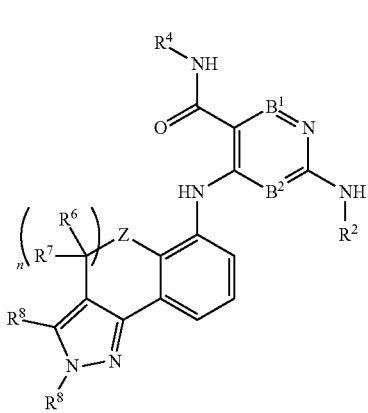

Formula (VIa-1)

or a pharmaceutically acceptable salt, tautomer, or solvate thereof.

In some embodiments, the compound has a structure of Formula (VIc-1):

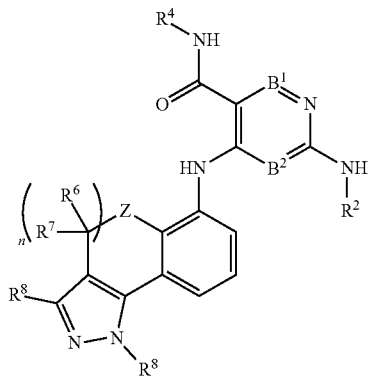

Formula (VIc-1)

or a pharmaceutically acceptable salt, tautomer, or solvate thereof.

In some embodiments, the compound has a structure of Formula (VIf-1):

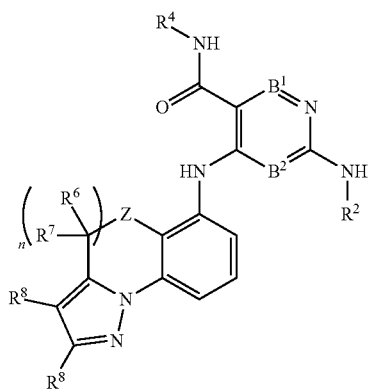

Formula (VIf-1)

or a pharmaceutically acceptable salt, tautomer, or solvate thereof.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —CN, —OH, —OR$^{17}$, —C(=O)R$^{16}$, —CO$_2$R$^{16}$, or —C(=O)N(R$^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —C(=O)R$^{16}$, —CO$_2$R$^{16}$, or —C(=O)N(R$^{16}$)$_2$. In some embodiments, each $R^8$ is independently hydrogen, —Cl, —F, methyl, ethyl, isopropyl, -CD$_3$, —CH$_2$OH, —CF$_3$, cyclopropyl, oxetanyl, azetidinyl, —CN, —OH, —CO$_2$H, or —CO$_2$CH$_3$; wherein if $R^8$ is attached to a nitrogen atom, then $R^8$ is hydrogen, methyl, ethyl, isopropyl, -CD$_3$, —CH$_2$OH, —CF$_3$, cyclopropyl, oxetanyl, azetidinyl, —CO$_2$H, or —CO$_2$CH$_3$. In some embodiments, each $R^8$ is independently hydrogen, methyl, -CD$_3$, —OH, —CH$_2$OH, —CF$_3$, oxetanyl, —CN, or —CO$_2$CH$_3$; wherein if $R^8$ is attached to a nitrogen atom, then $R^8$ is hydrogen, methyl, -CD$_3$, —CH$_2$OH, oxetanyl, or —CO$_2$CH$_3$.

In some embodiments, each $R^6$ and $R^7$ is independently hydrogen, deuterium, halogen, $C_1$-$C_4$ alkyl, or $C_1$-$C_4$ deuteroalkyl. In some embodiments, each $R^6$ and $R^7$ is independently hydrogen, deuterium, F, or methyl.

In some embodiments, Z is —NR$^{10}$—, —O—, or —SO$_2$—. In some embodiments, Z is —NR$^{10}$— or —O—. In some embodiments, Z is —NR$^{10}$—. In some embodiments, $R^{10}$ is hydrogen, $C_1$-$C_4$ alkyl, $C_1$-$C_4$ deuteroalkyl, or cyclopropyl. In some embodiments, Z is —O—.

In some embodiments, $R^2$ is a Ring B that is an unsubstituted or substituted heterocycle or unsubstituted or substituted carbocycle, wherein if Ring B is substituted then Ring B is substituted with q instances of $R^{13}$. In some embodiments, $R^2$ is a Ring B that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if Ring B is substituted then Ring B is substituted with q instances of $R^{13}$. In some embodiments, $R^2$ is a Ring B that is an unsubstituted or substituted phenyl, unsubstituted or substituted monocyclic 6-membered heteroaryl, or unsubstituted or substituted monocyclic 5-membered heteroaryl, wherein if Ring B is substituted then Ring B is substituted with q instances of $R^{13}$. In some embodiments, $R^2$ is a Ring B that is an unsubstituted or substituted phenyl or unsubstituted or substituted monocyclic 6-membered heteroaryl, wherein if Ring B is substituted then Ring B is substituted with q instances of $R^{13}$. In some embodiments, $R^2$ is a Ring B that is an unsubstituted or substituted phenyl, unsubstituted or substituted pyridinyl, unsubstituted or substituted pyrimidinyl, unsubstituted or substituted pyrazinyl, or unsubstituted or substituted pyridazinyl, wherein if Ring B is substituted then Ring B is substituted with q instances of $R^{13}$. In some embodiments, $R^2$ is a Ring B that is an unsubstituted or substituted pyridinyl or unsubstituted or substituted pyrimidinyl, wherein if Ring B is substituted then Ring B is substituted with q instances of $R^{13}$. In some embodiments, $R^2$ is a Ring B that is an unsubstituted or substituted pyridinyl, wherein if Ring B is substituted then Ring B is substituted with q instances of $R^{13}$.

In some embodiments, $R^2$ is

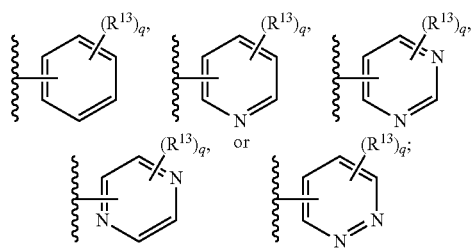

and q is 0, 1, 2, 3, or 4. In some embodiments, B is

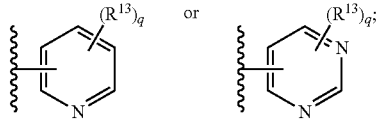

and q is 0, 1, 2, 3, or 4.

In some embodiments, the compound has a structure of Formula (VIII):

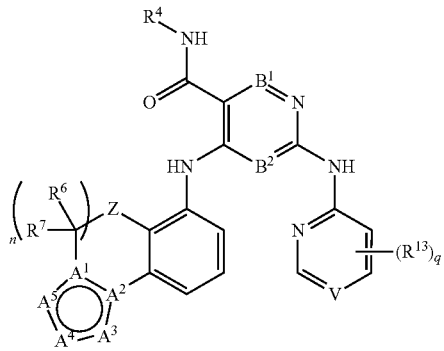

Formula (VIII)

or a pharmaceutically acceptable salt, tautomer, or solvate thereof, wherein: V is N, CH, or $CR^{13}$; q is 1, 2, or 3; $A^1$ and $A^2$ are each independently N or C; and $A^3$, $A^4$, and $A^5$ are each independently N, $NR^8$, or $CR^8$; wherein two adjacent ring atoms selected from $A^1$, $A^2$, $A^3$, $A^4$, and $A^5$ are N or $NR^8$; and the remaining atoms are C or $CR^8$.

In some embodiments, V is N. In some embodiments, V is CH or $CR^{13}$.

In some embodiments, each $R^{13}$ is independently halogen, unsubstituted or substituted $C_1$-$C_6$ alkyl, unsubstituted or substituted $C_1$-$C_6$ fluoroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SO_2R^{17}$, or —$SO_2N(R^{16})_2$. In some embodiments, each $R^{13}$ is independently —F, —Cl, —$CH_3$, or —$CF_3$.

In some embodiments, $R^2$ is —C(=O)$R^{14}$, —C(=O)$NR^{14}R^{15}$, or —C(=O)$OR^{14}$. In some embodiments, $R^2$ is —C(=O)$R^{14}$.

In some embodiments, the compound has a structure of Formula (IX):

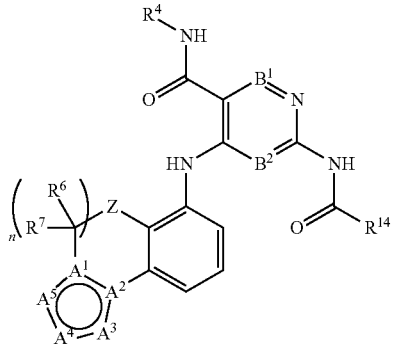

Formula (IX)

or a pharmaceutically acceptable salt, tautomer, or solvate thereof, wherein: $A^1$ and $A^2$ are each independently N or C; and $A^3$, $A^4$, and $A^5$ are each independently N, $NR^B$, or $CR^8$; wherein two adjacent ring atoms selected from $A^1$, $A^2$, $A^3$, $A^4$, and $A^5$ are N or $NR^B$; and the remaining atoms are C or $CR^8$.

In some embodiments, $R^{14}$ is unsubstituted or substituted $C_1$-$C_6$ alkyl, $C_1$-$C_6$ deuteroalkyl, unsubstituted or substituted $C_3$-$C_4$ cycloalkyl, or unsubstituted or substituted 4-membered heterocycloalkyl; wherein the substituted alkyl, substituted heteroalkyl, substituted cycloalkyl, or substituted heterocycloalkyl is substituted with one or more $R^s$ groups independently selected from the group consisting of deuterium, halogen, —CN, —$NH_2$, —OH, —$NH(CH_3)$, —$N(CH_3)_2$, —$CH_3$, —$CH_2CH_3$, —$CHF_2$, —$CF_3$, —$OCH_3$, —$OCHF_2$, and —$OCF_3$.

In some embodiments, $B^1$ is $CR^{12a}$; and $B^2$ is $CR^{12b}$; or $B^1$ is N; and $B^2$ is $CR^{12b}$; or $B^1$ is $CR^{12a}$; and $B^2$ is N; or $B^1$ is N; and $B^2$ is N. In some embodiments, $B^1$ is $CR^{12a}$; and $B^2$ is $CR^{12b}$; or $B^1$ is N; and $B^2$ is $CR^{12b}$. In some embodiments, $R^{12a}$ and $R^{12b}$ are each independently hydrogen, halogen, $C_1$-$C_4$ alkyl, $C_1$-$C_4$ fluoroalkyl, or —CN. In some embodiments, $R^{12a}$ and $R^{12b}$ are each hydrogen.

Any combination of the groups described above for the various variables is contemplated herein. Throughout the specification, groups and substituents thereof are chosen by one skilled in the field to provide stable moieties and compounds.

Also described herein are pharmaceutical compositions comprising a compound described herein, or a pharmaceutically acceptable salt, tautomer, or solvate thereof, and a pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule. In some embodiments, the pharmaceutical composition in the form of an ointment, a lotion, a cream, an oil, a gel, a transdermal patch, or other topical formulation. In additional embodiments, the pharmaceutical composition is in the form of a liquid solution, suspension, gel, depot, or other preparation that can be administered to the eye or surrounding tissue (e.g., eye drops).

Described herein are compounds of Formula (A1), or a pharmaceutically acceptable salt, tautomer, or solvate thereof useful in the treatment of TYK2-mediated disorders. Described herein are compounds of Formula (A1), or a pharmaceutically acceptable salt, tautomer, or solvate thereof, useful in the treatment of an inflammatory or autoimmune disease. In some embodiments, the disease is selected from rheumatoid arthritis, multiple sclerosis, psoriasis, psoriatic arthritis, lupus, systemic lupus erythematosus, Sjögren's syndrome, ankylosing spondylitis, vitiligo, atopic dermatitis, scleroderma, alopecia, hidradenitis suppurativa, uveitis, dry eye, intestinal bowel disease, Crohn's disease, ulcerative colitis, celiac disease, Bechet's disease, type 1 diabetes, systemic sclerosis, and idiopathic pulmonary fibrosis. In some embodiments, the disease is selected from psoriasis, psoriatic arthritis, vitiligo, atopic dermatitis, alopecia, and hidradenitis suppurativa. In some embodiments, the disease is selected from interferonopathies such as, by way of example, Alcardi-Goutieres syndrome.

In any of the aforementioned aspects are further embodiments in which the effective amount of the compound of Formula (I), or a pharmaceutically acceptable salt, or solvate thereof, is: (a) systemically administered to the mammal; and/or (b) administered orally to the mammal; and/or (c) intravenously administered to the mammal; and/or (d) administered by inhalation; and/or (e) administered by nasal administration; or and/or (f) administered by injection to the mammal; and/or (g) administered topically to the mammal; and/or (h) administered by ophthalmic administration; and/or (i) administered rectally to the mammal; and/or (j) administered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the embodiments disclosed herein, the mammal is a human.

In some embodiments, compounds provided herein are topically administered to a human.

Articles of manufacture, which include packaging material, a compound described herein, or a pharmaceutically acceptable salt thereof, within the packaging material, and a label that indicates that the compound or composition, or pharmaceutically acceptable salt, tautomers, pharmaceutically acceptable N-oxide, pharmaceutically active metabolite, pharmaceutically acceptable prodrug, or pharmaceutically acceptable solvate thereof, is used for modulating TYK2, or for the treatment, prevention or amelioration of one or more symptoms of a disease or condition that would benefit from modulating TYK2, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

TYK2 activation has been linked to many diseases and disorders, including inflammatory diseases and disorders, autoimmune diseases and disorders, respiratory diseases and disorders, and cancer.

In particular, IL-23 activation of TYK2 is associated with inflammatory diseases such as inflammatory bowel disease (IBD), Crohn's disease, celiac disease, and ulcerative colitis. As the downstream effector of IL-23, TYK2 also plays a role in psoriasis, ankylosing spondylitis, and Behcet's disease. TYK2 has also been associated with diseases and conditions of the skin, such as psoriasis, vitiligo, atopic dermatitis, hidradenitis suppurativa, scleroderma; or diseases and conditions of the eye, such as Sjögren's syndrome, uveitis, and dry eye.

TYK2 is associated with respiratory diseases and conditions such as asthma, chronic obstructive pulmonary disease (COPD), lung cancer, and cystic fibrosis. Goblet cell hyperplasia (GCH) and mucous hypersecretion is mediated by IL-13-induced activation of the TYK2/STAT6 pathway.

TYK2 is also associated with autoimmune diseases and conditions, such as multiple sclerosis (MS), lupus, and systemic lupus erythematosus (SLE). Loss of function mutation in TYK2, leads to decreased demyelination and increased remyelination of neurons, further suggesting a role for TYK2 inhibitors in the treatment of MS and other CNS demyelination disorders. Various type I IFN signaling pathways dependent on TYK2 signaling have implicated TYK2 in SLE and other autoimmune diseases and conditions.

TYK2 is associated with arthritis, including psoriatic arthritis and rheumatoid arthritis. Decreased TYK2 activity leads to protection of joints from collagen antibody-induced arthritis, a model of human rheumatoid arthritis.

TYK2 has also been shown to play an important role in maintaining tumor surveillance and TYK2 knockout mice showed compromised cytotoxic T cell response, and accelerated tumor development. These effects are largely due to the efficient suppression of natural killer (NK) and cytotoxic T lymphocytes, suggesting that TYK2 inhibitors are highly suitable for the treatment of autoimmune disorders or transplant rejection. Although other JAK family members such as JAK3 have similar roles in the immune system, TYK2 is a superior target because of its involvement in fewer and more closely related signaling pathways, leading to fewer off-target effects. However, studies in T-cell acute lymphoblastic leukemia (T-ALL) indicate that T-ALL is highly dependent on IL-10 via TYK2/STAT1 signaling to maintain cancer cell survival through upregulation of anti-apoptotic protein BCL2. Knockdown of TYK2, but not other JAK family members, reduced cell growth. Thus, selective inhibition of TYK2 has been suggested as a suitable target for patients with IL-10 and/or BCL2-addicted tumors, such as 70% of adult T-cell leukemia cases.

TYK2-mediated STAT3 signaling has also been shown to mediate neuronal cell death caused by amyloid-β (Aβ) peptide. Decreased TYK2 phosphorylation of STAT3 following Aβ administration lead to decreased neuronal cell death, and increased phosphorylation of STAT3 has been observed in postmortem brains of Alzheimer's patients.

Inhibition of JAK-STAT signaling pathways is also implicated in hair growth, and the reversal of the hair loss associated with alopecia areata.

Even though some TYK2 inhibitors are known, there is a continuing need to provide novel inhibitors having more effective or advantageous pharmaceutically relevant properties. For example, compounds with increased activity or increased selectivity over other JAK kinases (especially JAK2). In some embodiments provided herein, the present invention provides inhibitors of TYK2 which show selectivity over JAK1, JAK2, and/or JAK3. In some embodiments, compounds with this selectivity (particularly over JAK2) deliver a pharmacological response that favorably treats one or more of the diseases or conditions described herein without the side-effects associated with the inhibition of JAK2.

In some embodiments, the TYK2 inhibitors described herein are used in the treatment of a disease or condition in a mammal.

Compounds

Compounds described herein, including pharmaceutically acceptable salts, tautomers, and solvates thereof, are inhibitors of TYK2. In some embodiments, compounds described herein are selective for TYK2 over other JAKs. In some embodiments, compounds described herein bind selectively/specifically to the pseudokinase domain (JH2) of TYK2. In some embodiments, a compound described herein binds to an allosteric site of TYK2. In additional embodiments, a compound described herein may be useful in the treatment of TYK2 mediated diseases or disorders.

In one aspect, provided herein is a compound of Formula (I):

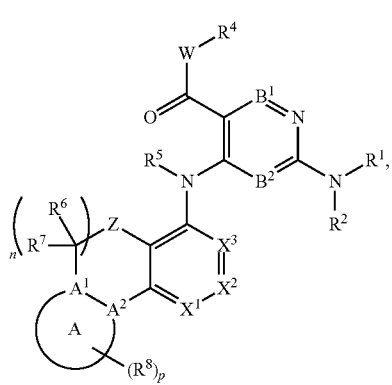

Formula (I)

or a pharmaceutically acceptable salt, tautomer, or solvate thereof, wherein:

Ring A is an unsubstituted or substituted pyrazole wherein $A^1$ and $A^2$ are independently N or C, wherein if Ring A is substituted then Ring A is substituted with p instances of $R^8$;
- each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —C(=O)R$^{16}$, —CO$_2$R$^{16}$, —C(=O)N(R$^{16}$)$_2$, —S(=O)R$^{17}$, —SO$_2$R$^{17}$, or —SO$_2$N(R$^{16}$)$_2$;

Z is —NR$^{10}$—, —O—, —S—, —S(=O)—, or —SO$_2$—;
$R^{10}$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

$X^1$, $X^2$, and $X^3$ are each independently CR$^{11}$ or N;
- each $R^{11}$ is independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

$B^1$ is N or CR$^{12a}$;
$B^2$ is N or CR$^{12b}$;

$R^{12a}$ and $R^{12b}$ are each independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

$R^1$ is hydrogen, $C_1$-$C_6$ alkyl, or $C_1$-$C_6$ fluoroalkyl;
$R^2$ is a Ring B that is an unsubstituted or substituted heterocycle or unsubstituted or substituted carbocycle, wherein if Ring B is substituted then Ring B is substituted with q instances of $R^{13}$;
- each $R^{13}$ is independently halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;
- or two $R^{13}$ groups on adjacent atoms of Ring B are taken together with the intervening atoms to which they are attached to form an unsubstituted or substituted 5- or 6-membered monocyclic carbocycle or an unsubstituted or substituted 5- or 6-membered monocyclic heterocycle;

or $R^2$ is —C(=O)R$^{14}$, —C(=O)NR$^{14}$R$^{15}$, or —C(=O)OR$^{14}$;
$R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle;
$R^{15}$ is hydrogen, $C_1$-$C_6$ alkyl, or $C_1$-$C_6$ fluoroalkyl;
or $R^{14}$ and $R^{15}$ are taken together with the intervening atoms to which they are attached to form an unsubstituted or substituted 5- or 6-membered monocyclic heterocycle;
or $R^1$ and $R^{15}$ are taken together with the intervening atoms to which they are attached to form an unsubstituted or substituted 5- or 6-membered monocyclic heterocycle;

W is —NR$^3$— or —O—;
$R^3$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle
$R^4$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;
or $R^3$ and $R^4$ are taken together with the N atom to which they are attached to form a substituted or unsubstituted N-containing heterocycle;
or $R^3$ and $R^{12a}$ are taken together with the intervening atoms to which they are attached to form a substituted or unsubstituted 5- or 6-membered heterocycle;
$R^5$ is hydrogen, $C_1$-$C_6$ alkyl, $C_1$-$C_6$ fluoroalkyl, $C_3$-$C_6$ cycloalkyl, or monocyclic heterocycle;

each $R^6$ and $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

or two $R^{16}$ on the same N atom are taken together with the N atom to which they are attached to form a substituted or unsubstituted N-containing heterocycle; and each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

wherein each substituted alkyl, substituted fluoroalkyl, substituted deuteroalkyl, substituted alkoxy, substituted fluoroalkoxy, substituted heteroalkyl, substituted carbocycle, and substituted heterocycle is substituted with one or more $R^s$ groups independently selected from the group consisting of deuterium, halogen, $C_1$-$C_6$ alkyl, monocyclic carbocycle, monocyclic heterocycle, —CN, —CH$_2$CN, —OR$^{18}$, —CH$_2$OR$^{18}$, —CO$_2$R$^{18}$, —CH$_2$CO$_2$R$^{18}$, —C(=O)N(R$^{18}$)$_2$, —CH$_2$C(=O)N(R$^{18}$)$_2$, —N(R$^{18}$)$_2$, —CH$_2$N(R$^{18}$)$_2$, —NR$^{18}$C(=O)R$^{18}$, —CH$_2$NR$^{18}$C(=O)R$^{18}$, —NR$^{18}$SO$_2$R$^{19}$, —CH$_2$NR$^{18}$SO$_2$R$^{19}$, —SR$^{18}$, —CH$_2$SR$^{18}$, —S(=O)R$^{19}$, —CH$_2$S(=O)R$^{19}$, —SO$_2$R$^{19}$, —CH$_2$SO$_2$R$^{19}$, —SO$_2$N(R$^{18}$)$_2$, or —CH$_2$SO$_2$N(R$^{18}$)$_2$;

each $R^{18}$ is independently selected from hydrogen, $C_1$-$C_6$ alkyl, $C_1$-$C_6$ fluoroalkyl, $C_1$-$C_6$ heteroalkyl, $C_3$-$C_6$ cycloalkyl, $C_2$-$C_6$ heterocycloalkyl, phenyl, benzyl, 5-membered heteroaryl and 6-membered heteroaryl;

or two $R^{18}$ groups are taken together with the N atom to which they are attached to form a N-containing heterocycle;

each $R^{19}$ is independently selected from $C_1$-$C_6$ alkyl, $C_1$-$C_6$ heteroalkyl, $C_3$-$C_6$ cycloalkyl, $C_2$-$C_6$ heterocycloalkyl, phenyl, benzyl, 5-membered heteroaryl, and 6-membered heteroaryl;

n is 1, 2, or 3;
p is 1 or 2; and
q is 1, 2, 3, or 4.

In some embodiments, the compound is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, 4-((2,5-dimethyl-4,5-dihydro-2H-pyrazolo[4,3-c]quinolin-4-yl)amino)-6-((2,6-dimethylpyrimidin-4-yl)amino)-N-methylnicotinamide, nor 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, the compound of Formula (I) is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, which has the following structure:

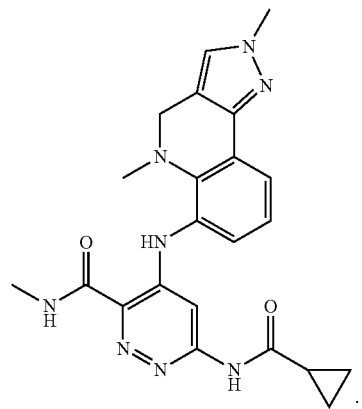 [SMILES: CNC(=O)c1nnc(NC(=O)C2CC2)cc1Nc1cccc2c1N(C)Cc1cn(C)nc1-2]

In some embodiments, the compound of Formula (I) is not 4-((2,5-dimethyl-4,5-dihydro-2H-pyrazolo[4,3-c]quinolin-6-yl)amino)-6-((5-fluoropyridin-2-yl)amino)-N-methylnicotinamide, which has the following structure:

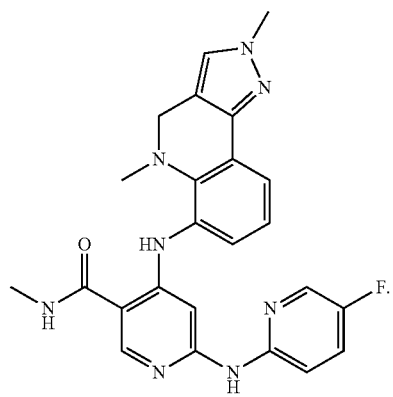 [SMILES: CNC(=O)c1cnc(Nc2ccc(F)cn2)cc1Nc1cccc2c1N(C)Cc1cn(C)nc1-2]

In some embodiments, the compound of Formula (I) is not 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide, which has the following structure:

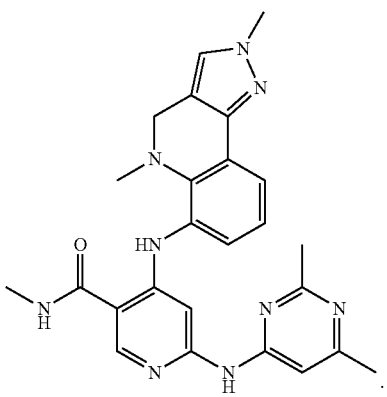

In some embodiments, the compound of Formula (I) is not 6-(cyclopropanecarboxamido)-4-((2,5-dimethyl-4,5-dihydropyrazolo[1,5-a]quinoxalin-6-yl)amino)-N-methylpyridazine-3-carboxamide, which has the following structure:

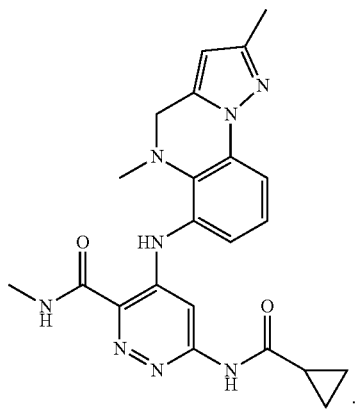 [SMILES: CNC(=O)c1nnc(NC(=O)C2CC2)cc1Nc1cccc2c1N(C)Cc1cc(C)nn1-2]

For any and all of the embodiments, substituents are selected from among a subset of the listed alternatives. For example, in some embodiments, $R^1$ is hydrogen, $C_1$-$C_6$ alkyl, or $C_1$-$C_6$ fluoroalkyl. In some embodiments, $R^1$ is hydrogen, $C_1$-$C_4$ alkyl, or $C_1$-$C_4$ fluoroalkyl. In some embodiments, $R^1$ is hydrogen or $C_1$-$C_6$ alkyl. In some embodiments, $R^1$ is hydrogen or $C_1$-$C_4$ alkyl. In some embodiments, $R^1$ is hydrogen, methyl, ethyl, propyl, isopropyl, or butyl. In some embodiments, $R^1$ is hydrogen or methyl. In some embodiments, $R^1$ is hydrogen. In some embodiments, $R^1$ is methyl.

In some embodiments, $R^5$ is hydrogen, $C_1$-$C_6$ alkyl, or $C_1$-$C_6$ fluoroalkyl. In some embodiments, $R^5$ is hydrogen, $C_1$-$C_4$ alkyl, or $C_1$-$C_4$ fluoroalkyl. In some embodiments, $R^5$ is hydrogen or $C_1$-$C_6$ alkyl. In some embodiments, $R^5$ is hydrogen or $C_1$-$C_4$ alkyl. In some embodiments, $R^5$ is hydrogen, methyl, ethyl, propyl, isopropyl, or butyl. In some embodiments, $R^5$ is hydrogen or methyl. In some embodiments, $R^5$ is hydrogen. In some embodiments, $R^5$ is methyl.

In some embodiments, W is —O—.

In some embodiments, W is —NR$^3$—.

In some embodiments, the compound is a compound of Formula (Ia) or Formula (Ib):

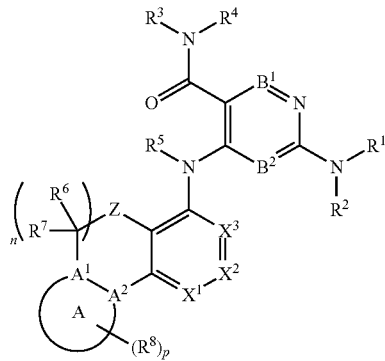

Formula (Ia)

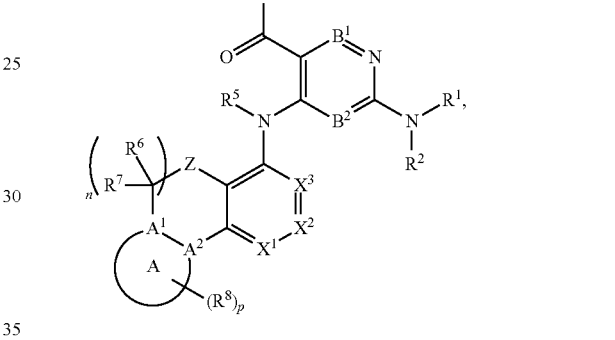

Formula (Ib)

or a pharmaceutically acceptable salt, tautomer, or solvate thereof.

In some embodiments, the compound is a compound of Formula (Ia), or a pharmaceutically acceptable salt, tautomer, or solvate thereof. In some embodiments, the compound is a compound of Formula (Ib), or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —CH$_3$, —CH$_2$D, -CHD$_2$, or -CD$_3$. In some embodiments, $R^4$ is hydrogen. In some embodiments, $R^4$ is —CH$_3$. In some embodiments, $R^4$ is -CD$_3$.

In some embodiments when W is —O—, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —CH$_3$, —CH$_2$D, -CHD$_2$, or -CD$_3$. In some embodiments, $R^4$ is hydrogen. In some embodiments, $R^4$ is —CH$_3$. In some embodiments, $R^4$ is -CD$_3$.

In some embodiments when W is —NR$^3$—, $R^3$ is hydrogen, $C_1$-$C_6$ alkyl, $C_1$-$C_6$ deuteroalkyl, or $C_1$-$C_6$ fluoroalkyl.

In some embodiments, $R^3$ is hydrogen, $C_1$-$C_6$ alkyl, or $C_1$-$C_6$ deuteroalkyl. In other embodiments, $R^3$ is hydrogen, $C_1$-$C_4$ alkyl, $C_1$-$C_4$ deuteroalkyl, or $C_1$-$C_4$ fluoroalkyl. In some embodiments, $R^3$ is hydrogen, $C_1$-$C_4$ alkyl, or $C_1$-$C_4$ deuteroalkyl. In some embodiments, $R^3$ is hydrogen, $C_1$-$C_2$ alkyl, or $C_1$-$C_2$ deuteroalkyl. In some embodiments, $R^3$ is hydrogen, —$CH_3$, —$CH_2D$, -$CHD_2$, or -$CD_3$. In some embodiments, $R^3$ is hydrogen. In some embodiments, $R^3$ is —$CH_3$. In some embodiments, $R^3$ is -$CD_3$.

In some embodiments when W is —$NR^3$—, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments when W is —$NR^3$—, $R^3$ and $R^4$ are each independently hydrogen, $C_1$-$C_6$ alkyl, $C_1$-$C_6$ deuteroalkyl, or $C_1$-$C_6$ fluoroalkyl. In some embodiments, $R^3$ and $R^4$ are each independently hydrogen, $C_1$-$C_6$ alkyl, or $C_1$-$C_6$ deuteroalkyl. In other embodiments, $R^3$ and $R^4$ are each independently hydrogen, $C_1$-$C_4$ alkyl, $C_1$-$C_4$ deuteroalkyl, or $C_1$-$C_4$ fluoroalkyl. In some embodiments, $R^3$ and $R^4$ are each independently hydrogen, $C_1$-$C_4$ alkyl, or $C_1$-$C_4$ deuteroalkyl. In some embodiments, $R^3$ and $R^4$ are each independently hydrogen, $C_1$-$C_2$ alkyl, or $C_1$-$C_2$ deuteroalkyl. In some embodiments, $R^3$ and $R^4$ are each independently hydrogen, —$CH_3$, —$CH_2D$, -$CHD_2$, or -$CD_3$. In some embodiments, $R^3$ is hydrogen. In some embodiments, $R^3$ is hydrogen; and $R^4$ is hydrogen, $C_1$-$C_4$ alkyl, or $C_1$-$C_4$ deuteroalkyl. In some embodiments, $R^3$ is hydrogen; and $R^4$ is hydrogen, $C_1$-$C_2$ alkyl, or $C_1$-$C_2$ deuteroalkyl. In some embodiments, $R^3$ is hydrogen; and $R^4$ is hydrogen, —$CH_3$, —$CH_2D$, -$CHD_2$, or -$CD_3$. In some embodiments, $R^3$ is hydrogen; and $R^4$ is hydrogen. In some embodiments, $R^3$ is hydrogen; and $R^4$ is $C_1$-$C_4$ alkyl, or $C_1$-$C_4$ deuteroalkyl. In some embodiments, $R^3$ is hydrogen; and $R^4$ is $C_1$-$C_2$ alkyl, or $C_1$-$C_2$ deuteroalkyl. In some embodiments, $R^3$ is hydrogen; and $R^4$ is —$CH_3$, -$CH_2D$, -$CHD_2$, or -$CD_3$. In some embodiments, $R^3$ is hydrogen; and $R^4$ is —$CH_3$. In some embodiments, $R^3$ is hydrogen; and $R^4$ is -$CD_3$.

In some embodiments when W is —$NR^3$—, $R^3$ and $R^4$ are taken together with the N atom to which they are attached to form a substituted or unsubstituted N-containing heterocycle. In some embodiments, $R^3$ and $R^4$ are taken together with the N atom to which they are attached to form a substituted or unsubstituted N-containing heterocycloalkyl. In some embodiments, $R^3$ and $R^4$ are taken together with the N atom to which they are attached to form a substituted or unsubstituted monocyclic N-containing heterocycloalkyl. In some embodiments, $R^3$ and $R^4$ are taken together with the N atom to which they are attached to form a substituted or unsubstituted 3- to 6-membered N-containing heterocycloalkyl.

In some embodiments, the compound is a compound of Formula (II) or Formula (III):

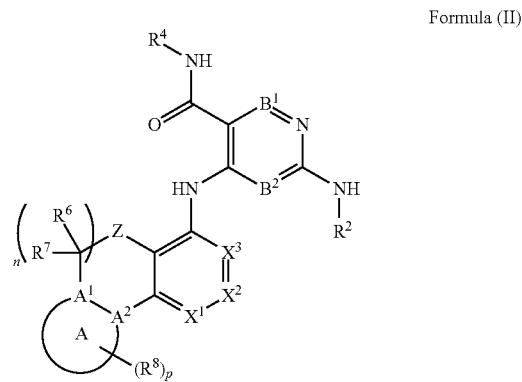

Formula (II)

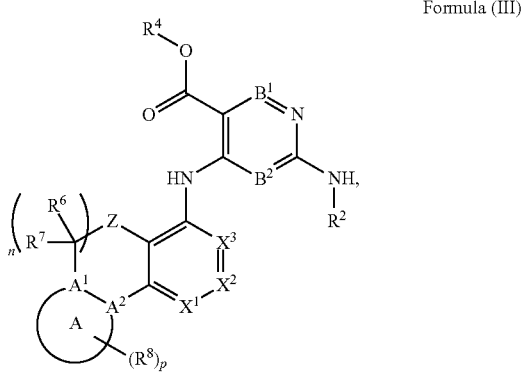

Formula (III)

or a pharmaceutically acceptable salt, tautomer, or solvate thereof.

In some embodiments, the compound is a compound of Formula (II), or a pharmaceutically acceptable salt, tautomer, or solvate thereof. In some embodiments, the compound is a compound of Formula (III), or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, $X^1$ is $CR^{11}$, $X^2$ is $CR^{11}$, and $X^3$ is $CR^{11}$; or $X^1$ is $CR^{11}$, $X^2$ is CR and $X^3$ is N; or $X^1$ is $CR^{11}$, $X^2$ is N, and $X^3$ is $CR^{11}$; or $X^1$ is $CR^{11}$, $X^2$ is N, and $X^3$ is N; or $X^1$ is N, $X^2$ is $CR^{11}$, and $X^3$ is $CR^{11}$; or $X^1$ is N, $X^2$ is $CR^{11}$, and $X^3$ is N; or $X^1$ is N, $X^2$ is N, and $X^3$ is $CR^{11}$. In some embodiments, $X^1$ is $CR^{11}$, $X^2$ is $CR^{11}$, and $X^3$ is $CR^{11}$. In some embodiments, $X^1$ is $CR^{11}$, $X^2$ is $CR^{11}$, and $X^3$ is N. In some embodiments, $X^1$ is $CR^{11}$, $X^2$ is N, and $X^3$ is $CR^{11}$. In some embodiments, $X^1$ is $CR^{11}$, $X^2$ is N, and $X^3$ is N. In some embodiments, $X^1$ is N, $X^2$ is $CR^{11}$, and $X^3$ is $CR^{11}$. In some embodiments, $X^1$ is N, $X^2$ is $CR^{11}$, and $X^3$ is N. In some embodiments, $X^1$ is N, $X^2$ is N, and $X^3$ is $CR^{11}$.

In some embodiments, $X^1$ is $CR^{11}$, $X^2$ is $CR^{11}$, and $X^3$ is $CR^{11}$; or $X^1$ is $CR^{11}$, $X^2$ is $CR^{11}$ and $X^3$ is N; or $X^1$ is $CR^{11}$, $X^2$ is N, and $X^3$ is $CR^{11}$; or $X^1$ is N, $X^2$ is $CR^{11}$, and $X^3$ is $CR^{11}$.

In some embodiments, each $R^{11}$ is independently hydrogen, halogen, $C_1$-$C_6$ alkyl, $C_1$-$C_6$ fluoroalkyl, —CN, —OH, —$OR^{17}$, —$CO_2R^{16}$, —$C(=O)N(R^{16})_2$, —$N(R^{16})_2$, —$SO_2R^{17}$, or —$SO_2N(R^{16})_2$. In some embodiments, each $R^{11}$ is independently hydrogen, halogen, $C_1$-$C_6$ alkyl, $C_1$-$C_6$ fluoroalkyl, —CN, —OH, —$OR^{17}$, —$C(=O)N(R^{16})_2$, —$N(R^{16})_2$, or —$SO_2N(R^{16})_2$. In some embodiments, each $R^{11}$ is independently hydrogen, halogen, $C_1$-$C_6$ alkyl, $C_1$-$C_6$ fluoroalkyl, —CN, —OH, —$OR^{17}$, or —$N(R^{16})_2$. In some embodiments, each $R^{11}$ is independently hydrogen, halogen, $C_1$-$C_4$ alkyl, $C_1$-$C_4$ fluoroalkyl, —CN, —OH, —$OR^{17}$, or —$N(R^{16})_2$. In some embodiments, each $R^{11}$ is independently hydrogen, halogen, $C_1$-$C_4$ alkyl, $C_1$-$C_4$ fluoroalkyl, or —CN. In some embodiments, each $R^{11}$ is independently hydrogen, halogen, or —CN. In some embodiments, each $R^{11}$ is independently hydrogen or halogen. In some embodiments, each $R^{11}$ is independently hydrogen, fluoro, or chloro. In some embodiments, each $R^{11}$ is independently hydrogen or fluoro. In some embodiments, each $R^{11}$ is hydrogen.

In some embodiments, $X^1$, $X^2$, and $X^3$ are each independently CH, CF, or N. In some embodiments, $X^1$, $X^2$, and $X^3$ are each independently CH or N. In some embodiments, $X^1$ is CH or CF, $X^2$ is CH or CF, and $X^3$ is CH or CF; or $X^1$ is CH or CF, $X^2$ is CH or CF, and $X^3$ is N; or $X^1$ is CH or CF, $X^2$ is N, and $X^3$ is CH or CF; or $X^1$ is N, $X^2$ is CH or CF, and $X^3$ is CH or CF. In some embodiments, $X^1$ is CH, $X^2$ is CH, and $X^3$ is CH; or $X^1$ is CH, $X^2$ is CH, and $X^3$ is N; or $X^1$ is CH, $X^2$ is N, and $X^3$ is CH; or $X^1$ is N, $X^2$ is CH, and $X^3$ is CH.

In some embodiments, $X^1$ is CH, $X^2$ is CH, CF, or N, and $X^3$ is CH. In some embodiments, $X^1$ is CH, $X^2$ is CF or N, and $X^3$ is CH. In some embodiments, $X^1$ is CH, CF, or N, $X^2$ is CH, and $X^3$ is CH. In some embodiments, $X^1$ is CF, or N, $X^2$ is CH, and $X^3$ is CH. In some embodiments, $X^1$ is CH, $X^2$ is CH, and $X^3$ is CH, CF, or N. In some embodiments, $X^1$ is CH, $X^2$ is CH, and $X^3$ is CF or N.

In some embodiments, the compound is a compound of Formula (IV) or Formula (V):

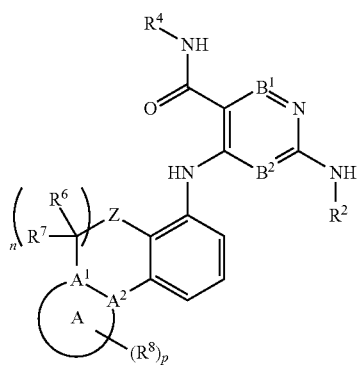

Formula (IV)

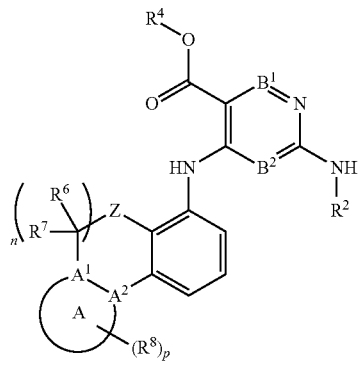

Formula (V)

or a pharmaceutically acceptable salt, tautomer, or solvate thereof.

In some embodiments, the compound is a compound of Formula (IV), or a pharmaceutically acceptable salt, tautomer, or solvate thereof. In some embodiments, the compound is a compound of Formula (V), or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —$C(=O)R^{16}$, —$CO_2R^{16}$, —$C(=O)N(R^{16})_2$, —$N(R^{16})_2$, —$NR^{16}C(=O)R^{17}$, —$SR^{16}$, —$S(=O)R^{17}$, —$SO_2R^{17}$, or —$SO_2N(R^{16})_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —$C(=O)R^{16}$, —$CO_2R^{16}$, —$C(=O)N(R^{16})_2$, —$S(=O)R^{17}$, —$SO_2R^{17}$, or —$SO_2N(R^{16})_2$. In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —CN, —OH, —$OR^{17}$, —$C(=O)R^{16}$, —$CO_2R^{16}$, or —$C(=O)N(R^{16})_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —$C(=O)R^{16}$, -$CO_2R^{16}$, or —$C(=O)N(R^{16})_2$. In some embodiments, each $R^8$ is independently hydrogen, —Cl, —F, methyl, ethyl, isopropyl, -CD$_3$, —CH$_2$OH, —CF$_3$, cyclopropyl, oxetanyl, azetidinyl, —CN, —OH, —CO$_2$H, or —CO$_2$CH$_3$; wherein if R$^8$ is attached to a nitrogen atom, then R$^8$ is hydrogen, methyl, ethyl, isopropyl, -CD$_3$, —CH$_2$OH, —CF$_3$, cyclopropyl, oxetanyl, azetidinyl, —CO$_2$H, or —CO$_2$CH$_3$. In some embodiments, each R$^8$ is independently hydrogen, methyl, -CD$_3$, —OH, —CH$_2$OH, —CF$_3$, oxetanyl, —CN, or —CO$_2$CH$_3$; wherein if R$^8$ is attached to a nitrogen atom, then R$^8$ is hydrogen, methyl, -CD$_3$, —CH$_2$OH, oxetanyl, or —CO$_2$CH$_3$.

In some embodiments, p is 0, 1, or 2. In some embodiments, p is 1 or 2. In some embodiments, p is 1. In some embodiments, p is 2. In some embodiments, p is 0; and Ring A is therefore unsubstituted.

In some embodiments, Ring A is

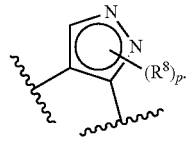

In some embodiments, Ring A is

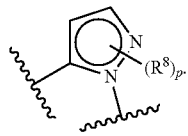

In some embodiments,

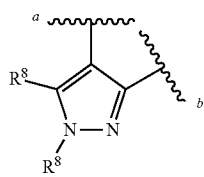

is

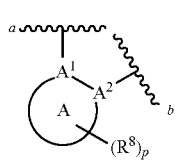

In some embodiments,

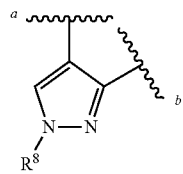

is

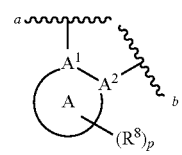

In some embodiments,

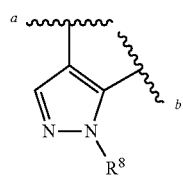

is

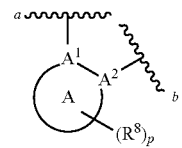

In some embodiment,

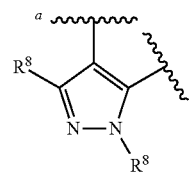

is

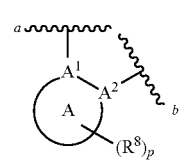

In some embodiments, is

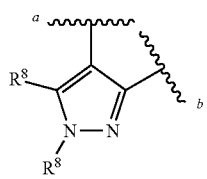

In some embodiments,

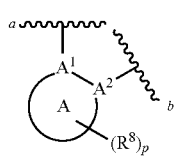

is

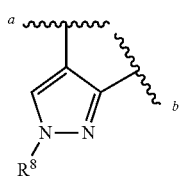

In some embodiments,

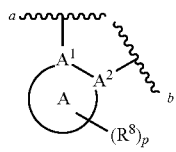

is

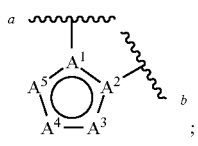

wherein $A^1$ and $A^2$ are each independently N or C; and $A^3$, $A^4$, and $A^5$ are each independently N, $NR^8$, or $CR^8$; wherein two adjacent ring atoms selected from $A^1$, $A^2$, $A^3$, $A^4$, and $A^5$ are N or $NR^8$; and the remaining atoms are C or $CR^8$.

In some embodiments, the compound is a compound of Formula (VI) or Formula (VII):

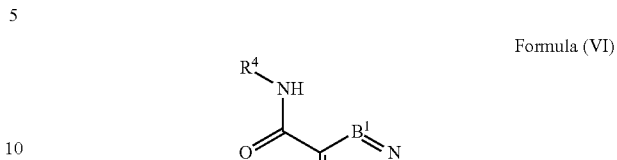

Formula (VI)

Formula (VII)

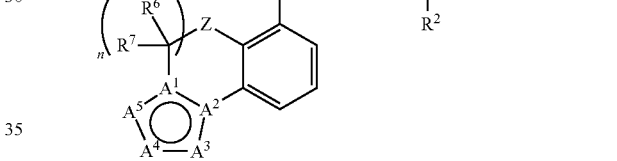

or a pharmaceutically acceptable salt, tautomer, or solvate thereof; wherein $A^1$ and $A^2$ are each independently N or C; and $A^3$, $A^4$, and $A^5$ are each independently N, $NR^8$, or $CR^8$; wherein two adjacent ring atoms selected from $A^1$, $A^2$, $A^3$, $A^4$, and $A^5$ are N or $NR^8$; and the remaining atoms are C or $CR^8$.

In some embodiments, the compound is a compound of Formula (VI), or a pharmaceutically acceptable salt, tautomer, or solvate thereof. In some embodiments, the compound is a compound of Formula (VII), or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments,
$A^1$ is C; $A^2$ is C; $A^3$ is N; $A^4$ is $NR^8$; and $A^5$ is $CR^8$;
or $A^1$ is C; $A^2$ is C; $A^3$ is $NR^8$; $A^4$ is N; and $A^5$ is $CR^8$;
or $A^1$ is C; $A^2$ is N; $A^3$ is N; $A^4$ is CR; and $A^5$ is $CR^8$.

In some embodiments, the compound is a compound of Formula (VIa-1):

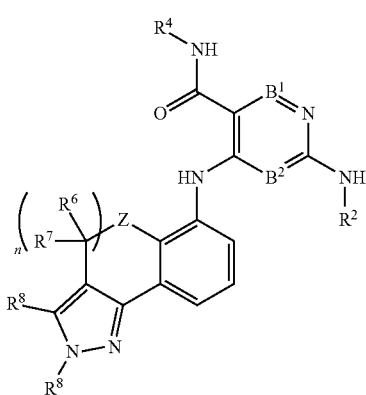

Formula (VIa-1)

or a pharmaceutically acceptable salt, tautomer, or solvate thereof.

In some embodiments, the compound of Formula (VIa-1) is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, nor 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, the compound is a compound of Formula (VIc-1):

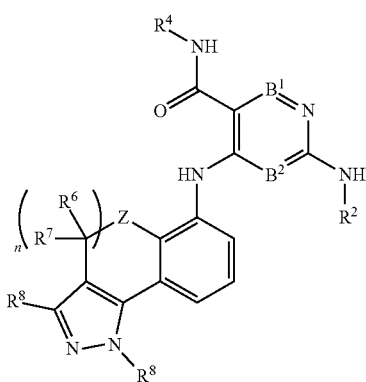

Formula (VIc-1)

or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, the compound is a compound of Formula (VIf-1):

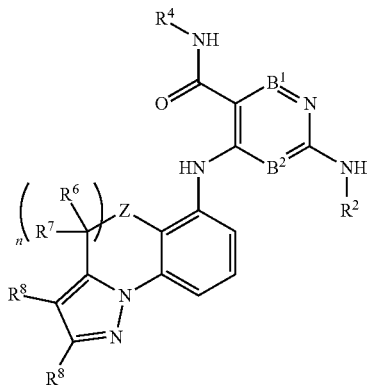

Formula (VIf-1)

or a pharmaceutically acceptable salt, tautomer, or solvate thereof.

In some embodiments, the compound of Formula (VIf-a) is not 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —C(=O)$R^{16}$, —$CO_2R^{16}$, —C(=O)N($R^{16}$)$_2$, —S(=O)$R^{17}$, —$SO_2R^{17}$, or —$SO_2$N($R^{16}$)$_2$.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —CN, —OH, —OR$^{17}$, —C(=O)R$^{16}$, —CO$_2$R$^{16}$, or —C(=O)N(R$^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —C(=O)R$^{16}$, —CO$_2$R$^{16}$, or —C(=O)N(R$^{16}$)$_2$.

In some embodiments, each $R^8$ is independently hydrogen, halogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —CN, —OH, —OR$^{17}$, —C(=O)R$^{16}$, —CO$_2$R$^{16}$, or —C(=O)N(R$^{16}$)$_2$; wherein if $R^8$ is attached to a nitrogen atom, then $R^8$ is hydrogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —C(=O)R$^{16}$, —CO$_2$R$^{16}$, or —C(=O)N(R$^{16}$)$_2$.

In some embodiments, each $R^8$ is independently hydrogen, —Cl, —F, methyl, ethyl, isopropyl, -CD$_3$, —CH$_2$OH, —CF$_3$, cyclopropyl, oxetanyl, azetidinyl, —CN, —OH, —CO$_2$H, or —CO$_2$CH$_3$; wherein if $R^8$ is attached to a nitrogen atom, then $R^8$ is hydrogen, methyl, ethyl, isopropyl, -CD$_3$, —CH$_2$OH, —CF$_3$, cyclopropyl, oxetanyl, azetidinyl, —CO$_2$H, or —CO$_2$CH$_3$.

In some embodiments, each $R^8$ is independently hydrogen, methyl, -CD$_3$, —OH, —CH$_2$OH, —CF$_3$, oxetanyl, —CN, or —CO$_2$CH$_3$; wherein if $R^8$ is attached to a nitrogen atom, then $R^8$ is hydrogen, methyl, -CD$_3$, —CH$_2$OH, oxetanyl, or —CO$_2$CH$_3$.

In some embodiments, each $R^8$ is independently hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —C(=O)R$^{16}$, —CO$_2$R$^{16}$, or —C(=O)N(R$^{16}$)$_2$. In some embodiments, each $R^8$ is independently hydrogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —C(=O)R$^{16}$, —CO$_2$R$^{16}$, or —C(=O)N(R$^{16}$)$_2$. In some embodiments, each $R^8$ is independently hydrogen, methyl, ethyl, isopropyl, -CD$_3$, —CH$_2$OH, —CF$_3$, cyclopropyl, oxetanyl, azetidinyl, —CN, —CO$_2$H, or —CO$_2$CH$_3$. In some embodiments, each $R^8$ is independently hydrogen, methyl, -CD$_3$, —CH$_2$OH, —CF$_3$, oxetanyl, —CN, or —CO$_2$CH$_3$. In some embodiments, each $R^8$ is independently hydrogen, $C_1$-$C_6$ alkyl, $C_1$-$C_6$ deuteroalkyl, or $C_1$-$C_6$ fluoroalkyl. In some embodiments, each $R^8$ is independently hydrogen, $C_1$-$C_4$ alkyl, $C_1$-$C_4$ deuteroalkyl, or $C_1$-$C_4$ fluoroalkyl. In some embodiments, each $R^8$ is independently hydrogen, methyl, ethyl, isopropyl, -CD$_3$, or —CF$_3$. In some embodiments, each $R^8$ is independently hydrogen, methyl, -CD$_3$, or —CF$_3$. In some embodiments, each $R^8$ is independently hydrogen or methyl.

In some embodiments, each $R^6$ and $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle, —CN, —OH, —OR$^{17}$, —C(=O)N(R$^{16}$)$_2$, —N(R$^{16}$)$_2$, —NR$^{16}$C(=O)R$^{17}$, —SO$_2$R$^{17}$, or —SO$_2$N(R$^{16}$)$_2$. In some embodiments, each $R^6$ and $R^7$ is independently halogen, $C_1$-$C_6$ alkyl, $C_1$-$C_6$ fluoroalkyl, —CN, —OH, —OR$^{17}$, and —N(R$^{16}$)$_2$. In some embodiments, each $R^6$ and $R^7$ is independently hydrogen, halogen, or $C_1$-$C_6$ alkyl. In some embodiments, each $R^6$ and $R^7$ is independently hydrogen or $C_1$-$C_6$ alkyl. In some embodiments, each $R^6$ and $R^7$ is independently hydrogen, deuterium, halogen, $C_1$-$C_4$ alkyl, or $C_1$-$C_4$ deuteroalkyl. In some embodiments, each $R^6$ and $R^7$ is independently hydrogen or $C_1$-$C_4$ alkyl. In some embodiments, each $R^6$ and $R^7$ is independently hydrogen, deuterium, F, Cl, -CD$_3$, or methyl. In some embodiments, each $R^6$ and $R^7$ is independently hydrogen, deuterium, F, or methyl. In some embodiments, each $R^6$ and $R^7$ is independently hydrogen or methyl. In some embodiments, one $R^6$ or $R^7$ is methyl. In some embodiments, one $R^6$ is methyl. In some embodiments, each $R^6$ and $R^7$ is hydrogen. In some embodiments, each $R^6$ and $R^7$ is deuterium. In some embodiments, each $R^6$ and $R^7$ is F.

In some embodiments, one $R^6$ and one $R^7$ attached to the same carbon atom are taken together with the carbon atom to which they are attached to form C=O or $C_3$-$C_4$ cycloalkyl. In some embodiments, one $R^6$ and one $R^7$ attached to the same carbon atom are taken together with the carbon atom to which they are attached to form C=O. In some embodiments, one $R^6$ and one $R^7$ attached to the same carbon atom are taken together with the carbon atom to which they are attached to form $C_3$-$C_4$ cycloalkyl. In some embodiments, one $R^6$ and one $R^7$ attached to the same carbon atom are taken together with the carbon atom to which they are attached to form a cyclopropyl.

In some embodiments, n is 1 or 2. In some embodiments, n is 1. In some embodiments, n is 2. In some embodiments, n is 3.

In some embodiments, Z is —NR$^{10}$—, —O—, —S—, or —SO$_2$—. In some embodiments, Z is —NR$^{10}$—, —O—, or —SO$_2$—. In some embodiments, Z is —NR$^{10}$—, —O—, or —S—. In some embodiments, Z is —NR$^{10}$— or —O—.

In some embodiments, Z is —NR$^{10}$—. In some embodiments, $R^{10}$ is hydrogen, $C_1$-$C_6$ alkyl, Ci-$C_6$ deuteroalkyl, $C_1$-$C_6$ fluoroalkyl, $C_3$-$C_6$ cycloalkyl, or 4- to 6-membered heterocycloalkyl. In some embodiments, $R^{10}$ is hydrogen, $C_1$-$C_6$ alkyl, $C_1$-$C_6$ fluoroalkyl, $C_3$-$C_6$ cycloalkyl, or 4- to 6-membered heterocycloalkyl. In some embodiments, $R^{10}$ is hydrogen, $C_1$-$C_4$ alkyl, $C_1$-$C_4$ deuteroalkyl, $C_1$-$C_4$ fluoroalkyl, $C_3$-$C_4$ cycloalkyl, or 4-membered heterocycloalkyl. In some embodiments, $R^{10}$ is hydrogen, $C_1$-$C_4$ alkyl, $C_1$-$C_4$ fluoroalkyl, $C_3$-$C_4$ cycloalkyl, or 4-membered heterocycloalkyl. In some embodiments, $R^{10}$ is hydrogen, $C_1$-$C_4$ alkyl, $C_1$-$C_4$ deuteroalkyl, cyclopropyl, cyclobutyl, oxetanyl, or azetidinyl. In some embodiments, $R^{10}$ is hydrogen, $C_1$-$C_4$ alkyl, cyclopropyl, cyclobutyl, oxetanyl, or azetidinyl. In some embodiments, $R^{10}$ is hydrogen, $C_1$-$C_4$ alkyl, $C_1$-$C_4$ deuteroalkyl, or cyclopropyl. In some embodiments, $R^{10}$ is hydrogen, $C_1$-$C_4$ alkyl, or cyclopropyl. In some embodiments, $R^{10}$ is hydrogen, $C_1$-$C_4$ alkyl, or $C_1$-$C_4$ deuteroalkyl. In some embodiments, $R^{10}$ is hydrogen, —CH$_3$, or -CD$_3$. In some embodiments, $R^{10}$ is $C_1$-$C_4$ alkyl or $C_1$-$C_4$ deuteroalkyl. In some embodiments, $R^{10}$ is —CH$_3$ or -CD$_3$. In some embodiments, $R^{10}$ is —CH$_3$. In some embodiments, $R^{10}$ is -CD$_3$.

In some embodiments, Z is NH, NCH$_3$, or NCD$_3$. In some embodiments, Z is NCH$_3$ or NCD$_3$. In some embodiments, Z is NCH$_3$. In some embodiments, Z is NCD$_3$.

In some embodiments, Z is —O—. In some embodiments, Z is —S—. In some embodiments, Z is —S(=O)—. In some embodiments, Z is —SO$_2$—.

In some embodiments, $R^2$ is a Ring B that is an unsubstituted or substituted heterocycle or unsubstituted or substituted carbocycle, wherein if Ring B is substituted then Ring B is substituted with q instances of $R^{13}$. In some embodiments, $R^2$ is a Ring B that is an unsubstituted or substituted monocyclic carbocycle, unsubstituted or substituted bicyclic carbocycle, unsubstituted or substituted monocyclic heterocycle, unsubstituted or substituted bicyclic heterocycle, unsubstituted or substituted spirocyclic carbocycle, unsubstituted or substituted spirocyclic heterocycle, unsubstituted or substituted bridged carbocycle, or unsubstituted or substituted bridged heterocycle, wherein if Ring B is substituted then Ring B is substituted with q instances of $R^{13}$.

In some embodiments, $R^2$ is a Ring B that is an unsubstituted or substituted monocyclic carbocycle, unsubstituted or substituted bicyclic carbocycle, unsubstituted or substituted monocyclic heterocycle, or unsubstituted or substituted bicyclic heterocycle, wherein if Ring B is substituted then Ring B is substituted with q instances of $R^{13}$.

In some embodiments, $R^2$ is a Ring B that is an unsubstituted or substituted phenyl, unsubstituted or substituted naphthyl, unsubstituted or substituted monocyclic 6-membered heteroaryl, unsubstituted or substituted monocyclic 5-membered heteroaryl, or unsubstituted or substituted bicyclic heteroaryl, wherein if Ring B is substituted then Ring B is substituted with q instances of $R^{13}$.

In some embodiments, $R^2$ is a Ring B that is an unsubstituted or substituted phenyl, unsubstituted or substituted monocyclic 6-membered heteroaryl, or unsubstituted or substituted monocyclic 5-membered heteroaryl, wherein if Ring B is substituted then Ring B is substituted with q instances of $R^{13}$.

In some embodiments, $R^2$ is a Ring B that is an unsubstituted or substituted monocyclic 5-membered heteroaryl, wherein if Ring B is substituted then Ring B is substituted with q instances of $R^{13}$. In some embodiments, $R^2$ is a Ring B that is an unsubstituted or substituted pyrrolyl, unsubstituted or substituted furanyl, unsubstituted or substituted thiophenyl, unsubstituted or substituted pyrazolyl, unsubstituted or substituted imidazolyl, unsubstituted or substituted oxazolyl, unsubstituted or substituted isoxazolyl, unsubstituted or substituted thiazolyl, unsubstituted or substituted isothiazolyl, unsubstituted or substituted triazolyl, unsubstituted or substituted oxadiazolyl, unsubstituted or substituted thiadiazolyl, or unsubstituted or substituted tetrazolyl, wherein if Ring B is substituted then Ring B is substituted with q instances of $R^{13}$. In some embodiments, $R^2$ is a Ring B that is an unsubstituted or substituted pyrrolyl, unsubstituted or substituted imidazolyl, unsubstituted or substituted pyrazolyl, unsubstituted or substituted triazolyl, or unsubstituted or substituted tetrazolyl, wherein if Ring B is substituted then Ring B is substituted with q instances of $R^{13}$. In some embodiments, $R^2$ is a Ring B that is an unsubstituted or substituted pyrrolyl, unsubstituted or substituted imidazolyl, or unsubstituted or substituted pyrazolyl, wherein if Ring B is substituted then Ring B is substituted with q instances of $R^{13}$.

In some embodiments, $R^2$ is a Ring B that is an unsubstituted or substituted phenyl or unsubstituted or substituted monocyclic 6-membered heteroaryl, wherein if Ring B is substituted then Ring B is substituted with q instances of $R^{13}$.

In some embodiments, $R^2$ is a Ring B that is an unsubstituted or substituted phenyl, unsubstituted or substituted pyridinyl, unsubstituted or substituted pyrimidinyl, unsubstituted or substituted pyrazinyl, or unsubstituted or substituted pyridazinyl, wherein if Ring B is substituted then Ring B is substituted with q instances of $R^{13}$.

In some embodiments, $R^2$ is a Ring B that is an unsubstituted or substituted monocyclic 6-membered heteroaryl, wherein if Ring B is substituted then Ring B is substituted with q instances of $R^{13}$. In some embodiments, $R^2$ is a Ring B that is an unsubstituted or substituted pyridinyl, unsubstituted or substituted pyrimidinyl, unsubstituted or substituted pyrazinyl, or unsubstituted or substituted pyridazinyl, wherein if Ring B is substituted then Ring B is substituted with q instances of $R^{13}$. In some embodiments, $R^2$ is a Ring B that is an unsubstituted or substituted pyridinyl or unsubstituted or substituted pyrimidinyl, wherein if Ring B is substituted then Ring B is substituted with q instances of $R^{13}$. In some embodiments, $R^2$ is a Ring B that is an unsubstituted or substituted pyridinyl, wherein if Ring B is substituted then Ring B is substituted with q instances of $R^{13}$. In some embodiments, $R^2$ is a Ring B that is an unsubstituted or substituted pyrimidinyl, wherein if Ring B is substituted then Ring B is substituted with q instances of $R^{13}$.

In some embodiments, $R^2$ is

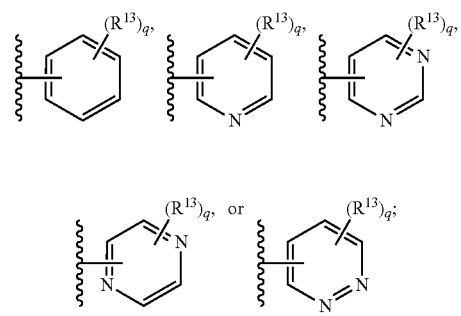

and q is 0-4. In some embodiments, $R^2$ is

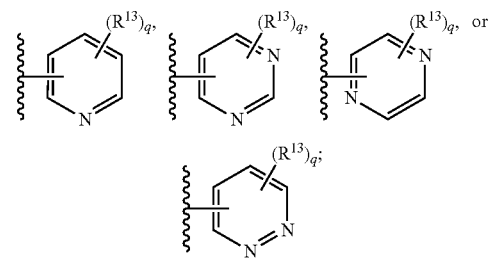

and q is 0-4. In some embodiments, $R^2$ is

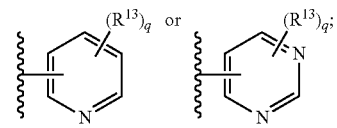

and q is 0-4.

In some embodiments, $R^2$ is

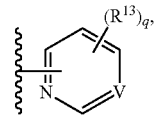

where V is CH, $CR^9$, or N; and q is 0, 1, 2, or 3. In some embodiments, $R^2$ is

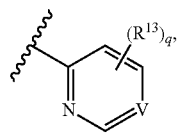

where V is CH, $CR^9$, or N; and q is 0, 1, 2, or 3.

In some embodiments, the compound is a compound of Formula (VIII):

Formula (VIII)

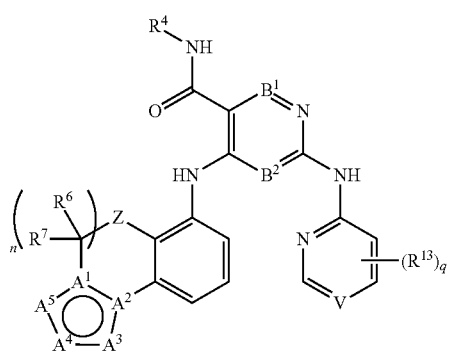

or a pharmaceutically acceptable salt, tautomer, or solvate thereof, wherein:
V is N, CH, or $CR^{13}$;
q is 1, 2, or 3;
$A^1$ and $A^2$ are each independently N or C; and
$A^3$, $A^4$, and $A^5$ are each independently N, $NR^B$, or $CR^8$; wherein two adjacent ring atoms selected from $A^1$, $A^2$, $A^3$, $A^4$, and $A^5$ are N or $NR^B$; and the remaining atoms are C or $CR^8$.

In some embodiments, the compound is a compound of Formula (VIIIa-1):

Formula (VIIIa-1)

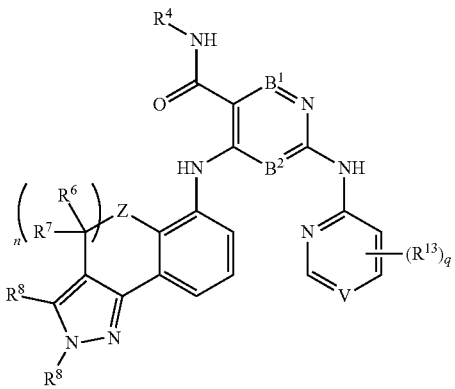

or a pharmaceutically acceptable salt, tautomer, or solvate thereof, wherein V is N, CH, or $CR^{13}$; and q is 1, 2, or 3.

In some embodiments, the compound of Formula (VIIIa-1) is not 4-((2,5-dimethyl-4,5-dihydro-2H-pyrazolo[4,3-c]quinolin-6-yl)amino)-6-((5-fluoropyridin-2-yl)amino)-N-methylnicotinamide, or 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide.

In some embodiments, the compound is a compound of Formula (VIIIc-1):

Formula (VIIIc-1)

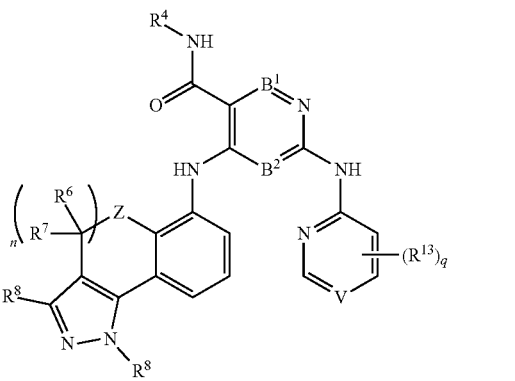

or a pharmaceutically acceptable salt, tautomer, or solvate thereof, wherein V is N, CH, or $CR^{13}$; and
q is 1, 2, or 3.

In some embodiments, the compound is a compound of Formula (VIIIf-1):

Formula (VIIIf-1)

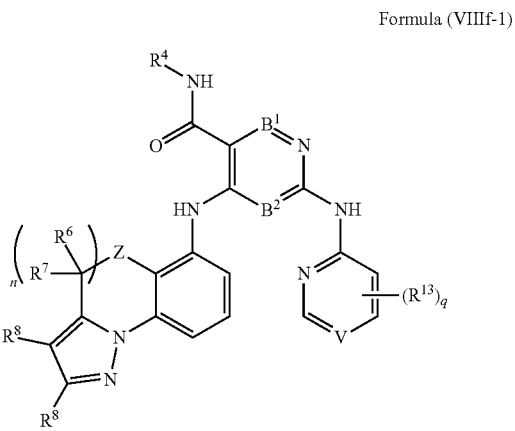

or a pharmaceutically acceptable salt, tautomer, or solvate thereof, wherein V is N, CH, or $CR^{13}$; and
q is 1, 2, or 3.

In some embodiments, V is N. In some embodiments, V is CH or $CR^{13}$. In some embodiments, V is CH. In some embodiments, V is $CR^{13}$.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, each $R^{13}$ is independently halogen, unsubstituted or substituted $C_1$-$C_6$ alkyl, unsubstituted or substituted $C_1$-$C_6$ fluoroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SO$_2$R$^{17}$, or —SO$_2$N(R$^{16}$)$_2$. In some embodiments, each R$^{13}$ is independently halogen, unsubstituted or substituted $C_1$-$C_6$ alkyl, unsubstituted or substituted $C_1$-$C_6$ fluoroalkyl, unsubstituted or substituted carbocycle, unsubstituted or substituted heterocycle, —C(=O)R$^{16}$, —CO$_2$R$^{16}$, or —C(=O)N(R$^{16}$)$_2$. In some embodiments, each R$^{13}$ is independently halogen, $C_1$-$C_6$ alkyl, $C_1$-$C_6$ fluoroalkyl, $C_3$-$C_6$ cycloalkyl, 4- to 6-membered heterocycloalkyl, —C(=O)R$^{16}$, —CO$_2$R$^{16}$, or —C(=O)N(R$^{16}$)$_2$. In some embodiments, each R$^{13}$ is independently halogen, $C_1$-$C_4$ alkyl, or $C_1$-$C_4$fluoroalkyl. In some embodiments, each R$^{13}$ is independently —F, —Cl, —CH$_3$, or —CF$_3$.

In some embodiments, q is 0, 1, 2, or 3. In some embodiments, q is 1, 2, or 3. In some embodiments, q is 1 or 2. In some embodiments, q is 1. In some embodiments, q is 2. In some embodiments, q is 0; and Ring B is therefore unsubstituted.

In some embodiments, R$^2$ is —C(=O)R$^{14}$, —C(=O)NR$^{14}$R$^{15}$, or —C(=O)OR$^{14}$.

In some embodiments, R$^2$ is —C(=O)R$^{14}$.

In some embodiments, R$^2$ is —C(=O)NR$^{14}$R$^{15}$ or —C(=O)OR$^{14}$.

In some embodiments, the compound is a compound of Formula (IX), Formula (X), or Formula (XI):

Formula (IX)

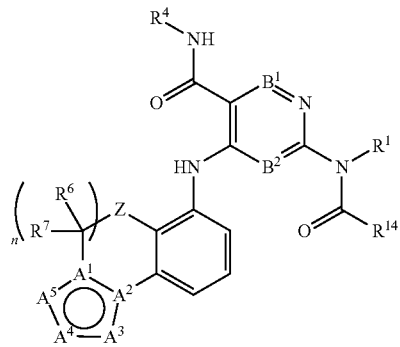

Formula (X)

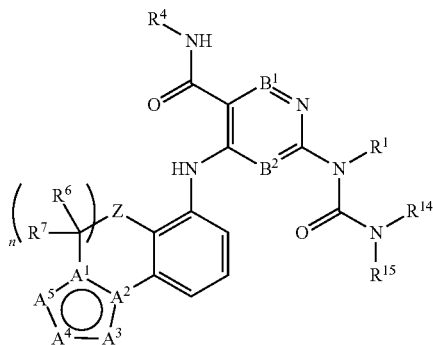

Formula (XI)

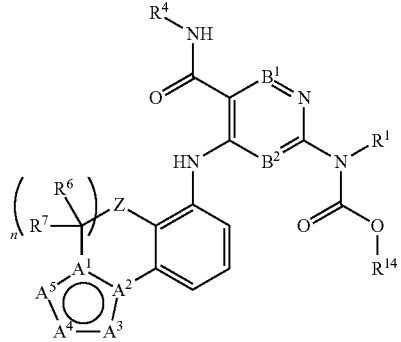

or a pharmaceutically acceptable salt, tautomer, or solvate thereof; wherein A$^1$ and A$^2$ are each independently N or C; and A$^3$, A$^4$, and A$^5$ are each independently N, NR$^B$, or CR$^8$; wherein two adjacent ring atoms selected from A$^1$, A$^2$, A$^3$, A$^4$, and A$^5$ are N or NR$^B$; and the remaining atoms are C or CR$^8$.

In some embodiments, the compound is a compound of Formula (IX), or a pharmaceutically acceptable salt, tautomer, or solvate thereof. In some embodiments, the compound is a compound of Formula (X), or a pharmaceutically acceptable salt, tautomer, or solvate thereof. In some embodiments, the compound is a compound of Formula (XI), or a pharmaceutically acceptable salt, tautomer, or solvate thereof.

In some embodiments, R$^4$ is hydrogen, $C_1$-$C_6$ alkyl, $C_1$-$C_6$ deuteroalkyl, or $C_1$-$C_6$ fluoroalkyl. In some embodiments, R$^4$ is hydrogen, $C_1$-$C_6$ alkyl, or $C_1$-$C_6$ deuteroalkyl. In other embodiments, R$^4$ is hydrogen, $C_1$-$C_4$ alkyl, $C_1$-$C_4$ deuteroalkyl, or $C_1$-$C_4$ fluoroalkyl. In some embodiments, R$^4$ is hydrogen, $C_1$-$C_4$ alkyl, or $C_1$-$C_4$ deuteroalkyl. In some embodiments, R$^4$ is hydrogen, $C_1$-$C_2$ alkyl, or $C_1$-$C_2$ deuteroalkyl. In some embodiments, R$^4$ is hydrogen, —CH$_3$, —CH$_2$D, -CHD$_2$, or -CD$_3$. In some embodiments, R$^4$ is hydrogen. In some embodiments, R$^4$ is —CH$_3$. In some embodiments, R$^4$ is -CD$_3$.

In some embodiments, R$^1$ is hydrogen, $C_1$-$C_6$ alkyl, or $C_1$-$C_6$ fluoroalkyl. In some embodiments, R$^1$ is hydrogen, $C_1$-$C_4$ alkyl, or $C_1$-$C_4$ fluoroalkyl. In some embodiments, R$^1$ is hydrogen or $C_1$-$C_6$ alkyl. In some embodiments, R$^1$ is hydrogen or $C_1$-$C_4$ alkyl. In some embodiments, R$^1$ is hydrogen, methyl, ethyl, propyl, isopropyl, or butyl. In some embodiments, R$^1$ is hydrogen or methyl. In some embodiments, R$^1$ is hydrogen. In some embodiments, R$^1$ is methyl.

In some embodiments, R$^1$ and R$^{15}$ are taken together with the intervening atoms to which they are attached to form an unsubstituted or substituted 5- or 6-membered monocyclic heterocycle. In some embodiments, R$^1$ and R$^{15}$ are taken together with the intervening atoms to which they are attached to form an unsubstituted or substituted 5- or 6-membered monocyclic heterocycloalkyl. In some embodiments, R$^1$ and R$^{15}$ are taken together with the intervening atoms to which they are attached to form an unsubstituted or substituted 5-membered monocyclic heterocycle. In some embodiments, R$^1$ and R$^{15}$ are taken together with the intervening atoms to which they are attached to form an unsubstituted or substituted 5-membered monocyclic heterocycloalkyl.

In some embodiments, R$^1$ is hydrogen.

In some embodiments, the compound is a compound of Formula (IXa-1):

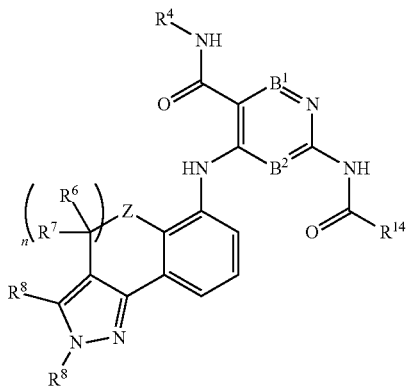

Formula (IXa-1)

or a pharmaceutically acceptable salt, tautomer, or solvate thereof.

In some embodiments, the compound of Formula (IXa-1) is not 6-(cyclopropanecarboxamido)-4-((2,5-dimethyl-4,5-dihydro-2H-pyrazolo[4,3-c]quinolin-6-yl)amino)-N-methylpyridazine-3-carboxamide.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, the compound is a compound of Formula (IXc-1):

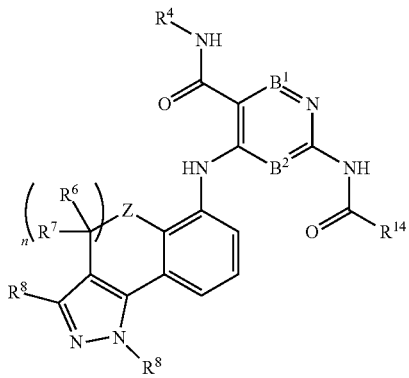

Formula (IXc-1)

or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, the compound is a compound of Formula (IXf-1):

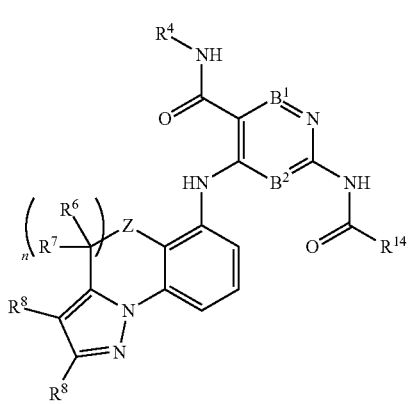

Formula (IXf-1)

or a pharmaceutically acceptable salt, tautomer, or solvate thereof.

In some embodiments, the compound of Formula (IXf-1) is not 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, $R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle. In some embodiments, $R^{14}$ is unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle. In some embodiments, $R^{14}$ is unsubstituted or substituted $C_1$-$C_6$ alkyl, $C_1$-$C_6$ deuteroalkyl, unsubstituted or substituted $C_1$-$C_6$ heteroalkyl, unsubstituted or substituted $C_3$-$C_6$ cycloalkyl, or unsubstituted or substituted 4- to 6-membered heterocycloalkyl.

In some embodiments, $R^{14}$ is hydrogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle. In some embodiments, $R^{14}$ is unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle. In some embodiments, $R^{14}$ is unsubstituted or substituted $C_1$-$C_6$ alkyl, unsubstituted or substituted $C_1$-$C_6$ heteroalkyl, unsubstituted or substituted $C_3$-$C_6$ cycloalkyl, or unsubstituted or substituted 4- to 6-membered heterocycloalkyl.

In some embodiments, $R^{14}$ is unsubstituted or substituted $C_1$-$C_6$ alkyl, $C_1$-$C_6$ deuteroalkyl, unsubstituted or substituted $C_3$-$C_6$ cycloalkyl, or unsubstituted or substituted 4- to 6-membered heterocycloalkyl; wherein the substituted alkyl, substituted heteroalkyl, substituted cycloalkyl, or substituted heterocycloalkyl is substituted with one or more $R^s$ groups. In some embodiments, $R^{14}$ is unsubstituted or substituted $C_1$-$C_6$ alkyl, unsubstituted or substituted $C_3$-$C_6$ cycloalkyl, or unsubstituted or substituted 4- to 6-membered heterocycloalkyl; wherein the substituted alkyl, substituted heteroalkyl, substituted cycloalkyl, or substituted heterocycloalkyl is substituted with one or more $R^s$ groups. In some embodiments, $R^{14}$ is unsubstituted or substituted $C_1$-$C_6$ alkyl, $C_1$-$C_6$ deuteroalkyl, unsubstituted or substituted $C_3$-$C_6$ cycloalkyl, or unsubstituted or substituted 4- to 6-membered heterocycloalkyl; wherein the substituted alkyl, substituted heteroalkyl, substituted cycloalkyl, or substituted heterocycloalkyl is substituted with one or more $R^s$ groups independently selected from the group consisting of deuterium, halogen, $C_1$-$C_6$ alkyl, —CN, —$OR^{18}$, and —$N(R^{18})_2$. In some embodiments, $R^{14}$ is unsubstituted or substituted $C_1$-$C_6$ alkyl, unsubstituted or substituted $C_3$-$C_6$ cycloalkyl, or unsubstituted or substituted 4- to 6-membered heterocycloalkyl; wherein the substituted alkyl, substituted heteroalkyl, substituted cycloalkyl, or substituted heterocycloalkyl is substituted with one or more $R^s$ groups independently selected from the group consisting of deuterium, halogen, $C_1$-$C_6$ alkyl, —CN, —$OR^{18}$, and —$N(R^{18})_2$. In some embodiments, $R^{14}$ is unsubstituted or substituted $C_1$-$C_6$ alkyl, unsubstituted or substituted $C_3$-$C_4$ cycloalkyl, or unsubstituted or substituted 4-membered heterocycloalkyl; wherein the substituted alkyl, substituted heteroalkyl, substituted cycloalkyl, or substituted heterocycloalkyl is substituted with one or more $R^s$ groups independently selected from the group consisting of deuterium, halogen, —CN, —$NH_2$, —OH, —$NH(CH_3)$, —$N(CH_3)_2$, —$CH_3$, —$CH_2CH_3$, —$CHF_2$, —$CF_3$, —$OCH_3$, —$OCHF_2$, and —$OCF_3$. In some embodiments, $R^{14}$ is methyl, -$CD_3$, ethyl, isopropyl, t-butyl, cyclopropyl, cyclobutyl, azetidinyl, oxetanyl,

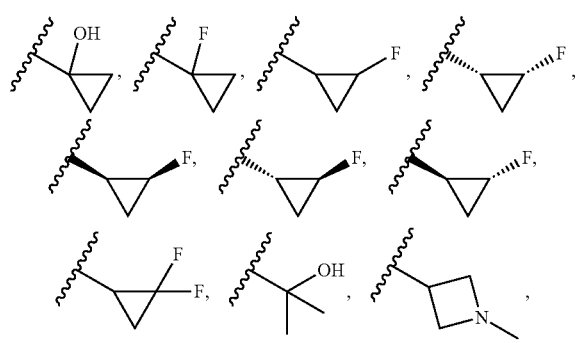

In some embodiments, $R^{14}$ is methyl, -$CD_3$, ethyl, isopropyl, t-butyl, cyclopropyl, cyclobutyl, azetidinyl, oxetanyl,

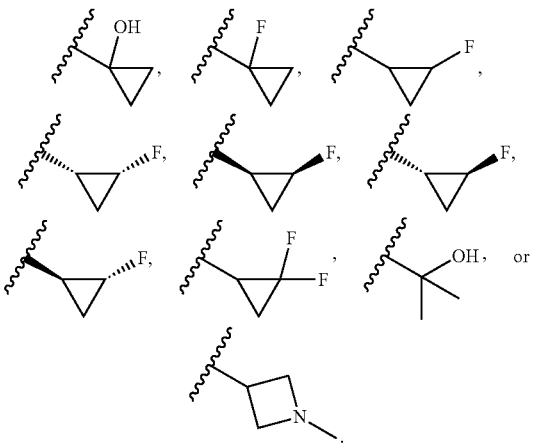

In some embodiments, $R^{14}$ is methyl, ethyl, isopropyl, t-butyl, cyclopropyl, azetidinyl, oxetanyl,

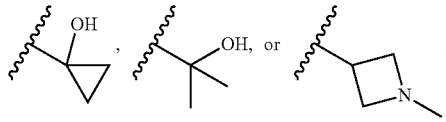

In some embodiments, when $R^2$ is —C(=O)$NR^{14}R^{15}$, $R^{14}$ and $R^{15}$ are taken together with the intervening atoms to which they are attached to form an unsubstituted or substituted 4- to 6-membered monocyclic heterocycle. In some embodiments, $R^{14}$ and $R^{15}$ are taken together with the intervening atoms to which they are attached to form an unsubstituted or substituted 4- to 6-membered monocyclic heterocycloalkyl.

In some embodiments, $B^1$ is $CR^{12a}$; and $B^2$ is $CR^{12b}$; or $B^1$ is N; and $B^2$ is $CR^{12b}$; or $B^1$ is $CR^{12a}$; and $B^2$ is N; or $B^1$ is N; and $B^2$ is N. In some embodiments, $B^1$ is $CR^{12a}$; and $B^2$ is $CR^{12b}$. In some embodiments, $B^1$ is N; and $B^2$ is $CR^{12b}$. In some embodiments, $B^1$ is $CR^{12a}$; and $B^2$ is N. In some embodiments, $B^1$ is N; and $B^2$ is N.

In some embodiments, $B^1$ is $CR^{12a}$; and $B^2$ is $CR^{12b}$; or $B^1$ is N; and $B^2$ is $CR^{12b}$.

In some embodiments, $R^{12a}$ and $R^{12b}$ are each independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2N(R^{16})_2$.

In some embodiments, $R^{12a}$ and $R^{12b}$ are each independently hydrogen, halogen, $C_1$-$C_6$ alkyl, $C_1$-$C_6$ fluoroalkyl, —CN, —OH, —OR$^{17}$, —CO$_2$R$^{16}$, —C(=O)N(R$^{16}$)$_2$, —N(R$^{16}$)$_2$, —SO$_2$R$^{17}$, or —SO$_2$N(R$^{16}$)$_2$. In some embodiments, R$^{12a}$ and R$^{12b}$ are each independently hydrogen, halogen, C$_1$-C$_6$ alkyl, C$_1$-C$_6$ fluoroalkyl, —CN, —OH, —OR$^{17}$, —C(=O)N(R$^{16}$)$_2$, —N(R$^{16}$)$_2$, or —SO$_2$N(R$^{16}$)$_2$. In some embodiments, R$^{12a}$ and R$^{12b}$ are each independently hydrogen, halogen, C$_1$-C$_6$ alkyl, C$_1$-C$_6$ fluoroalkyl, —CN, —OH, —OR$^{17}$, or —N(R$^{16}$)$_2$. In some embodiments, R$^{12a}$ and R$^{12b}$ are each independently hydrogen, halogen, C$_1$-C$_4$ alkyl, C$_1$-C$_4$ fluoroalkyl, —CN, —OH, —OR$^{17}$, or —N(R$^{16}$)$_2$. In some embodiments, R$^{12a}$ and R$^{12b}$ are each independently hydrogen, halogen, C$_1$-C$_4$ alkyl, C$_1$-C$_4$ fluoroalkyl, or —CN. In some embodiments, R$^{12a}$ and R$^{12b}$ are each independently hydrogen, halogen, or —CN. In some embodiments, R$^{12a}$ and R$^{12b}$ are each independently hydrogen or halogen. In some embodiments, R$^{12a}$ and R$^{12b}$ are each independently hydrogen, fluoro, or chloro. In some embodiments, R$^{12a}$ and R$^{12b}$ are each independently hydrogen or fluoro. In some embodiments, R$^{12a}$ and R$^{12b}$ are each hydrogen.

In some embodiments, B$^1$ and B$^2$ are each independently CH, CF, or N. In some embodiments, B$^1$ and B$^2$ are each independently CH or N.

In some embodiments, B$^1$ is CH or CF; and B$^2$ is CH or CF; or B$^1$ is N; and B$^2$ is CH or CF; or B$^1$ is CH or CF; and B$^2$ is N; or B$^1$ is N; and B$^2$ is N. In some embodiments, B$^1$ is CH; and B$^2$ is CH; or B$^1$ is N; and B$^2$ is CH; or B$^1$ is CH; and B$^2$ is N; or B$^1$ is N; and B$^2$ is N.

In some embodiments, R$^3$ and R$^{12a}$ are taken together with the intervening atoms to which they are attached to form a substituted or unsubstituted 5- or 6-membered heterocycle. In some embodiments, R$^3$ and R$^{12a}$ are taken together with the intervening atoms to which they are attached to form a substituted or unsubstituted 5-membered heterocycle. In some embodiments, R$^3$ and R$^{12a}$ are taken together with the intervening atoms to which they are attached to form a substituted or unsubstituted pyrazolidinone ring. In some embodiments,

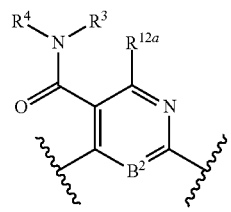

is

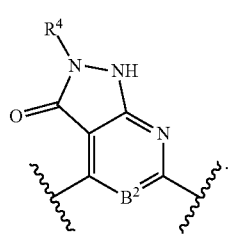

In some embodiments,

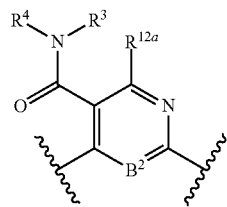

is

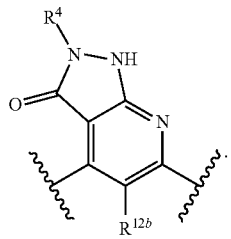

In some embodiments,

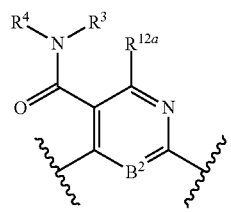

is

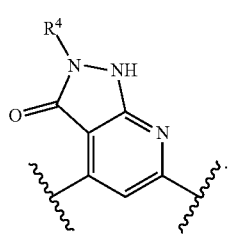

In some embodiments, the compound is a compound of Formula (XII):

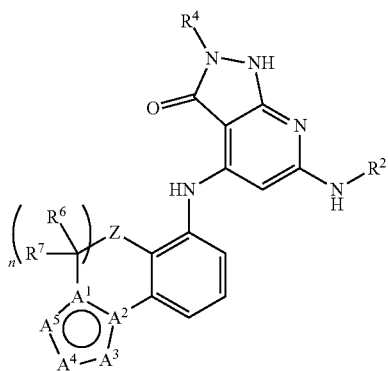

Formula (XII)

or a pharmaceutically acceptable salt, tautomer, or solvate thereof; wherein $A^1$ and $A^2$ are each independently N or C; and $A^3$, $A^4$, and $A^5$ are each independently N, $NR^8$, or $CR^8$; wherein two adjacent ring atoms selected from $A^1$, $A^2$, $A^3$, $A^4$, and $A^5$ are N or $NR^8$; and the remaining atoms are C or $CR^8$.

In some embodiments, $A^1$ is C; $A^2$ is C; $A^3$ is N; $A^4$ is $NR^8$; and $A^5$ is CH.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, $R^2$ is a Ring B that is an unsubstituted or substituted heterocycle or unsubstituted or substituted carbocycle, wherein if Ring B is substituted then Ring B is substituted with q instances of $R^{13}$. In some embodiments, $R^2$ is a Ring B that is an unsubstituted or substituted monocyclic 6-membered heteroaryl, wherein if Ring B is substituted then Ring B is substituted with q instances of $R^{13}$. In some embodiments, $R^2$ is a Ring B that is an unsubstituted or substituted pyridinyl or unsubstituted or substituted pyrimidinyl, wherein if Ring B is substituted then Ring B is substituted with q instances of $R^{13}$.

In some embodiments, $R^2$ is —C(=O)$R^{14}$, —C(=O)$NR^{14}R^{15}$, or —C(=O)O$R^{14}$. In some embodiments, $R^2$ is —C(=O)$R^{14}$.

In some embodiments, each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, or substituted or unsubstituted monocyclic 3- to 8-membered heterocycloalkyl; or two $R^{16}$ on the same N atom are taken together with the N atom to which they are attached to form a substituted or unsubstituted N-containing heterocycloalkyl. In some embodiments, each $R^{16}$ is independently hydrogen, $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl; or two $R^{16}$ on the same N atom are taken together with the N atom to which they are attached to form a 4- to 6-membered N-containing heterocycloalkyl.

In some embodiments, each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, or substituted or unsubstituted monocyclic 3- to 8-membered heterocycloalkyl. In some embodiments, each $R^{17}$ is independently $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl.

In some embodiments, the compound is a compound of Formula (XV):

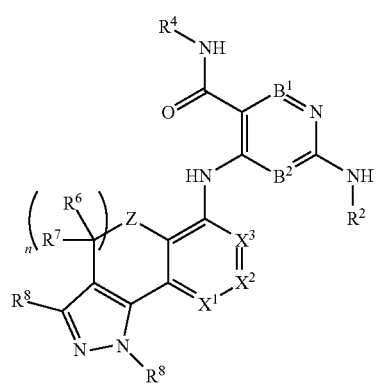

Formula (XV)

or a pharmaceutically acceptable salt, tautomer, or solvate thereof, wherein:

each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —O$R^{17}$, —C(=O)$R^{16}$, —CO$_2R^{16}$, —C(=O)N($R^{16}$)$_2$, —N($R^{16}$)$_2$, —N$R^{16}$C(=O)$R^{17}$, —S$R^{16}$, —S(=O)$R^{17}$, —SO$_2R^{17}$, or —SO$_2$N($R^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —C(=O)$R^{16}$, —CO$_2R^{16}$, —C(=O)N($R^{16}$)$_2$, —S(=O)$R^{17}$, —SO$_2R^{17}$, or —SO$_2$N($R^{16}$)$_2$;

Z is —N$R^{10}$—, —O—, —S—, —S(=O)—, or —SO$_2$—;

$R^{10}$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

$X^1$, $X^2$, and $X^3$ are each independently $CR^{11}$ or N;

each $R^1$ is independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —O$R^{17}$, —C(=O)$R^{16}$, —CO$_2R^{16}$, —C(=O)N($R^{16}$)$_2$, —N($R^{16}$)$_2$, —N$R^{16}$C(=O)$R^{17}$, —S$R^{16}$, —S(=O)$R^{17}$, —SO$_2R^{17}$, or —SO$_2$N($R^{16}$)$_2$;

$B^1$ is N or $CR^{12a}$;

$B^2$ is N or $CR^{12b}$;

$R^{12a}$ and $R^{12b}$ are each independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

$R^2$ is a Ring B that is an unsubstituted or substituted heterocycle or unsubstituted or substituted carbocycle, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

or two $R^{13}$ groups on adjacent atoms of Ring B are taken together with the intervening atoms to which they are attached to form an unsubstituted or substituted 5- or 6-membered monocyclic carbocycle or an unsubstituted or substituted 5- or 6-membered monocyclic heterocycle;

or $R^2$ is —C(=O)$R^{14}$, —C(=O)$NR^{14}R^{15}$, or —C(=O)$OR^{14}$;

$R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle;

$R^{15}$ is hydrogen, $C_1$-$C_6$ alkyl, or $C_1$-$C_6$ fluoroalkyl;

$R^4$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

each $R^6$ and $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

or two $R^{16}$ on the same N atom are taken together with the N atom to which they are attached to form a substituted or unsubstituted N-containing heterocycle; and each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

wherein each substituted alkyl, substituted fluoroalkyl, substituted deuteroalkyl, substituted alkoxy, substituted fluoroalkoxy, substituted heteroalkyl, substituted carbocycle, and substituted heterocycle is substituted with one or more $R^s$ groups independently selected from the group consisting of deuterium, halogen, $C_1$-$C_6$ alkyl, monocyclic carbocycle, monocyclic heterocycle, —CN, —$CH_2$CN, —$OR^{18}$, —$CH_2OR^{18}$, —$CO_2R^{18}$, —$CH_2CO_2R^{18}$, —C(=O)N($R^{18}$)$_2$, —$CH_2$C(=O)N($R^{18}$)$_2$, —N($R^{18}$)$_2$, —$CH_2$N($R^{18}$)$_2$, —$NR^{18}$C(=O)$R^{18}$, —$CH_2NR^{18}$C(=O)$R^{18}$, —$NR^{18}SO_2R^{19}$, —$CH_2NR^{18}SO_2R^{19}$, —$SR^{18}$, —$CH_2SR^{18}$, —S(=O)$R^{19}$, —$CH_2$S(=O)$R^{19}$, —$SO_2R^{19}$, —$CH_2SO_2R^{19}$, —$SO_2$N($R^{18}$)$_2$, or —$CH_2SO_2$N($R^{18}$)$_2$;

each $R^{18}$ is independently selected from hydrogen, $C_1$-$C_6$ alkyl, $C_1$-$C_6$ fluoroalkyl, $C_1$-$C_6$ heteroalkyl, $C_3$-$C_6$ cycloalkyl, $C_2$-$C_6$ heterocycloalkyl, phenyl, benzyl, 5-membered heteroaryl and 6-membered heteroaryl;

or two $R^{18}$ groups are taken together with the N atom to which they are attached to form a N-containing heterocycle;

each $R^{19}$ is independently selected from $C_1$-$C_6$ alkyl, $C_1$-$C_6$ heteroalkyl, $C_3$-$C_6$ cycloalkyl, $C_2$-$C_6$ heterocycloalkyl, phenyl, benzyl, 5-membered heteroaryl, and 6-membered heteroaryl;

n is 1, 2, or 3; and q is 1, 2, 3, or 4.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —CN, —OH, —$OR^{17}$, —C(=O)$R^{16}$, —$CO_2R^{16}$, or —C(=O)N($R^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —C(=O)$R^{16}$, —$CO_2R^{16}$, or —C(=O)N($R^{16}$)$_2$;

Z is —$NR^{10}$— or —O—;

$R^{10}$ is hydrogen, $C_1$-$C_4$ alkyl, $C_1$-$C_4$ deuteroalkyl, or cyclopropyl;

$X^1$, $X^2$, and $X^3$ are each independently $CR^{11}$ or N;

each $R^{11}$ is independently hydrogen, halogen, $C_1$-$C_6$ alkyl, $C_1$-$C_6$ fluoroalkyl, —CN, —OH, —$OR^{17}$, or —N($R^{16}$)$_2$;

$B^1$ is N or $CR^{12a}$;

$B^2$ is N or $CR^{12b}$;

$R^{12a}$ and $R^{12b}$ are each independently hydrogen, halogen, $C_1$-$C_4$ alkyl, $C_1$-$C_4$ fluoroalkyl, or —CN;

$R^2$ is a Ring B that is an unsubstituted or substituted phenyl, unsubstituted or substituted monocyclic 6-membered heteroaryl, or unsubstituted or substituted monocyclic 5-membered heteroaryl, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_1$-$C_6$ fluoroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SO$_2$R$^{17}$, or —SO$_2$N(R$^{16}$)$_2$;

or $R^2$ is —C(=O)R$^{14}$;

$R^{14}$ is unsubstituted or substituted $C_1$-$C_6$ alkyl, $C_1$-$C_6$ deuteroalkyl, unsubstituted or substituted $C_3$-$C_4$ cycloalkyl, or unsubstituted or substituted 4-membered heterocycloalkyl; wherein the substituted alkyl, substituted heteroalkyl, substituted cycloalkyl, or substituted heterocycloalkyl is substituted with one or more R$^s$ groups independently selected from the group consisting of deuterium, halogen, —CN, —NH$_2$, —OH, —NH(CH$_3$), —N(CH$_3$)$_2$, —CH$_3$, —CH$_2$CH$_3$, —CHF$_2$, —CF$_3$, —OCH$_3$, —OCHF$_2$, and —OCF$_3$;

each $R^6$ and $R^7$ is independently hydrogen, deuterium, halogen, $C_1$-$C_4$ alkyl, or $C_1$-$C_4$ deuteroalkyl;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl;

or two $R^{16}$ on the same N atom are taken together with the N atom to which they are attached to form a 4- to 6-membered N-containing heterocycloalkyl; and each $R^{17}$ is independently $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —CH$_3$, —CH$_2$D, -CHD$_2$, or -CD$_3$. In some embodiments, $R^4$ is hydrogen. In some embodiments, $R^4$ is —CH$_3$. In some embodiments, $R^4$ is -CD$_3$.

In some embodiments, $X^1$ is CR$^{11}$, $X^2$ is CR$^{11}$, and $X^3$ is CR$^{11}$; or $X^1$ is CR$^{11}$, $X^2$ is CR$^{11}$ and $X^3$ is N; or $X^1$ is CR$^{11}$, $X^2$ is N, and $X^3$ is CR$^{11}$; or $X^1$ is N, $X^2$ is CR$^{11}$, and $X^3$ is CR$^{11}$. In some embodiments, $X^1$ is CR$^{11}$, $X^2$ is CR$^{11}$, and $X^3$ is CR$^{11}$. In some embodiments, $X^1$ is CR$^{11}$, $X^2$ is CR$^{11}$, and $X^3$ is N. In some embodiments, $X^1$ is CR$^{11}$, $X^2$ is N, and $X^3$ is CR$^{11}$. In some embodiments, $X^1$ is N, $X^2$ is CR$^{11}$, and $X^3$ is CR$^{11}$.

In some embodiments, each $R^4$ is independently hydrogen, halogen, $C_1$-$C_4$ alkyl, $C_1$-$C_4$ fluoroalkyl, or —CN. In some embodiments, each $R^{11}$ is independently hydrogen, halogen, or —CN. In some embodiments, each $R^{11}$ is independently hydrogen or halogen. In some embodiments, each $R^{11}$ is independently hydrogen, fluoro, or chloro. In some embodiments, each $R^{11}$ is independently hydrogen or fluoro. In some embodiments, each $R^{11}$ is hydrogen.

In some embodiments, the compound of Formula (XV) is a compound of Formula (VIc-1):

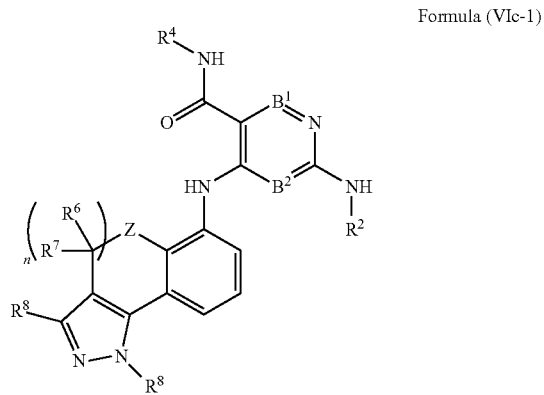

Formula (VIc-1)

or a pharmaceutically acceptable salt, tautomer, or solvate thereof.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —CH$_3$, —CH$_2$D, -CHD$_2$, or -CD$_3$. In some embodiments, $R^4$ is hydrogen. In some embodiments, $R^4$ is —CH$_3$. In some embodiments, $R^4$ is -CD$_3$.

In some embodiments, each $R^8$ is independently hydrogen, halogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —CN, —OH, —OR$^{17}$, —C(=O)R$^{16}$, —CO$_2$R$^{16}$, or —C(=O)N(R$^{16}$)$_2$; wherein if $R^8$ is attached to a nitrogen atom, then $R^8$ is hydrogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —C(=O)R$^{16}$, —CO$_2$R$^{16}$, or —C(=O)N(R$^{16}$)$_2$. In some embodiments, each $R^8$ is independently hydrogen, —Cl, —F, methyl, ethyl, isopropyl, -CD$_3$, —CH$_2$OH, —CF$_3$, cyclopropyl, oxetanyl, azetidinyl, —CN, —OH, —CO$_2$H, or —CO$_2$CH$_3$; wherein if $R^8$ is attached to a nitrogen atom, then $R^8$ is hydrogen, methyl, ethyl, isopropyl, -CD$_3$, —CH$_2$OH, —CF$_3$, cyclopropyl, oxetanyl, azetidinyl, —CO$_2$H, or —CO$_2$CH$_3$. In some embodiments, each $R^8$ is independently hydrogen, methyl, -CD$_3$, —OH, —CH$_2$OH, —CF$_3$, oxetanyl, —CN, or —CO$_2$CH$_3$; wherein if $R^8$ is attached to a nitrogen atom, then $R^8$ is hydrogen, methyl, -CD$_3$, —CH$_2$OH, oxetanyl, or —CO$_2$CH$_3$.

In some embodiments, each $R^6$ and $R^7$ is independently hydrogen, deuterium, F, Cl, -CD$_3$, or methyl. In some embodiments, each $R^6$ and $R^7$ is independently hydrogen, deuterium, F, or methyl. In some embodiments, each $R^6$ and $R^7$ is independently hydrogen or methyl. In some embodiments, one $R^6$ or $R^7$ is methyl. In some embodiments, one $R^6$ is methyl. In some embodiments, each $R^6$ and $R^7$ is hydrogen. In some embodiments, each $R^6$ and $R^7$ is deuterium. In some embodiments, each $R^6$ and $R^7$ is F.

In some embodiments, one $R^6$ and one $R^7$ attached to the same carbon atom are taken together with the carbon atom to which they are attached to form C=O or $C_3$-$C_4$ cycloalkyl. In some embodiments, one $R^6$ and one $R^1$ attached to the same carbon atom are taken together with the carbon atom to which they are attached to form C=O. In some embodiments, one $R^6$ and one $R^7$ attached to the same carbon atom are taken together with the carbon atom to which they are attached to form $C_3$-$C_4$ cycloalkyl. In some embodiments, one $R^6$ and one $R^7$ attached to the same carbon atom are taken together with the carbon atom to which they are attached to form a cyclopropyl.

In some embodiments, n is 1 or 2. In some embodiments, n is 1. In some embodiments, n is 2. In some embodiments, n is 3.

In some embodiments, Z is —$NR^{10}$—. In some embodiments, $R^{10}$ is hydrogen, $C_1$-$C_4$ alkyl, $C_1$-$C_4$ deuteroalkyl, or cyclopropyl. In some embodiments, $R^{10}$ is hydrogen, $C_1$-$C_4$ alkyl, or cyclopropyl. In some embodiments, $R^{10}$ is hydrogen, $C_1$-$C_4$ alkyl, or $C_1$-$C_4$ deuteroalkyl. In some embodiments, $R^{10}$ is hydrogen, —$CH_3$, or -$CD_3$. In some embodiments, $R^{10}$ is $C_1$-$C_4$ alkyl or $C_1$-$C_4$ deuteroalkyl. In some embodiments, $R^{10}$ is —$CH_3$ or -$CD_3$. In some embodiments, $R^{10}$ is —$CH_3$. In some embodiments, $R^{10}$ is -$CD_3$.

In some embodiments, Z is NH, $NCH_3$, or $NCD_3$. In some embodiments, Z is $NCH_3$ or $NCD_3$. In some embodiments, Z is $NCH_3$. In some embodiments, Z is $NCD_3$.

In some embodiments, Z is —O—.

In some embodiments, $R^2$ is as defined herein.

In some embodiments, the compound is a compound of Formula (XVII):

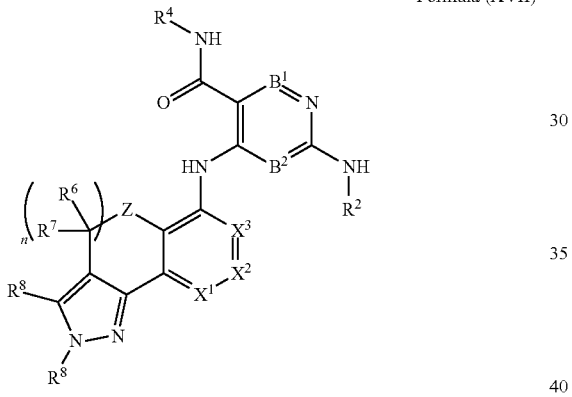

Formula (XVII)

or a pharmaceutically acceptable salt, tautomer, or solvate thereof, wherein:

each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{11}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —C(=O)$R^{16}$, —$CO_2R^{16}$, —C(=O)N($R^{16}$)$_2$, —S(=O)$R^{17}$, —$SO_2R^{17}$, or —$SO_2$N($R^{16}$)$_2$;

Z is —$NR^{10}$—, —O—, —S—, —S(=O)—, or —$SO_2$—;

$R^{10}$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

$X^1$, $X^2$, and $X^3$ are each independently $CR^{11}$ or N;

each $R^{11}$ is independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

$B^1$ is N or $CR^{12a}$;

$B^2$ is N or $CR^{12b}$;

$R^{12a}$ and $R^{12b}$ are each independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

$R^2$ is a Ring B that is an unsubstituted or substituted heterocycle or unsubstituted or substituted carbocycle, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

or two $R^{13}$ groups on adjacent atoms of Ring B are taken together with the intervening atoms to which they are attached to form an unsubstituted or substituted 5- or 6-membered monocyclic carbocycle or an unsubstituted or substituted 5- or 6-membered monocyclic heterocycle;

or $R^2$ is —C(=O)$R^{14}$, —C(=O)$NR^{14}R^{15}$, or —C(=O)$OR^{14}$;

$R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle;

$R^{15}$ is hydrogen, $C_1$-$C_6$ alkyl, or $C_1$-$C_6$ fluoroalkyl;

$R^4$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

each $R^6$ and $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SR^{16}$, —S(=O)$R^{17}$, —$SO_2R^{17}$, or —$SO_2$N($R^{16}$)$_2$;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

or two $R^{16}$ on the same N atom are taken together with the N atom to which they are attached to form a substituted or unsubstituted N-containing heterocycle; and each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

wherein each substituted alkyl, substituted fluoroalkyl, substituted deuteroalkyl, substituted alkoxy, substituted fluoroalkoxy, substituted heteroalkyl, substituted carbocycle, and substituted heterocycle is substituted with one or more $R^s$ groups independently selected from the group consisting of deuterium, halogen, $C_1$-$C_6$ alkyl, monocyclic carbocycle, monocyclic heterocycle, —CN, —$CH_2CN$, —$OR^{18}$, —$CH_2OR^{18}$, —$CO_2R^{18}$, —$CH_2CO_2R^{18}$, —C(=O)N($R^{18}$)$_2$, —$CH_2C$(=O)N($R^{18}$)$_2$, —N($R^{18}$)$_2$, —$CH_2$N($R^{18}$)$_2$, —$NR^{18}$C(=O)$R^{18}$, —$CH_2NR^{18}$C(=O)$R^{18}$, —$NR^{18}SO_2R^{19}$, —$CH_2NR^{18}SO_2R^{19}$, —$SR^{18}$, —$CH_2SR^{18}$, —S(=O)$R^{19}$, —$CH_2$S(=O)$R^{19}$, —$SO_2R^{19}$, —$CH_2SO_2R^{19}$, —$SO_2N$($R^{18}$)$_2$, or —$CH_2SO_2N$($R^{18}$)$_2$;

each $R^{18}$ is independently selected from hydrogen, $C_1$-$C_6$ alkyl, $C_1$-$C_6$ fluoroalkyl, $C_1$-$C_6$ heteroalkyl, $C_3$-$C_6$ cycloalkyl, $C_2$-$C_6$ heterocycloalkyl, phenyl, benzyl, 5-membered heteroaryl and 6-membered heteroaryl;

or two $R^{18}$ groups are taken together with the N atom to which they are attached to form a N-containing heterocycle;

each $R^{19}$ is independently selected from $C_1$-$C_6$ alkyl, $C_1$-$C_6$ heteroalkyl, $C_3$-$C_6$ cycloalkyl, $C_2$-$C_6$ heterocycloalkyl, phenyl, benzyl, 5-membered heteroaryl, and 6-membered heteroaryl;

n is 1, 2, or 3; and q is 1, 2, 3, or 4.

In some embodiments, the compound of Formula (XVII) is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, nor 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —CN, —OH, —$OR^{17}$, —C(=O)$R^{16}$, —$CO_2R^{16}$, or —C(=O)N($R^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —C(=O)$R^{16}$, —$CO_2R^{16}$, or —C(=O)N($R^{16}$)$_2$;

Z is —$NR^{10}$— or —O—;

$R^{10}$ is hydrogen, $C_1$-$C_4$ alkyl, $C_1$-$C_4$ deuteroalkyl, or cyclopropyl;

$X^1$, $X^2$, and $X^3$ are each independently $CR^{11}$ or N;

each $R^{11}$ is independently hydrogen, halogen, $C_1$-$C_6$ alkyl, $C_1$-$C_6$ fluoroalkyl, —CN, —OH, —$OR^{17}$, or —N($R^{16}$)$_2$;

$B^1$ is N or $CR^{12a}$;

$B^2$ is N or $CR^{12b}$;

$R^{12a}$ and $R^{12b}$ are each independently hydrogen, halogen, $C_1$-$C_4$ alkyl, $C_1$-$C_4$ fluoroalkyl, or —CN;

$R^2$ is a Ring B that is an unsubstituted or substituted phenyl, unsubstituted or substituted monocyclic 6-membered heteroaryl, or unsubstituted or substituted monocyclic 5-membered heteroaryl, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_1$-$C_6$ fluoroalkyl, unsubstituted or substituted carbocycle, unsubstituted or substituted heterocycle, —CN, —OH, —$OR^{17}$, —C(=O)$R^{16}$, —$CO_2R^{16}$, —C(=O)N($R^{16}$)$_2$, —N($R^{16}$)$_2$, —$NR^{16}$C(=O)$R^{17}$, —$SO_2R^{17}$, or —$SO_2N$($R^{16}$)$_2$;

or $R^2$ is —C(=O)$R^{14}$;

$R^{14}$ is unsubstituted or substituted $C_1$-$C_6$ alkyl, $C_1$-$C_6$ deuteroalkyl, unsubstituted or substituted $C_3$-$C_4$ cycloalkyl, or unsubstituted or substituted 4-membered heterocycloalkyl; wherein the substituted alkyl, substituted heteroalkyl, substituted cycloalkyl, or substituted heterocycloalkyl is substituted with one or more $R^s$ groups independently selected from the group consisting of deuterium, halogen, —CN, —$NH_2$, —OH, —NH($CH_3$), —N($CH_3$)$_2$, —$CH_3$, —$CH_2CH_3$, —$CHF_2$, —$CF_3$, —$OCH_3$, —$OCHF_2$, and —$OCF_3$;

each $R^6$ and $R^7$ is independently hydrogen, deuterium, halogen, $C_1$-$C_4$ alkyl, or $C_1$-$C_4$ deuteroalkyl;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl;

or two $R^{16}$ on the same N atom are taken together with the N atom to which they are attached to form a 4- to 6-membered N-containing heterocycloalkyl; and each $R^{17}$ is independently $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, $X^1$ is $CR^{11}$, $X^2$ is $CR^{11}$, and $X^3$ is $CR^{11}$; or $X^1$ is $CR^{11}$, $X^2$ is $CR^{11}$, and $X^3$ is N; or $X^1$ is $CR^{11}$, $X^2$ is N, and $X^3$ is $CR^{11}$; or $X^1$ is N, $X^2$ is $CR^{11}$, and $X^3$ is $CR^{11}$. In some embodiments, $X^1$ is $CR^{11}$, $X^2$ is $CR^{11}$, and $X^3$ is $CR^{11}$. In some embodiments, $X^1$ is $CR^{11}$, $X^2$ is $CR^{11}$, and $X^3$ is N. In some embodiments, $X^1$ is $CR^{11}$, $X^2$ is N, and $X^3$ is $CR^{11}$. In some embodiments, $X^1$ is N, $X^2$ is $CR^{11}$, and $X^3$ is $CR^{11}$.

In some embodiments, each $R^{11}$ is independently hydrogen, halogen, $C_1$-$C_4$ alkyl, $C_1$-$C_4$ fluoroalkyl, or —CN. In some embodiments, each $R^{11}$ is independently hydrogen, halogen, or —CN. In some embodiments, each $R^{11}$ is independently hydrogen or halogen. In some embodiments, each $R^{11}$ is independently hydrogen, fluoro, or chloro. In some embodiments, each $R^{11}$ is independently hydrogen or fluoro. In some embodiments, each $R^{11}$ is hydrogen.

In some embodiments, the compound of Formula (XV) is a compound of Formula (VIc-1):

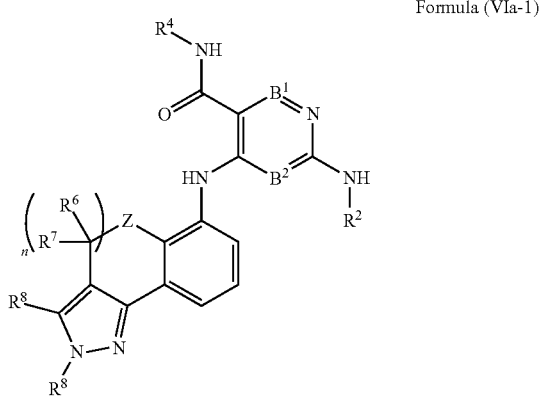

Formula (VIa-1)

or a pharmaceutically acceptable salt, tautomer, or solvate thereof.

In some embodiments, the compound of Formula (VIa-1) is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, nor 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, each $R^8$ is independently hydrogen, halogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —CN, —OH, —$OR^{17}$, —C(=O)$R^{16}$, —$CO_2R^{16}$, or —C(=O)N($R^{16}$)$_2$; wherein if $R^8$ is attached to a nitrogen atom, then $R^8$ is hydrogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —C(=O)$R^{16}$, —$CO_2R^{16}$, or —C(=O)N($R^{16}$)$_2$. In some embodiments, each $R^8$ is independently hydrogen, —Cl, —F, methyl, ethyl, isopropyl, -$CD_3$, —$CH_2OH$, —$CF_3$, cyclopropyl, oxetanyl, azetidinyl, —CN, —OH, —$CO_2H$, or —$CO_2CH_3$; wherein if $R^8$ is attached to a nitrogen atom, then $R^8$ is hydrogen, methyl, ethyl, isopropyl, -$CD_3$, —$CH_2OH$, —$CF_3$, cyclopropyl, oxetanyl, azetidinyl, —$CO_2H$, or —$CO_2CH_3$. In some embodiments, each $R^8$ is independently hydrogen, methyl, -$CD_3$, —OH, —$CH_2OH$, —$CF_3$, oxetanyl, —CN, or —$CO_2CH_3$; wherein if $R^8$ is attached to a nitrogen atom, then $R^8$ is hydrogen, methyl, -$CD_3$, —$CH_2OH$, oxetanyl, or —$CO_2CH_3$.

In some embodiments, each $R^6$ and $R^7$ is independently hydrogen, deuterium, F, $C_1$, -$CD_3$, or methyl. In some embodiments, each $R^6$ and $R^7$ is independently hydrogen, deuterium, F, or methyl. In some embodiments, each $R^6$ and $R^7$ is independently hydrogen or methyl. In some embodiments, one $R^6$ or $R^7$ is methyl. In some embodiments, one $R^6$ is methyl. In some embodiments, each $R^6$ and $R^7$ is hydrogen. In some embodiments, each $R^6$ and $R^7$ is deuterium. In some embodiments, each $R^6$ and $R^7$ is F.

In some embodiments, one $R^6$ and one $R^7$ attached to the same carbon atom are taken together with the carbon atom to which they are attached to form C=O or $C_3$-$C_4$ cycloalkyl. In some embodiments, one $R^6$ and one $R^7$ attached to the same carbon atom are taken together with the carbon atom to which they are attached to form C=O. In some embodiments, one $R^6$ and one $R^7$ attached to the same carbon atom are taken together with the carbon atom to which they are attached to form $C_3$-$C_4$ cycloalkyl. In some embodiments, one $R^6$ and one $R^7$ attached to the same carbon atom are taken together with the carbon atom to which they are attached to form a cyclopropyl.

In some embodiments, n is 1 or 2. In some embodiments, n is 1. In some embodiments, n is 2. In some embodiments, n is 3.

In some embodiments, Z is —$NR^{10}$—. In some embodiments, $R^{10}$ is hydrogen, $C_1$-$C_4$ alkyl, $C_1$-$C_4$ deuteroalkyl, or cyclopropyl. In some embodiments, $R^{10}$ is hydrogen, $C_1$-$C_4$ alkyl, or cyclopropyl. In some embodiments, $R^{10}$ is hydrogen, $C_1$-$C_4$ alkyl, or $C_1$-$C_4$ deuteroalkyl. In some embodiments, $R^{10}$ is hydrogen, —$CH_3$, or -$CD_3$. In some embodiments, $R^{10}$ is $C_1$-$C_4$ alkyl or $C_1$-$C_4$ deuteroalkyl. In some embodiments, $R^{10}$ is —$CH_3$ or -$CD_3$. In some embodiments, $R^{10}$ is —$CH_3$. In some embodiments, $R^{10}$ is -$CD_3$.

In some embodiments, Z is NH, $NCH_3$, or $NCD_3$. In some embodiments, Z is $NCH_3$ or $NCD_3$. In some embodiments, Z is $NCH_3$. In some embodiments, Z is $NCD_3$.

In some embodiments, Z is —O—.

In some embodiments, $R^2$ is as defined herein.

In some embodiments, the compound is a compound of Formula (XVIII):

Formula (XVIII)

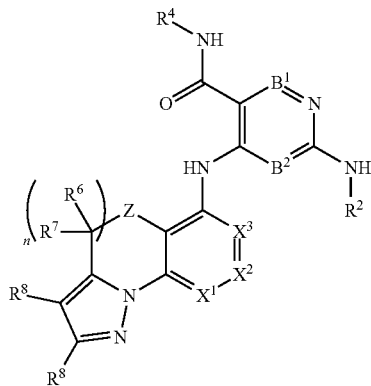

or a pharmaceutically acceptable salt, tautomer, or solvate thereof, wherein:

each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —C(=O)R$^{16}$, —CO$_2$R$^{16}$, —C(=O)N(R$^{16}$)$_2$, —S(=O)R$^{17}$, —SO$_2$R$^{17}$, or —SO$_2$N(R$^{16}$)$_2$;

Z is —NR$^{10}$—, —O—, —S—, —S(=O)—, or —SO$_2$—;

$R^{10}$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

$X^1$, $X^2$, and $X^3$ are each independently $CR^{11}$ or N;

each $R^{11}$ is independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

$B^1$ is N or $CR^{12a}$;

$B^2$ is N or $CR^{12b}$;

$R^{12a}$ and $R^{12b}$ are each independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

$R^2$ is a Ring B that is an unsubstituted or substituted heterocycle or unsubstituted or substituted carbocycle, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

or two $R^{13}$ groups on adjacent atoms of Ring B are taken together with the intervening atoms to which they are attached to form an unsubstituted or substituted 5- or 6-membered monocyclic carbocycle or an unsubstituted or substituted 5- or 6-membered monocyclic heterocycle;

or $R^2$ is —C(=O)R$^{14}$, —C(=O)NR$^{14}$R$^{15}$, or —C(=O)OR$^{14}$;

$R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocycle, unsubstituted or substituted bicyclic carbocycle, unsubstituted or substituted monocyclic heterocycle, or unsubstituted or substituted bicyclic heterocycle;

$R^{15}$ is hydrogen, $C_1$-$C_6$ alkyl, or $C_1$-$C_6$ fluoroalkyl;

$R^4$ is hydrogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle;

each $R^6$ and $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, or monocyclic heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —SO$_2$R$^{17}$, or —SO$_2$N(R$^{16}$)$_2$;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;

or two $R^{16}$ on the same N atom are taken together with the N atom to which they are attached to form a substituted or unsubstituted N-containing heterocycle; and each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, substituted or unsubstituted monocyclic 3- to 8-membered heterocycloalkyl, substituted or unsubstituted phenyl, or substituted or unsubstituted monocyclic heteroaryl;
wherein each substituted alkyl, substituted fluoroalkyl, substituted deuteroalkyl, substituted alkoxy, substituted fluoroalkoxy, substituted heteroalkyl, substituted carbocycle, and substituted heterocycle is substituted with one or more $R^s$ groups independently selected from the group consisting of deuterium, halogen, $C_1$-$C_6$ alkyl, monocyclic carbocycle, monocyclic heterocycle, —CN, —CH$_2$CN, —OR$^{18}$, —CH$_2$OR$^{18}$, —CO$_2$R$^{18}$, —CH$_2$CO$_2$R$^{18}$, —C(=O)N(R$^{18}$)$_2$, —CH$_2$C(=O)N(R$^{18}$)$_2$, —N(R$^{18}$)$_2$, —CH$_2$N(R$^{18}$)$_2$, —NR$^{18}$C(=O)R$^{18}$, —CH$_2$NR$^{18}$C(=O)R$^{18}$, —NR$^{18}$SO$_2$R$^{19}$, —CH$_2$NR$^{18}$SO$_2$R$^{19}$, —SR$^{18}$, —CH$_2$SR$^{18}$, —S(=O)R$^{19}$, —CH$_2$S(=O)R$^{19}$, —SO$_2$R$^{19}$, —CH$_2$SO$_2$R$^{19}$, —SO$_2$N(R$^{18}$)$_2$, or —CH$_2$SO$_2$N(R$^{18}$)$_2$;

each $R^{18}$ is independently selected from hydrogen, $C_1$-$C_6$ alkyl, $C_1$-$C_6$ fluoroalkyl, $C_1$-$C_6$ heteroalkyl, $C_3$-$C_6$ cycloalkyl, $C_2$-$C_6$ heterocycloalkyl, phenyl, benzyl, 5-membered heteroaryl and 6-membered heteroaryl;

or two $R^{18}$ groups are taken together with the N atom to which they are attached to form a N-containing heterocycle;

each $R^{19}$ is independently selected from $C_1$-$C_6$ alkyl, $C_1$-$C_6$ heteroalkyl, $C_3$-$C_6$ cycloalkyl, $C_2$-$C_6$ heterocycloalkyl, phenyl, benzyl, 5-membered heteroaryl, and 6-membered heteroaryl;

n is 1, 2, or 3; and q is 1, 2, 3, or 4.

In some embodiments, the compound of Formula (VXIII) is not 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —CN, —OH, —OR$^{17}$, —C(=O)R$^{16}$, —CO$_2$R$^{16}$, or —C(=O)N(R$^{16}$)$_2$; wherein if $R^8$ is attached to a nitrogen atom, then $R^8$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocycle, unsubstituted or substituted heterocycle, —C(=O)R$^{16}$, —CO$_2$R$^{16}$, or —C(=O)N(R$^{16}$)$_2$;

Z is —NR$^{10}$— or —O—;

$R^{10}$ is hydrogen, $C_1$-$C_4$ alkyl, $C_1$-$C_4$ deuteroalkyl, or cyclopropyl;

$X^1$, $X^2$, and $X^3$ are each independently CR$^{11}$ or N;

each $R^{11}$ is independently hydrogen, halogen, $C_1$-$C_6$ alkyl, $C_1$-$C_6$ fluoroalkyl, —CN, —OH, —OR$^{17}$, or —N(R$^{16}$)$_2$;

$B^1$ is N or CR$^{12a}$;

$B^2$ is N or CR$^{12b}$;

$R^{12a}$ and $R^{12b}$ are each independently hydrogen, halogen, $C_1$-$C_4$ alkyl, $C_1$-$C_4$ fluoroalkyl, or —CN;

$R^2$ is a Ring B that is an unsubstituted or substituted phenyl, unsubstituted or substituted monocyclic 6-membered heteroaryl, or unsubstituted or substituted monocyclic 5-membered heteroaryl, wherein if Ring B is substituted then Ring B is substituted with q instances of $R^{13}$;

each $R^{13}$ is independently halogen, unsubstituted or substituted $C_1$-$C_6$ alkyl, unsubstituted or substituted $C_1$-$C_6$ fluoroalkyl, unsubstituted or substituted carbocycle, unsubstituted or substituted heterocycle, —CN, —OH, —OR$^{17}$, —C(=O)R$^{16}$, —CO$_2$R$^{16}$, —C(=O)N(R$^{16}$)$_2$, —N(R$^{16}$)$_2$, —NR$^{16}$C(=O)R$^{17}$, —SO$_2$R$^{17}$, or —SO$_2$N(R$^{16}$)$_2$;

or $R^2$ is —C(=O)R$^{14}$;

$R^{14}$ is unsubstituted or substituted $C_1$-$C_6$ alkyl, $C_1$-$C_6$ deuteroalkyl, unsubstituted or substituted $C_3$-$C_4$ cycloalkyl, or unsubstituted or substituted 4-membered heterocycloalkyl; wherein the substituted alkyl, substituted heteroalkyl, substituted cycloalkyl, or substituted heterocycloalkyl is substituted with one or more $R^s$ groups independently selected from the group consisting of deuterium, halogen, —CN, —NH$_2$, —OH, —NH(CH$_3$), —N(CH$_3$)$_2$, —CH$_3$, —CH$_2$CH$_3$, —CHF$_2$, —CF$_3$, —OCH$_3$, —OCHF$_2$, and —OCF$_3$;

each $R^6$ and $R^7$ is independently hydrogen, deuterium, halogen, $C_1$-$C_4$ alkyl, or $C_1$-$C_4$ deuteroalkyl;

or one $R^6$ and one $R^7$ attached to the same carbon atom are taken together with the carbon atom to which they are attached to form C=O or $C_3$-$C_4$ cycloalkyl;

each $R^{16}$ is independently hydrogen, $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl;

or two $R^{16}$ on the same N atom are taken together with the N atom to which they are attached to form a 4- to 6-membered N-containing heterocycloalkyl; and each $R^{17}$ is independently $C_1$-$C_6$ alkyl, $C_1$-$C_6$ fluoroalkyl, $C_1$-$C_6$ heteroalkyl, $C_3$-$C_7$ cycloalkyl, or monocyclic 3- to 8-membered heterocycloalkyl.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —CH$_3$, —CH$_2$D, -CHD$_2$, or -CD$_3$. In some embodiments, $R^4$ is hydrogen. In some embodiments, $R^4$ is —CH$_3$. In some embodiments, $R^4$ is -CD$_3$.

In some embodiments, $X^1$ is CR$^{11}$, $X^2$ is CR$^{11}$, and $X^3$ is CR$^{11}$; or $X^1$ is CR$^{11}$, $X^2$ is CR$^{11}$ and $X^3$ is N; or $X^1$ is CR$^{11}$, $X^2$ is N, and $X^3$ is CR$^{11}$; or $X^1$ is N, $X^2$ is CR$^{11}$, and $X^3$ is CR$^{11}$. In some embodiments, $X^1$ is CR$^{11}$, $X^2$ is CR$^{11}$, and $X^3$ is CR$^{11}$. In some embodiments, $X^1$ is CR$^{11}$, $X^2$ is CR$^{11}$ and $X^3$ is N. In some embodiments, $X^1$ is CR$^{11}$, $X^2$ is N, and $X^3$ is CR$^{11}$. In some embodiments, $X^1$ is N, $X^2$ is CR$^{11}$, and $X^3$ is CR$^{11}$.

In some embodiments, each $R^{11}$ is independently hydrogen, halogen, $C_1$-$C_4$ alkyl, $C_1$-$C_4$ fluoroalkyl, or —CN. In some embodiments, each $R^{11}$ is independently hydrogen, halogen, or —CN. In some embodiments, each $R^{11}$ is independently hydrogen or halogen. In some embodiments, each $R^{11}$ is independently hydrogen, fluoro, or chloro. In some embodiments, each $R^{11}$ is independently hydrogen or fluoro. In some embodiments, each $R^{11}$ is hydrogen.

In some embodiments, the compound of Formula (XV) is a compound of Formula (VIc-1):

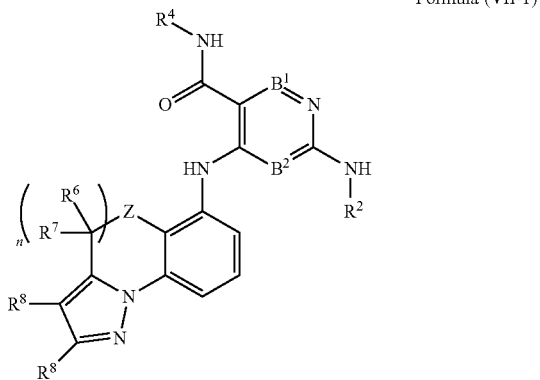

Formula (VIf-1)

or a pharmaceutically acceptable salt, tautomer, or solvate thereof.

In some embodiments, the compound of Formula (VIf-1) is not 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, $R^4$ is hydrogen, $C_1$-$C_6$ alkyl, $C_1$-$C_6$ deuteroalkyl, or $C_1$-$C_6$ fluoroalkyl. In some embodiments, $R^4$ is hydrogen, $C_1$-$C_6$ alkyl, or $C_1$-$C_6$ deuteroalkyl. In other embodiments, $R^4$ is hydrogen, $C_1$-$C_4$ alkyl, $C_1$-$C_4$ deuteroalkyl, or $C_1$-$C_4$ fluoroalkyl. In some embodiments, $R^4$ is hydrogen, $C_1$-$C_4$ alkyl, or $C_1$-$C_4$ deuteroalkyl. In some embodiments, $R^4$ is hydrogen, $C_1$-$C_2$ alkyl, or $C_1$-$C_2$ deuteroalkyl. In some embodiments, $R^4$ is hydrogen, —$CH_3$, —$CH_2D$, -$CHD_2$, or -$CD_3$. In some embodiments, $R^4$ is hydrogen. In some embodiments, $R^4$ is —$CH_3$. In some embodiments, $R^4$ is -$CD_3$.

In some embodiments, each $R^8$ is independently hydrogen, halogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —CN, —OH, —$OR^{17}$, —C(=O)$R^{16}$, —$CO_2R^{16}$, or —C(=O)N($R^{16}$)$_2$; wherein if $R^8$ is attached to a nitrogen atom, then $R^8$ is hydrogen, $C_1$-$C_6$ alkyl, $C_1$-$C_6$ deuteroalkyl, $C_1$-$C_6$ fluoroalkyl, $C_3$-$C_6$ cycloalkyl, 4- to 6-membered heterocycloalkyl, —C(=O)$R^{16}$, —$CO_2R^{16}$, or —C(=O)N($R^{16}$)$_2$. In some embodiments, each $R^8$ is independently hydrogen, —Cl, —F, methyl, ethyl, isopropyl, -$CD_3$, —$CH_2OH$, —$CF_3$, cyclopropyl, oxetanyl, azetidinyl, —CN, —OH, —$CO_2H$, or —$CO_2CH_3$; wherein if $R^8$ is attached to a nitrogen atom, then $R^8$ is hydrogen, methyl, ethyl, isopropyl, -$CD_3$, —$CH_2OH$, —$CF_3$, cyclopropyl, oxetanyl, azetidinyl, —$CO_2H$, or —$CO_2CH_3$. In some embodiments, each $R^8$ is independently hydrogen, methyl, -$CD_3$, —OH, —$CH_2OH$, —$CF_3$, oxetanyl, —CN, or —$CO_2CH_3$; wherein if $R^8$ is attached to a nitrogen atom, then $R^8$ is hydrogen, methyl, -$CD_3$, —$CH_2OH$, oxetanyl, or —$CO_2CH_3$.

In some embodiments, each $R^6$ and $R^7$ is independently hydrogen, deuterium, F, Cl, -$CD_3$, or methyl. In some embodiments, each $R^6$ and $R^7$ is independently hydrogen, deuterium, F, or methyl. In some embodiments, each $R^6$ and $R^7$ is independently hydrogen or methyl. In some embodiments, one $R^6$ or $R^7$ is methyl. In some embodiments, one $R^6$ is methyl. In some embodiments, each $R^6$ and $R^7$ is hydrogen. In some embodiments, each $R^6$ and $R^7$ is deuterium. In some embodiments, each $R^6$ and $R^7$ is F.

In some embodiments, one $R^6$ and one $R^7$ attached to the same carbon atom are taken together with the carbon atom to which they are attached to form C=O or $C_3$-$C_4$ cycloalkyl. In some embodiments, one $R^6$ and one $R^7$ attached to the same carbon atom are taken together with the carbon atom to which they are attached to form C=O. In some embodiments, one $R^6$ and one $R^7$ attached to the same carbon atom are taken together with the carbon atom to which they are attached to form $C_3$-$C_4$ cycloalkyl. In some embodiments, one $R^6$ and one $R^7$ attached to the same carbon atom are taken together with the carbon atom to which they are attached to form a cyclopropyl.

In some embodiments, n is 1 or 2. In some embodiments, n is 1. In some embodiments, n is 2. In some embodiments, n is 3.

In some embodiments, Z is —$NR^{10}$—. In some embodiments, $R^{10}$ is hydrogen, $C_1$-$C_4$ alkyl, $C_1$-$C_4$ deuteroalkyl, or cyclopropyl. In some embodiments, $R^{10}$ is hydrogen, $C_1$-$C_4$ alkyl, or cyclopropyl. In some embodiments, $R^{10}$ is hydrogen, $C_1$-$C_4$ alkyl, or $C_1$-$C_4$ deuteroalkyl. In some embodiments, $R^{10}$ is hydrogen, —$CH_3$, or -$CD_3$. In some embodiments, $R^{10}$ is $C_1$-$C_4$ alkyl or $C_1$-$C_4$ deuteroalkyl. In some embodiments, $R^{10}$ is —$CH_3$ or -$CD_3$. In some embodiments, $R^{10}$ is —$CH_3$. In some embodiments, $R^{10}$ is -$CD_3$.

In some embodiments, Z is NH, $NCH_3$, or $NCD_3$. In some embodiments, Z is $NCH_3$ or $NCD_3$. In some embodiments, Z is $NCH_3$. In some embodiments, Z is $NCD_3$.

In some embodiments, Z is —O—.

In some embodiments, $R^2$ is as defined herein.

In some embodiments, compounds described herein have the following structure:

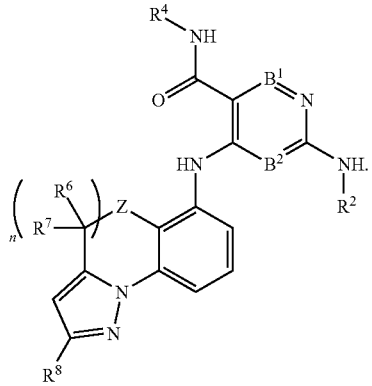

In some embodiments, $B^1$, $B^2$, $R^2$, $R^4$, Z, n, $R^6$, $R^7$, and $R^8$ are as described herein. In some embodiments, $B^1$, $B^2$, $R^2$, $R^4$, Z, n, $R^6$, $R^7$, and $R^8$ are as described in Table 1. In some embodiments, the compound is not 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, nor 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide.

In some embodiments, compounds described herein have the following structure:

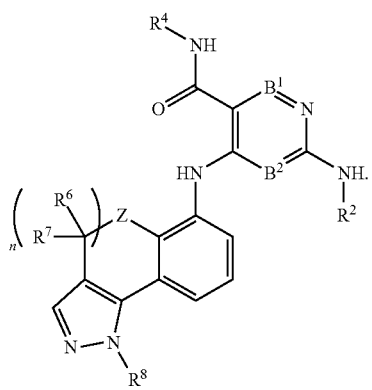

In some embodiments, $B^1$, $B^2$, $R^2$, $R^4$, Z, n, $R^6$, $R^7$, and $R^8$ are as described herein. In some embodiments, $B^1$, $B^2$, $R^2$, $R^4$, Z, n, $R^6$, $R^7$, and $R^8$ are as described in Table 2.

In some embodiments, compounds described herein have the following structure:

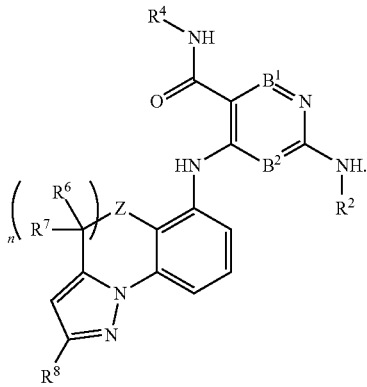

In some embodiments $B^1$, $B^2$, $R^2$, $R^4$, Z, n, $R^6$, $R^7$, and $R^8$ are as described herein. In some embodiments $B^1$, $B^2$, $R^2$, $R^4$, Z, n, $R^6$, $R^7$, and $R^8$ are as described in Table 3. In some embodiments, the compound is not 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, compounds described herein have the following structure:

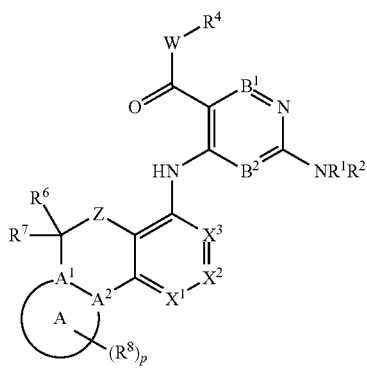

In some embodiments, $B^1$, $B^2$, $NR^1R^2$, W, $R^4$, $X^1$, $X^2$, $X^3$, Z, $R^6$, $R^7$, $A^1$, $A^2$, Ring A, $R^8$ and p are as described herein. In some embodiments, $B^1$, $B^2$, $NR^1R^2$, W, $R^4$, $X^1$, $X^2$, $X^3$, Z, $R^6$, $R^7$, and

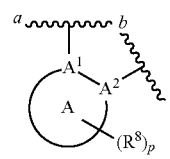

are as described herein. In some embodiments, $B^1$, $B^2$, $NR^1R^2$, W, $R^4$, $X^1$, $X^2$, $X^3$, Z, $R^6$, $R^7$, $A^1$, $A^2$, Ring A, $R^8$ and p are as described in Table 4. In some embodiments, $B^1$, $B^2$, $NR^1R^2$, W, $R^4$, $X^1$, $X^2$, $X^3$, Z, $R^6$, $R^7$, and

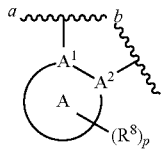

are as described in Table 4. In some embodiments, the compound is not 6-(cyclopropanecarboxamido)-4-((2,5-dimethyl-4,5-dihydro-2H-pyrazolo[4,3-c]quinolin-6-yl) amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide, nor 6-(cyclopropanecarboxamido)-4-((2,5-dimethyl-4,5-dihydropyrazolo[1,5-a]quinoxalin-6-yl)amino)-N-methylpyridazine-3-carboxamide.

In some embodiments, compounds described herein have the following structure:

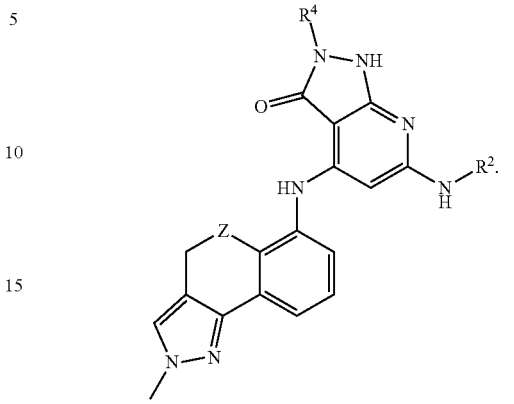

In some embodiments $W^2$, $W^4$, and Z, are as described herein. In some embodiments $R^2$, $W^4$, and Z are as described in Table 5.

Any combination of the groups described above for the various variables is contemplated herein. Throughout the specification, groups and substituents thereof are chosen by one skilled in the field to provide stable moieties and compounds.

Exemplary compounds described herein include the compounds described in the following Tables:

TABLE 1

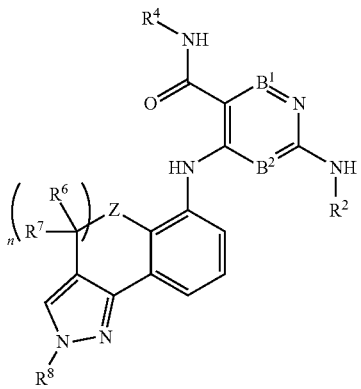

| Cpd No. | $B^1$ | $B^2$ | $R^2$ | $R^4$ | Z | n | $R^6$ | $R^7$ | $R^8$ |
|---|---|---|---|---|---|---|---|---|---|
| 1 | N | CH | 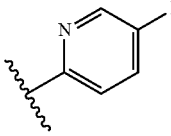 | F | —$CH_3$ | O | 1 | H | H | —$CH_3$ |
| 2 | N | CH | 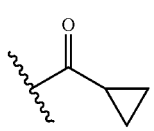 [SMILES: *C(=O)C1CC1] | | —$CH_3$ | O | 1 | H | H | —$CH_3$ |

TABLE 1-continued
| # | | | | | | | | |
|---|---|---|---|---|---|---|---|---|
| 3 | N | CH | 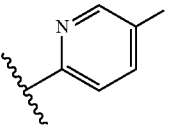 | —CH₃ | O | 1 | H | H | 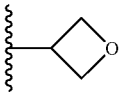 |
| 4 | N | CH | 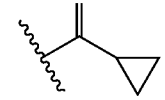 | —CH₃ | O | 1 | H | H | 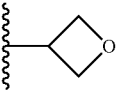 [SMILES: *C1COC1] |
| 5 | N | CH | 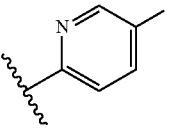 | —CD₃ | O | 1 | H | H | —CH₃ |
| 6 | CH | CH | 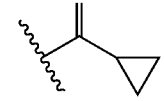 | —CD₃ | O | 1 | H | H | —CH₃ |
| 7 | CH | CH | 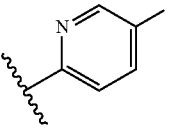 | —CD₃ | O | 1 | H | H | —CH₃ |
| 8 | N | CH | 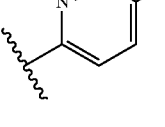 | H | O | 1 | H | H | —CH₃ |
| 9 | CH | CH | 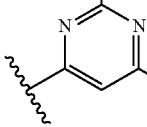 | —CD₃ | O | 1 | H | H | —CH₃ |
| 10 | N | CH | 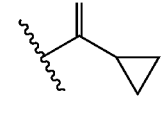 | —CH₃ | O | 1 | —CH₃ | H | —CH₃ |
| 11 | N | CH | 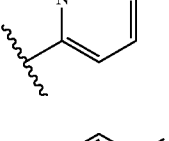 | —CH₃ | O | 1 | —CH₃ | H | —CH₃ |
| 12 | N | CH | 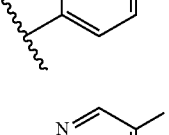 | —CH₃ | NCH₃ | 1 | H | H | —CH₃ |
| 13 | CH | CH | 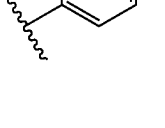 | —CD₃ | NCH₃ | 1 | H | H | —CH₃ |

TABLE 1-continued

| # | | | | | | | | |
|---|---|---|---|---|---|---|---|---|
| 14 | CH | CH | cyclopropyl ketone | —CD₃ | NCH₃ | 1 | H | H | —CH₃ |
| 15 | N | CH | cyclopropyl ketone | —CD₃ | NCH₃ | 1 | H | H | —CH₃ |
| 16 | CH | CH | dimethylpyrimidinyl | —CD₃ | NCH₃ | 1 | H | H | —CH₃ |
| 17 | CH | CH | cyclopropyl ketone | H | NCH₃ | 1 | H | H | —CH₃ |
| 18 | CH | N | cyclopropyl ketone | —CD₃ | NCH₃ | 1 | H | H | —CH₃ |
| 19 | CH | CH | cyclopropyl ketone | —CD₃ | NCH₃ | 1 | H | H | —CD₃ |
| 20 | N | CH | cyclopropyl ketone | —CD₃ | NCH₃ | 1 | H | H | —CD₃ |
| 21 | CH | CH | hydroxycyclopropyl ketone | —CD₃ | NCH₃ | 1 | H | H | —CH₃ |
| 22 | CH | N | cyclopropyl ketone | —CD₃ | NCH₃ | 1 | H | H | —CH₃ |
| 23 | CH | CH | cyclopropyl ketone | —CD₃ | NCH₃ | 1 | H | H | —H |
| 24 | CH | CH | oxetanyl ketone | —CD₃ | NCH₃ | 1 | H | H | —CH₃ |
| 25 | CH | CH | N-methyl amide | —CD₃ | NCH₃ | 1 | H | H | —CH₃ |

TABLE 1-continued
| | | | | | | | | |
|---|---|---|---|---|---|---|---|---|
| 26 | CH | CH | 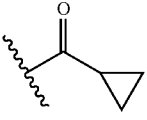 | —CD₃ | NCD₃ | 1 | H | H | —CH₃ |
| 27 | N | CH | 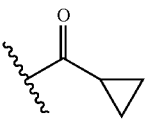 | —CD₃ | NCH₃ | 1 | H | H | —H |
| 28 | N | CH | 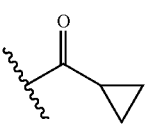 | —CD₃ | NCD₃ | 1 | H | H | —CH₃ |
| 29 | CH | CH | 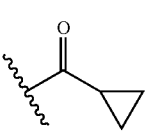 | —CD₃ | NCH₃ | 1 | H | H | 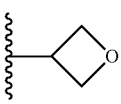 [SMILES: *C1COC1] |
| 30 | CH | CH | 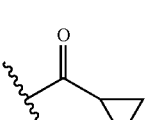 | —CD₃ | NCH₃ | 1 | (S)-CH₃ | H | —CH₃ |
| 31 | CH | CH | 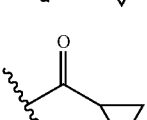 | —CD₃ | NCH₃ | 1 | (R)-CH₃ | H | —CH₃ |
| 32 | CH | CH | 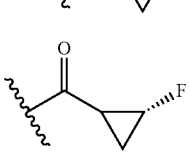 | —CD₃ | NCH₃ | 1 | H | H | —CH₃ |
| 33 | N | CH | 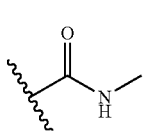 [SMILES: *C(=O)NC] | —CD₃ | NCH₃ | 1 | D | D | —CH₃ |
| 34 | N | CH | 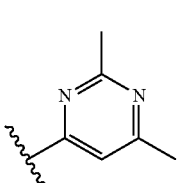 | —CH₃ | NCH₃ | 1 | H | H | —CH₃ |
| 35 | CH | CH | 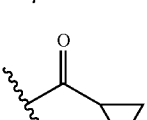 | —CD₃ | NCH₃ | 1 | D | D | —CH₃ |
| 36 | CH | CH | 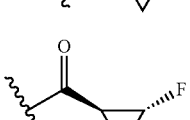 | —CD₃ | NCH₃ | 1 | H | H | —CH₃ |
| 37 | CH | CH | 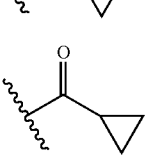 | —CD₃ | NCH₃ | 1 | H | H | —CH(CH₃)₂ |

TABLE 1-continued

| # | | | | | | | | |
|---|---|---|---|---|---|---|---|---|
| 38 | N | CH | 5-fluoropyridin-2-yl | —CH₃ | O | 2 | H | H | —CH₃ |
| 39 | CH | CH | 3-hydroxy-3-methyl-2-oxobutyl | —CD₃ | NCH₃ | 1 | H | H | —CH₃ |
| 40 | CH | CH | (1-methylazetidin-3-yl)carbonyl | —CD₃ | NCH₃ | 1 | H | H | —CH₃ |
| 41 | CH | CH | methoxycarbonyl | —CD₃ | NCH₃ | 1 | H | H | —CH₃ |
| 42 | N | N | cyclopropylcarbonyl | —CD₃ | NCH₃ | 1 | H | H | —CH₃ |
| 43 | CH | CH | cyclopropylcarbonyl | —CD₃ | NCH₃ | 1 | CH₃ | H | —CH₃ |
| 44 | CH | CH | cyclopropylcarbonyl | —CD₃ | NCH₃ | 1 | CH₃ | H | —CD₃ |
| 45 | CH | CH | cyclopropylcarbonyl | —CD₃ | NCD₃ | 1 | H | H | —CD₃ |
| 46 | CH | CH | cyclopropylcarbonyl | —CD₃ | NCH₃ | 1 | D | D | —CD₃ |
| 47 | CH | CH | cyclopropylcarbonyl | —CD₃ | NCH₃ | 1 | F | F | —CH₃ |
| 48 | CH | CH | cyclopropylcarbonyl | —CD₃ | NCH₃ | 1 | F | F | —CD₃ |
| 91 | N | CH | cyclopropylcarbonyl | —CD₃ | NCH₃ | 1 | H | H | —CH(CH₃)₂ |

Compounds in Table 1 are named:
1: 6-((5-fluoropyridin-2-yl)amino)-N-methyl-4-((2-methyl-2,4-dihydrochromeno[4,3-c]pyrazol-6-yl)amino)pyridazine-3-carboxamide;
2: 6-(cyclopropanecarboxamido)-N-methyl-4-((2-methyl-2,4-dihydrochromeno[4,3-c]pyrazol-6-yl)amino)pyridazine-3-carboxamide;
3: 6-[(5-fluoropyridin-2-yl)amino]-N-methyl-4-{[2-(oxetan-3-yl)-2H,4H-chromeno[4,3-c]pyrazol-6-yl]amino}pyridazine-3-carboxamide;
4: 6-(cyclopropanecarboxamido)-N-methyl-4-((2-(oxetan-3-yl)-2,4-dihydrochromeno[4,3-c]pyrazol-6-yl)amino)pyridazine-3-carboxamide;
5: 6-((5-fluoropyridin-2-yl)amino)-N-(methyl-d3)-4-((2-methyl-2,4-dihydrochromeno[4,3-c]pyrazol-6-yl)amino)pyridazine-3-carboxamide;
6: 6-(cyclopropanecarboxamido)-N-(methyl-d3)-4-((2-methyl-2,4-dihydrochromeno[4,3-c]pyrazol-6-yl)amino)nicotinamide;
7: 6-((5-fluoropyridin-2-yl)amino)-N-(methyl-d3)-4-((2-methyl-2,4-dihydrochromeno[4,3-c]pyrazol-6-yl)amino)nicotinamide;
8: 6-((5-fluoropyridin-2-yl)amino)-4-((2-methyl-2,4-dihydrochromeno[4,3-c]pyrazol-6-yl)amino)pyridazine-3-carboxamide;
9: 6-((2,6-dimethylpyrimidin-4-yl)amino)-N-(methyl-d3)-4-((2-methyl-2,4-dihydrochromeno[4,3-c]pyrazol-6-yl)amino)nicotinamide;
10: 6-(cyclopropanecarboxamido)-4-((2,4-dimethyl-2,4-dihydrochromeno[4,3-c]pyrazol-6-yl)amino)-N-methylpyridazine-3-carboxamide;
11: 4-((2,4-dimethyl-2,4-dihydrochromeno[4,3-c]pyrazol-6-yl)amino)-6-((5-fluoropyridin-2-yl)amino)-N-methylpyridazine-3-carboxamide;
12: (4-((2,5-dimethyl-4,5-dihydro-2H-pyrazolo[4,3-c]quinolin-6-yl)amino)-6-((5-fluoropyridin-2-yl)amino)-N-methylpyridazine-3-carboxamide);
13: 4-((2,5-dimethyl-4,5-dihydro-2H-pyrazolo[4,3-c]quinolin-6-yl)amino)-6-((5-fluoropyridin-2-yl)amino)-N-(methyl-d3)nicotinamide;
14: [6-(cyclopropanecarboxamido)-4-((2,5-dimethyl-4,5-dihydro-2H-pyrazolo[4,3-c]quinolin-6-yl)amino)-N-(methyl-d3)nicotinamide];
15: 6-(cyclopropanecarboxamido)-4-((2,5-dimethyl-4,5-dihydro-2H-pyrazolo[4,3-c]quinolin-6-yl)amino)-N-(methyl-d3)pyridazine-3-carboxamide;
16: 4-((2,5-dimethyl-4,5-dihydro-2H-pyrazolo[4,3-c]quinolin-6-yl)amino)-6-((2,6-dimethylpyrimidin-4-yl)amino)-N-(methyl-d3)nicotinamide;
17: 6-(cyclopropanecarboxamido)-4-((2,5-dimethyl-4,5-dihydro-2H-pyrazolo[4,3-c]quinolin-6-yl)amino)nicotinamide;
18: 6-(cyclopropanecarboxamido)-4-((2,5-dimethyl-4,5-dihydro-2H-pyrazolo[4,3-c]quinolin-6-yl)amino)-N-methylnicotinamide;
19: 6-(cyclopropanecarboxamido)-N-(methyl-d3)-4-((5-methyl-2-(methyl-d3)-4,5-dihydro-2H-pyrazolo[4,3-c]quinolin-6-yl)amino)nicotinamide;
20: 6-(cyclopropanecarboxamido)-N-(methyl-d3)-4-((5-methyl-2-(methyl-d3)-4,5-dihydro-2H-pyrazolo[4,3-c]quinolin-6-yl)amino)pyridazine-3-carboxamide
21: 4-((2,5-dimethyl-4,5-dihydro-2H-pyrazolo[4,3-c]quinolin-6-yl)amino)-6-(1-hydroxycyclopropane-1-carboxamido)-N-(methyl-d3)nicotinamide;
22: 2-(cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide;
23: 6-(cyclopropanecarboxamido)-N-(methyl-d3)-4-((5-methyl-4,5-dihydro-2H-pyrazolo[4,3-c]quinolin-6-yl)amino)nicotinamide;
24: 4-((2,5-dimethyl-4,5-dihydro-2H-pyrazolo[4,3-c]quinolin-6-yl)amino)-N-(methyl-d3)-6-(oxetane-3-carboxamido)nicotinamide;
25: 4-((2,5-dimethyl-4,5-dihydro-2H-pyrazolo[4,3-c]quinolin-6-yl)amino)-N-(methyl-d3)-6-(3-methylureido)nicotinamide;
26: 6-(cyclopropanecarboxamido)-N-(methyl-d3)-4-((2-methyl-5-(methyl-d3)-4,5-dihydro-2H-pyrazolo[4,3-c]quinolin-6-yl)amino)nicotinamide;
27: 6-(cyclopropanecarboxamido)-N-(methyl-d3)-4-((5-methyl-4,5-dihydro-2H-pyrazolo[4,3-c]quinolin-6-yl)amino)pyridazine-3-carboxamide;
28: 6-(cyclopropanecarboxamido)-N-(methyl-d3)-4-((2-methyl-5-(methyl-d3)-4,5-dihydro-2H-pyrazolo[4,3-c]quinolin-6-yl)amino)pyridazine-3-carboxamide;
29: 6-(cyclopropanecarboxamido)-N-(methyl-d3)-4-((5-methyl-2-(oxetan-3-yl)-4,5-dihydro-2H-pyrazolo[4,3-c]quinolin-6-yl)amino)nicotinamide;
30: (S)-6-(cyclopropanecarboxamido)-N-(methyl-d3)-4-((2,4,5-trimethyl-4,5-dihydro-2H-pyrazolo[4,3-c]quinolin-6-yl)amino)nicotinamide;
31: (R)-6-(cyclopropanecarboxamido)-N-(methyl-d3)-4-((2,4,5-trimethyl-4,5-dihydro-2H-pyrazolo[4,3-c]quinolin-6-yl)amino)nicotinamide;
32: 4-((2,5-dimethyl-4,5-dihydro-2H-pyrazolo[4,3-c]quinolin-6-yl)amino)-6-((2R)-2-fluorocyclopropane-1-carboxamido)-N-(methyl-d3)nicotinamide;
33: 4-((2,5-dimethyl-4,5-dihydro-2H-pyrazolo[4,3-c]quinolin-6-yl-4,4-d2)amino)-N-(methyl-d3)-6-(3-methylureido)pyridazine-3-carboxamide;
34: 4-((2,5-dimethyl-4,5-dihydro-2H-pyrazolo[4,3-c]quinolin-6-yl)amino)-6-((2,6-dimethylpyrimidin-4-yl)amino)-N-methylpyridazine-3-carboxamide;
35: 6-(cyclopropanecarboxamido)-4-((2,5-dimethyl-4,5-dihydro-2H-pyrazolo[4,3-c]quinolin-6-yl-4,4-d2)amino)-N-(methyl-d3)nicotinamide;
36: rel-4-((2,5-dimethyl-4,5-dihydro-2H-pyrazolo[4,3-c]quinolin-6-yl)amino)-6-((1R,2S)-2-fluorocyclopropane-1-carboxamido)-N-(methyl-d3)nicotinamide;
37: 6-(cyclopropanecarboxamido)-4-((2-isopropyl-5-methyl-4,5-dihydro-2H-pyrazolo[4,3-c]quinolin-6-yl)amino)-N-(methyl-d3)nicotinamide.
38: 6-((5-fluoropyridin-2-yl)amino)-N-methyl-4-((2-methyl-4,5-dihydro-2H-benzo[2,3]oxepino[4,5-c]pyrazol-7-yl)amino)pyridazine-3-carboxamide;
39: 4-((2,5-dimethyl-4,5-dihydro-2H-pyrazolo[4,3-c]quinolin-6-yl)amino)-6-(2-hydroxy-2-methylpropanamido)-N-(methyl-d3)nicotinamide;
40: 4-((2,5-dimethyl-4,5-dihydro-2H-pyrazolo[4,3-c]quinolin-6-yl)amino)-N-(methyl-d3)-6-(1-methylazetidine-3-carboxamido)nicotinamide;
41: methyl (4-((2,5-dimethyl-4,5-dihydro-2H-pyrazolo[4,3-c]quinolin-6-yl)amino)-5-((methyl-d3)carbamoyl)pyridin-2-yl)carbamate;
42: 3-(cyclopropanecarboxamido)-5-((2,5-dimethyl-4,5-dihydro-2H-pyrazolo[4,3-c]quinolin-6-yl)amino)-N-(methyl-d3)-1,2,4-triazine-6-carboxamide;
43: 6-(cyclopropanecarboxamido)-N-(methyl-d3)-4-((2,4,5-trimethyl-4,5-dihydro-2H-pyrazolo[4,3-c]quinolin-6-yl)amino)nicotinamide;
44: 6-(cyclopropanecarboxamido)-4-((4,5-dimethyl-2-(methyl-d3)-4,5-dihydro-2H-pyrazolo[4,3-c]quinolin-6-yl)amino)-N-(methyl-d3)nicotinamide;

45: 4-((2,5-bis(methyl-d3)-4,5-dihydro-2H-pyrazolo[4,3-c]quinolin-6-yl)amino)-6-(cyclopropanecarboxamido)-N-(methyl-d3)nicotinamide;
46: 6-(cyclopropanecarboxamido)-N-(methyl-d3)-4-((5-methyl-2-(methyl-d3)-4,5-dihydro-2H-pyrazolo[4,3-c]quinolin-6-yl-4,4-d2)amino)nicotinamide;
47: 6-(cyclopropanecarboxamido)-4-((4,4-difluoro-2,5-dimethyl-4,5-dihydro-2H-pyrazolo[4,3-c]quinolin-6-yl)amino)-N-(methyl-d3)nicotinamide;
48: 6-(cyclopropanecarboxamido)-4-((4,4-difluoro-5-methyl-2-(methyl-d3)-4,5-dihydro-2H-pyrazolo[4,3-c]quinolin-6-yl)amino)-N-(methyl-d3)nicotinamide; and
91: 6-(cyclopropanecarboxamido)-4-((2-isopropyl-5-methyl-4,5-dihydro-2H-pyrazolo[4,3-c]quinolin-6-yl)amino)-N-(methyl-d3)pyridazine-3-carboxamide.

In some embodiments, provided herein is a pharmaceutically acceptable salt of a compound that is described in Table 1.

TABLE 2

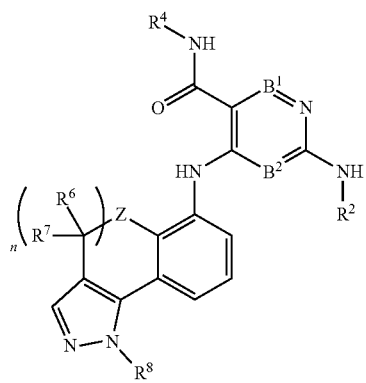

TABLE 2-continued

| Cpd No. | B$^1$ | B$^2$ | R$^2$ | R$^4$ | Z | n | R$^6$ | R$^7$ | R$^8$ |
|---|---|---|---|---|---|---|---|---|---|
| 49 | N | CH | 5-fluoropyridin-2-yl | —CH$_3$ | O | 1 | H | H | —CH$_3$ |
| 50 | N | CH | cyclopropyl ketone | —CH$_3$ | O | 1 | H | H | —CH$_3$ |
| 51 | CH | CH | cyclopropyl ketone | —CD$_3$ | NCH$_3$ | 1 | H | H | —CH$_3$ |

Compounds in Table 2 are named:
49: 6-((5-fluoropyridin-2-yl)amino)-N-methyl-4-((1-methyl-1,4-dihydrochromeno[4,3-c]pyrazol-6-yl)amino)pyridazine-3-carboxamide;
50: 6-(cyclopropanecarboxamido)-N-methyl-4-((1-methyl-1,4-dihydrochromeno[4,3-c]pyrazol-6-yl)amino)pyridazine-3-carboxamide; and
51: 6-(cyclopropanecarboxamido)-4-((1,5-dimethyl-4,5-dihydro-1H-pyrazolo[4,3-c]quinolin-6-yl)amino)-N-(methyl-d3)nicotinamide.

In some embodiments, provided herein is a pharmaceutically acceptable salt of a compound that is described in Table 2.

TABLE 3

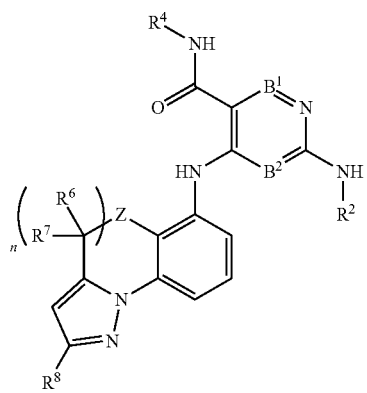

| Cpd No. | B$^1$ | B$^2$ | R$^2$ | R$^4$ | Z | n | R$^6$ | R$^7$ | R$^8$ |
|---|---|---|---|---|---|---|---|---|---|
| 52 | N | CH | cyclopropyl ketone | —CD$_3$ | NCH$_3$ | 1 | H | H | —CH$_3$ |
| 53 | CH | CH | cyclopropyl ketone | —CD$_3$ | NCH$_3$ | 1 | H | H | —CH$_3$ |

TABLE 3-continued

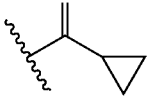

| Cpd No. | B¹ | B² | R² | R⁴ | Z | n | R⁶ | R⁷ | R⁸ |
|---|---|---|---|---|---|---|---|---|---|
| 54 | N | CH | 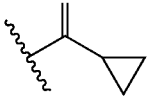 | —CD₃ | NCH₃ | 1 | H | H | —CF₃ |
| 55 | CH | CH | 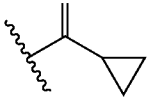 | —CD₃ | NCH₃ | 1 | H | H | —CF₃ |
| 56 | N | CH | 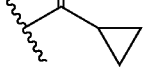 | —CD₃ | NCH₃ | 1 | D | D | —CH₃ |
| 57 | CH | CH | 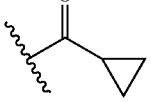 | —CD₃ | NCH₃ | 1 | D | D | —CH₃ |
| 58 | N | CH | 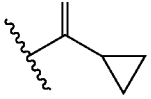 | —CD₃ | NCH₃ | 1 | D | D | —H |
| 59 | CH | CH | 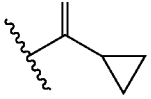 | —CD₃ | NCH₃ | 1 | D | D | —H |

Compounds in Table 3 are named:

52: 6-(cyclopropanecarboxamido)-4-((2,5-dimethyl-4,5-dihydropyrazolo[1,5-a]quinoxalin-6-yl)amino)-N-(methyl-d3)pyridazine-3-carboxamide;

53: 6-(cyclopropanecarboxamido)-4-((2,5-dimethyl-4,5-dihydropyrazolo[1,5-a]quinoxalin-6-yl)amino)-N-(methyl-d3)nicotinamide;

54: 6-(cyclopropanecarboxamido)-N-(methyl-d3)-4-((5-methyl-2-(trifluoromethyl)-4,5-dihydropyrazolo[1,5-a]quinoxalin-6-yl)amino)pyridazine-3-carboxamide;

55: 6-(cyclopropanecarboxamido)-N-(methyl-d3)-4-((5-methyl-2-(trifluoromethyl)-4,5-dihydropyrazolo[1,5-a]quinoxalin-6-yl)amino)nicotinamide;

56: 6-(cyclopropanecarboxamido)-4-((2,5-dimethyl-4,5-dihydropyrazolo[1,5-a]quinoxalin-6-yl-4,4-d2)amino)-N-(methyl-d3)pyridazine-3-carboxamide;

57: 6-(cyclopropanecarboxamido)-4-((2,5-dimethyl-4,5-dihydropyrazolo[1,5-a]quinoxalin-6-yl-4,4-d2)amino)-N-(methyl-d3)nicotinamide;

58: 6-(cyclopropanecarboxamido)-N-(methyl-d3)-4-((5-methyl-4,5-dihydropyrazolo[1,5-a]quinoxalin-6-yl-4,4-d2)amino)pyridazine-3-carboxamide; and 59: 6-(cyclopropanecarboxamido)-N-(methyl-d3)-4-((5-methyl-4,5-dihydropyrazolo[1,5-a]quinoxalin-6-yl-4,4-d2)amino)nicotinamide.

In some embodiments, provided herein is a pharmaceutically acceptable salt of a compound that is described in Table 3.

TABLE 4

| Cpd No. | B¹ | B² | NR¹R² | W | R⁴ | X¹ | X² | X³ | Z | R⁶ | R⁷ | A(R⁸)p |
|---|---|---|---|---|---|---|---|---|---|---|---|---|
| 60 | CH | CH | N-H-C(=O)-cyclopropyl | O | —CH₃ | CH | CH | CH | NCH₃ | H | H | 1-methyl-pyrazole (a at 4, b at 3) |
| 61 | CH | CH | imidazolidin-2-one, N-isopropyl | NH | —CD₃ | CH | CH | CH | NCH₃ | H | H | 1-methyl-pyrazole (a at 4, b at 3) |
| 62 | N | CH | N(CH₃)-C(=O)-cyclopropyl | NH | —CD₃ | N | CH | CH | NCH₃ | D | D | 1-methyl-pyrazole (a at 4, b at 3) |
| 63 | CH | CH | imidazolidin-2-one, N-isopropyl | NH | —CD₃ | CH | CH | CH | NCH₃ | D | D | 1-methyl-pyrazole (a at 4, b at 3) |
| 64 | CH | CH | N-H-C(=O)-cyclopropyl | NH | —CD₃ | CH | CH | N | NCH₃ | H | H | 1-methyl-pyrazole (a at 4, b at 3) |
| 65 | N | CH | N-H-C(=O)-cyclopropyl | NH | —CD₃ | CH | CH | N | NCH₃ | H | H | 1-methyl-pyrazole (a at 4, b at 3) |

TABLE 4-continued
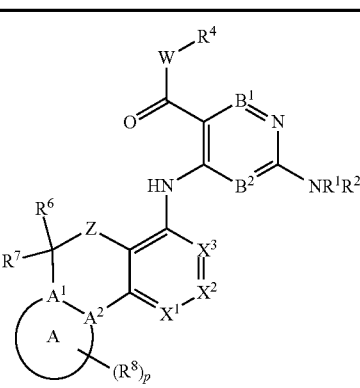
| Cpd No. | B¹ | B² | NR¹R² | W | R⁴ | X¹ | X² | X³ | Z | R⁶ | R⁷ | 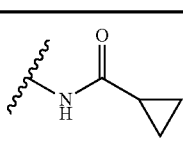 |
|---|---|---|---|---|---|---|---|---|---|---|---|---|
| 66 | CH | CH | 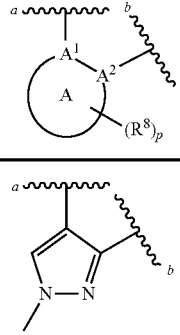 | NH | —CD₃ | CH | CH | N | NCD₃ | H | H | 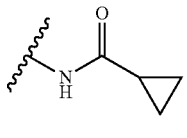 [SMILES: *NC(=O)C1CC1] |
| 67 | N | CH | 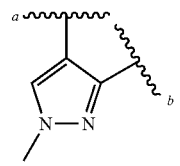 [SMILES: *c1cn(C)nc1*] | NH | —CD₃ | CH | CH | N | NCD₃ | H | H | 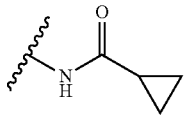 [SMILES: *NC(=O)C1CC1] |
| 68 | N | CH | 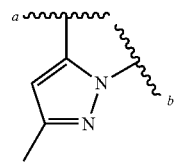 | NH | —CD₃ | CH | CH | N | NCH₃ | H | H | 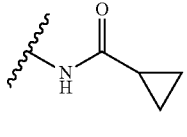 [SMILES: *NC(=O)C1CC1] |
| 69 | N | CH | 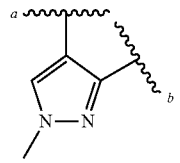 [SMILES: *c1cn(C)nc1*] | NH | —CD₃ | CH | CH | N | NCH₃ | (S)-CH₃ | H | 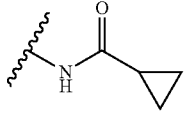 [SMILES: *NC(=O)C1CC1] |
| 70 | N | CH | 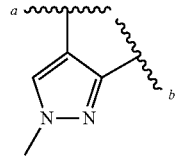 [SMILES: *c1cn(C)nc1*] | NH | —CD₃ | CH | CH | N | NCH₃ | (R)-CH₃ | H | 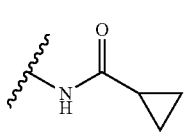 [SMILES: *NC(=O)C1CC1] |
| 71 | CH | CH | 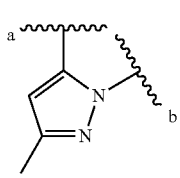 [SMILES: *c1cc(C)nn1*] | NH | —CD₃ | CH | CH | N | NCH₃ | H | H |  |

TABLE 4-continued
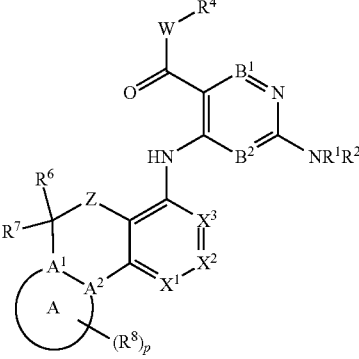
| Cpd No. | B¹ | B² | NR¹R² | W | R⁴ | X¹ | X² | X³ | Z | R⁶ | R⁷ | 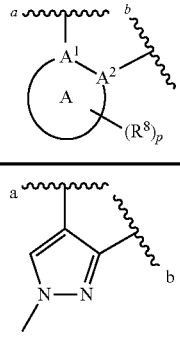 |
|---|---|---|---|---|---|---|---|---|---|---|---|---|
| 72 | N | CH | 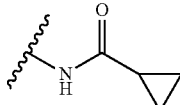 | NH | —CD$_3$ | CH | CH | N | NCH$_3$ | D | D | 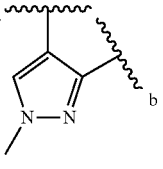 |
| 73 | N | CH | 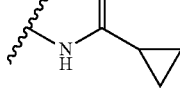 | NH | —CD$_3$ | CH | CH | N | NCH$_3$ | D | D | 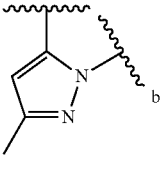 |
| 74 | N | CH | 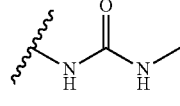 | NH | —CD$_3$ | CH | CH | N | NCH$_3$ | D | D | 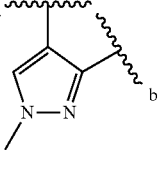 |
| 75 | N | CH | 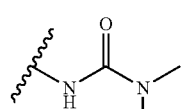 | NH | —CD$_3$ | CH | CH | N | NCH$_3$ | D | D | 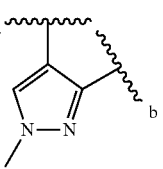 |
| 76 | CH | CH | 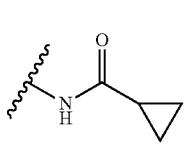 [SMILES: *NC(=O)C1CC1] | NH | —CD$_3$ | CH | CH | N | NCH$_3$ | D | D | 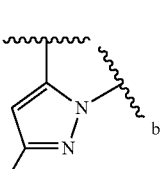 |
| 77 | CH | CH | 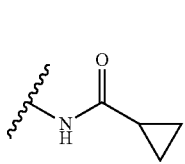 [SMILES: *NC(=O)C1CC1] | NH | —CD$_3$ | CH | CH | N | NCH$_3$ | D | D | 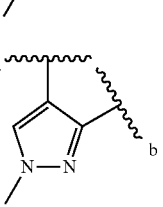 |

TABLE 4-continued
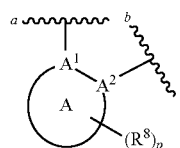
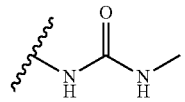
| Cpd No. | B¹ | B² | NR¹R² | W | R⁴ | X¹ | X² | X³ | Z | R⁶ | R⁷ | |
|---|---|---|---|---|---|---|---|---|---|---|---|---|
| 78 | N | CH | 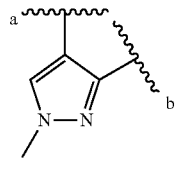 [SMILES: *c1cn(C)nc1*] | NH | —CD₃ | CH | CH | N | NCH₃ | (R)-CH₃ | H | 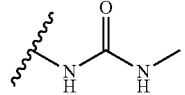 |
| 79 | N | CH | 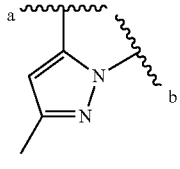 [SMILES: *c1cc(C)nn1*] | NH | —CD₃ | CH | CH | N | NCH₃ | H | H | 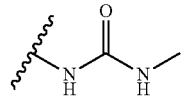 |
| 80 | N | CH | 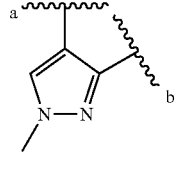 [SMILES: *c1cn(C)nc1*] | NH | —CD₃ | CH | CH | N | NCH₃ | (S)-CH₃ | H | 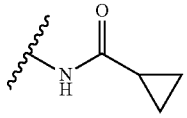 [SMILES: *NC(=O)C1CC1] |
| 81 | N | CH | 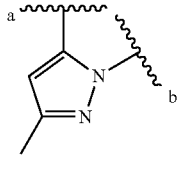 [SMILES: *c1cc(C)nn1*] | NH | —CD₃ | CH | CH | N | NCH₃ | (R)-CH₃ | H | 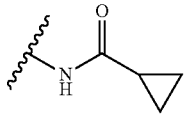 [SMILES: *NC(=O)C1CC1] |
| 82 | CH | CH | 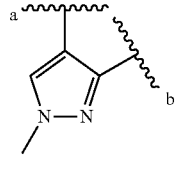 [SMILES: *c1cn(C)nc1*] | NH | —CD₃ | CH | CF | CH | NCH₃ | H | H | 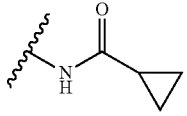 [SMILES: *NC(=O)C1CC1] |
| 83 | CH | CH | 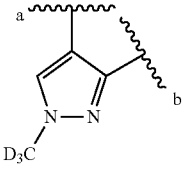 | NH | —CD₃ | CH | CF | CH | NCH₃ | H | H | 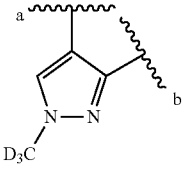 |

TABLE 4-continued

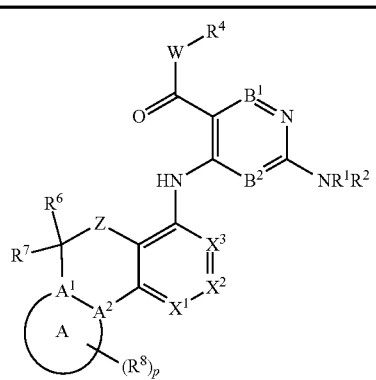

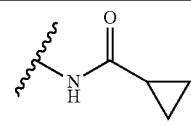

| Cpd No. | B¹ | B² | NR¹R² | W | R⁴ | X¹ | X² | X³ | Z | R⁶ | R⁷ | |
|---|---|---|---|---|---|---|---|---|---|---|---|---|
| 84 | CH | CH | 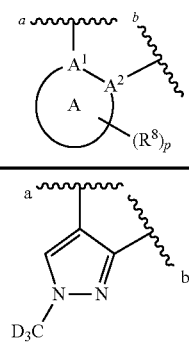 | NH | —CD₃ | CH | N | CH | NCH₃ | H | H |  |
| 85 | N | CH |  | NH | —CD₃ | CH | N | CH | NCH₃ | H | H | 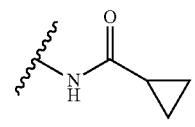 [SMILES: *NC(=O)C1CC1] |
| 86 | CH | CH | 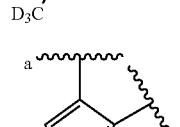 | NH | —CD₃ | CH | CH | N | NCH₃ | H | H | 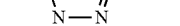 |
| 87 | N | CH |  | NH | —CD₃ | CH | CH | N | NCH₃ | H | H | 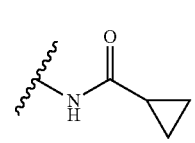 [SMILES: *NC(=O)C1CC1] |

Compounds in Table 4 are named:

60: methyl 6-(cyclopropanecarboxamido)-4-((2,5-dimethyl-4,5-dihydro-2H-pyrazolo[4,3-c]quinolin-6-yl)amino)nicotinate;

61: 4-((2,5-dimethyl-4,5-dihydro-2H-pyrazolo[4,3-c]quinolin-6-yl)amino)-6-(3-isopropyl-2-oxoimidazolidin-1-yl)-N-(methyl-d3)nicotinamide;

62: 4-((2,5-dimethyl-4,5-dihydro-2H-pyrazolo[4,3-c][1,7]naphthyridin-6-yl-4,4-d2)amino)-N-(methyl-d3)-6-(N-methylcyclopropanecarboxamido)pyridazine-3-carboxamide;

63: 4-((2,5-dimethyl-4,5-dihydro-2H-pyrazolo[4,3-c]quinolin-6-yl-4,4-d2)amino)-6-(3-isopropyl-2-oxoimidazolidin-1-yl)-N-(methyl-d3)nicotinamide;

64: 6-(cyclopropanecarboxamido)-4-((2,5-dimethyl-4,5-dihydro-2H-pyrazolo[4,3-c][1,7]naphthyridin-6-yl)amino)-N-(methyl-d3)nicotinamide;

65: 6-(cyclopropanecarboxamido)-4-((2,5-dimethyl-4,5-dihydro-2H-pyrazolo[4,3-c][1,7]naphthyridin-6-yl)amino)-N-(methyl-d3)pyridazine-3-carboxamide;

66: 6-(cyclopropanecarboxamido)-N-(methyl-d3)-4-((2-methyl-5-(methyl-d3)-4,5-dihydro-2H-pyrazolo[4,3-c][1,7]naphthyridin-6-yl)amino)nicotinamide;

67: 6-(cyclopropanecarboxamido)-N-(methyl-d3)-4-((2-methyl-5-(methyl-d3)-4,5-dihydro-2H-pyrazolo[4,3-c][1,7]naphthyridin-6-yl)amino)pyridazine-3-carboxamide;

68: 6-(cyclopropanecarboxamido)-4-((2,5-dimethyl-4,5-dihydropyrazolo[1,5-a]pyrido[3,4-e]pyrazin-6-yl)amino)-N-(methyl-d3)pyridazine-3-carboxamide;
69: (S)-6-(cyclopropanecarboxamido)-N-(methyl-d3)-4-((2,4,5-trimethyl-4,5-dihydro-2H-pyrazolo[4,3-c][1,7]naphthyridin-6-yl)amino)pyridazine-3-carboxamide;
70: (R)-6-(cyclopropanecarboxamido)-N-(methyl-d3)-4-((2,4,5-trimethyl-4,5-dihydro-2H-pyrazolo[4,3-c][1,7]naphthyridin-6-yl)amino)pyridazine-3-carboxamide;
71: 6-(cyclopropanecarboxamido)-4-((2,5-dimethyl-4,5-dihydropyrazolo[1,5-a]pyrido[3,4-e]pyrazin-6-yl)amino)-N-(methyl-d3)nicotinamide;
72: 6-(cyclopropanecarboxamido)-4-((2,5-dimethyl-4,5-dihydro-2H-pyrazolo[4,3-c][1,7]naphthyridin-6-yl-4,4-d2)amino)-N-(methyl-d3)pyridazine-3-carboxamide;
73: 6-(cyclopropanecarboxamido)-4-((2,5-dimethyl-4,5-dihydropyrazolo[1,5-a]pyrido[3,4-e]pyrazin-6-yl-4,4-d2)amino)-N-(methyl-d3)pyridazine-3-carboxamide;
74: 4-((2,5-dimethyl-4,5-dihydro-2H-pyrazolo[4,3-c][1,7]naphthyridin-6-yl-4,4-d2)amino)-N-(methyl-d3)-6-(3-methylureido)pyridazine-3-carboxamide;
75: 4-((2,5-dimethyl-4,5-dihydro-2H-pyrazolo[4,3-c][1,7]naphthyridin-6-yl-4,4-d2)amino)-6-(3,3-dimethylureido)-N-(methyl-d3)pyridazine-3-carboxamide;
76: 6-(cyclopropanecarboxamido)-4-((2,5-dimethyl-4,5-dihydropyrazolo[1,5-a]pyrido[3,4-e]pyrazin-6-yl-4,4-d2)amino)-N-(methyl-d3)nicotinamide;
77: 6-(cyclopropanecarboxamido)-4-((2,5-dimethyl-4,5-dihydro-2H-pyrazolo[4,3-c][1,7]naphthyridin-6-yl-4,4-d2)amino)-N-(methyl-d3)nicotinamide;
78: (R)-N-(methyl-d3)-6-(3-methylureido)-4-((2,4,5-trimethyl-4,5-dihydro-2H-pyrazolo[4,3-c][1,7]naphthyridin-6-yl)amino)pyridazine-3-carboxamide;
79: 4-((2,5-dimethyl-4,5-dihydropyrazolo[1,5-a]pyrido[3,4-e]pyrazin-6-yl)amino)-N-(methyl-d3)-6-(3-methylureido)pyridazine-3-carboxamide;
80: (S)—N-(methyl-d3)-6-(3-methylureido)-4-((2,4,5-trimethyl-4,5-dihydro-2H-pyrazolo[4,3-c][1,7]naphthyridin-6-yl)amino)pyridazine-3-carboxamide;
81: (R)-6-(cyclopropanecarboxamido)-N-(methyl-d3)-4-((2,4,5-trimethyl-4,5-dihydropyrazolo[1,5-a]pyrido[3,4-e]pyrazin-6-yl)amino)pyridazine-3-carboxamide;
82: 6-(cyclopropanecarboxamido)-4-((8-fluoro-2,5-dimethyl-4,5-dihydro-2H-pyrazolo[4,3-c]quinolin-6-yl)amino)-N-(methyl-d3)nicotinamide;
83: 6-(cyclopropanecarboxamido)-4-((8-fluoro-5-methyl-2-(methyl-d3)-4,5-dihydro-2H-pyrazolo[4,3-c]quinolin-6-yl)amino)-N-(methyl-d3)nicotinamide;
84: 6-(cyclopropanecarboxamido)-N-(methyl-d3)-4-((5-methyl-2-(methyl-d3)-4,5-dihydro-2H-pyrazolo[4,3-c][1,6]naphthyridin-6-yl)amino)nicotinamide;
85: 6-(cyclopropanecarboxamido)-N-(methyl-d3)-4-((5-methyl-2-(methyl-d3)-4,5-dihydro-2H-pyrazolo[4,3-c][1,6]naphthyridin-6-yl)amino)pyridazine-3-carboxamide;
86: 6-(cyclopropanecarboxamido)-N-(methyl-d3)-4-((5-methyl-2-(methyl-d3)-4,5-dihydro-2H-pyrazolo[4,3-c][1,7]naphthyridin-6-yl)amino)nicotinamide; and
87: 6-(cyclopropanecarboxamido)-N-(methyl-d3)-4-((5-methyl-2-(methyl-d3)-4,5-dihydro-2H-pyrazolo[4,3-c][1,7]naphthyridin-6-yl)amino)pyridazine-3-carboxamide.

In some embodiments, provided herein is a pharmaceutically acceptable salt of a compound that is described in Table 4.

TABLE 5

| Compound No. | $R^2$ | $R^4$ | Z |
|---|---|---|---|
| 88 | cyclopropanecarbonyl | —CH$_3$ | O |
| 89 | cyclopropanecarbonyl | —CH$_3$ | NCH$_3$ |
| 90 | cyclopropanecarbonyl | —CD$_3$ | NCH$_3$ |

Compounds in Table 5 are named:
88: N-(2-methyl-4-((2-methyl-2,4-dihydrochromeno[4,3-c]pyrazol-6-yl)amino)-3-oxo-2,3-dihydro-1H-pyrazolo[3,4-b]pyridin-6-yl)cyclopropanecarboxamide;
89: N-(4-((2,5-dimethyl-4,5-dihydro-2H-pyrazolo[4,3-c]quinolin-6-yl)amino)-2-methyl-3-oxo-2,3-dihydro-1H-pyrazolo[3,4-b]pyridin-6-yl)cyclopropanecarboxamide; and
90: N-(4-((2,5-dimethyl-4,5-dihydro-2H-pyrazolo[4,3-c]quinolin-6-yl)amino)-2-(methyl-d3)-3-oxo-2,3-dihydro-1H-pyrazolo[3,4-b]pyridin-6-yl)cyclopropanecarboxamide.

In some embodiments, provided herein is a pharmaceutically acceptable salt of a compound that is described in Table 5.

In one aspect, compounds described herein are in the form of pharmaceutically acceptable salts. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic at the concentration or amount used, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties*, Selection and Use, Weinheim/Zürich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviors. Also, because the salt-forming molecule can be in equilibrium with a neutral form, passage through biological membranes can be adjusted.

In some embodiments, pharmaceutically acceptable salts are obtained by reacting a compound of Formula (I) with an acid. In some embodiments, the compound of Formula (I) (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound of Formula (I) is prepared as a chloride salt, sulfate salt, bromide salt, mesylate salt, maleate salt, citrate salt or phosphate salt.

In some embodiments, pharmaceutically acceptable salts are obtained by reacting a compound of Formula (I) with a base. In some embodiments, the compound of Formula (I) is acidic and is reacted with a base. In such situations, an acidic proton of the compound of Formula (I) is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), or pharmaceutically acceptable salts of compounds having the structure of Formula (I), as well as active metabolites of these compounds having the same type of activity.

In some embodiments, sites on the organic radicals (e.g. alkyl groups, aromatic rings) of compounds of Formula (I) are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, sulfur, fluorine chlorine, iodine, phosphorus, such as, for example, $^{2}H$, $^{3}H$, $^{13}C$, $^{14}C$, $^{15}N$, $^{18}O$, $^{17}O$, $^{35}$, $^{18}F$, $^{36}Cl$, $^{123}I$, $^{124}I$, $^{125}I$, $^{131}I$, $^{32}P$ and $^{33}P$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds of Formula (I) possess one or more stereocenters and each stereocenter exists independently in either the R or S configuration. In some embodiments, the compound of Formula (I) exists in the R configuration. In some embodiments, the compound of Formula (I) exists in the S configuration. The compounds presented herein include all diastereomeric, individual enantiomers, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns or the separation of diastereomers by either non-chiral or chiral chromatographic columns or crystallization and recrystallization in a proper solvent or a mixture of solvents. In certain embodiments, compounds of Formula (I) are prepared as their individual stereoisomers by reacting a racemic mixture of the compound with an optically active resolving agent to form a pair of diastereoisomeric compounds/salts, separating the diastereomers and recovering the optically pure individual enantiomers. In some embodiments, resolution of individual enantiomers is carried out using covalent diastereomeric derivatives of the compounds described herein. In another embodiment, diastereomers are separated by separation/resolution techniques based upon differences in solubility. In other embodiments, separation of stereoisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley And Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, N-alkyloxyacyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound of Formula (I) as set forth herein are included within the scope of the claims. In some cases, some of the herein-described compounds is a prodrug for another derivative or active compound.

In some embodiments, any one of the hydroxyl group(s), amino group(s) and/or carboxylic acid group(s) are functionalized in a suitable manner to provide a prodrug moiety. In some embodiments, the prodrug moiety is as described above.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulfhydryl groups. Metabolites of the compounds disclosed herein are optionally identified either by administration of compounds to a host and analysis of tissue samples from the host, or by incubation of compounds with hepatic cells in vitro and analysis of the resulting compounds.

In some instances, heterocyclic rings may exist in tautomeric forms. In such situations, it is understood that the structures of said compounds are illustrated or named in one tautomeric form but could be illustrated or named in the alternative tautomeric form. The alternative tautomeric forms are expressly included in this disclosure, such as, for example, the structures illustrated below. For example, pyridones could exist in the following tautomeric forms:

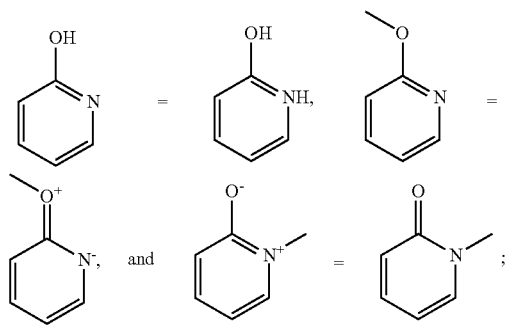

all of which are encapsulated within the group, "substituted pyridines." Similarly, triazolones could exist in the following tautomeric forms, which include zwitterionic forms:

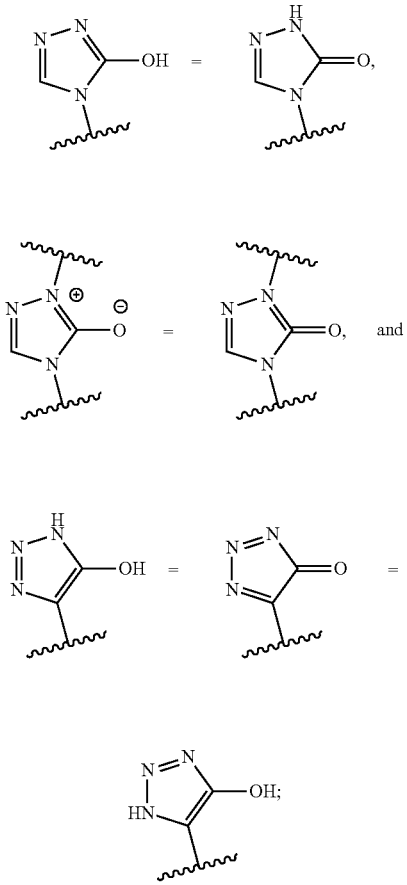

all of which are encapsulated within the group, "substituted 5-membered heteroaryl." Similarly, pyrazoles, triazoles, pyrimidines, and the like are known to tautomerize; for the purpose of this disclosure, all tautomeric forms (including charged and zwitterionic tautomers) are considered within the scope of the present disclosure.

Synthesis of Compounds

Compounds of Formula (I) described herein are synthesized using standard synthetic techniques or using methods known in the art in combination with methods described herein.

Unless otherwise indicated, conventional methods of mass spectroscopy, NMR, HPLC are employed.

Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions.

In some embodiments, compounds described herein are prepared as described in Scheme A.

Scheme A

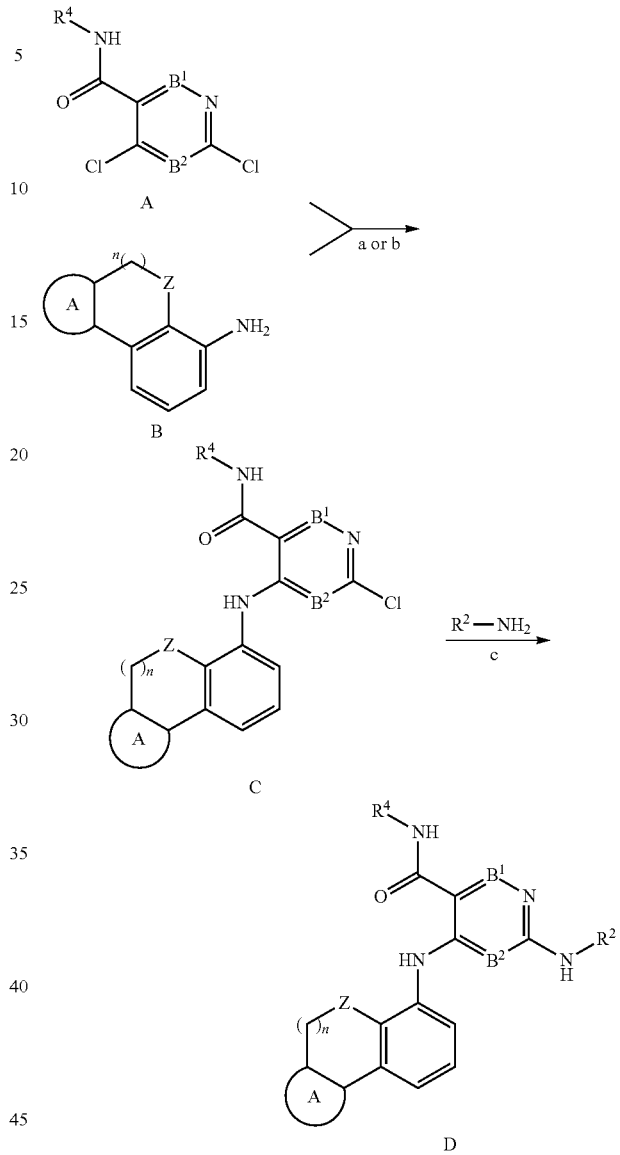

variables are as defined in Formula (I).

In some embodiments, nucleophilic substitution of one chloro group of intermediate A with the free amino group of B affords intermediate C. In some embodiments, for example when intermediate A is a pyridazine compound ($B^1$=N), this substitution can be carried out with a suitable Lewis acid such as $Zn(OAc)_2$. In other embodiments, for example when intermediate B is a pyridine compound ($B^1$=CH), this substitution is carried out by deprotonation of the amino group with a suitable base, such as LDA. In still other embodiments, intermediate C may be accessed by a cross-coupling reaction of intermediates A and B. Cross-coupling reactions may be organometallic cross-couplings such as Suzuki-Miyaura reactions, Buchwald-Hartwig reactions, Heck reactions, Ullman couplings, Chan-Lam couplings, and the like. Finally, in some embodiments, intermediate C is converted to the final compound D (e.g., compound 1) via a cross-coupling reaction. Cross-coupling reactions may be organometallic cross-couplings such as Suzuki-Miyaura reactions, Buchwald-Hartwig reactions, Heck reactions, Ullman couplings, Chan-Lam couplings, and the like.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ ... $C_1$-$C_x$. By way of example only, a group designated as "$C_1$-$C_6$" indicates that there are one to six carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$ alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers to a divalent alkyl radical. Any of the above mentioned monovalent alkyl groups may be an alkylene by abstraction of a second hydrogen atom from the alkyl. In some embodiments, an alkylene is a $C_1$-$C_6$ alkylene. In other embodiments, an alkylene is a $C_1$-$C_4$alkylene. Typical alkylene groups include, but are not limited to, —$CH_2$—, —$CH_2CH_2$—, —$CH_2CH_2CH_2$—, —$CH_2CH_2CH_2CH_2$—, and the like. In some embodiments, an alkylene is —$CH_2$—.

An "alkoxy" group refers to a (alkyl)O— group, where alkyl is as defined herein.

The term "alkylamine" refers to the —N(alkyl)$_x$Hy group, where x is 0 and y is 2, or where x is 1 and y is 1, or where x is 2 and y is 0.

An "hydroxyalkyl" refers to an alkyl in which one hydrogen atom is replaced by a hydroxyl. In some embodiments, a hydroxyalkyl is a $C_1$-$C_4$hydroxyalkyl. Typical hydroxyalkyl groups include, but are not limited to, —$CH_2OH$, —$CH_2CH_2OH$, —$CH_2CH_2CH_2OH$, —$CH_2CH_2CH_2CH_2OH$, and the like.

An "aminoalkyl" refers to an alkyl in which one hydrogen atom is replaced by an amino. In some embodiments, aminoalkyl is a $C_1$-$C_4$aminoalkyl. Typical aminoalkyl groups include, but are not limited to, —$CH_2NH_2$, —$CH_2CH_2NH_2$, —$CH_2CH_2CH_2NH_2$, —$CH_2CH_2CH_2CH_2NH_2$, and the like.

The term "alkenyl" refers to a type of alkyl group in which at least one carbon-carbon double bond is present. In one embodiment, an alkenyl group has the formula —C(R)=$CR^2$, wherein R refers to the remaining portions of the alkenyl group, which may be the same or different. In some embodiments, R is H or an alkyl. In some embodiments, an alkenyl is selected from ethenyl (i.e., vinyl), propenyl (i.e., allyl), butenyl, pentenyl, pentadienyl, and the like. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkenyl group has the formula —C≡C—R, wherein R refers to the remaining portions of the alkynyl group. In some embodiments, R is H or an alkyl. In some embodiments, an alkynyl is selected from ethynyl, propynyl, butynyl, pentynyl, hexynyl, and the like. Non-limiting examples of an alkynyl group include —C≡CH, —C≡$CCH_3$—C≡$CCH_2CH_3$, —$CH_2$C≡CH.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a $C_1$-$C_6$heteroalkyl.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. Carbocycles include aryls and cycloalkyls.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a phenyl, naphthyl, indanyl, indenyl, or tetrahydronaphthyl. In some embodiments, an aryl is a $C_6$-$C_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a $C_3$-$C_6$cycloalkyl. In some embodiments, a cycloalkyl is a $C_3$-$C_4$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoroalkyl is a $C_1$-$C_6$fluoroalkyl.

The term "heterocycle" or "heterocyclic" refers to heteroaromatic rings (also known as heteroaryls) and heterocycloalkyl rings containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1(2H)-onyl, 3,4-dihydroquinolin-2(1H)-onyl, isoindoline-1,3-dithionyl, benzo[d]oxazol-2(3H)-onyl, 1H-benzo[d]imidazol-2(3H)-onyl, benzo[d]thiazol-2(3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (=O) moieties, such as pyrrolidin-2-one. In some embodiments, at least one of the two rings of a bicyclic heterocycle is aromatic. In some embodiments, both rings of a bicyclic heterocycle are aromatic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a $C_1$-$C_9$heteroaryl. In some embodiments, monocyclic heteroaryl is a $C_1$-$C_5$heteroaryl. In some embodiments, monocyclic heteroaryl is a 5-membered or 6-membered heteroaryl. In some embodiments, bicyclic heteroaryl is a $C_6$-$C_9$heteroaryl.

A "heterocycloalkyl" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl is monocyclic or bicyclic. In some embodiments, a heterocycloalkyl is monocyclic and is a 3, 4, 5, 6, 7, or 8-membered ring. In some embodiments, a heterocycloalkyl is monocyclic and is a 3, 4, 5, or 6-membered ring. In some embodiments, a heterocycloalkyl is monocyclic and is a 3 or 4-membered ring. In some embodiments, a heterocycloalkyl contains 0-2 N atoms in the ring. In some embodiments, a heterocycloalkyl contains 0-2 N atoms, 0-2 O atoms and 0-1 S atoms in the ring.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from halogen, —CN, —NH$_2$, —NH(alkyl), —N(alkyl)$_2$, —OH, —CO$_2$H, -CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$(C$_1$-C$_4$alkyl), —C(=O)NH$_2$, —C(=O)NH(C$_1$-C$_4$alkyl), —C(=O)N(C$_1$—C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, -SC$_1$-C$_4$alkyl, —S(=O)C$_1$-C$_4$alkyl, and —S(=O)$_2$C$_1$-C$_4$alkyl. In some embodiments, optional substituents are independently selected from halogen, —CN, —NH$_2$, —OH, —NH(CH$_3$), —N(CH$_3$)$_2$, —CH$_3$, —CH$_2$CH$_3$, —CHF$_2$, —CF$_3$, —OCH$_3$, —OCHF$_2$, and —OCF$_3$. In some embodiments, substituted groups are substituted with one or two of the preceding groups. In some embodiments, an optional substituent on an aliphatic carbon atom (acyclic or cyclic) includes oxo (=O).

In some embodiments, each substituted alkyl, substituted fluoroalkyl, substituted heteroalkyl, substituted carbocycle, and substituted heterocycle is substituted with one or more R$^s$ groups independently selected from the group consisting of deuterium, halogen, C$_1$-C$_6$ alkyl, monocyclic carbocycle, monocyclic heterocycle, —CN, —OR$^{18}$, —CO$_2$R$^{18}$, —C(=O)N(R$^{18}$)$_2$, —N(R$^{18}$)$_2$, —NR$^{18}$C(=O)R$^{19}$, —SR$^{18}$, —S(=O)R$^{19}$, —SO$_2$R$^{19}$, or —SO$_2$N(R$^{18}$)$_2$; each R$^{18}$ is independently selected from hydrogen, C$_1$-C$_6$ alkyl, C$_1$-C$_6$ fluoroalkyl, C$_1$-C$_6$ heteroalkyl, C$_3$-C$_6$ cycloalkyl, C$_2$-C$_6$ heterocycloalkyl, phenyl, benzyl, 5-membered heteroaryl and 6-membered heteroaryl; or two R$^{18}$ groups are taken together with the N atom to which they are attached to form a N-containing heterocycle; each R$^{19}$ is independently selected from C$_1$-C$_6$ alkyl, C$_1$-C$_6$ fluoroalkyl, C$_1$-C$_6$ heteroalkyl, C$_3$-C$_6$ cycloalkyl, C$_2$-C$_6$ heterocycloalkyl, phenyl, benzyl, 5-membered heteroaryl and 6-membered heteroaryl.

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is an inhibitor.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound of Formula (I), or a pharmaceutically acceptable salt thereof, and a co-agent, are both administered to a patient simultaneously in the form of a single entity or dosage. The term "non-fixed combination" means that the active ingredients, e.g. a compound of Formula (I), or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "article of manufacture" and "kit" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development or progression of the disease or condition, relieving the disease or condition, causing regression of the disease or condition, relieving a secondary condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed.

(Lippincott Williams & Wilkins 1999), herein incorporated by reference for such disclosure.

A compound or a pharmaceutical composition of the present disclosure is, in some embodiments, useful for the treatment of a TYK2 mediated disease or disorder. In some embodiments, the pharmaceutical composition is effective at treating a disease or disorder wherein TYK2 is overexpressed or hyperactive. In some embodiments, the pharmaceutical composition is effective at treating a disease or disorder which would benefit from a reduction in TYK2 activity or expression.

In some embodiments, the pharmaceutical composition is useful in the treatment of disease or disorder associated with high levels of cytokines driven by TYK2, such as interferons (e.g. IFN-α, IFN-β, IFN-κ, IFN-δ, IFN-ε, IFN-τ, IFN-co, and IFN-ζ (also known as limitin), and interleukins (e.g. IL-4, IL-6, IL-10, IL-11, IL-12, IL-13, IL-22, IL-23, IL-27, IL-31, oncostatin M, ciliary neurotrophic factor, cardiotrophin 1, cardiotrophin-like cytokine, and LIF. In some embodiments, the disease or disorder is an inflammatory disease or disorder, an autoimmune disease or disorder, a respiratory disease or disorder, type 1 diabetes, and interferonopathies such as Alcardi-Goutieres syndrome, or combinations thereof.

In some embodiments, the pharmaceutical composition is useful in the treatment of an inflammatory disease or disorder. In some embodiments, the inflammatory disease or disorder is an auto-inflammatory disease or disorder, a host-mediated inflammatory disease or disorder, an injury-related inflammatory disease or disorder, an infection-related inflammatory disease or disorder, a hyperproliferative (e.g., cancer, fibrosis) mediated inflammatory disease or disorder. In some embodiments, the inflammatory disease or disorder or infection-related inflammatory disease or disorder is a respiratory disease or disorder. In some embodiments, the respiratory disease or disorder is associated with a viral in microbial infection. In some embodiments, the respiratory disease or disorder is a problematic immune response to a viral or microbial infection. In some embodiments, the respiratory disease or disorder is associated with a coronavirus such as MERS-CoV, SARS-CoV-1, or SARS-CoV-2. In some embodiments, the pharmaceutical composition is effective in decreasing symptoms associated with COVID-19, or an immune response associated therewith.

In some embodiments, the pharmaceutical composition is useful in the treatment of an autoimmune disease or disorders. In some embodiments, an autoimmune disease or disorder is rheumatoid arthritis, multiple sclerosis, psoriasis, psoriatic arthritis, lupus, systemic lupus erythematosus, Sjögren's syndrome, ankylosing spondylitis, vitiligo, atopic dermatitis, scleroderma, alopecia, hidradenitis suppurativa, uveitis, dry eye, intestinal bowel disease, Crohn's disease, ulcerative colitis, celiac disease, Bechet's disease, type 1 diabetes, systemic sclerosis, and idiopathic pulmonary fibrosis. In some embodiments, an autoimmune disease or disorder is lupus or systemic lupus erythematosus. In some embodiments, an autoimmune disease or disorder is psoriasis. In some embodiments, an autoimmune disease or disorder is irritable bowel disease (IBS) or irritable bowel disease with diarrhea (IBS-D). In some embodiments, an autoimmune disease or disorder is dry eye or uveitis. In some embodiments, an autoimmune disease or disorder is Crohn's disease. In some embodiments, an autoimmune disease or disorder is atopic dermatitis.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, topical application such as creams or ointments. Additional examples of local administration of the present compounds include eye drops, ocular creams, gels or hydrogels, implants, transdermal patches, or drug depots. In some embodiments, a pharmaceutical composition is administered orally (e.g., in a liquid formulation, tablet, capsule, nebulized liquid, aerosolized liquid, dry powder spray).

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions may also be formulated as a depot preparation. Such long acting formulations may be administered by implantation (for example subcutaneously). Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

Pharmaceutical compositions may be administered topically, that is by non-systemic administration. This includes the application of a compound of the present invention externally to the epidermis or the buccal cavity and the installation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compound described herein, or a pharmaceutically acceptable salt, tautomer, or solvate thereof, are used in the preparation of medicaments for the treatment of diseases or conditions in a mammal that would benefit from modulation of TYK2 activity. Methods for treating any of the diseases or conditions described herein in a mammal in need of such treatment, involves administration of pharmaceutical compositions that include at least one compound described herein, or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-2000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, described herein are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

Combination Treatments

In certain instances, it is appropriate to administer at least one compound described herein, or a pharmaceutically acceptable salt thereof, in combination with one or more other therapeutic agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may simply be additive of the two therapeutic agents or the patient may experience a synergistic benefit.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject.

EXAMPLES

As used above, and throughout the description of the invention, the following abbreviations, unless otherwise indicated, shall be understood to have the following meanings:

Abbreviations

ACN acetonitrile
CAN ceric ammonium nitrate
DCM dichloromethane
DIBAL diisobutylaluminum hydride
DIPEA N,N-diisopropylethylamine
DMA dimethylacetamide
DMF N,N-dimethylformamide
DMSO dimethylsulfoxide
EtOAc ethyl acetate
EGTA ethylene glycol-bis(O-aminoethyl ether)-N,N,N',N'-tetraacetic acid
ES electrospray
FBS fetal bovine serum
GST glutathione S-transferase
HEK human embryonic kidney
HEPES 4-(2-hydroxyethyl)-1-piperazineethanesulfonic acid
HMDS bis(trimethylsilyl)amide
HPLC high pressure liquid chromatography
HTRF homogenous time resolved fluorescence
$IC_{50}$ half maximal inhibitory concentration
IFN interferon
IL interleukin
IPA isopropyl alcohol
JAK Janus kinase
LCMS liquid chromatography-mass spectrometry
MDI metered drug inhalant
MW microwave
NMR nuclear magnetic resonance
SEAP secreted embryonic alkaline phosphatase
STAT signal transducer and activator of transcription
T3P propanephosphonic acid anhydride
TBAF tetra-n-butylammonium fluoride
TBDMS tert-butyldimethylsilyl
TBDPS tert-butyldiphenylsilyl
TEA triethylamine
TFA trifluoroacetic acid
THF tetrahydrofuran
TLC thin-layer chromatography
TYK non-receptor tyrosine-protein kinase The following examples are provided for illustrative purposes only and not to limit the scope of the claims provided herein.

Synthesis of Compounds

Example 1: Preparation of 2-methyl-2,4-dihydro-chromeno[4,3-c]pyrazol-6-amine (I-1)

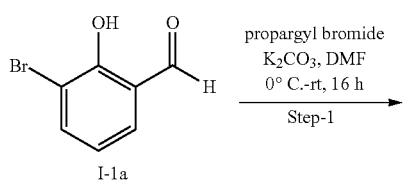

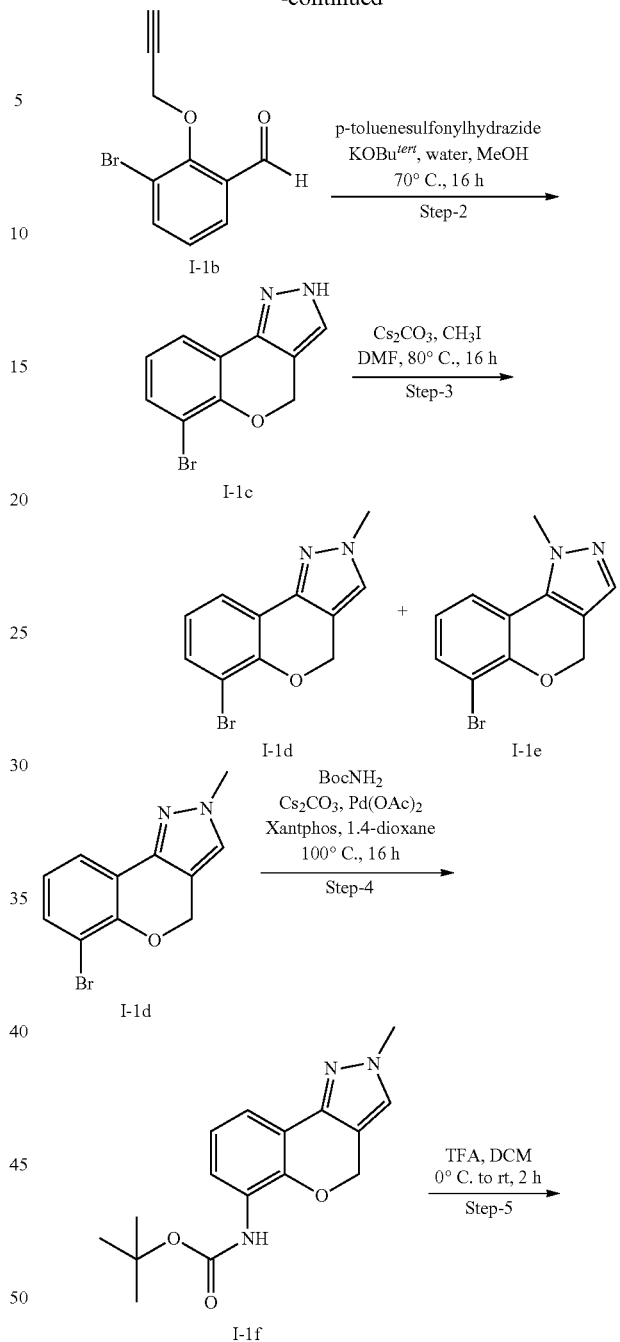

Step-1: 3-bromo-2-(prop-2-yn-1-yloxy)benzaldehyde (I-1b): To a stirred solution of 3-bromo-2-hydroxybenzaldehyde I-1a (10.0 g, 49.7 mmol) in DMF (50.0 mL) was added anhydrous $K_2CO_3$ (20.6 g, 149 mmol) at 0° C. and stirred for 10 min. To this was then added propargyl bromide (7.54 mL, 99.5 mmol) and the reaction mixture was allowed to stir at room temperature for 16 h. The progress of the reaction was monitored by TLC. After complete consumption of starting material, water (250 mL) was added to it and extraction was carried out using EtOAc (100 mL×3). The combined organic extracts were washed with water (100 mL×3), brine (100 mL), dried over anhydrous $Na_2SO_4$, filtered and concentrated under reduced pressure to afford 3-bromo-2-(prop-2-yn-1-yloxy)benzaldehyde I-1b (11.3 g) as a yellow solid. LCMS (ES) m/z: 239.1 [M+H]⁺.

Step-2: 6-bromo-2,4-dihydrochromeno[4,3-c]pyrazole (I-1c): To a stirred solution of I-1b (11.3 g, 47.3 mmol) in MeOH (25.0 mL) and water (25.0 mL) was added KOtBu (8.03 g, 70.9 mmol) and p-toluenesulfonylhydrazide (17.6 g, 93.8 mmol) at room temperature. The reaction mixture was then stirred at 70° C. for 16 h. The progress of the reaction was monitored by TLC. After complete consumption of starting material, the reaction mixture was cooled to room temperature and water (250 mL) was added to it. Extraction was carried out using EtOAc (100 mL×3); the combined organic extracts were washed with brine (100 mL×2), dried over anhydrous $Na_2SO_4$, filtered and concentrated under reduced pressure. The resulting crude was purified by Combi-Flash (using gradient elution of 0-20% EtOAc in hexane) to afford 6-bromo-2,4-dihydrochromeno[4,3-c]pyrazole I-1c (10 g) as an off-white solid. LCMS (ES) m/z; 251.0 [M+H]⁺.

Step-3: 6-bromo-2-methyl-2,4-dihydrochromeno[4,3-c]pyrazole (I-1d) and 6-bromo-1-methyl-1,4-dihydrochromeno[4,3-c]pyrazole (I-1e): To a solution of I-1c (4.00 g, 15.9 mmol) in DMF (60.0 mL) was added $Cs_2CO_3$ (10.4 g, 31.9 mmol) under nitrogen atmosphere and stirred for 30 min. To this was then added MeI (1.20 mL, 19.1 mmol) and the reaction mixture was stirred at 80° C. for 16 h in a sealed tube. The progress of the reaction was monitored by TLC. After completion, it was cooled to room temperature and water (50 mL) was added to it. Extraction was carried out using EtOAc (3×50 mL); the combined organic extracts were washed with water (50 mL×3), brine (50 mL), dried over anhydrous $Na_2SO_4$, filtered and concentrated under reduced pressure. The resulting crude was purified by Combi-Flash (using gradient elution of 0-20% EtOAc in hexane) to afford 6-bromo-2-methyl-2,4-dihydrochromeno [4,3-c]pyrazole I-1d (3.4 g) as an off-white solid {LCMS (ES) m/z; 265.0 [M+H]⁺. ¹H NMR (400 MHz, DMSO-$d_6$) δ 7.61 (s, 1H); 7.58 (d, J=7.2 Hz, 1H); 7.46 (d, J=7.6 Hz, 1H); 6.93 (t, J=7.6 Hz, 1H); 5.36 (s, 2H); 3.89 (s, 3H)} and 6-bromo-1-methyl-1,4-dihydrochromeno[4,3-c]pyrazole 1-1e (0.8 g) as an off-white solid {LCMS (ES) m/z; 265.0 [M+H]⁺. ¹H NMR (400 MHz, DMSO-$d_6$) δ 7.72 (d, J=8.0 Hz, 1H); 7.55 (d, J=8.0 Hz, 1H); 7.34 (s, 1H); 6.99 (t, J=8.0 Hz, 1H); 5.30 (s, 2H); 3.87 (s, 3H)}.

Step-4: tert-butyl (2-methyl-2,4-dihydrochromeno[4,3-c]pyrazol-6-yl)carbamate (I-1f): Argon gas was purged through a stirred suspension of I-1d (3.40 g, 12.8 mmol), tert-butyl carbamate (2.25 g, 19.2 mmol) and $Cs_2CO_3$ (8.36 g, 25.6 mmol) in 1,4-dioxane (20.00 mL) for 15 min. To this was then added [5-(diphenylphosphanyl)-9,9-dimethyl-9H-xanthen-4-yl]diphenylphosphane (1.48 g, 2.56 mmol) and $Pd(OAc)_2$ (576 mg, 2.56 mmol). The reaction mixture was then stirred at 100° C. for 16 h in a sealed tube. It was then cooled to room temperature, filtered through Celite bed and washed with EtOAc (50 mL×2). The combined filtrate was concentrated under reduced pressure and the residue was purified by Combi-Flash (using gradient elution of 0-50% EtOAc in hexane) to afford tert-butyl (2-methyl-2,4-dihydrochromeno[4,3-c]pyrazol-6-yl)carbamate I-1f (2.30 g) as a pale yellow solid. LCMS (ES) m/z; 301.9 [M+H]⁺.

Step-5: 2-methyl-2,4-dihydrochromeno[4,3-c]pyrazol-6-amine (I-1): To a stirred solution of I-1f (2.30 g, 7.63 mmol) in DCM (40.0 mL) was added trifluoroacetic acid (10.0 mL) at 0° C. under nitrogen atmosphere and the reaction mixture was allowed to warm to room temperature over 2 h. The progress of the reaction was monitored by TLC. After completion, volatiles were removed under reduced pressure and saturated $NaHCO_3$ solution (50 mL) was added to the residue. Extraction was carried out using EtOAc (3×30 mL); the combined organic extracts were washed with water (30 mL), brine (30 mL), dried over anhydrous $Na_2SO_4$, filtered and evaporated under reduced pressure to afford 2-methyl-2,4-dihydrochromeno[4,3-c]pyrazol-6-amine I-1 (1.20 g) as a pale yellow solid LCMS (ES) m/z; 202.1 [M+H]⁺. ¹H NMR (400 MHz, DMSO-$d_6$) δ 7.53 (s, 1H); 6.81 (d, J=7.2 Hz, 1H); 6.70 (t, J=7.2 Hz, 1H); 6.57 (d, J=7.6 Hz, 1H); 5.19 (s, 2H); 4.75 (br s, 2H); 3.86 (s, 3H).

Example 2: Preparation of 1-methyl-1,4-dihydrochromeno[4,3-c]pyrazol-6-amine (I-2)

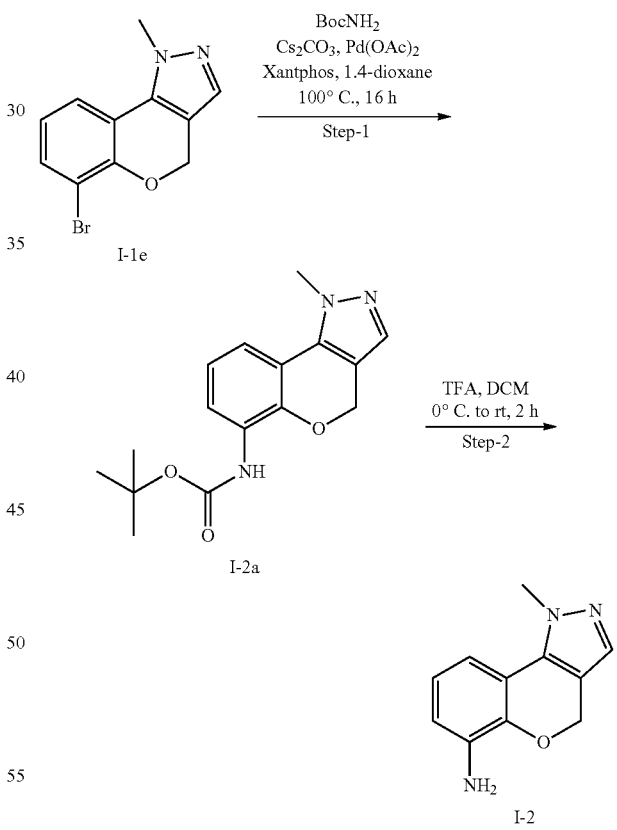

Step-1: tert-butyl (1-methyl-1,4-dihydrochromeno[4,3-c]pyrazol-6-yl)carbamate (I-2a): I-2a (0.8 g) was synthesized by following experimental procedure described for the synthesis of I-1 (step-4) using I-1e (1.4 g, 5.28 mmol) as the starting material. LCMS (ES) m/z; 302.1 [M+H]⁺.

Step-2: 1-methyl-1,4-dihydrochromeno[4,3-c]pyrazol-6-amine (1-2): 1-2 (0.4 g) was synthesized by following experimental procedure described for the synthesis of I-1 using I-2a (0.8 g, 2.65 mmol) as the starting material. LCMS (ES) m/z; 201.9 [M+H]⁺. ¹H NMR (400 MHz, DMSO-d₆) δ 7.31 (s, 1H); 6.91 (dd, J₁=1.6 Hz, J₂=7.6 Hz, 1H); 6.81 (t, J=8.0 Hz, 1H); 6.67 (dd, J₁=1.6 Hz, J₂=8.0 Hz, 1H); 5.15 (s, 2H); 4.86 (br s, 2H); 4.04 (s, 3H).

Example 3: Preparation of 2-(oxetan-3-yl)-2,4-dihydrochromeno[4,3-c]pyrazol-6-amine (I-3)

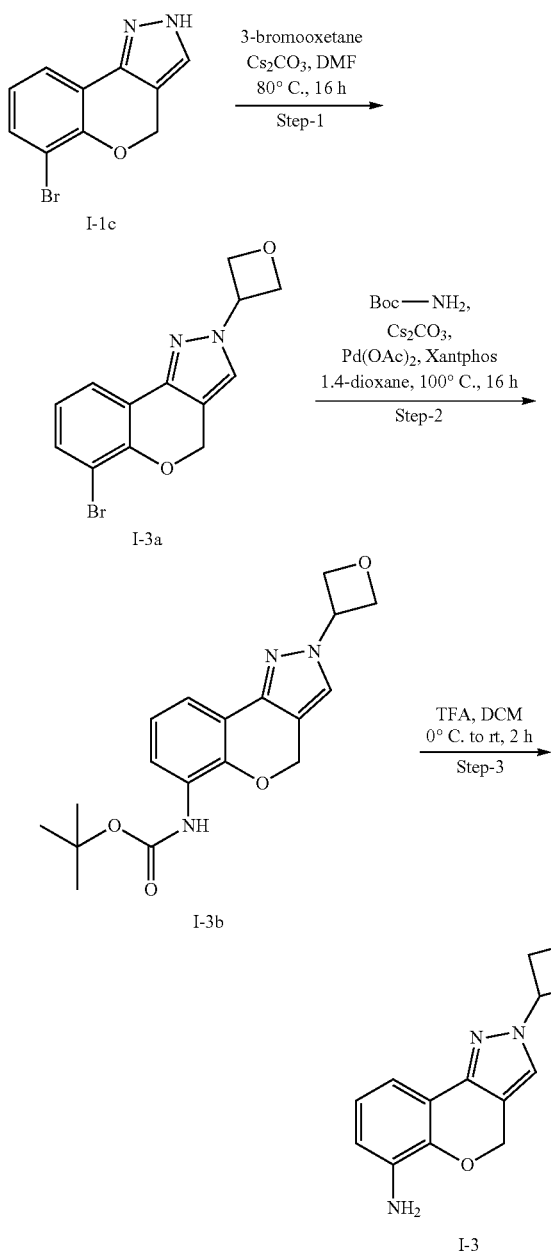

Step-1: 6-bromo-2-(oxetan-3-yl)-2,4-dihydrochromeno[4,3-c]pyrazole (I-3a): To a stirred solution of I-1c (2.20 g, 8.76 mmol) in DMF (20.0 mL) was added Cs₂CO₃ (5.71 g, 17.5 mmol) and 3-bromooxetane (2.40 g, 17.5 mmol) at room temperature under nitrogen atmosphere. The resulting mixture was then stirred at 80° C. for 16 h in a sealed tube. The progress of the reaction was monitored by TLC. After complete consumption of starting material, it was cooled to room temperature and water (50 mL) was added to it. Extraction was carried out using EtOAc (3×50 mL); the combined organic extracts were washed with water (50 mL×3), brine (50 mL), dried over anhydrous Na₂SO₄, filtered and concentrated under reduced pressure. The resultant crude was purified by Combi-Flash (using gradient elution of 0-20% EtOAc in hexane) to afford desired compound 6-bromo-2-(oxetan-3-yl)-2,4-dihydrochromeno[4,3-c]pyrazole I-3a (1.9 g) as an off-white solid. LCMS (ES) m/z; 306.9 [M+H]⁺.

Step-2: tert-butyl (2-(oxetan-3-yl)-2,4-dihydrochromeno[4,3-c]pyrazol-6-yl)carbamate (I-3b): I-3b (0.92 g) was synthesized by following procedure as described for the synthesis of I-1 (step-4) using I-3a (1.7 g, 5.53 mmol) as the starting material. LCMS (ES) m/z; 344.0 [M+H]⁺.

Step-3: 2-(oxetan-3-yl)-2,4-dihydrochromeno[4,3-c]pyrazol-6-amine (I-3): I-3 (0.55 g) was synthesized by following procedure as described for the synthesis of I-1 (step-5) using I-3b (0.92 g, 2.68 mmol) as the starting material. LCMS (ES) m/z; 244.2 [M+H]⁺. ¹H NMR (400 MHz, DMSO-d₆) δ 7.72 (s, 1H); 6.90 (dd, J₁=1.6 Hz, J₂=8.0 Hz, 1H); 6.87 (t, J=8.0 Hz, 1H); 6.70 (dd, J₁=1.6 Hz, J₂=8.0 Hz, 1H); 5.58 (pentet, J=7.2 Hz, 1H); 5.18 (s, 2H); 4.90 (d, J=7.2 Hz, 4H); 4.85 (br s, 2H).

Example 4: Preparation of 2,4-dimethyl-2,4-dihydrochromeno[4,3-c]pyrazol-6-amine (I-4)

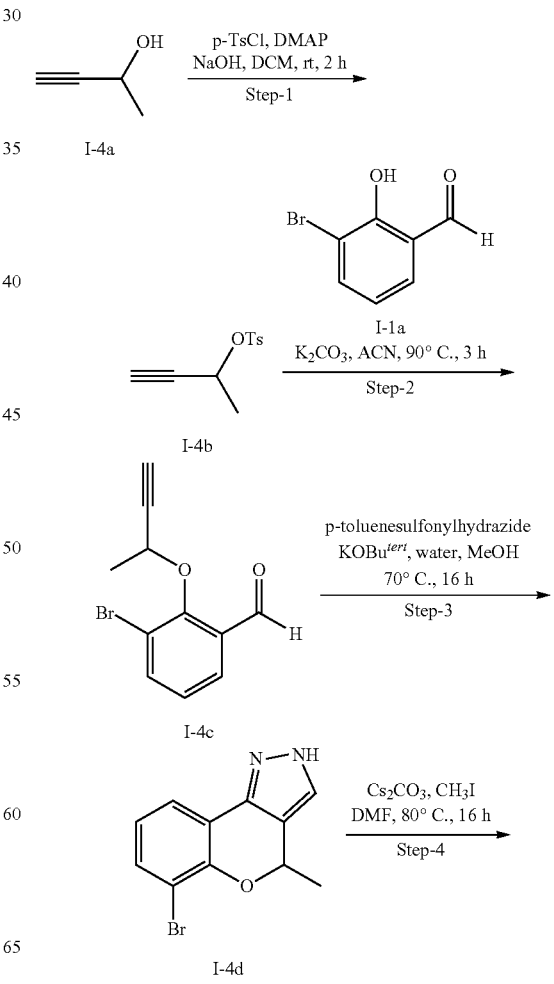

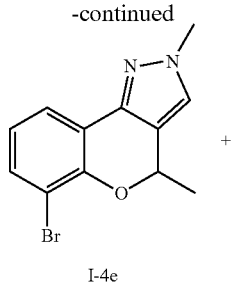

I-4e

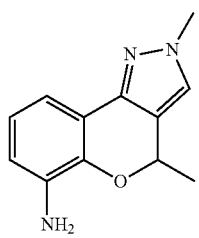

I-4

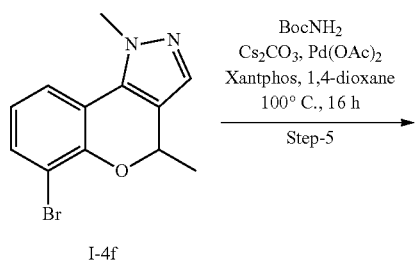

I-4f

BocNH₂
Cs₂CO₃, Pd(OAc)₂
Xantphos, 1,4-dioxane
100° C., 16 h
Step-5

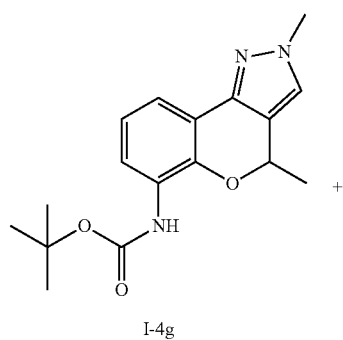

I-4g

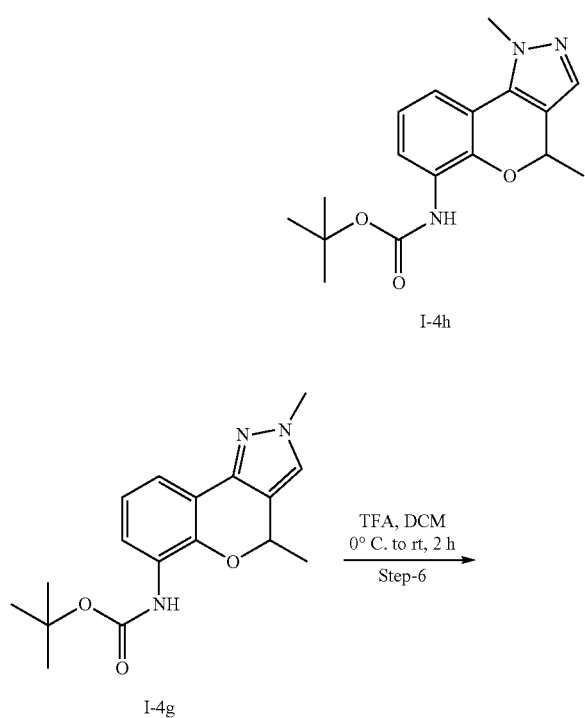

I-4g

TFA, DCM
0° C. to rt, 2 h
Step-6

Step-1: but-3-yn-2-yl 4-methylbenzenesulfonate (I-4b): To a solution of N,N-dimethylpyridin-4-amine (261 mg, 0.03 eq., 2.14 mmol) in DCM (50 mL) were successively added aqueous but-3-yn-2-ol (5.59 mL, 71.3 mmol), aqueous sodium hydroxide (12.5 mL) and 4-methylbenzene-1-sulfonyl chloride (13.6 g, 71.3 mmol) at 0° C. and then the mixture was stirred at room temperature for 2 h. After completion, water (100 mL) was added to it and extraction was carried out using DCM (50 mL×3). The combined organic extracts were washed with brine (50 mL), dried over anhydrous Na₂SO₄, filtered and concentrated under reduced pressure. The residue was purified by Combi-Flash (using gradient elution of 0-10% EtOAc in hexane) to afford desired compound but-3-yn-2-yl 4-methylbenzene-1-sulfonate I-4b (7.5 g) as a colorless oil. ¹H NMR (400 MHz, DMSO-d₆) δ 7.82 (d, J=8.4 Hz, 2H); 7.33 (d, J=8.4 Hz, 2H); 5.18-5.15 (m, 1H); 2.44 (s, 3H); 3.41 (s, 1H); 1.58 (s, 3H).

Step-2: 3-bromo-2-(but-3-yn-2-yloxy)benzaldehyde (I-4c): To a stirred solution of I-1a (5.0 g, 24.9 mmol) in ACN (30 mL) was added anhydrous K₂CO₃ (5.16 g, 37.3 mmol) and I-4b (7.25 g, 36.1 mmol) at room temperature. The reaction mixture was then stirred at 90° C. for 3 h. After completion (as indicated by TLC), volatiles were removed under reduced pressure and water (100 mL) was added to the residue. Extraction was carried out using EtOAc (3×50 mL); the combined organic extracts were washed with water (50 mL), brine (30 mL), dried over anhydrous Na₂SO₄, filtered and evaporated under reduced pressure. The residue was purified by Combi-Flash (using gradient elution of 0-10% EtOAc in hexane) to afford desired compound 3-bromo-2-(but-3-yn-2-yloxy)benzaldehyde I-4c (4.00 g, 15.8 mmol) as a colorless oil. LCMS (ES) m/z; 253.0 [M+H]⁺.

Step-3: 6-bromo-4-methyl-2,4-dihydrochromeno[4,3-c]pyrazole (I-4d): I-4d (2.62 g) was synthesized by following procedure as described for the synthesis of I-1 (step-2) using I-4c (2.5 g, 9.88 mmol) as the starting material. LCMS (ES) m/z; 264.8 [M+H]⁺.

Step-4: 6-bromo-2,4-dimethyl-2,4-dihydrochromeno[4,3-c]pyrazole (I-14e) and 6-bromo-1,4-dimethyl-1,4-dihydrochromeno[4,3-c]pyrazole (I-4f): A mixture of I-4e and I-4f (1.1 g) was synthesized by following procedure as described for the synthesis of I-1 (step-3) using I-4d (2.62 g, 9.88 mmol) as the starting material. LCMS (ES) m/z; 279.0 [M+H]⁺.

Step-5: tert-butyl (2,4-dimethyl-2,4-dihydrochromeno[4,3-c]pyrazol-6-yl)carbamate (I-4g) and tert-butyl (1,4-dimethyl-1,4-dihydrochromeno[4,3-c]pyrazol-6-yl)carbamate (I-4h): I-4g (0.42 g) and I-4h (0.28 g) were synthesized by following procedure as described for the synthesis of I-1 (step-4) using a mixture of I-4e and I-4f (1.1 g, 3.94 mmol) as the starting material. LCMS (ES) m/z; 316.2 [M+H]⁺.

Step-6: 2,4-dimethyl-2,4-dihydrochromeno[4,3-c]pyrazol-6-amine (I-4): I-4 (0.21 g) was synthesized by following procedure as described for the synthesis of I-1 (step-5) using I-4g (0.42 g, 1.33 mmol) as the starting material. LCMS (ES) m/z; 216.1 [M+H]+. 1H NMR (400 MHz, DMSO-$d_6$) δ 7.56 (s, 1H); 6.82 (dd, $J_1$=1.2 Hz, $J_2$=7.6 Hz, 1H); 6.69 (t, J=7.6 Hz, 1H); 6.57 (dd, $J_1$=1.2 Hz, $J_2$=7.6 Hz, 1H); 5.34 (q, J=6.4 Hz, 1H); 4.72 (s, 2H); 3.89 (s, 3H); 1.57 (d, J=6.4 Hz, 3H).
Example 5: Preparation of 2,5-dimethyl-4,5-dihydro-2H-pyrazolo[4,3-c]quinolin-6-amine (I-5)
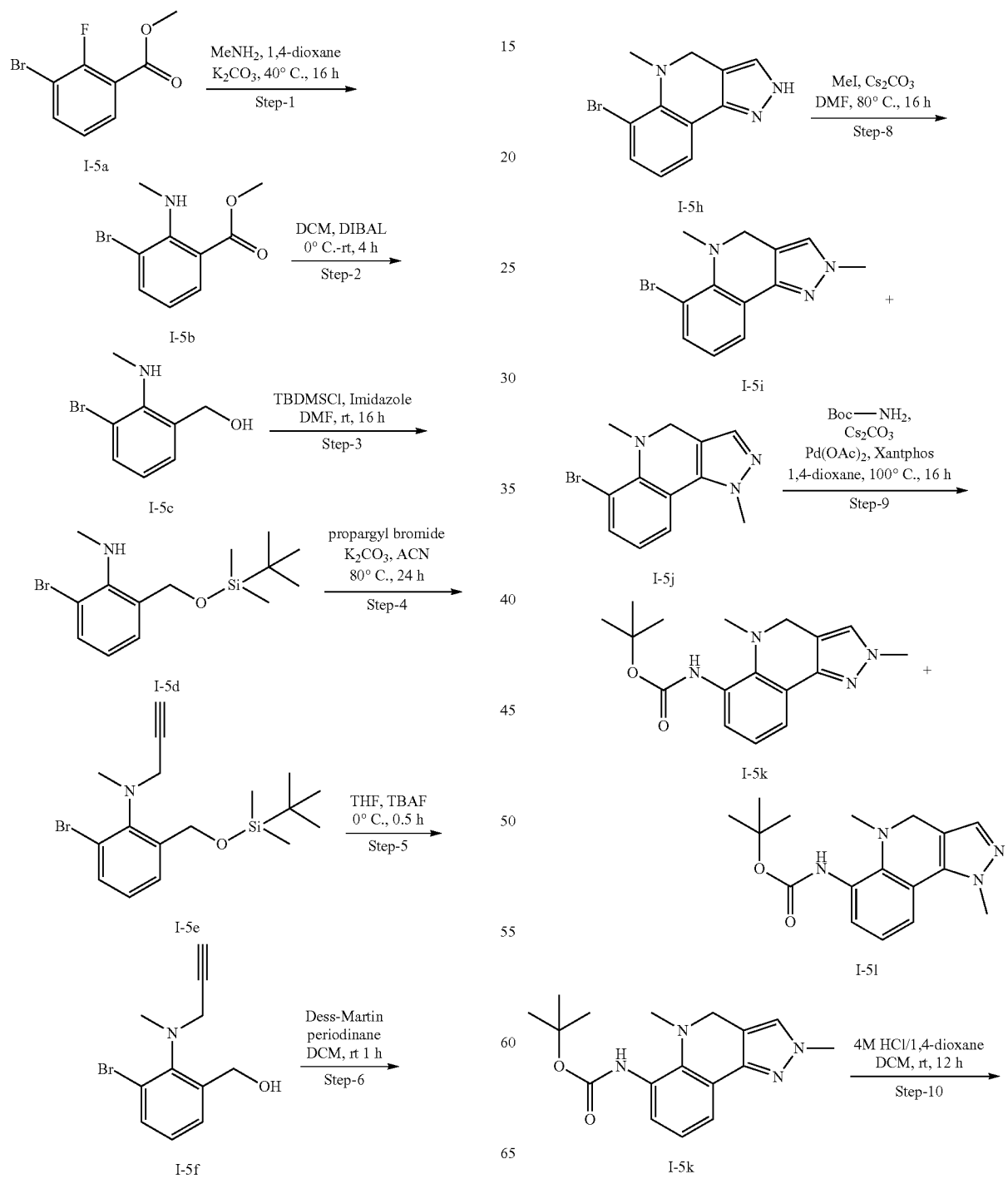

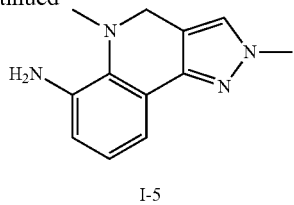

I-5

Step-1: Methyl 3-bromo-2-(methylamino)benzoate (I-5b): To a stirred solution of methyl 3-bromo-2-fluorobenzoate I-5a (5.0 g, 21.5 mmol) in 1,4-dioxane (20 mL) was added potassium carbonate (5.93 g, 42.9 mmol) and a solution of 2M MeNH$_2$ in THF (21.5 mL, 42.9 mmol) at room temperature. The reaction mixture was then stirred at 40° C. in a sealed tube for 16 h, while monitoring progress by LCMS. After completion, volatiles were removed under reduced pressure and the residue was partitioned between DCM (100 mL) and water (50 mL). The organic layer was separated and washed with brine (50 mL), dried over anhydrous Na$_2$SO$_4$, filtered and concentrated under reduced pressure to provide desired compound methyl 3-bromo-2-(methylamino) benzoate I-5b (5.0 g) as a yellow oil. LCMS (ES) m/z: 244.0 [M+H]+; 246.0.

Step-2: (3-bromo-2-(methylamino)phenyl)methanol (I-5c): To a stirred solution of I-5b (9.50 g, 38.9 mmol) in anhydrous DCM (100 mL) was added a 1M solution of DIBAL-H (117 mL, 117 mmol) drop wise at 0° C. The reaction mixture was then allowed to warm to room temperature over 4 h, while monitoring reaction progress by TLC. After completion, it was cooled to 0° C. and quenched slowly with addition of 10% aqueous solution of citric acid (30 mL). Extraction was carried out using DCM (100 mL×2); the combined organic extracts were washed with brine (100 mL), dried over anhydrous Na$_2$SO$_4$, filtered and concentrated under reduced pressure. The resulting crude was purified by Combi-Flash (using gradient elution of 0-60% EtOAc in hexane) to afford desired compound (3-bromo-2-(methylamino)phenyl)methanol I-5c (6.5 g) as a colorless oil. LCMS (ES) m/z; 216.0 [M+H]+, 217.8.

Step-3: 2-bromo-6-(((tert-butyldimethylsilyl)oxy)methyl)-N-methylaniline (I-5d): To a stirred solution of I-5c (6.50 g, 30.1 mmol) in anhydrous DMF (60 mL) was added 1H-imidazole (3.07 g, 45.1 mmol) and TBDMSCl (5.67 g, 37.6 mmol) at room temperature. The reaction mixture was then stirred at room temperature for 16 h. Saturated NaHCO$_3$ solution (50 mL) was added to it and extraction was carried out using diethyl ether (70 mL×3). The combined organic extracts were washed with water (50 mL×3), brine (50 mL), dried over anhydrous MgSO$_4$, filtered and concentrated under reduced pressure. The residue was purified by Combi-Flash (using gradient elution of 0-50% EtOAc in hexane) to afford desired compound 2-bromo-6-(((tert-butyldimethylsilyl)oxy)methyl)-N-methylaniline I-5d (6.5 g) as a pale yellow oil. $^1$H NMR (400 MHz, CDCl$_3$) δ 7.41 (d, J=8.0 Hz, 1H); 7.30 (d, J=8.0 Hz, 1H); 6.82 (t, J=8.0 Hz, 1H); 4.74 (s, 2H); 3.95 (s, 1H); 2.82 (s, 3H); 0.92 (s, 9H); 0.08 (s, 6H).

Step-4: 2-bromo-6-(((tert-butyldimethylsilyl)oxy)methyl)-N-methyl-N-(prop-2-yn-1-yl)aniline (I-5e): To a stirred solution of I-5d (6.50 g, 19.7 mmol) in ACN (65 mL) was added anhydrous K$_2$CO$_3$ (8.16 g, 59.0 mmol) and propargyl bromide (4.47 mL, 59.0 mmol) at room temperature. The reaction mixture was then stirred at 80° C. for 24 h, while monitoring reaction progress by TLC. After completion, it was cooled to room temperature, the base was filtered off through Celite and washed with ACN (10 mL×2). The filtrate was concentrated under reduced pressure and the residue was diluted with EtOAc (100 mL). The organic layer was washed with water (50 mL), brine (50 mL), dried over anhydrous Na$_2$SO$_4$, filtered and concentrated under reduced pressure. The residue was purified by Combi-Flash (using gradient elution of 0-50% EtOAc in hexane) to afford desired compound 2-bromo-6-{[(tert-butyldimethylsilyl)oxy]methyl}-N-methyl-N-(prop-2-yn-1-yl)aniline I-5e (7.0 g) as a brown solid. $^1$H NMR (400 MHz, CDCl$_3$) δ 7.50 (d, J=7.6 Hz, 1H); 7.43 (d, J=8.0 Hz, 1H); 7.09 (t, J=8.0 Hz, 1H); 4.95-4.77 (m, 2H); 4.00-3.82 (m, 2H); 2.90 (s, 3H); 2.19 (t, J=2.4 Hz, 1H); 0.92 (s, 9H); 0.08 (s, 6H).

Step-5: (3-bromo-2-(methyl(prop-2-yn-1-yl)amino)phenyl)methanol (I-5f): 1M solution of TBAF in THF (22.8 mL, 22.8 mmol) was added to a stirred solution of I-5e (7.00 g, 19.0 mmol) in THF (70 mL) at 0° C. and the reaction mixture was stirred for 30 min. After complete consumption of starting material (as indicated by TLC), saturated NH$_4$Cl solution (50 mL) was added to it and extraction was carried out using EtOAc (70 mL×2). The combined organic extracts were washed with brine (70 mL), dried over MgSO$_4$, filtered and concentrated under reduced pressure. The residue was purified by Combi-Flash (using gradient elution of 0-100% EtOAc in hexane) to afford desired compound (3-bromo-2-[methyl(prop-2-yn-1-yl)amino]phenyl)methanol I-5f (4.5 g) as a colorless oil. LCMS (ES) m/z; 254.0 [M+H]+, 256.0.

Step-6: 3-bromo-2-(methyl(prop-2-yn-1-yl)amino)benzaldehyde (I-5g): To a stirred solution of I-5f (4.50 g, 17.7 mmol) in DCM (50.0 mL) was added DMP (11.3 g, 26.6 mmol) at 0° C. and the reaction mixture was allowed to warm to room temperature over 1 h. The reaction progress was monitored by LCMS. After completion, it was filtered through Celite bed and washed with DCM (20 mL×2). The resulting filtrate was washed with saturated NaHCO$_3$ solution (30 mL), water (30 mL), brined (30 mL), dried over anhydrous Na$_2$SO$_4$, filtered and concentrated under reduced pressure. The residue was purified by Combi-Flash (using gradient elution of 0-50% EtOAc in hexane) to afford desired compound 3-bromo-2-[methyl(prop-2-yn-1-yl)amino]benzaldehyde I-5g (3.60 g) as a yellow oil. LCMS (ES) m/z; 252.0 [M+H]+, 254.0

Step-7: 6-bromo-5-methyl-4,5-dihydro-2H-pyrazolo[4,3-c]quinolone (I-5h): To a stirred solution of I-5g (3.60 g, 14.3 mmol) in MeOH (20.0 mL) and water (20.0 mL) was added KOtBu (2.75 g, 24.3 mmol) and p-toluenesulfonylhydrazide (3.99 g, 21.4 mmol) sequentially at room temperature. The reaction mixture was stirred at 70° C. for 16 h, while monitoring reaction progress by TLC. After complete consumption of starting material, it was cooled to room temperature and MeOH was removed under reduced pressure. Water (30 mL) was added to the residue and extraction was carried out using EtOAc (3×50 mL). The combined organic extracts were washed with brine (50 mL), dried over anhydrous Na$_2$SO$_4$, filtered and concentrated under reduced pressure. The residue was then stirred in pentane (30 mL), filtered and dried to afford desired compound 6-bromo-5-methyl-4,5-dihydro-2H-pyrazolo[4,3-c]quinolone I-5h (3.5 g) as an off-white solid. LCMS (ES) m/z; 264.0 [M+H]+, 266.0.

Step-8: 6-bromo-2,5-dimethyl-4,5-dihydro-2H-pyrazolo[4,3-c]quinolone (I-5i) & 6-bromo-1,5-dimethyl-4,5-dihydro-1H-pyrazolo[4,3-c]quinolone (I-5j): To a stirred solution of I-5h (5.00 g, 18.9 mmol) in DMF (60.0 mL) was added Cs$_2$CO$_3$ (12.3 g, 37.9 mmol) and iodomethane (1.42 mL, 22.7 mmol). The reaction mixture was then stirred at 80° C. for 16 h in a sealed tube. After complete consumption of starting material, it was cooled to room temperature and water (60 mL) was added to it. Extraction was carried out using EtOAc (50 mL×3); the combined organic extracts were washed with water (50 mL×3), brine (50 mL), dried over anhydrous $Na_2SO_4$, filtered and concentrated under reduced pressure to afford 4.16 g of mixture of 6-bromo-2,5-dimethyl-2H,4H,5H-pyrazolo[4,3-c]quinolone (I-5i) and 6-bromo-1,5-dimethyl-4,5-dihydro-1H-pyrazolo[4,3-c]quinolone (I-5j). LCMS (ES) m/z; 278.1 [M+H]+, 280.1.

Step-9: tert-butyl (2,5-dimethyl-4,5-dihydro-2H-pyrazolo[4,3-c]quinolin-6-yl)carbamate (I-11k) and tert-butyl (1,5-dimethyl-4,5-dihydro-1H-pyrazolo[4,3-c]quinolin-6-yl)carbamate (I-5l): Argon gas was purged through a stirred suspension of (I-5i+I-5j) (4.00 g, 14.4 mmol), tert-butyl carbamate (2.53 g, 21.6 mmol) and $Cs_2CO_3$ (9.37 g, 28.8 mmol) in 1,4-dioxane (50.0 mL) for 15 min. To this was then added [5-(diphenylphosphanyl)-9,9-dimethyl-9H-xanthen-4-yl]diphenylphosphane (1.66 g, 2.88 mmol) and $Pd(OAc)_2$ (646 mg, 2.88 mmol). The reaction mixture was then stirred at 100° C. for 16 h in a sealed tube. It was then cooled to room temperature, filtered through a pad of Celite and washed with EtOAc (50 mL×2). The filtrate was concentrated under reduced pressure and the residue was purified by Combi-Flash (using gradient elution of 0-50% EtOAc in hexane) to afford tert-butyl N-{2,5-dimethyl-2H,4H,5H-pyrazolo[4,3-c]quinolin-6-yl}carbamate I-5k (2.0 g) (as an off-white solid) and tert-butyl (1,5-dimethyl-4,5-dihydro-1H-pyrazolo[4,3-c]quinolin-6-yl)carbamate I-5l (0.8 g). LCMS (ES) m/z; 314.9 [M+H]$^+$.

Step-10: 2,5-dimethyl-4,5-dihydro-2H-pyrazolo[4,3-c]quinolin-6-amine (I-5): To a stirred solution of I-5k (1.00 g, 3.18 mmol) in DCM (10.0 mL) was added a 4M solution HCl in 1,4-dioxane (5.00 mL) at 0° C. The reaction mixture was stirred at room temperature for 16 h. After completion, volatiles were removed under reduced pressure and saturated sodium bicarbonate solution (30 mL) was added to the residue. Extraction was carried out using EtOAc (3×30 mL); the combined organic extracts were washed with water (30 mL), brine (30 mL), dried over anhydrous $Na_2SO_4$, filtered and evaporated under reduced pressure. The residue was purified by Combi-Flash (using gradient elution of 0-80% EtOAc in hexane) to afford desired compound 2,5-dimethyl-4,5-dihydro-2H-pyrazolo[4,3-c]quinolin-6-amine I-5 (0.5 g) as semi-solid. LCMS (ES) m/z; 215.2 [M+H]$^+$. $^1$H NMR (400 MHz, DMSO-$d_6$) δ 7.49 (s, 1H); 6.94-6.80 (m, 2H); 6.57 (dd, $J_1$=1.6 Hz, $J_2$=7.6 Hz, 1H); 4.87 (s, 2H); 3.93 (s, 2H); 3.83 (s, 3H); 2.34 (s, 3H).

Example 6: Preparation of 1,5-dimethyl-4,5-dihydro-1H-pyrazolo[4,3-c]quinolin-6-amine (I-6)

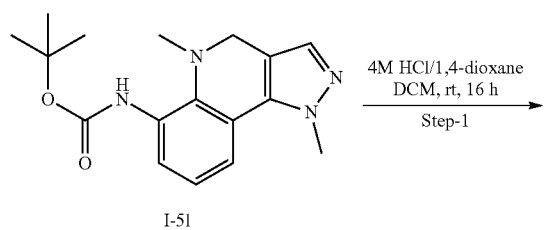

I-5l

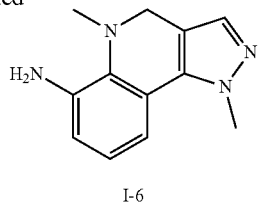

I-6

Step-1: 1,5-dimethyl-4,5-dihydro-1H-pyrazolo[4,3-c]quinolin-6-amine (I-6): To a stirred solution of I-5l (contaminated with I-5k) (0.8 g, 2.54 mmol) in DCM (10.0 mL) was added a 4M solution of HCl in 1,4-dioxane (5.00 mL) at 0° C. The reaction mixture was stirred at room temperature for 16 h. After completion, volatiles were removed under reduced pressure and saturated $NaHCO_3$ solution (20 mL) was added to the residue. Extraction was carried out using EtOAc (3×30 mL); the combined organic extracts were washed with water (30 mL), brine (30 mL), dried over anhydrous $Na_2SO_4$, filtered and concentrated under reduced pressure. The residue was purified by Combi-Flash (using gradient elution of 0-80% EtOAc in hexane) to afford desired compound 1,5-dimethyl-4,5-dihydro-1H-pyrazolo[4,3-c]quinolin-6-amine I-6 (contaminated with I-5) (0.5 g) as a semi-solid (mixture of regioisomers was carried forward for the next step). LCMS (ES) m/z; 214.9 [M+H]$^+$.

Example 7: Preparation of 5-methyl-2-(methyl-d3)-4,5-dihydro-2H-pyrazolo[4,3-c]quinolin-6-amine (I-7)

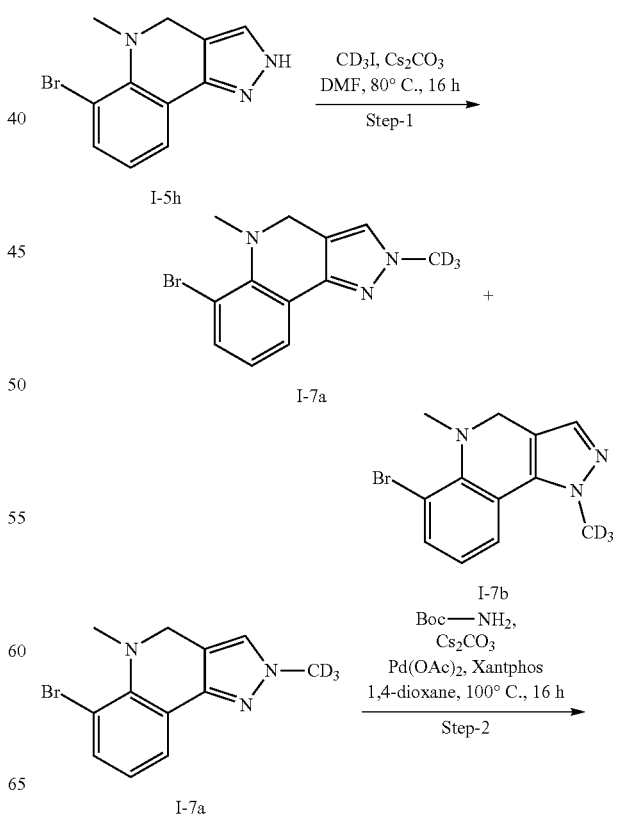

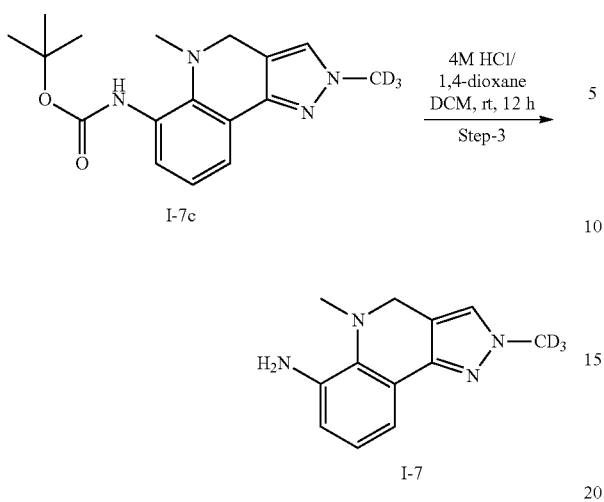

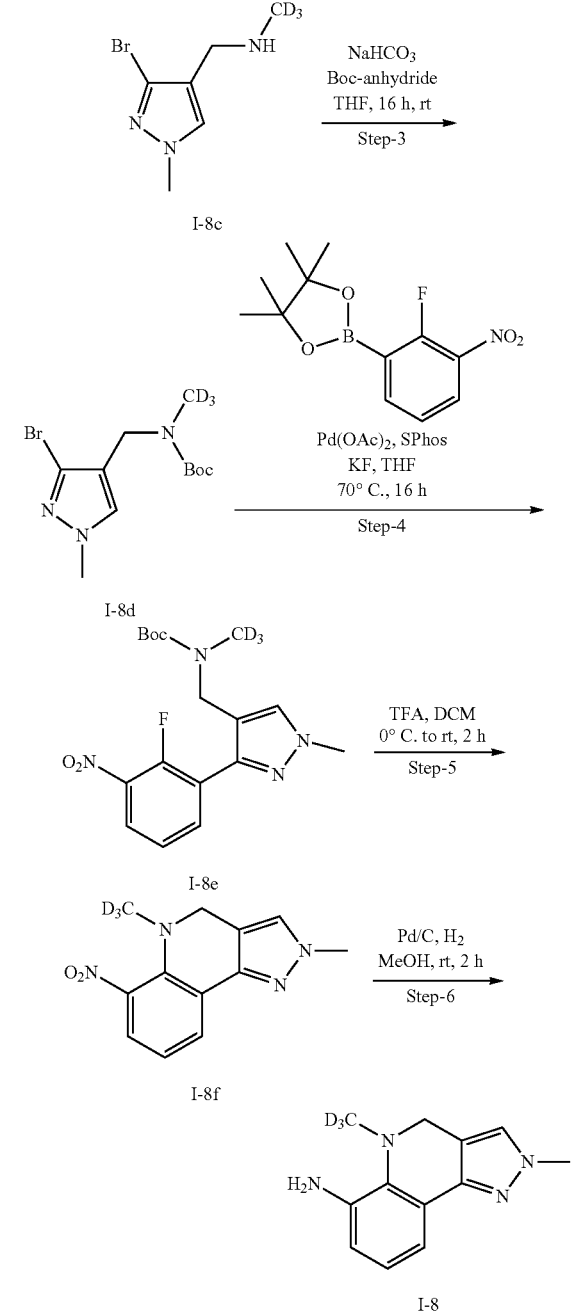

Step-1: 6-bromo-5-methyl-2-(methyl-d3)-4,5-dihydro-2H-pyrazolo[4,3-c]quinolone (I-7a) and 6-bromo-5-methyl-1-(methyl-d3)-4,5-dihydro-1H-pyrazolo[4,3-c]quinolone (I-7b): I-7a (4.0 g) and I-7b (1.5 g) were synthesized by following procedure as described for the synthesis of I-5 (step-8) using I-5h (6.0 g, 22.7 mmol) as the starting material. LCMS (ES) m/z; 281.0 [M+H]⁺.

Step-2: tert-butyl (5-methyl-2-(methyl-d3)-4,5-dihydro-2H-pyrazolo[4,3-c]quinolin-6-yl)carbamate (I-7c): I-7c (3.0 g) was synthesized by following procedure as described for the synthesis of I-1 (step-4) using I-7a (3.5 g, 12.4 mmol) as the starting material. LCMS (ES) m/z; 318.0 [M+H]⁺.

Step-3: 5-methyl-2-(methyl-d3)-4,5-dihydro-2H-pyrazolo[4,3-c]quinolin-6-amine (I-7): I-7 (1.1 g) was synthesized by following procedure as described for the synthesis of I-5 (step-10) using I-7c (3.0 g, 9.45 mmol) as the starting material. LCMS (ES) m/z; 218.2 [M+H]⁺. ¹H NMR (400 MHz, DMSO-d₆) δ 7.49 (s, 1H); 6.89-6.81 (m, 1H); 6.56 (dd, J₁=1.6 Hz, J₂=8.0 Hz, 1H); 4.88 (s, 2H); 3.92 (s, 2H); 2.48 (s, 3H).

Example 8: Preparation of 2-methyl-5-(methyl-d3)-4,5-dihydro-2H-pyrazolo[4,3-c]quinolin-6-amine (I-8)

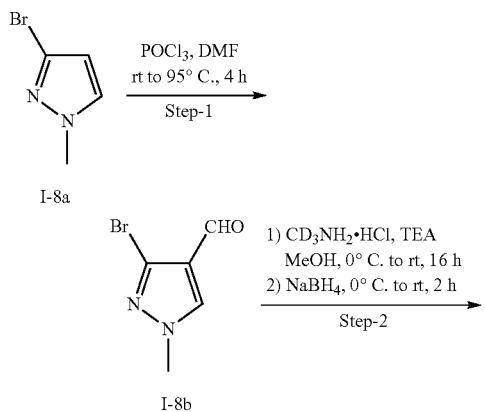

Step-1: 3-bromo-1-methyl-1H-pyrazole-4-carbaldehyde (I-8b): To a stirred solution of I-8a (10.0 g, 6.21 mmol) in DMF (30.0 mL) was slowly added POCl₃ (30.0 mL) at 0° C. Then, the reaction mixture was stirred at 95° C. for 4 h. After complete consumption of starting material, it was quenched with saturated NaHCO₃ solution (300 mL) and extracted with EtOAc (3×100 mL). The combined organic extracts were washed with water (100 mL), brine (100 mL), dried over anhydrous Na₂SO₄, filtered and concentrated under vacuum. The resulting crude was purified by Combi-Flash (using gradient elution 0-20% EtOAc in Heptane) to afford desired compound 3-bromo-1-methyl-1H-pyrazole-4-carbaldehyde I-8b (10.8 g) as an off-white solid. LCMS (ES) m/z: 188.9 [M+H]⁺.

Step-2-3: tert-butyl ((3-bromo-1-methyl-1H-pyrazol-4-yl)methyl)(methyl-d3)carbamate (I-8d): To a stirred solution of I-8b (5.0 g, 26.5 mmol) in MeOH (50 mL) were added TEA (7.37 mL, 52.9 mmol) and methyl-d3-amine hydrochloride (3.73 g, 52.9 mmol) at 0° C. The reaction mixture was stirred for 16 h at room temperature before it was cooled to 0° C. To this was then added NaBH$_4$ (1.95 g, 52.9 mmol) portion-wise and the reaction mixture was allowed to warm to room temperature over 2 h. Saturated NaHCO$_3$ solution (10 mL) was then added to it and washed with EtOAc (20 mL×2). (Boc)$_2$O (27.7 mL, 121 mmol) was then added to the aqueous NaHCO$_3$ solution and stirred at room temperature for 16 h. After completion, it was diluted with water (50 mL) and extraction was carried out using EtOAc (50 mL×3). The combined organic extracts were washed with brine (50 mL), dried over anhydrous Na$_2$SO$_4$, filtered and concentrated under reduced pressure. The residue was purified by Combi-Flash (using gradient elution of 0-10% EtOAc in hexane) to afford desired compound tert-butyl ((3-bromo-1-methyl-1H-pyrazol-4-yl)methyl)(methyl-d3)carbamate I-8d (7.00 g) as a colorless oil. LCMS (ES) m/z; 307.0 [M+H]$^+$.

Step-4: tert-butyl ((3-(2-fluoro-3-nitrophenyl)-1-methyl-1H-pyrazol-4-yl)methyl)(methyl-d3)carbamate (I-8e): Argon gas was purged through a stirred suspension of I-8d (2.5 g, 8.14 mmol), 2-(2-fluoro-3-nitrophenyl)-4,4,5,5-tetramethyl-1,3,2-dioxaborolane (3.26 g, 12.2 mmol) and KF (1.42 g, 24.4 mmol) in THF (40.0 mL) for 15 min. To this was then added Pd(OAc)$_2$ (0.0914 g, 0.407 mmol) and dicyclohexyl({2',6'-dimethoxy-[1,1'-biphenyl]-2-yl})phosphane (0.334 g, 0.814 mmol). The reaction mixture was then stirred at 70° C. for 16 h in a sealed tube. It was then cooled to room temperature, filtered through celite bed and washed with EtOAc (50 mL×2). The combined filtrate was concentrated under reduced pressure and the residue was purified by Combi-Flash (using gradient elution of 0-30% EtOAc in hexane) to afford tert-butyl ((3-(2-fluoro-3-nitrophenyl)-1-methyl-1H-pyrazol-4-yl)methyl)(methyl-d3)carbamate I-8e (2.3 g) as a yellow oil. LCMS (ES) m/z; 368.2 [M+H]$^+$.

Step-5: 2-methyl-5-(methyl-d3)-6-nitro-4,5-dihydro-2H-pyrazolo[4,3-c]quinolone (I-8f): To a stirred solution of I-8e (2.3 g, 6.26 mmol) in DCM (30.0 mL) was added trifluoroacetic acid (15.0 mL) at 0° C. under nitrogen atmosphere and the reaction mixture was allowed to warm to room temperature over 2 h. The progress of the reaction was monitored by TLC. After completion, volatiles were removed under reduced pressure and saturated NaHCO$_3$ solution (50 mL) was added to the residue. Extraction was carried out using EtOAc (2×30 mL); the combined organic extracts were washed with water (20 mL), brine (10 mL), dried over anhydrous Na$_2$SO$_4$, filtered and evaporated under reduced pressure to afford 2-methyl-5-(methyl-d3)-6-nitro-4,5-dihydro-2H-pyrazolo[4,3-c]quinolone I-8f (1.4 g) as a pale yellow solid. LCMS (ES) m/z; 248.1 [M+H]$^+$.

Step-6: 2-methyl-5-(methyl-d3)-4,5-dihydro-2H-pyrazolo[4,3-c]quinolin-6-amine (I-8): To a stirred solution of I-8f (1.4 g, 5.66 mmol) in methanol (20.0 mL) was added 10% Pd/C (241 mg) at room temperature. It was then allowed to stir under hydrogen atmosphere (H$_2$ balloon) for 2 h. After completion, the reaction mixture was filtered through celite bed and washed with methanol (20 mL×2). The combined filtrate was concentrated under reduced pressure. The resulting residue was purified by Combi-Flash (using gradient elution of 0-55% EtOAc in hexane) to afford 2-methyl-5-(methyl-d3)-4,5-dihydro-2H-pyrazolo[4,3-c]quinolin-6-amine I-8 (1.2 g) as a brown gummy liquid. LCMS (ES) m/z; 218.2 [M+H]$^+$. $^1$H NMR (400 MHz, DMSO-d$_6$) δ 7.51 (s, 1H); 6.92 (dd, J$_1$=1.6 Hz, J$_2$=7.6 Hz, 1H); 6.86 (t, J=7.6 Hz, 1H); 6.60 (dd, J$_1$=1.6 Hz, J$_2$=7.6 Hz, 1H); 4.90 (s, 2H); 3.95 (s, 2H); 3.86 (s, 3H).

Example 9: Preparation of 2-methyl-5-(methyl-d3)-4,5-dihydro-2H-pyrazolo[4,3-c][1,7]naphthyridin-6-amine (I-9)

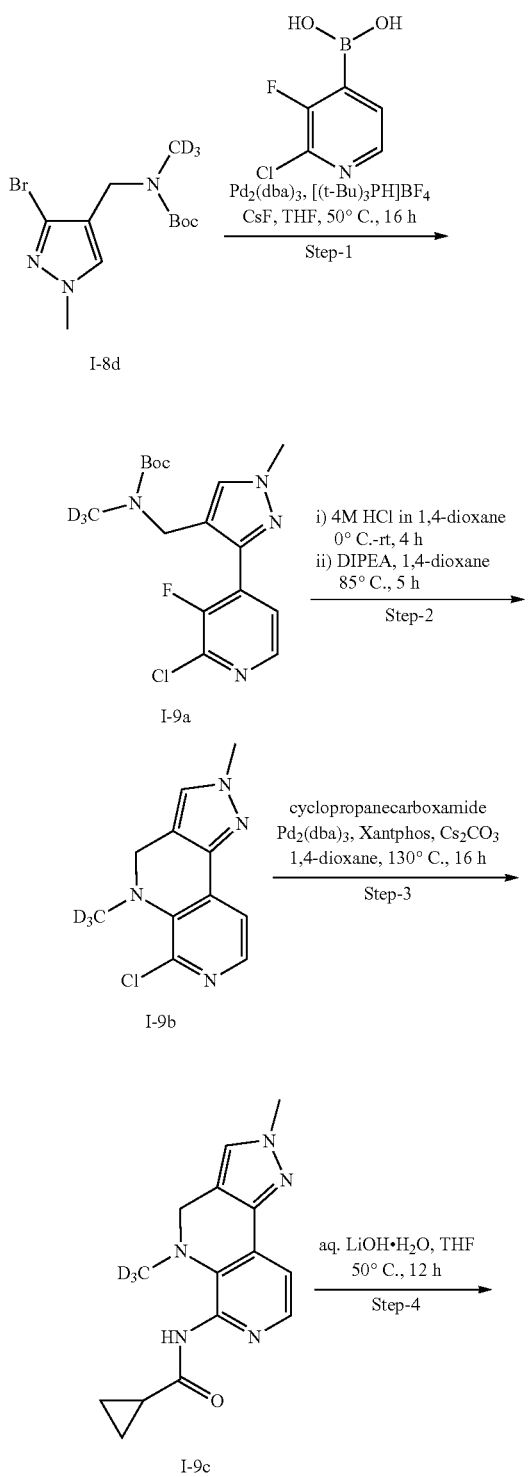

-continued

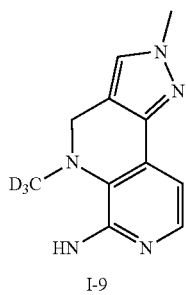

I-9

Step-1: tert-butyl ((3-(2-chloro-3-fluoropyridin-4-yl)-1-methyl-1H-pyrazol-4-yl)methyl)(methyl-d3)carbamate (I-9a): Argon gas was purged through a solution of I-8d (2.5 g, 8.14 mmol), (2-chloro-3-fluoropyridin-4-yl)boronic acid (3.57 g, 20.3 mmol) and CsF (3.71 g, 24.4 mmol) in THF (30 mL) for 15 min. To this then added tri-tert-butylphosphonium tetrafluoroborate (142 mg, 0.488 mmol) and tris(1,5-diphenylpenta-1,4-dien-3-one) dipalladium (373 mg, 0.407 mmol). The reaction mixture was then stirred at 50° C. for 16 h in a sealed tube. After completion, the reaction mixture was filtered through celite bed and washed with EtOAc (50 mL×2). The combined filtrate was concentrated under reduced pressure. The resulting residue was purified by Combi-Flash (using gradient elution of 0-30% EtOAc in hexane) to afford tert-butyl ((3-(2-chloro-3-fluoropyridin-4-yl)-1-methyl-1H-pyrazol-4-yl)methyl)(methyl-d3)carbamate I-9a (1.9 g) as a brown gummy liquid. LCMS (ES) m/z; 358.1 [M+H]$^+$.

Step-2: 6-chloro-2-methyl-5-(methyl-d3)-4,5-dihydro-2H-pyrazolo[4,3-c][1,7]naphthyridine (I-9b): A 4M solution of HCl in 1,4-dioxane (50 mL) was added to I-9a (1.9 g, 5.31 mmol) and stirred at room temperature for 16 h. After completion, volatiles were removed under reduced pressure and dried (co-evaporation with 1,4-dioxane). To this was then added 1,4-dioxane (20 mL) and DIPEA (4.98 mL, 29.1 mmol) at room temperature and the reaction mixture was then stirred at 85° C. for 5 h. After completion, volatiles were removed under reduced pressure and the residue was purified by Combi-Flash (using gradient elution of 0-55% EtOAc in hexane) to afford the desired compound 6-chloro-2-methyl-5-(methyl-d3)-4,5-dihydro-2H-pyrazolo[4,3-c][1,7]naphthyridine I-9b (1.5 g) as a yellow thick oil. LCMS (ES) m/z; 238.1 [M+H]$^+$.

Step-3: N-(2-methyl-5-(methyl-d3)-4,5-dihydro-2H-pyrazolo[4,3-c][1,7]naphthyridin-6-yl)cyclopropanecarboxamide (I-9c): Argon gas was purged through a stirred suspension of I-9b (1 g, 4.21 mmol), cyclopropanecarboxamide (0.72 g, 8.41 mmol) and Cs$_2$CO$_3$ (4.11 g, 12.6 mmol) in 1,4-dioxane (20 mL) for 15 min. To this was then added [5-(diphenylphosphanyl)-9,9-dimethyl-9H-xanthen-4-yl]diphenylphosphane (0.24 g, 0.421 mmol) and Pd$_2$(dba)$_3$ (0.38 g, 0.421 mmol). The reaction mixture was then stirred at 130° C. for 16 h in a sealed tube. It was then cooled to room temperature, filtered through celite bed and washed with EtOAc (50 mL×2). The filtrate was concentrated under reduced pressure and the residue was purified by Combi-Flash (using gradient elution of 0-80% EtOAc in Hexane) to afford N-(2-methyl-5-(methyl-d3)-4,5-dihydro-2H-pyrazolo[4,3-c][1,7]naphthyridin-6-yl)cyclopropanecarboxamide I-9c (0.8 g) as a pale yellow solid. LCMS (ES) m/z; 287.1 [M+H]$^+$.

Step-4: 2-methyl-5-(methyl-d3)-4,5-dihydro-2H-pyrazolo[4,3-c][1,7]naphthyridin-6-amine (I-9): To a stirred solution of I-9c (0.7 g, 2.44 mmol) in THF (10 mL) was added LiOH (0.29 g, 12.2 mmol) in water (5.0 mL) at room temperature. It was then stirred at 50° C. for 16 h. After completion, the reaction was diluted with water (20 mL) and extracted with 10% MeOH in DCM (50 mL×2). The combined organic extracts were washed with brine (50 mL), dried over anhydrous Na$_2$SO$_4$, filtered and evaporated under reduced pressure. The residue was purified by Combi-Flash (using gradient elution of 0-10% MeOH in DCM) to afford desired compound 2-methyl-5-(methyl-d3)-4,5-dihydro-2H-pyrazolo[4,3-c][1,7]naphthyridin-6-amine I-9 (0.4 g) as a pale yellow solid. LCMS (ES) m/z; 219.2 [M+H]$^+$. $^1$H NMR (400 MHz, DMSO-d$_6$) δ 7.78 (d, J=5.6 Hz, 1H); 7.40 (s, 1H); 7.12 (d, J=5.6 Hz, 1H); 5.54 (s, 2H); 4.07 (s, 2H); 3.98 (s, 3H).

Example 10: Preparation of 2,5-dimethyl-4,5-dihydro-2H-pyrazolo[4,3-c][1,7]naphthyridin-6-amine (I-10)

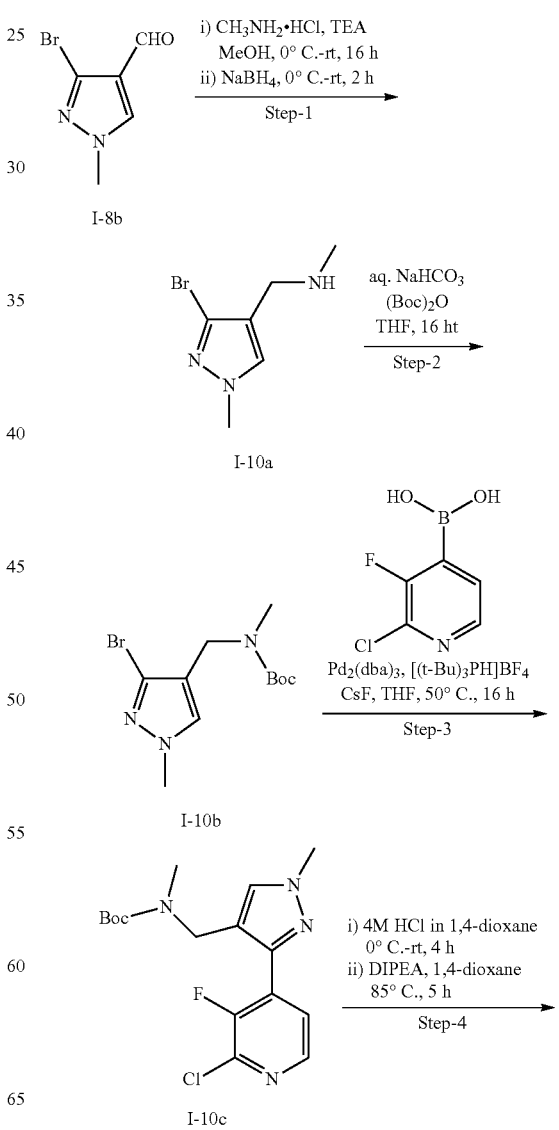

129

-continued

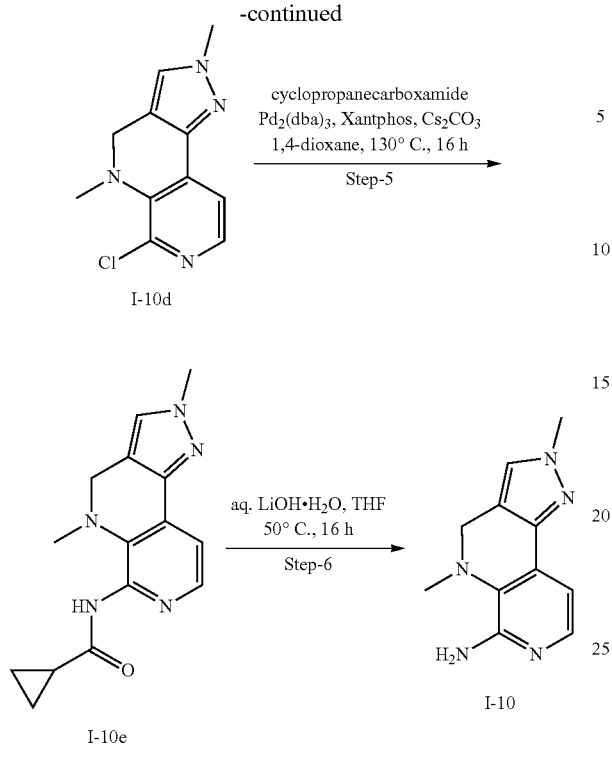

130

Example 11: Preparation of 2,5-dimethyl-4,5-dihydro-2H-pyrazolo[4,3-c]quinolin-4,4-d2-6-amine (I-11)

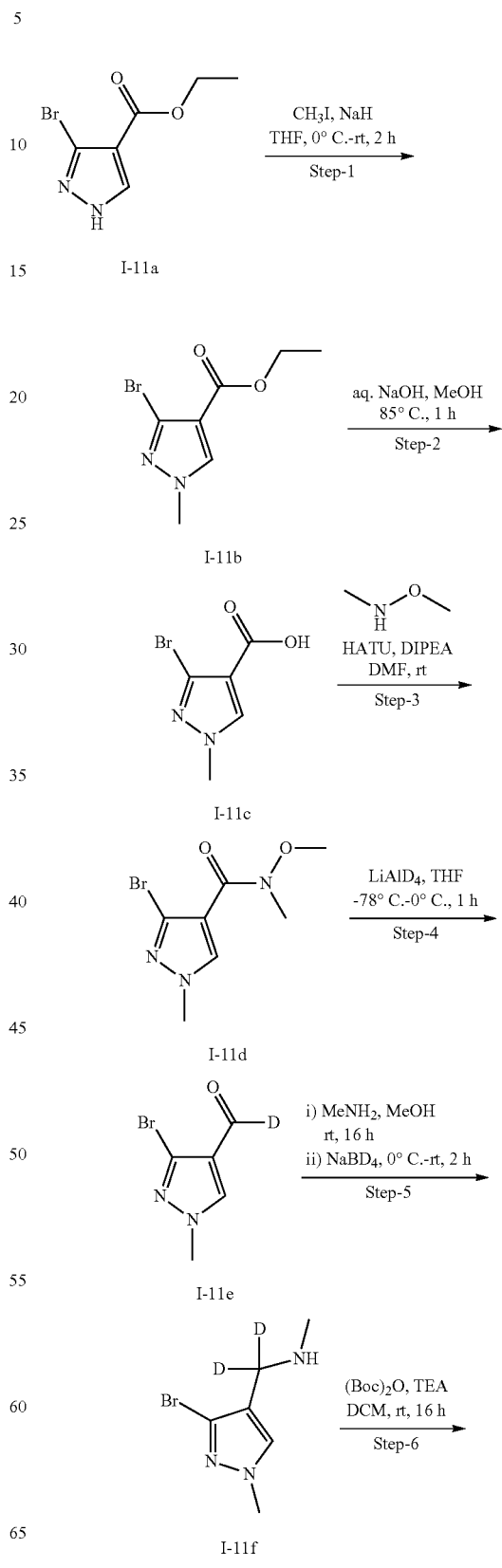

Step-1-2: tert-butyl ((3-bromo-1-methyl-1H-pyrazol-4-yl)methyl)(methyl)carbamate (I-10b): I-10b (5.7 g) was synthesized by following procedure as described for the synthesis of I-8 (step-2-3) using I-8b (5.7 g, 30.2 mmol) and methyl amine hydrochloride (6.11 g, 30.2 mmol) as the starting materials. LCMS (ES) m/z; 304.0 [M+H]$^+$.

Step-3: tert-butyl ((3-(2-chloro-3-fluoropyridin-4-yl)-1-methyl-1H-pyrazol-4-yl)methyl)(methyl)carbamate (I-10c): I-10c (4.8 g) was synthesized by following procedure as described for the synthesis of I-9 (step-1) using I-10b (5.7 g, 18.7 mmol) and (2-chloro-3-fluoropyridin-4-yl)boronic acid (8.7 g, 18.7 mmol) as the starting materials. LCMS (ES) m/z; 355.1 [M+H]$^+$.

Step-4: 6-chloro-2,5-dimethyl-4,5-dihydro-2H-pyrazolo[4,3-c][1,7]naphthyridine (I-10d): I-10d (2.8 g) was synthesized by following procedure as described for the synthesis of I-9 (step-2) using I-10c (4.8 g, 13.5 mmol) as the starting material. LCMS (ES) m/z; 235.1 [M+H]$^+$.

Step-5: N-(2,5-dimethyl-4,5-dihydro-2H-pyrazolo[4,3-c][1,7]naphthyridin-6-yl)cyclopropanecarboxamide (I-10e): I-10e (1.5 g) was synthesized by following procedure as described for the synthesis of I-9 (step-3) using I-10d (1.5 g, 6.39 mmol) and cyclopropanecarboxamide (1.09 g, 12.8 mmol) as the starting materials. LCMS (ES) m/z; 284.2 [M+H]$^+$.

Step-6: 2,5-dimethyl-4,5-dihydro-2H-pyrazolo[4,3-c][1,7]naphthyridin-6-amine (I-10): I-10 (1.2 g) was synthesized by following procedure as described for the synthesis of I-9 (step-4) using I-10e (2.0 g, 7.06 mmol) as the starting material. LCMS (ES) m/z; 216.2 [M+H]$^+$. $^1$H NMR (400 MHz, DMSO-d$_6$) δ 7.73 (d, J=5.2 Hz, 1H); 7.59 (s, 1H); 6.82 (d, J=5.2 Hz, 1H); 5.76 (s, 2H); 4.01 (s, 2H); 3.8 (s, 3H); 2.46 (s, 3H).

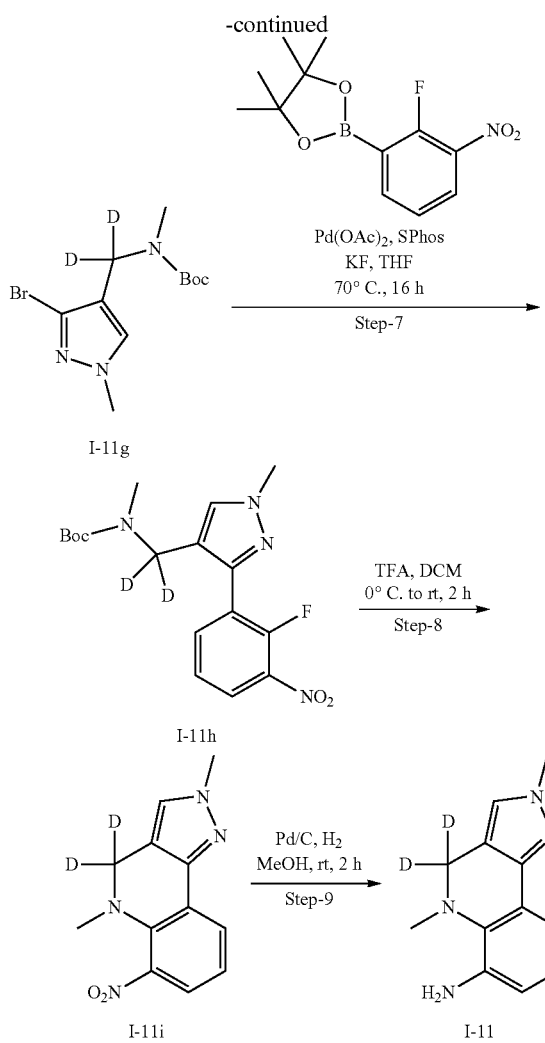

Step-3: 3-bromo-N-methoxy-N,1-dimethyl-1H-pyrazole-4-carboxamide (I-11d): To a stirred solution of I-11c (8 g, 39 mmol) in DMF (80 mL) were added DIPEA (20 mL, 117 mmol) and HATU (29.7 g, 78 mmol) at 0° C. To this was then added N,O-dimethylhydroxylamine hydrochloride (7.61 g, 78 mmol) and the reaction mixture was stirred at room temperature for 2 h. After complete consumption of starting material, water (20 mL) was added to it and extracted with EtOAc (75×3 mL). The combined organic extracts were washed with brine (50 mL×2), dried over $Na_2SO_4$, filtered and concentrated under reduced pressure. The resulting crude was purified by Combi-Flash (using gradient elution of 0-50% EtOAc in Heptane) to afford 3-bromo-N-methoxy-N,1-dimethyl-1H-pyrazole-4-carboxamide I-11d (5 g) as an off-white solid. LCMS (ES) m/z; 248.0 $[M+H]^+$.

Step-4: 3-bromo-1-methyl-1H-pyrazole-4-carbaldehyde-d (I-11e): To a stirred solution of I-11d (10 g, 40.3 mmol) in anhydrous THF (100 mL) was added LiAlD4 (1.69 g, 40.3 mmol) portion-wise at −78° C. and the reaction mixture was allowed to warm to 0° C. over 1 h. After completion, saturated $NH_4Cl$ solution (20 mL) was added to it and extraction was carried out using EtOAc (50 mL×3). The combined organic extracts were washed with brine (50 mL×2), dried over $Na_2SO_4$, filtered and concentrated under reduced pressure. The resulting residue was purified by Combi-Flash (using gradient elution of 0-50% EtOAc in Heptane) to afford 3-bromo-1-methyl-1H-pyrazole-4-carbaldehyde-d I-11e (6 g) as an-off white solid. LCMS (ES) m/z; 190.0 $[M+H]^+$.

Step-5: 1-(3-bromo-1-methyl-1H-pyrazol-4-yl)-N-methylmethan-d2-amine (I-11f): To a stirred solution of I-11e (7.0 g, 36.8 mmol) in MeOH (70 mL) was added TEA (10.3 mL, 52.9 mmol) and methyl amine hydrochloride (4.97 g, 73.7 mmol) at 0° C. Then, the reaction mixture was stirred for 16 h at room temperature. It was then cooled to 0° C. and $NaBD_4$ (3.08 g, 73.7 mmol) was added to it portion-wise. The reaction mixture was allowed to warm to room temperature over 2 h. Saturated $NaHCO_3$ solution (10 mL) was then added to it and washed with EtOAc (20 mL×2). The resulting aqueous $NaHCO_3$ solution containing 1-(3-bromo-1-methyl-1H-pyrazol-4-yl)-N-methylmethan-d2-amine I-11f was carried forward for the next step.

Step-6: tert-butyl ((3-bromo-1-methyl-1H-pyrazol-4-yl)methyl-d2)(methyl)carbamate (I-11g): I-11g (7.5 g) was synthesized by following procedure as described for the synthesis of I-8 (step-3). LCMS (ES) m/z; 306.0 $[M+H]^+$.

Step-7: tert-butyl ((3-(2-fluoro-3-nitrophenyl)-1-methyl-1H-pyrazol-4-yl)methyl-d2)(methyl)carbamate (I-11h): I-11h (1.0 g) was synthesized by following procedure as described for the synthesis of I-8 (step-4) using I-11g (1.1 g, 3.59 mmol) and 2-(2-fluoro-3-nitrophenyl)-4,4,5,5-tetramethyl-1,3,2-dioxaborolane (1.44 g, 5.39 mmol) as the starting materials. LCMS (ES) m/z; 367.1 $[M+H]^+$.

Step-8: 2,5-dimethyl-6-nitro-4,5-dihydro-2H-pyrazolo[4,3-c]quinoline-4,4-d2 (I-i1i): I-11i (0.66 g) was synthesized by following procedure as described for the synthesis of I-8 (step-5) using I-11h (1.1 g, 3 mmol) as the starting material. LCMS (ES) m/z; 247.1 $[M+H]^+$.

Step-9: 2,5-dimethyl-4,5-dihydro-2H-pyrazolo[4,3-c]quinolin-4,4-d2-6-amine (I-11): I-11 (0.5 g) was synthesized by following procedure as described for the synthesis of I-8 (step-6) using I-11i (0.66 g, 2.68 mmol) as the starting material. LCMS (ES) m/z; 217.0 $[M+H]^+$. $^1$H NMR (400 MHz, DMSO-$d_6$) δ 7.52 (s, 1H); 6.91 (dd, $J_1$=1.6 Hz, $J_2$=7.6 Hz, 1H); 6.85 (t, J=7.6 Hz, 1H); 6.91 (dd, $J_1$=1.6 Hz, $J_2$=7.6 Hz, 1H); 4.90 (s, 2H); 3.86 (s, 3H); 2.37 (s, 3H).

Example 12: Preparation of 2,5-dimethyl-4,5-dihydro-2H-pyrazolo[4,3-c][1,7]naphthyridin-4,4-d2-6-amine (I-12)

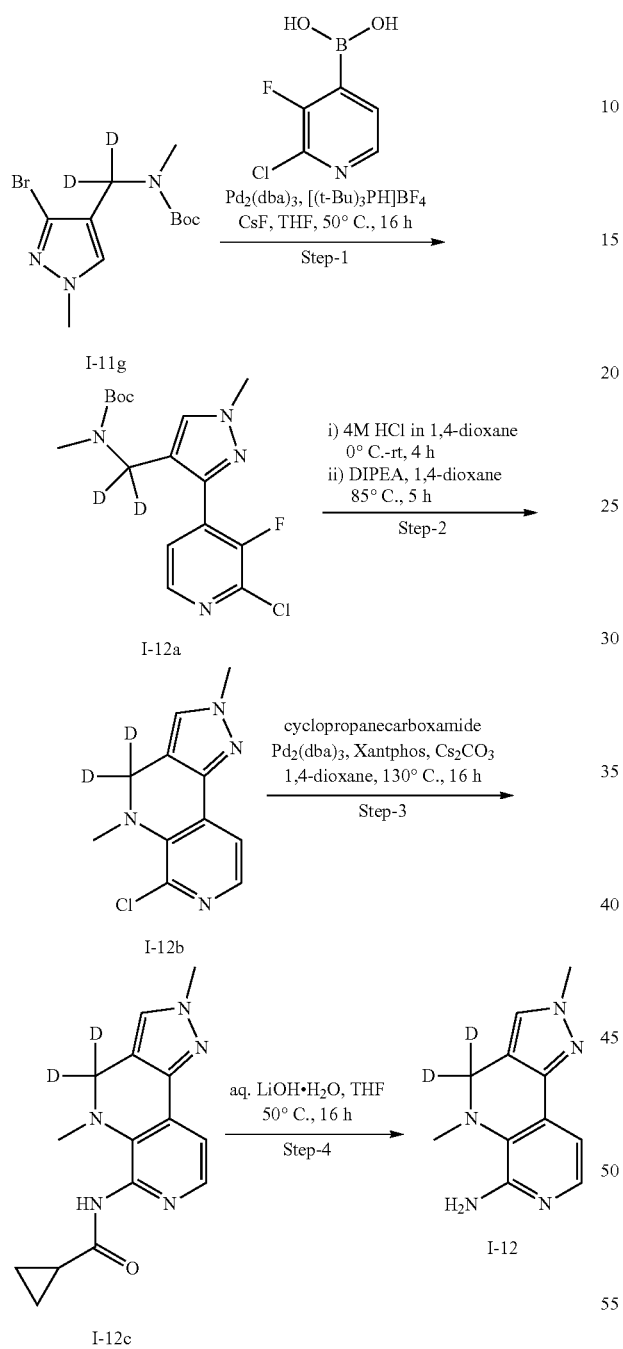

Step-1: tert-butyl ((3-(2-chloro-3-fluoropyridin-4-yl)-1-methyl-1H-pyrazol-4-yl)methyl-d2)(methyl)carbamate (I-12a): I-12a (3.8 g) was synthesized by following procedure as described for the synthesis of I-9 (step-1) using I-11g (4.5 g, 14.7 mmol) and (2-chloro-3-fluoropyridin-4-yl)boronic acid (6.44 g, 36.7 mmol) as the starting materials. LCMS (ES) m/z; 357.0 [M+H]⁺.

Step-2: 6-chloro-2,5-dimethyl-4,5-dihydro-2H-pyrazolo[4,3-c][1,7]naphthyridine-4,4-d2 (I-12b): I-12b (0.6 g) was synthesized by following procedure as described for the synthesis of I-9 (step-2) using I-12a (2.0 g, 5.61 mmol) as the starting material. LCMS (ES) m/z; 237.0 [M+H]⁺.

Step-3: N-(2,5-dimethyl-4,5-dihydro-2H-pyrazolo[4,3-c][1,7]naphthyridin-6-yl-4,4-d2)cyclopropanecarboxamide (I-12c): I-12c (0.4 g) was synthesized by following procedure as described for the synthesis of I-9 (step-3) using I-12b (0.63 g, 2.06 mmol) and cyclopropanecarboxamide (1.73 g, 5.32 mmol) as the starting materials. LCMS (ES) m/z; 286.2 [M+H]⁺.

Step-4: 2,5-dimethyl-4,5-dihydro-2H-pyrazolo[4,3-c][1,7]naphthyridin-4,4-d2-6-amine (I-12): I-12 (0.28 g) was synthesized by following procedure as described for the synthesis of I-9 (step-4) using I-12c (0.63 g, 2.21 mmol) as the starting material. LCMS (ES) m/z; 218.0 [M+H]⁺. ¹H NMR (400 MHz, DMSO-d₆) δ 7.73 (d, J=5.2 Hz, 1H); 7.59 (s, 1H); 6.82 (d, J=4.8 Hz, 1H); 5.68 (s, 2H); 3.89 (s, 3H); 2.41 (s, 3H).

Example 13: Preparation of 5-methyl-2-(oxetan-3-yl)-4,5-dihydro-2H-pyrazolo[4,3-c]quinolin-6-amine (I-13)

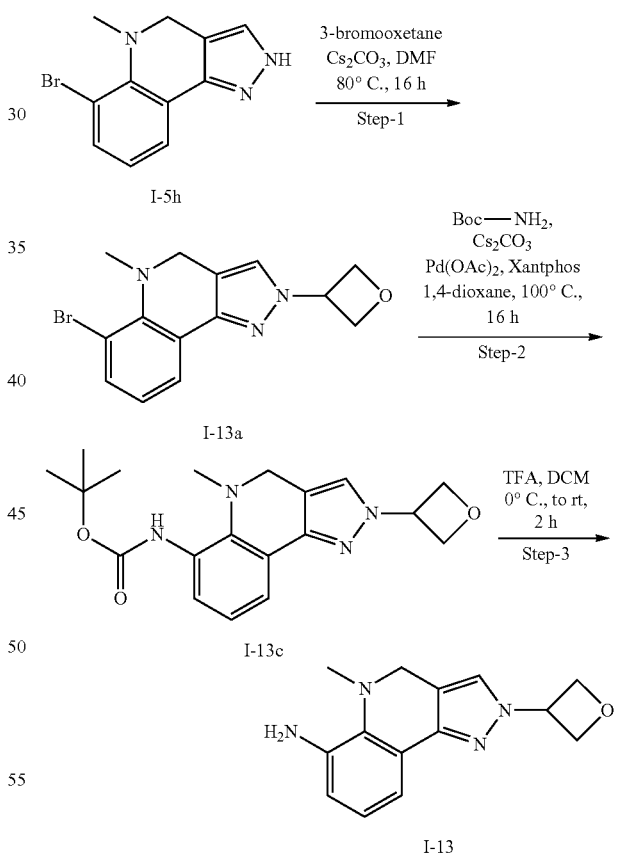

Step-1: 6-bromo-5-methyl-2-(oxetan-3-yl)-4,5-dihydro-2H-pyrazolo[4,3-c]quinolone (I-13a): I-13a (0.6 g) was synthesized by following procedure as described for the synthesis of I-3 (step-1) using I-5h (1.35 g, 5.11 mmol) and 3-bromooxetane (0.85 mL, 10.2 mmol) as the starting materials. LCMS (ES) m/z; 320.1 [M+H]⁺.

Step-2: tert-butyl (5-methyl-2-(oxetan-3-yl)-4,5-dihydro-2H-pyrazolo[4,3-c]quinolin-6-yl)carbamate (I-13b): I-13b (0.5 g) was synthesized by following procedure as described for the synthesis of I-1 (step-4) using I-13a (0.6 g, 1.87 mmol) as the starting material. LCMS (ES) m/z; 357.1 [M+H]⁺.

Step-3: 5-methyl-2-(oxetan-3-yl)-4,5-dihydro-2H-pyrazolo[4,3-c]quinolin-6-amine (I-13): I-13 (0.2 g) was synthesized by following procedure as described for the synthesis of I-1 (step-5) using I-13b (0.5 g, 1.4 mmol) as the starting material. LCMS (ES) m/z; 257.0 [M+H]⁺. ¹H NMR (400 MHz, DMSO-d₆) δ 7.72 (s, 1H); 6.96 (d, J=6.8 Hz, 1H); 6.86 (t, J=8.0 Hz, 1H); 6.60 (d, J=6.8 Hz, 1H); 5.57 (m, 1H); 4.92 (s, 2H); 4.90 (m, 4H); 3.98 (s, 2H); 2.48 (s, 3H).

Example 14: Preparation of 2,4,5-trimethyl-4,5-dihydro-2H-pyrazolo[4,3-c]quinolin-6-amine (I-14)

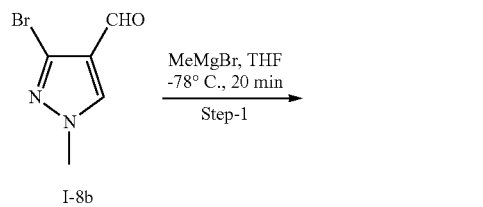

Step-1: 1-(3-bromo-1-methyl-1H-pyrazol-4-yl)ethan-1-ol (I-14a): To a stirred solution of I-8b (25 g, 132.3 mmol) in anhydrous THF (250 mL) was added a 1M solution of MeMgBr in Et₂O (198.3 mL, 198.4 mmol) at −78° C. and the reaction mixture was allowed to warm to room temperature over 20 min. After complete consumption of starting material, it was quenched with addition of saturated NH₄Cl solution (100 mL) and extraction was carried out using EtOAc (70 mL×3). The combined extracts were washed with water (100 mL), brine (100 mL), dried over anhydrous Na₂SO₄, filtered and concentrated under reduced pressure to afford desired compound 1-(3-bromo-1-methyl-1H-pyrazol-4-yl) ethan-1-ol I-14a (23 g) as a brown semi-solid. LCMS (ES) m/z; 205.0 [M+H]⁺.

Step-2: 1-(3-bromo-1-methyl-1H-pyrazol-4-yl)ethan-1-one (I-14b): I-14b (15.5 g) was synthesized by following procedure as described for the synthesis of I-5 (step-6) using I-14a (23 g, 122.0 mmol) as the starting material. LCMS (ES) m/z; 203.0 [M+H]⁺.

Step-3: 1-(3-bromo-1-methyl-1H-pyrazol-4-yl)-N-methylethan-1-amine (I-14c): To a stirred solution of I-14b (15.5 g, 76.35 mmol) in THF (150 mL) was added titanium (IV) isopropoxide (45.2 mL, 152.70 mmol) in a sealed tube at 0° C. To this then added 2M solution of MeNH$_2$ in THF (76.3 mL, 152.70 mmol) and the reaction mixture was stirred at 60° C. for 16 h. It was then cooled to room temperature and volatiles were removed under reduced pressure. It was then diluted with MeOH (180 mL) and to this was added sodium borohydride (8.66 g, 229.06 mmol) at 0° C. The reaction mixture was then allowed to warm to room temperature over 2 h. After completion, saturated NaHCO$_3$ solution (100 mL) was added to it and washed with EtOAc (30 mL×2). The aqueous NaHCO$_3$ solution containing 1-(3-bromo-1-methyl-1H-pyrazol-4-yl)-N-methylethan-1-amine I-14c was carried forward for the next step.

Step-4: tert-butyl (1-(3-bromo-1-methyl-1H-pyrazol-4-yl)ethyl)(methyl)carbamate (I-14d): I-14d (19 g) was synthesized by following procedure as described for the synthesis of I-8 (step-3). LCMS (ES) m/z; 318.0 [M+H]$^+$.

Step-5: tert-butyl (1-(3-(2-fluoro-3-nitrophenyl)-1-methyl-1H-pyrazol-4-yl)ethyl)(methyl)carbamate (I-14e): I-14e (6.0 g) was synthesized by following procedure as described for the synthesis of I-8 (step-4) using I-14d (5.5 g, 17.3 mmol) and 2-(2-fluoro-3-nitrophenyl)-4,4,5,5-tetramethyl-1,3,2-dioxaborolane (6.92 g, 25.9 mmol) as the starting materials. LCMS (ES) m/z; 379.0 [M+H]$^+$.

Step-6: 2,4,5-trimethyl-6-nitro-4,5-dihydro-2H-pyrazolo[4,3-c]quinoline (I-14f): I-14f (3.0 g) was synthesized by following procedure as described for the synthesis of I-8 (step-5) using I-14e (6.0 g, 15.9 mmol) as the starting material. LCMS (ES) m/z; 259.0 [M+H]$^+$.

Step-7: 2,4,5-trimethyl-4,5-dihydro-2H-pyrazolo[4,3-c]quinolin-6-amine (I-14): I-14 (2.2 g) was synthesized by following procedure as described for the synthesis of I-8 (step-6) using I-14f (3.0 g, 11.6 mmol) as the starting material. LCMS (ES) m/z; 229.2 [M+H]$^+$. $^1$H NMR (400 MHz, DMSO-d$_6$) δ 7.25 (d, J=8.0 Hz, 1H); 7.15 (s, 1H); 6.99 (t, J=8.0 Hz, 1H); 6.68 (d, J=8.0 Hz, 1H); 4.26 (br s, 2H); 4.10 (q, J=7.2 Hz, 1H); 3.94 (s, 3H); 2.46 (s, 3H); 1.19 (d, J=7.2 Hz, 3H).

Example 15: Preparation of 2,4,5-trimethyl-4,5-dihydro-2H-pyrazolo[4,3-c][1,7]naphthyridin-6-amine (I-15)

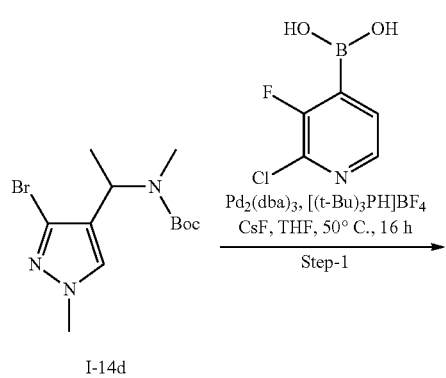

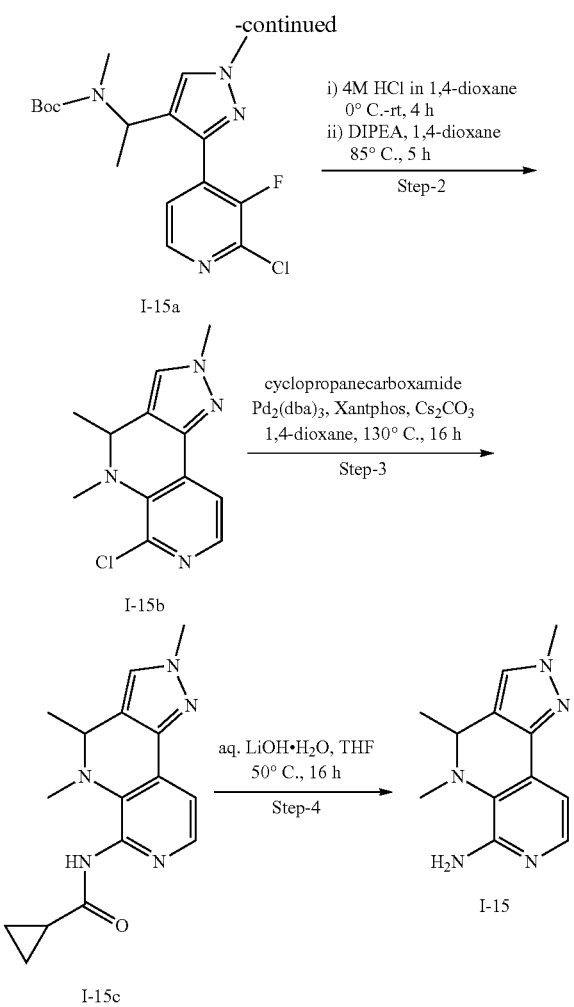

Step-1: tert-butyl (1-(3-(2-chloro-3-fluoropyridin-4-yl)-1-methyl-1H-pyrazol-4-yl)ethyl)(methyl)carbamate (I-15a): I-15a (3.0 g) was synthesized by following procedure as described for the synthesis of I-9 (step-1) using I-14d (5.0 g, 15.7 mmol) and (2-chloro-3-fluoropyridin-4-yl)boronic acid (4.13 g, 23.6 mmol) as the starting materials. LCMS (ES) m/z; 369.1 [M+H]$^+$.

Step-2: 6-chloro-2,4,5-trimethyl-4,5-dihydro-2H-pyrazolo[4,3-c][1,7]naphthyridine (I-15b): I-15b (5.0 g) was synthesized by following procedure as described for the synthesis of I-9 (step-2) using I-15a (12.0 g, 32.5 mmol) as the starting material. LCMS (ES) m/z; 249.1 [M+H]$^+$.

Step-3: N-(2,4,5-trimethyl-4,5-dihydro-2H-pyrazolo[4,3-c][1,7]naphthyridin-6-yl)cyclopropanecarboxamide (I-15c): I-15c (0.6 g) was synthesized by following procedure as described for the synthesis of I-9 (step-3) using I-15b (1.0 g, 4.02 mmol) and cyclopropanecarboxamide (0.68 g, 8.04 mmol) as the starting materials. LCMS (ES) m/z; 298.0 [M+H]$^+$.

Step-4: 2,4,5-trimethyl-4,5-dihydro-2H-pyrazolo[4,3-c][1,7]naphthyridin-6-amine (I-15): I-15 (2.1 g) was synthesized by following procedure as described for the synthesis of I-9 (step-4) using I-15c (3.36 g, 11.3 mmol) as the starting material. LCMS (ES) m/z; 230.1 [M+H]$^+$. $^1$H NMR (400 MHz, DMSO-d$_6$) δ 7.70 (d, J=5.2 Hz, 1H); 7.57 (s, 1H); 6.79 (d, J=4.8 Hz, 1H); 5.63 (br s, 2H); 4.11 (q, J=6.8 Hz, 1H); 3.86 (s, 3H); 2.35 (s, 3H); 1.4 (d, J=7.2 Hz, 3H).

Racemate I-15 (2.1 g) was resolved by chiral HPLC separation [Column: CHIRALPAK IC (250 mm×30 mm×5 m); Mobile phase: n-Hexane:IPA with 0.1% DEA (80:20); Flow rate: 40 mL/min)] to afford two enantiomers {I-15A (0.6 g) and I-15B (0.6 g)}; peak-1; Rt; 12.06 min and I-15B (0.6 g): peak-2; Rt; 16.23 min}, which were used further without their absolute configuration determination.

Example 16: Preparation of 2,5-dimethyl-4,5-dihydropyrazolo[1,5-a]quinoxalin-6-amine (I-16)

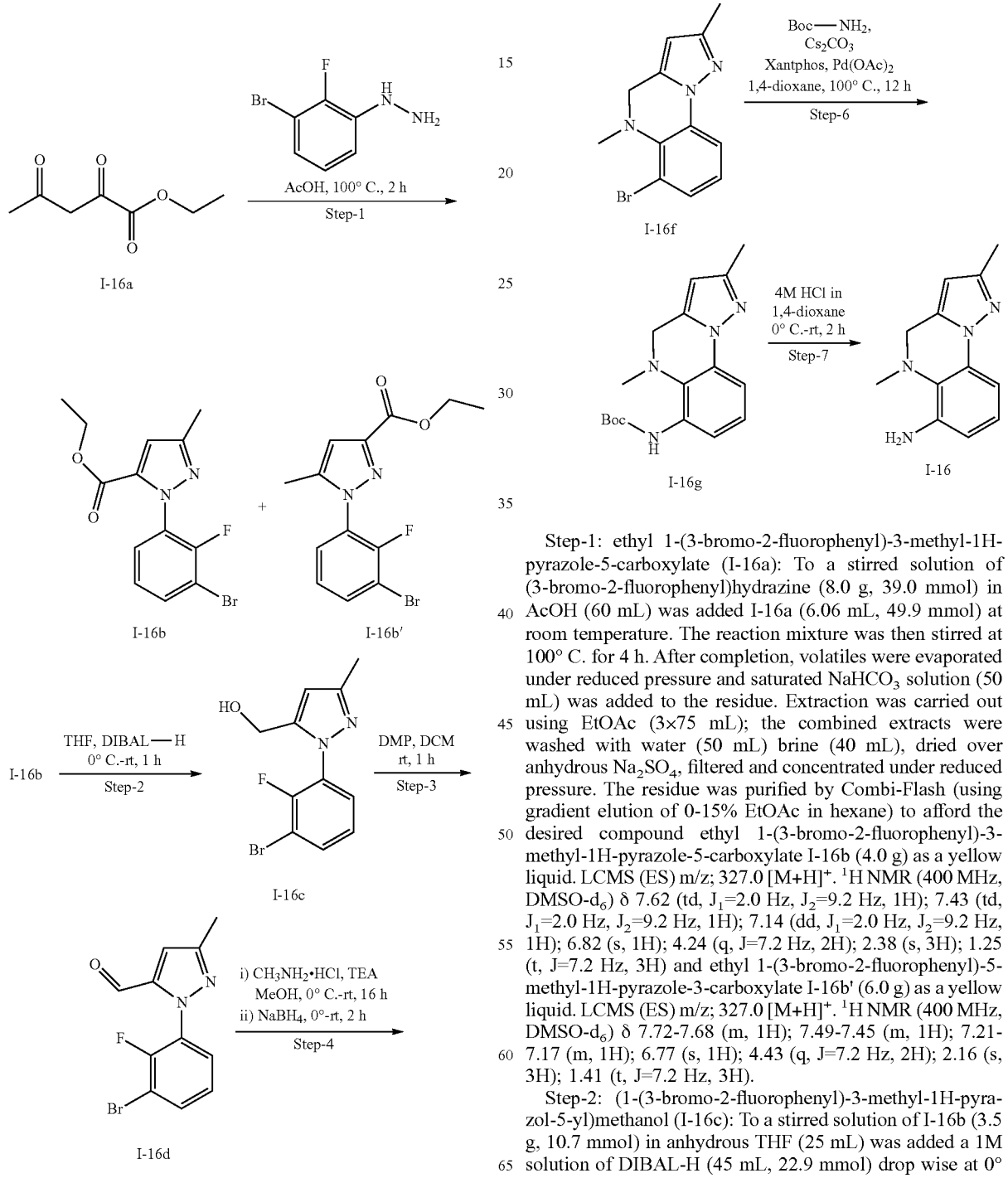

Step-1: ethyl 1-(3-bromo-2-fluorophenyl)-3-methyl-1H-pyrazole-5-carboxylate (I-16a): To a stirred solution of (3-bromo-2-fluorophenyl)hydrazine (8.0 g, 39.0 mmol) in AcOH (60 mL) was added I-16a (6.06 mL, 49.9 mmol) at room temperature. The reaction mixture was then stirred at 100° C. for 4 h. After completion, volatiles were evaporated under reduced pressure and saturated NaHCO$_3$ solution (50 mL) was added to the residue. Extraction was carried out using EtOAc (3×75 mL); the combined extracts were washed with water (50 mL) brine (40 mL), dried over anhydrous Na$_2$SO$_4$, filtered and concentrated under reduced pressure. The residue was purified by Combi-Flash (using gradient elution of 0-15% EtOAc in hexane) to afford the desired compound ethyl 1-(3-bromo-2-fluorophenyl)-3-methyl-1H-pyrazole-5-carboxylate I-16b (4.0 g) as a yellow liquid. LCMS (ES) m/z; 327.0 [M+H]$^+$. $^1$H NMR (400 MHz, DMSO-d$_6$) δ 7.62 (td, J$_1$=2.0 Hz, J$_2$=9.2 Hz, 1H); 7.43 (td, J$_1$=2.0 Hz, J$_2$=9.2 Hz, 1H); 7.14 (dd, J$_1$=2.0 Hz, J$_2$=9.2 Hz, 1H); 6.82 (s, 1H); 4.24 (q, J=7.2 Hz, 2H); 2.38 (s, 3H); 1.25 (t, J=7.2 Hz, 3H) and ethyl 1-(3-bromo-2-fluorophenyl)-5-methyl-1H-pyrazole-3-carboxylate I-16b' (6.0 g) as a yellow liquid. LCMS (ES) m/z; 327.0 [M+H]$^+$. $^1$H NMR (400 MHz, DMSO-d$_6$) δ 7.72-7.68 (m, 1H); 7.49-7.45 (m, 1H); 7.21-7.17 (m, 1H); 6.77 (s, 1H); 4.43 (q, J=7.2 Hz, 2H); 2.16 (s, 3H); 1.41 (t, J=7.2 Hz, 3H).

Step-2: (1-(3-bromo-2-fluorophenyl)-3-methyl-1H-pyrazol-5-yl)methanol (I-16c): To a stirred solution of I-16b (3.5 g, 10.7 mmol) in anhydrous THF (25 mL) was added a 1M solution of DIBAL-H (45 mL, 22.9 mmol) drop wise at 0° C. The reaction mixture was then allowed to warm to room temperature over 1 h, while monitoring reaction progress by TLC. After completion, it was cooled to 0° C. and quenched slowly with addition of 10% aqueous solution of citric acid (20 mL). Extraction was carried out using DCM (100 mL×2); the combined organic extracts were washed with brine (50 mL), dried over anhydrous Na$_2$SO$_4$, filtered and concentrated under reduced pressure. The resulting crude was purified by Combi-Flash (using gradient elution of 0-40% EtOAc in hexane) to afford desired compound (1-(3-bromo-2-fluorophenyl)-3-methyl-1H-pyrazol-5-yl) methanol I-16c (3.0 g) as a yellow thick oil. LCMS (ES) m/z; 285.1 [M+H]$^+$.

Step-3: 1-(3-bromo-2-fluorophenyl)-3-methyl-1H-pyrazole-5-carbaldehyde (I-16d): I-16d (2.5 g) was synthesized by following procedure as described for the synthesis of I-5 (step-6) using I-16c (3.0 g, 10.12 mmol) as the starting material. LCMS (ES) m/z; 283.0 [M+H]$^+$.

Step-4: 1-(1-(3-bromo-2-fluorophenyl)-3-methyl-1H-pyrazol-5-yl)-N-methylmethanamine (I-16e): I-16e (2.2 g) was synthesized by following procedure as described for the synthesis of I-8 (step-2) using I-16d (2.5 g, 9.18 mmol) and methyl amine hydrochloride (0.86 g mg, 12.7 mmol) as the starting materials. LCMS (ES) m/z; 298.2 [M+H]$^+$.

Step-5: 6-bromo-2,5-dimethyl-4,5-dihydropyrazolo[1,5-a]quinoxaline (I-16f): To a stirred solution of I-16e (2.2 g, 9.39 mmol) in 1,4-dioxane (10 mL) was added DIPEA (3.1 mL, 18.1 mmol) and the reaction mixture was stirred at 80° C. for 6 h. After completion, it was cooled to room temperature and volatiles were removed under reduced pressure. Water (50 mL) was added to the residue and extraction was carried out using EtOAc (2×50 mL). The combined organic extracts were washed with brine (30 mL), dried over anhydrous Na$_2$SO$_4$, filtered and concentrated under reduced pressure. The residue was purified by Combi-Flash (using gradient elution of 0-50% EtOAc in hexane) to afford the desired compound 6-bromo-2,5-dimethyl-4,5-dihydropyrazolo[1,5-a]quinoxaline I-16f (2.0 g) as a yellow oil. LCMS (ES) m/z; 278.2 [M+H]$^+$.

Step-6: tert-butyl (2,5-dimethyl-4,5-dihydropyrazolo[1,5-a]quinoxalin-6-yl)carbamate (I-16g): I-16g (0.8 g) was synthesized by following procedure as described for the synthesis of I-1 (step-4) using I-16f (2.0 g, 8.01 mmol) as the starting material. LCMS (ES) m/z; 315.4 [M+H]$^+$.

Step-7: 2,5-dimethyl-4,5-dihydropyrazolo[1,5-a]quinoxalin-6-amine (I-16): I-16 (0.5 g) was synthesized by following procedure as described for the synthesis of I-1 (step-5) using I-16g (0.8 g, 4.45 mmol) as the starting material. LCMS (ES) m/z; 215.4 [M+H]$^+$. $^1$H NMR (400 MHz, DMSO-d$_6$) δ 6.93-6.86 (m, 2H); 6.53-6.46 (m, 1H); 6.06 (s, 1H); 5.08 (s, 2H); 4.08 (s, 2H); 2.31 (s, 3H); 2.19 (s, 3H).

Example 17: Preparation of 2,5-dimethyl-4,5-dihydropyrazolo[1,5-a]quinoxalin-4,4-d2-6-amine (I-17)

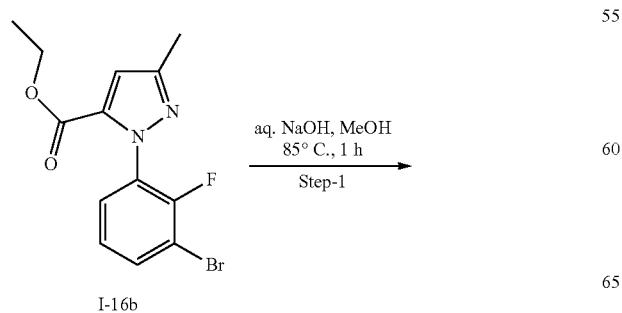

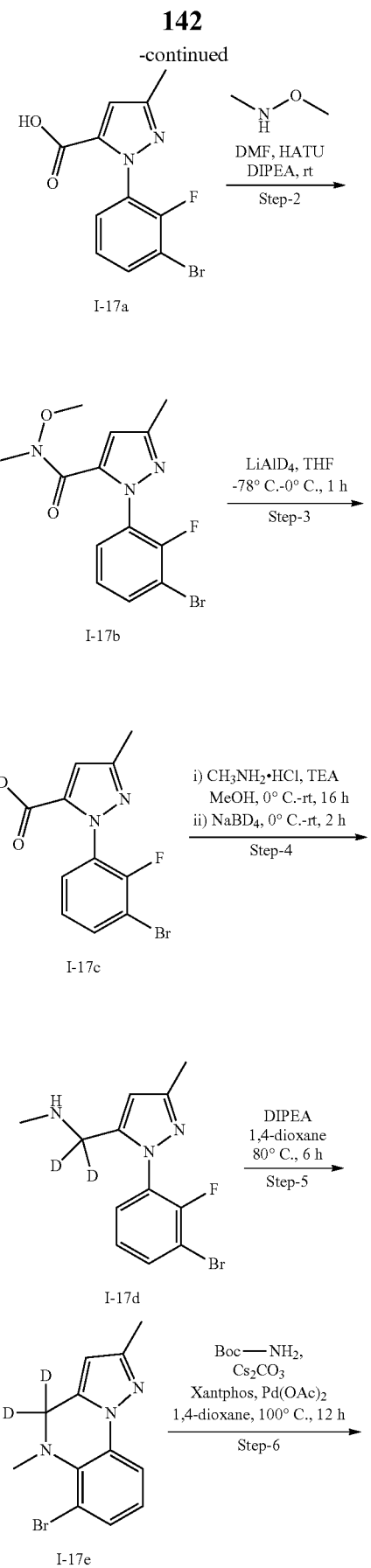

Example 18: Preparation of 2,5-dimethyl-4,5-dihydropyrazolo[1,5-a]pyrido[3,4-e]pyrazin-6-amine (I-88)

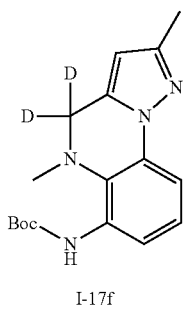
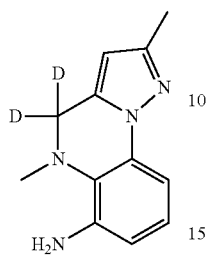
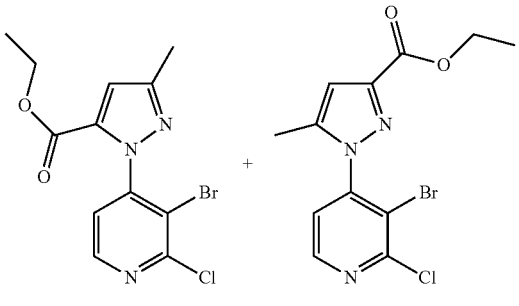

Step-1: 1-(3-bromo-2-fluorophenyl)-3-methyl-1H-pyrazole-5-carboxylic acid (I-17a): I-17a (4.0 g) was synthesized by following procedure as described for the synthesis of I-11 (step-2) using I-16b (4.5 g, 13.8 mmol) as the starting material. LCMS (ES) m/z; 299.0 [M+H]⁺.

Step-2: 1-(3-bromo-2-fluorophenyl)-N-methoxy-N,3-dimethyl-1H-pyrazole-5-carboxamide (I-17b): I-17b (3.5 g) was synthesized by following procedure as described for the synthesis of I-11 (step-3) using I-17a (3.5 g, 11.7 mmol) as the starting material. LCMS (ES) m/z; 342.1 [M+H]⁺.

Step-3: 1-(3-bromo-2-fluorophenyl)-3-methyl-1H-pyrazole-5-carbaldehyde-d (I-17c): I-17c (2.8 g) was synthesized by following procedure as described for the synthesis of I-11 (step-4) using I-17b (3.5 g, 10.2 mmol) as the starting material. LCMS (ES) m/z; 284.0 [M+H]⁺.

Step-4: 1-(1-(3-bromo-2-fluorophenyl)-3-methyl-1H-pyrazol-5-yl)-N-methylmethan-d2-amine (I-17d): I-17d (1.5 g) was synthesized by following procedure as described for the synthesis of I-11 (step-5) using I-17c (3 g, 10.6 mmol) as the starting material. LCMS (ES) m/z; 300.1 [M+H]⁺.

Step-5: 6-bromo-2,5-dimethyl-4,5-dihydropyrazolo[1,5-a]quinoxaline-4,4-d2 (I-17e): I-17e (1.5 g) was synthesized by following procedure as described for the synthesis of I-16 (step-5) using I-17d (2.2 g, 7.33 mmol) as the starting material. LCMS (ES) m/z; 279.9 [M+H]⁺.

Step-6: tert-butyl (2,5-dimethyl-4,5-dihydropyrazolo[1,5-a]quinoxalin-6-yl-4,4-d2)carbamate (1-17f): I-17f (1.2 g) was synthesized by following procedure as described for the synthesis of I-1 (step-4) using I-17e (1.0 g, 3.57 mmol) as the starting material. LCMS (ES) m/z; 317.2 [M+H]⁺.

Step-7: 2,5-dimethyl-4,5-dihydropyrazolo[1,5-a]quinoxalin-4,4-d2-6-amine (I-17): I-17 (1.1 g) was synthesized by following procedure as described for the synthesis of I-1 (step-5) using I-17f (1.5 g, 4.74 mmol) as the starting material. LCMS (ES) m/z; 217.2 [M+H]⁺. ¹H NMR (400 MHz, DMSO-d₆) δ 7.42 (d, J=8.0 Hz, 1H); 7.17 (t, J=8.0 Hz, 1H); 6.95 (d, J=8.0 Hz 1H); 6.14 (s, 1H); 5.12 (s, 2H); 3.14 (s, 3H); 2.25 (s, 3H).

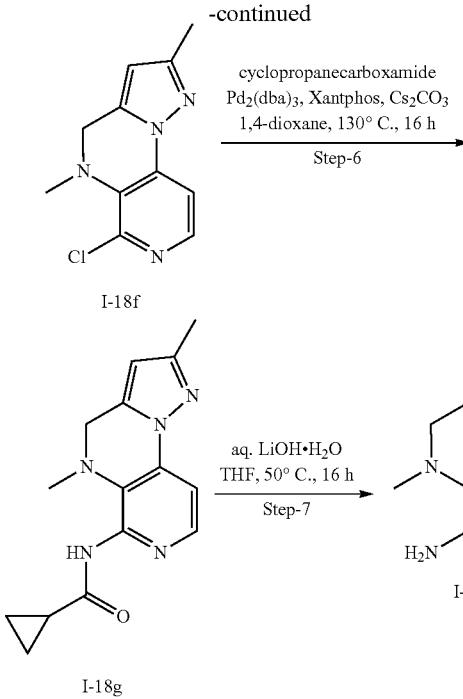

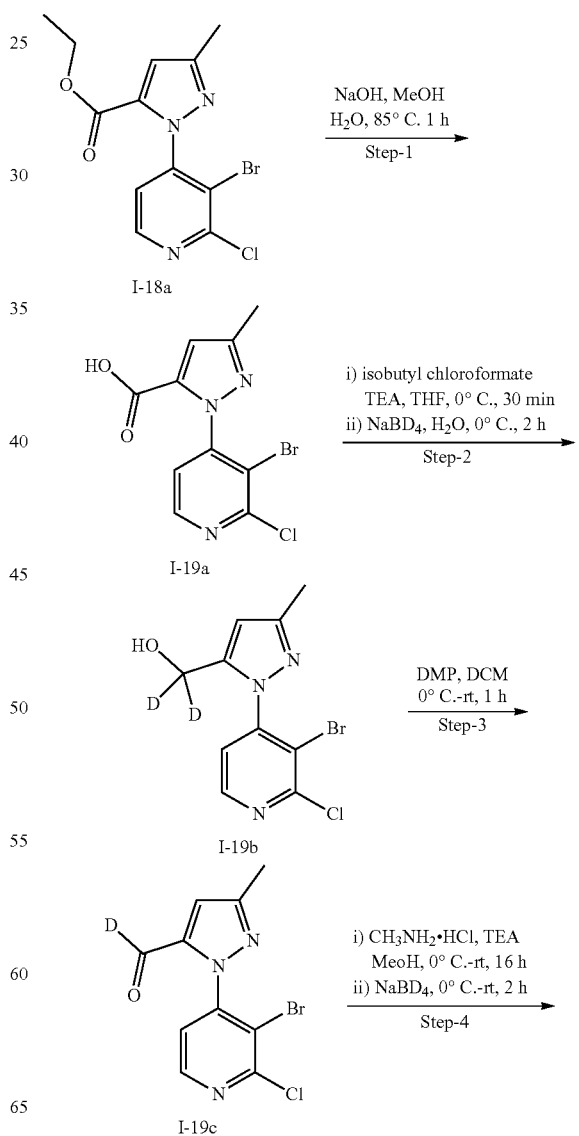

0-80% EtOAc in hexane) to afford the desired compound 6-chloro-2,5-dimethyl-4,5-dihydropyrazolo[1,5-a]pyrido[3,4-e]pyrazine I-18f (0.8 g) as a yellow oil. LCMS (ES) m/z; 235.4 [M+H]+.

Step-6: N-(2,5-dimethyl-4,5-dihydropyrazolo[1,5-a]pyrido[3,4-e]pyrazin-6-yl)cyclopropanecarboxamide (I-18g): I-18g (0.7 g) was synthesized by following procedure as described for the synthesis of I-9 (step-3) using I-18f (1.7 g 7.63 mmol) as the starting material. LCMS (ES) m/z; 284.3 [M+H]+.

Step-7: 2,5-dimethyl-4,5-dihydropyrazolo[1,5-a]pyrido[3,4-e]pyrazin-6-amine (I-18): I-18 (0.4 g) was synthesized by following procedure as described for the synthesis of I-9 (step-4) using I-18g (0.7 g, 2.47 mmol) as the starting material. LCMS (ES) m/z; 216.2 [M+H]+. $^1$H NMR (400 MHz, DMSO-$d_6$) δ 7.74 (d, J=5.2 Hz, 1H); 6.86 (d, J=5.2 Hz, 1H); 6.13 (s, 1H); 5.90 (s, 2H); 4.13 (s, 2H); 2.42 (s, 3H); 2.24 (s, 3H).

Example 19: Preparation of 2,5-dimethyl-4,5-dihydropyrazolo[1,5-a]pyrido[3,4-e]pyrazin-4,4-d2-6-amine (I-19)

Step-1: ethyl 1-(3-bromo-2-chloropyridin-4-yl)-3-methyl-1H-pyrazole-5-carboxylate (I-18a): I-18a (6.0 g) was synthesized by following procedure as described for the synthesis of I-16 (step-1) using I-16a (7.5 mL, 50.3 mmol) and 3-bromo-2-chloro-4-hydrazineylpyridine (12.5 g, 56.2 mmol) as the starting materials. LCMS (ES) m/z; 344.0 [M+H]+. $^1$H NMR (400 MHz, DMSO-$d_6$) δ 8.44 (d, J=4.8 Hz, 1H); 7.29 (d, J=4.8 Hz, 1H); 6.86 (s, 1H); 4.25 (q, J=7.2 Hz, 2H); 2.37 (s, 3H); 1.24 (t, J=7.2 Hz, 3H).

Step-2: (1-(3-bromo-2-chloropyridin-4-yl)-3-methyl-1H-pyrazol-5-yl)methanol (I-18c): I-18c (1.9 g) was synthesized by following procedure as described for the synthesis of I-16 (step-2) using I-18a (3.0 g, 8.71 mmol) as the starting materials. LCMS (ES) m/z; 302.2 [M+H]+.

Step-3: 1-(3-bromo-2-chloropyridin-4-yl)-3-methyl-1H-pyrazole-5-carbaldehyde (I-38d): I-18d (3.2 g) was synthesized by following procedure as described for the synthesis of I-5 (step-6) using I-18c (3.4 g, 11.24 mmol) as the starting material. LCMS (ES) m/z; 300.5 [M+H]+.

Step-4: 1-(1-(3-bromo-2-chloropyridin-4-yl)-3-methyl-1H-pyrazol-5-yl)-N-methylmethanamine (I-18e): I-18e (3.0 g) was synthesized by following procedure as described for the synthesis of I-8 (step-2) using I-18d (3.0 g, 9.98 mmol) and methyl amine hydrochloride (2.02 g, 29.9 mmol) as the starting materials. LCMS (ES) m/z; 314.9 [M+H]+.

Step-5: 6-chloro-2,5-dimethyl-4,5-dihydropyrazolo[1,5-a]pyrido[3,4-e]pyrazine (I-18f): Argon gas was purged through a stirred suspension of I-18e (1.0 g, 3.17 mmol) and CsOAc (1.22 g, 6.34 mmol) in DMSO (10 mL) for 15 min. To this was then added copper powder (20.1 mg, 0.317 mmol) at room temperature and the reaction mixture was then stirred at 100° C. for 16 h in a sealed tube. It was then cooled to room temperature and saturated NaHCO$_3$ solution (30 mL) was added to it. Extraction was carried out using EtOAc (3×50 mL); the combined extracts were washed with water (50 mL) brine (40 mL), dried over anhydrous Na$_2$SO$_4$, filtered and concentrated under reduced pressure. The residue was purified by Combi-Flash (using gradient elution of -continued

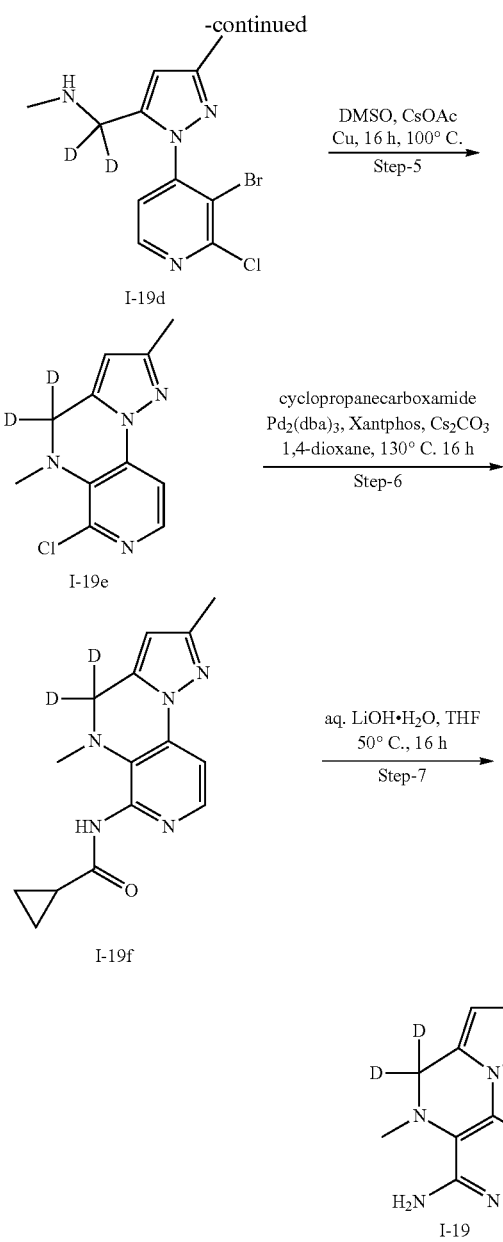

trated under reduced pressure. The resulting crude was purified by Combi-Flash (using gradient elution of 0-30% EtOAc in hexane) to afford desired compound (1-(3-bromo-2-chloropyridin-4-yl)-3-methyl-1H-pyrazol-5-yl)methan-d2-ol I-19b (3.5 g) as an off-white solid. LCMS (ES) m/z; 304.4 [M+H]$^+$.

Step-3: 1-(2-bromo-3-fluoropyridin-4-yl)-3-methyl-1H-pyrazole-5-carbaldehyde-d (I-19c): I-19c (1.4 g) was synthesized by following procedure as described for the synthesis of I-5 (step-6) using I-19b (2.3 g, 7.55 mmol) as the starting material. LCMS (ES) m/z; 285.1 [M+H]$^+$.

Step-4: 1-(1-(3-bromo-2-chloropyridin-4-yl)-3-methyl-1H-pyrazol-5-yl)-N-methylmethan-d2-amine (I-19d): I-19d (1.2 g) was synthesized by following procedure as described for the synthesis of I-11 (step-5) using I-19c (1.1 g, 3.65 mmol) as the starting material. LCMS (ES) m/z; 317.1 [M+H]$^+$.

Step-5: 6-chloro-2,5-dimethyl-4,5-dihydropyrazolo[1,5-a]pyrido[3,4-e]pyrazine-4,4-d2 (I-19e): I-19e (2.0 g) was synthesized by following procedure as described for the synthesis of I-18 (step-5) using I-19d (2.6 g, 8.19 mmol) as the starting material. LCMS (ES) m/z; 237.4 [M+H]$^+$.

Step-6: N-(2,5-dimethyl-4,5-dihydropyrazolo[1,5-a]pyrido[3,4-e]pyrazin-6-yl-4,4-d2)cyclopropanecarboxamide (I-19f): I-19f (1.8 g) was synthesized by following procedure as described for the synthesis of I-9 (step-3) using I-19e (2.0 g, 13.01 mmol) and cyclopropanecarboxamide (0.65 g, 7.6 mmol) as the starting materials. LCMS (ES) m/z; 286.4 [M+H]$^+$.

Step-7: 2,5-dimethyl-4,5-dihydropyrazolo[1,5-a]pyrido[3,4-e]pyrazin-4,4-d2-6-amine (I-19): I-19 (0.8 g) was synthesized by following procedure as described for the synthesis of I-9 (step-4) using I-19f (1.8 g, 6.31 mmol) as the starting material. LCMS (ES) m/z; 218.4 [M+H]$^+$. $^1$H NMR (400 MHz, DMSO-d$_6$) δ 7.92 (d, J=5.6 Hz, 1H); 7.18 (d, J=5.6 Hz, 1H); 6.06 (s, 1H); 4.99 (s, 2H); 2.56 (s, 3H); 2.39 (s, 3H).

Example 20: Preparation of 5-methyl-4,5-dihydropyrazolo[1,5-a]quinoxalin-4,4-d2-6-amine (I-20)

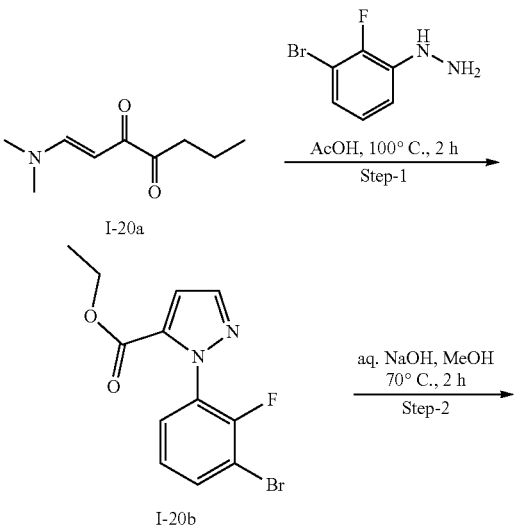

Step-1: 1-(3-bromo-2-chloropyridin-4-yl)-3-methyl-1H-pyrazole-5-carboxylic acid (I-19a): I-19a (6.5 g) was synthesized by following procedure as described for the synthesis of I-11 (step-2) using I-18a (12.0 g, 51.03 mmol) as the starting material. LCMS (ES) m/z; 316.4 [M+H]$^+$.

Step-2: (1-(3-bromo-2-chloropyridin-4-yl)-3-methyl-1H-pyrazol-5-yl)methan-d2-ol (I-19b): To stirred solution of I-19a (6.0 g, 17.4 mmol) in THF (50 mL) were added TEA (7.33 mL, 52.1 mmol) and isobutyl chloroformate (5.65 mL, 43.4 mmol) at 0° C. It was then allowed to stir for 30 min. After complete consumption of starting material, the reaction mixture was filtered through celite bed and the resulting filtrate was then added drop wise to a solution of NaBD$_4$ (1.2 g, 26.1 mmol) in water (5 ml) at 0° C. The reaction mixture was then allowed to stir at room temperature for 1 h. After completion, saturated NH$_4$Cl solution (50 mL) was added to it and extraction was carried out using EtOAc (70 mL×3). The combined organic extracts were washed with brine (50 mL), dried over anhydrous Na$_2$SO$_4$, filtered and concen- -continued

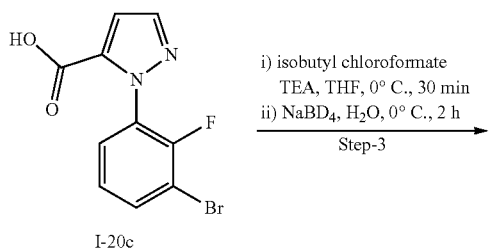

I-20c i) isobutyl chloroformate
TEA, THF, 0° C., 30 min
ii) NaBD₄, H₂O, 0° C., 2 h
Step-3

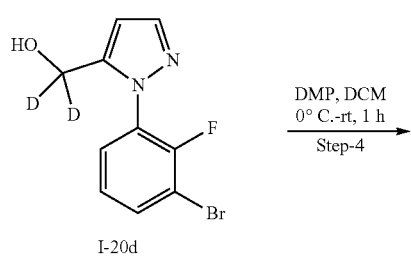

I-20d

DMP, DCM
0° C.-rt, 1 h
Step-4

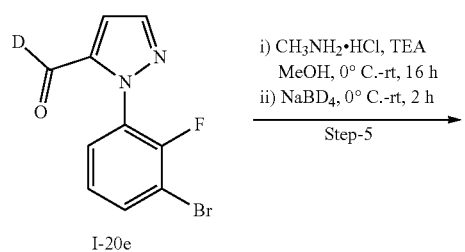

I-20e i) CH₃NH₂·HCl, TEA
MeOH, 0° C.-rt, 16 h
ii) NaBD₄, 0° C.-rt, 2 h
Step-5

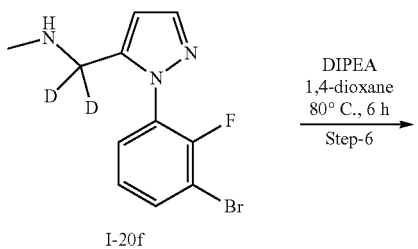

I-20f

DIPEA
1,4-dioxane
80° C., 6 h
Step-6

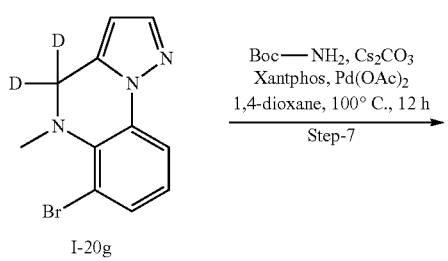

I-20g

Boc—NH₂, Cs₂CO₃
Xantphos, Pd(OAc)₂
1,4-dioxane, 100° C., 12 h
Step-7

-continued

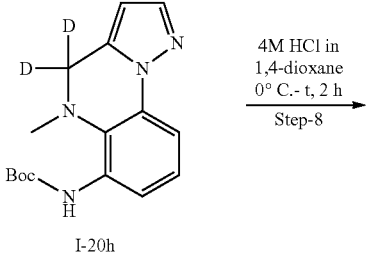

I-20h

4M HCl in
1,4-dioxane
0° C.-t, 2 h
Step-8

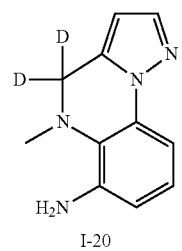

I-20

Step-1: ethyl 1-(3-bromo-2-fluorophenyl)-1H-pyrazole-5-carboxylate (I-20b): I-20b (7.5 g) was synthesized by following procedure as described for the synthesis of I-16 (step-1) using I-20a (6.68 g, 39.0 mmol) and (3-bromo-2-fluorophenyl)hydrazine (8.0 g, 39.0 mmol) as the starting materials. LCMS (ES) m/z; 313.2 [M+H]⁺.

Step-2: 1-(3-bromo-2-fluorophenyl)-1H-pyrazole-5-carboxylic acid (I-20c): I-20c (6.2 g) was synthesized by following procedure as described for the synthesis of I-17 (step-1) using I-20b (6.5 g, 21.7 mmol) as the starting material. LCMS (ES) m/z; 285.0 [M+H]⁺.

Step-3: (1-(3-bromo-2-fluorophenyl)-1H-pyrazol-5-yl)methan-d2-ol (I-20d): I-20d (4.3 g) was synthesized by following procedure as described for the synthesis of I-19 (step-2) using I-20c (6.2 g, 21.7 mmol) as the starting material. LCMS (ES) m/z; 273.2 [M+H]⁺.

Step-4: 1-(3-bromo-2-fluorophenyl)-1H-pyrazole-5-carbaldehyde-d (I-20e): I-20e (2.1 g) was synthesized by following procedure as described for the synthesis of I-5 (step-6) using I-20d (4.3 g, 15.7 mmol) as the starting material. LCMS (ES) m/z; 270.0 [M+H]⁺.

Step-5: 1-(1-(3-bromo-2-fluorophenyl)-1H-pyrazol-5-yl)-N-methylmethan-d2-amine (I-20f): I-20f (2.0 g) was synthesized by following procedure as described for the synthesis of I-11 (step-5) using I-20e (2.1 g, 7.78 mmol) as the starting material. LCMS (ES) m/z; 286.1 [M+H]⁺.

Step-6: 6-bromo-5-methyl-4,5-dihydropyrazolo[1,5-a]quinoxaline-4,4-d2 (I-20g): I-20g (1.7 g) was synthesized by following procedure as described for the synthesis of I-16 (step-5) using I-20f (2.0 g, 6.99 mmol) as the starting material. LCMS (ES) m/z; 266.1 [M+H]⁺.

Step-7: tert-butyl (5-methyl-4,5-dihydropyrazolo[1,5-a]quinoxalin-6-yl-4,4-d2)carbamate (I-20h): I-20h (1.3 g) was synthesized by following procedure as described for the synthesis of I-1 (step-4) using I-20g (1.7 g, 6.39 mmol) as the starting material. LCMS (ES) m/z; 303.1 [M+H]⁺.

Step-8: 5-methyl-4,5-dihydropyrazolo[1,5-a]quinoxalin-4,4-d2-6-amine (I-20): I-20 (0.8 g) was synthesized by following procedure as described for the synthesis of I-1 (step-5) using I-20h (1.3 g 4.3 mmol) as the starting material. LCMS (ES) m/z; 203.1 [M+H]⁺. ¹H NMR (400 MHz, DMSO-d₆) δ 7.65 (d, J=1.6 Hz, 1H); 7.00 (dd, J₁=1.2 Hz, J₂=7.6 Hz, 1H); 6.92 (t, J=8.0 Hz, 1H); 6.54 (dd, J₁=1.2 Hz, J₂=8.0 Hz, 1H); 6.28 (d, J=1.6 Hz, 1H); 5.13 (s, 2H); 2.36 (s, 3H).

Example 21: Preparation of 5-methyl-2-(trifluoromethyl)-4,5-dihydropyrazolo[1,5-a]quinoxalin-6-amine (I-21)

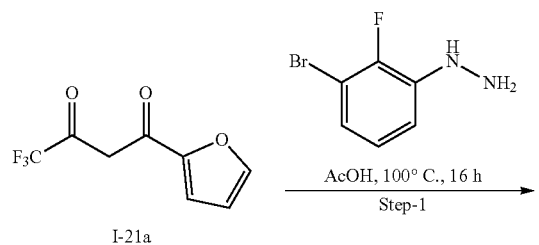

I-21a

AcOH, 100° C., 16 h
Step-1

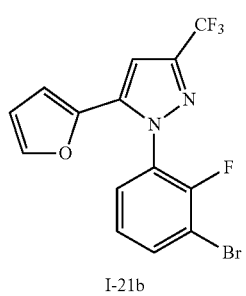

I-21b

+

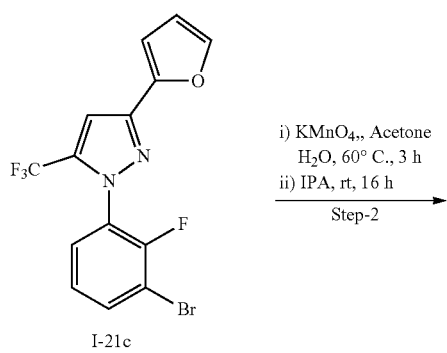

I-21c i) KMnO$_4$, Acetone
H$_2$O, 60° C., 3 h
ii) IPA, rt, 16 h
Step-2

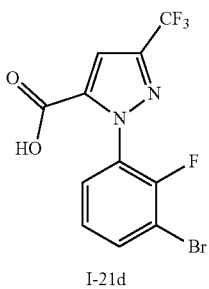

I-21d

+

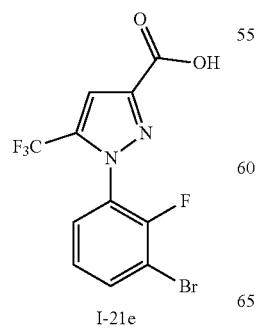

I-21e

-continued

I-21d
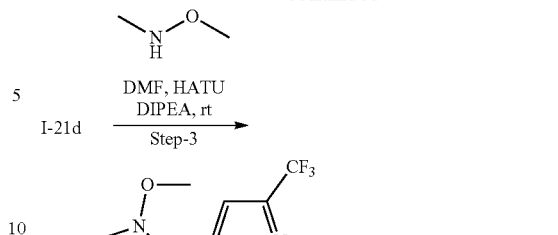
DMF, HATU
DIPEA, rt
Step-3

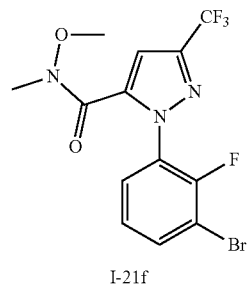 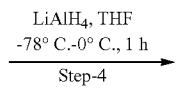

I-21f

LiAlH$_4$, THF
−78° C.-0° C., 1 h
Step-4

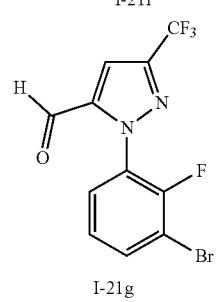 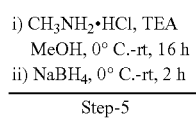

I-21g i) CH$_3$NH$_2$·HCl, TEA
MeOH, 0° C.-rt, 16 h
ii) NaBH$_4$, 0° C.-rt, 2 h
Step-5

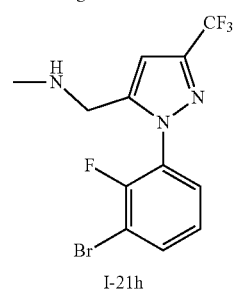 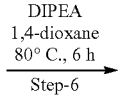

I-21h

DIPEA
1,4-dioxane
80° C., 6 h
Step-6

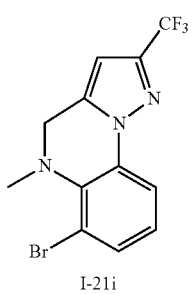 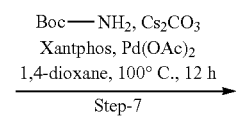

I-21i

Boc—NH$_2$, Cs$_2$CO$_3$
Xantphos, Pd(OAc)$_2$
1,4-dioxane, 100° C., 12 h
Step-7

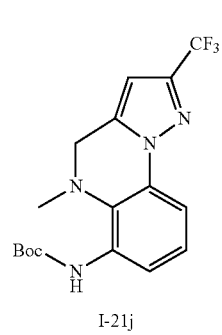 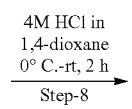

I-21j

4M HCl in
1,4-dioxane
0° C.-rt, 2 h
Step-8

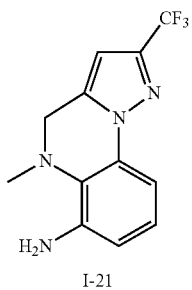

I-21

Step-1: 1-(3-bromo-2-fluorophenyl)-5-(furan-2-yl)-3-(trifluoromethyl)-1H-pyrazole (I-21b) and 1-(3-bromo-2-fluorophenyl)-3-(furan-2-yl)-5-(trifluoromethyl)-1H-pyrazole (I-21c): To a stirred solution of I-21a (15.1 g, 73.2 mmol) in AcOH (150 mL) was added (3-bromo-2-fluorophenyl)hydrazine (10 g, 48.8 mmol) at room temperature and the reaction mixture was the stirred at 100° C. for 4 h. After completion, volatiles were removed under vacuum and water (100 mL) was added to the residue. Extraction was carried out using EtOAc (70 mL×3); the combined extracts were washed with water brine (100 ml), dried over anhydrous Na$_2$SO$_4$ and concentrated under reduced pressure. The residue was purified by Combi-Flash (using gradient elution of 0-20% EtOAc in Heptane) to get an inseparable mixture of 1-(3-bromo-2-fluorophenyl)-5-(furan-2-yl)-3-(trifluoromethyl)-1H-pyrazole I-21b and 1-(3-bromo-2-fluorophenyl)-3-(furan-2-yl)-5-(trifluoromethyl)-1H-pyrazole I-21c (17 g) as an orange liquid. LCMS (ES) m/z; 375.1 [M+1]+.

Step-2: 1-(3-bromo-2-fluorophenyl)-3-(trifluoromethyl)-1H-pyrazole-5-carboxylic acid (I-21d) and 1-(3-bromo-2-fluorophenyl)-5-(trifluoromethyl)-1H-pyrazole-3-carboxylic acid (I-21e): To a stirred solution of I-41b+I-41c (17 g, 45.3 mmol) in acetone (200 mL) and water (200 mL) was added potassium permanganate (50.1 g, 317 mmol) portion wise at 0° C. The reaction mixture was stirred at 60° C. for 3 h. After complete consumption of starting material, it was cooled to room temperature and IPA (100 mL) was added to it. It was the stirred at room temperature for 16 h. The reaction mixture was then filtered through celite bed and washed with EtOAc (50 mL). The filtrate was concentrated under reduced pressure and the resulting residue was acidified to pH 2 using 1N HCl. Extraction was carried out using EtOAc (60 mL×2); the combined extracts were washed with water brine (50 ml), dried over anhydrous Na$_2$SO$_4$ and concentrated under reduced pressure. The residue was purified by Combi-Flash (using gradient elution of 0-70% EtOAc in Heptane) to get the desired compound 1-(3-bromo-2-fluorophenyl)-3-(trifluoromethyl)-1H-pyrazole-5-carboxylic acid I-21d (6.0 g) as a pale yellow solid. LCMS (ES) m/z; 353.0 [M+H]+. $^1$H NMR (400 MHz, DMSO-d$_6$) δ 14.14 (s, 1H); 7.93-7.90 (m, 1H); 7.70 (t, J=6.8 Hz 1H); 7.58 (s, 1H); 7.34 (t, J=7.2 Hz, 1H) and 1-(3-bromo-2-fluorophenyl)-5-(trifluoromethyl)-1H-pyrazole-3-carboxylic acid I-21e (2.3 g) as a yellow solid. LCMS (ES) m/z; 353.0 [M+H]+.

Step-3: 1-(3-bromo-2-fluorophenyl)-N-methoxy-N-methyl-3-(trifluoromethyl)-1H-pyrazole-5-carboxamide (I-21f): I-21f (6.0 g) was synthesized by following procedure as described for the synthesis of I-11 (step-3) using I-21d (6.0 g, 17 mmol) as the starting material. LCMS (ES) m/z; 396.0 [M+H]+.

Step-4: 1-(3-bromo-2-fluorophenyl)-3-(trifluoromethyl)-1H-pyrazole-5-carbaldehyde (I-21g): I-21g (3.0 g) was synthesized by following procedure as described for the synthesis of I-11 (step-4) using I-21f (6.0 g, 15.1 mmol) as the starting material. LCMS (ES) m/z; 337.0 [M+H]+.

Step-5: 1-(1-(3-bromo-2-fluorophenyl)-3-(trifluoromethyl)-1H-pyrazol-5-yl)-N-methylmethanamine (I-21h): I-21h (3.0 g) was synthesized by following procedure as described for the synthesis of I-8 (step-2) using I-21g (3.0 g, 8.9 mmol) as the starting material. LCMS (ES) m/z; 352.1 [M+H]+.

Step-6: 6-bromo-5-methyl-2-(trifluoromethyl)-4,5-dihydropyrazolo[1,5-a]quinoxaline (I-21i): I-21i (2.0 g) was synthesized by following procedure as described for the synthesis of I-16 (step-5) using I-21g (3.0 g, 8.52 mmol) as the starting material. LCMS (ES) m/z; 332.1 [M+H]+.

Step-7: tert-butyl (5-methyl-2-(trifluoromethyl)-4,5-dihydropyrazolo[1,5-a]quinoxalin-6-yl)carbamate (I-21j): I-21j (1.5 g) was synthesized by following procedure as described for the synthesis of I-1 (step-4) using I-21i (2.0 g, 6.02 mmol) as the starting material. LCMS (ES) m/z; 369.2 [M+H]+.

Step-8: 5-methyl-2-(trifluoromethyl)-4,5-dihydropyrazolo[1,5-a]quinoxalin-6-amine (I-21): I-21 (0.7 g) was synthesized by following procedure as described for the synthesis of I-1 (step-5) using I-21j (1.5 g, 4.07 mmol) as the starting material. LCMS (ES) m/z; 269.1 [M+H]+. $^1$H NMR (400 MHz, DMSO-d$_6$) δ 7.02-6.95 (m, 2H); 6.77 (s, 1H); 6.63 (d, J=7.6 Hz 1H); 5.25 (s, 2H); 4.23 (s, 2H); 2.39 (s, 3H).

Example 22: Preparation of 4,6-dichloro-N-methylpyridazine-3-carboxamide (A-1)

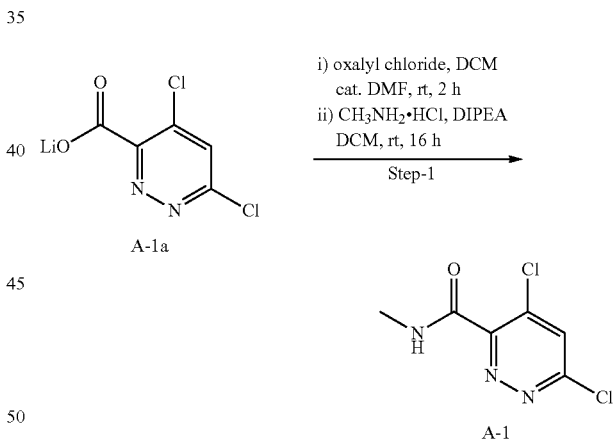

To a stirred solution of A-1a (10.0 g, 50.3 mmol) in anhydrous DCM (100 mL) was added catalytic amount of DMF (2 to 3 drops) and oxalyl chloride (9.11 mL, 101.0 mmol) drop wise at 0° C. The reaction mixture was then allowed to warm to room temperature over 2 h. After completion, volatiles were removed under reduced pressure and the residue was dried. It was then dissolved in anhydrous DCM (50 mL) and added to a stirred solution of methylamine hydrochloride (5.09 g, 75.4 mmol) and DIPEA (13.2 mL, 75.4 mmol) in DCM (50 mL) at 0° C. under nitrogen atmosphere. The reaction mixture was then stirred at room temperature for 16 h. Water (50 mL) was then added to it and the organic layer was separated. It was then washed with saturated NaHCO$_3$ solution (30 mL), brine (50 mL), dried over anhydrous Na$_2$SO$_4$, filtered and concentrated under reduced pressure. The residue was then purified by Combi-Flash (using gradient elution of 0-40% EtOAc in hexane) to afford desired compound 4,6-dichloro-N-methylpyridazine-3-carboxamide A-1 (3.2 g) as an off-white solid. LCMS (ES) m/z; 206.0 [M+H]$^+$.

Example 23: Preparation of 4,6-dichloro-N-(methyl-d3)pyridazine-3-carboxamide (A-2)

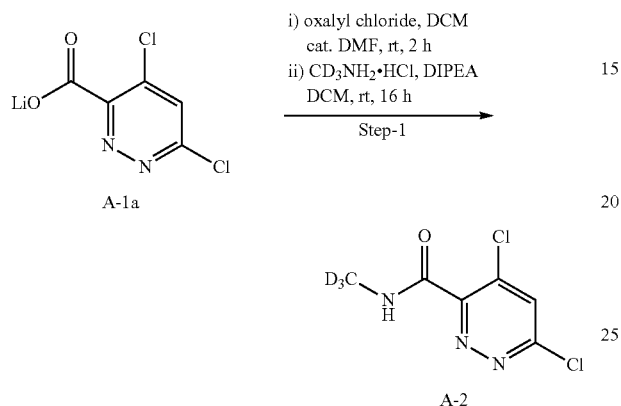

To a stirred solution of A-1a (5.0 g, 25.1 mmol) in anhydrous DCM (40 mL) was added catalytic amount of DMF (2 to 3 drops) and oxalyl chloride (4.6 mL, 50.3 mmol) drop wise at 0° C. The reaction mixture was then allowed to warm to room temperature over 2 h. After completion, volatiles were removed under reduced pressure and the residue was dried. It was then dissolved in anhydrous DCM (25 mL) and added to a stirred solution of methan-d$_3$-amine hydrochloride (2.13, 30.2 mmol) and DIPEA (13.2 mL, 75.4 mmol) in anhydrous DCM (25 mL) at 0° C. under nitrogen atmosphere. The reaction mixture was then stirred at room temperature for 16 h. Water (50 mL) was then added to it and the organic layer was separated. It was then washed with saturated NaHCO$_3$ solution (30 mL), brine (50 mL), dried over anhydrous Na$_2$SO$_4$, filtered and concentrated under reduced pressure. The residue was then purified by Combi-Flash (using gradient elution of 0-40% EtOAc in hexane) to afford desired compound 4,6-dichloro-N-(methyl-d3)pyridazine-3-carboxamide A-2 (2.6 g) as an off-white solid. LCMS (ES) m/z; 209.0 [M+H]$^+$.

Example 24: Preparation of 4,6-dichloro-N-(methyl-d3)nicotinamide (A-3)

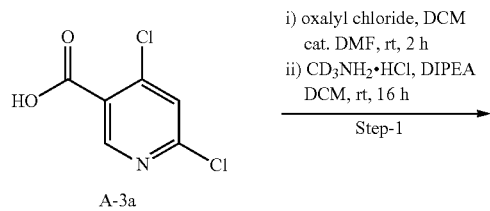

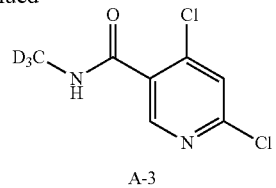

A-3 (2.6 g) was synthesized as described for the synthesis of A-2 using A-3a (3 g) as the starting material. LCMS (ES) m/z 208.0 [M+H]$^+$.

Example 25: Preparation of 4,6-dichloropyridazine-3-carboxamide (A-4)

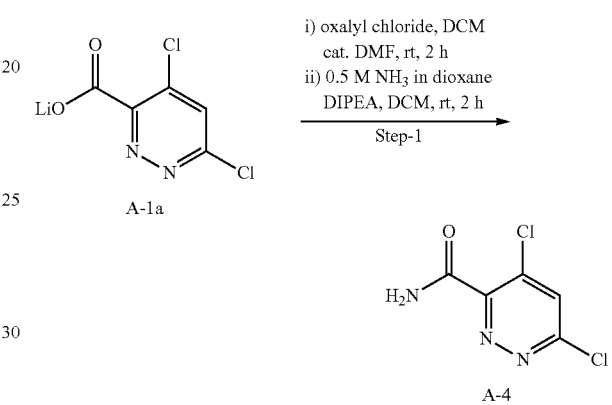

To a stirred solution of A-1a (2.5 g, 12.6 mmol) in anhydrous DCM (50 mL) was added catalytic amount of DMF (2 to 3 drops) and oxalyl chloride (2.5 mL, 25.1 mmol) drop wise at 0° C. The reaction mixture was then allowed to warm to room temperature over 2 h. After completion, volatiles were removed under reduced pressure and the residue was dried. It was then dissolved in anhydrous DCM (25 mL) and added to a stirred solution of 0.5 M ammonia in dioxane (10.0 mL and DIPEA (6.5 mL, 37.3 mmol) in anhydrous DCM (25 mL) at 0° C. under nitrogen atmosphere. The reaction mixture was then stirred at room temperature for 2 h. Water (50 mL) was then added to it and the organic layer was separated. It was then washed with saturated NaHCO$_3$ solution (30 mL), brine (50 mL), dried over anhydrous Na$_2$SO$_4$, filtered and concentrated under reduced pressure. The residue was then purified by Combi-Flash (using gradient elution of 0-60% EtOAc in hexane) to afford desired compound 4,6-dichloropyridazine-3-carboxamide A-4 (4.2 g) as an off-white solid. LCMS (ES) m/z; 193.0 [M+H]$^+$.

Example 26: Preparation of 4,6-dichloro-N-methylnicotinamide (A-5)

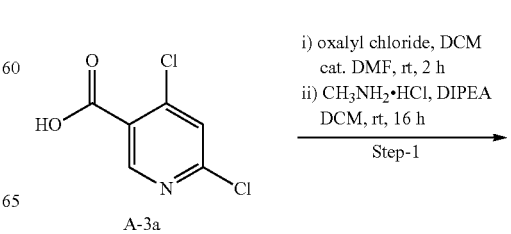

-continued

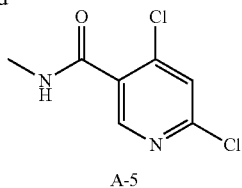

A-5 (2.5 g) was synthesized as described for the synthesis of A-1 using A-3a (3 g) as the starting material. LCMS (ES) m/z; 204.9 [M+H]⁺.

Example 27: Preparation of 4,6-dichloronicotinamide (A-6)

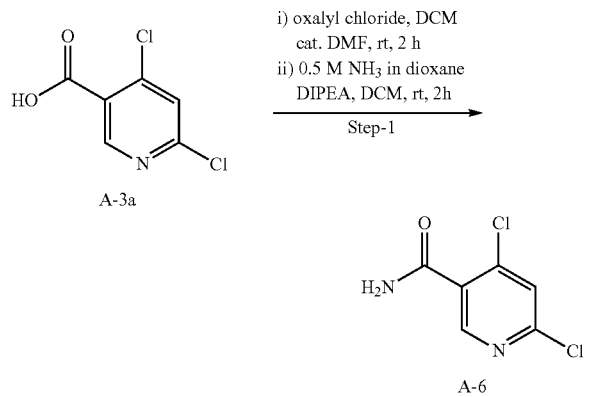

A-6 (0.14 g) was synthesized as described for the synthesis of A-4 using A-3a (0.25 g) as the starting material. LCMS (ES) m/z; 190.9 [M+H]⁺.

Example 28: Preparation of 4-bromo-6-chloro-N-(methyl-d3)nicotinamide (A-7)

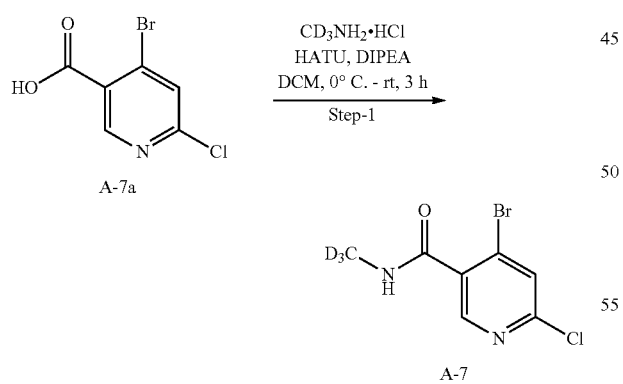

To a stirred solution of A-7a (4.75 g, 20.1 mmol) in DCM (15 mL) was added HATU (11.5 g, 30.1 mmol) and DIPEA (10.4 mL, 60.3 mmol) at 0° C. To this was then added methan-d₃-amine hydrochloride (1.7 g, 24.1 mmol) and the reaction mixture was allowed to stir at room temperature for 3 h. After completion, water (50 mL) was added to it and extraction was carried out using DCM (75 mL×2). The combined organic extracts were washed with brine (50 mL), dried over anhydrous Na₂SO₄, filtered and concentrated under vacuum. The resulting crude was purified by Combi-Flash (using gradient elution 0-20% EtOAc in Heptane) to afford desired compound 4-bromo-6-chloro-N-(methyl-d3) nicotinamide A-7 (3.1 g) as an off-white solid. LCMS (ES) m/z; 252.0 [M+H]⁺.

Example 29: Preparation of 6-((5-fluoropyridin-2-yl)amino)-N-methyl-4-((2-methyl-2,4-dihydro-chromeno[4,3-c]pyrazol-6-yl)amino)pyridazine-3-carboxamide (Compound 1)

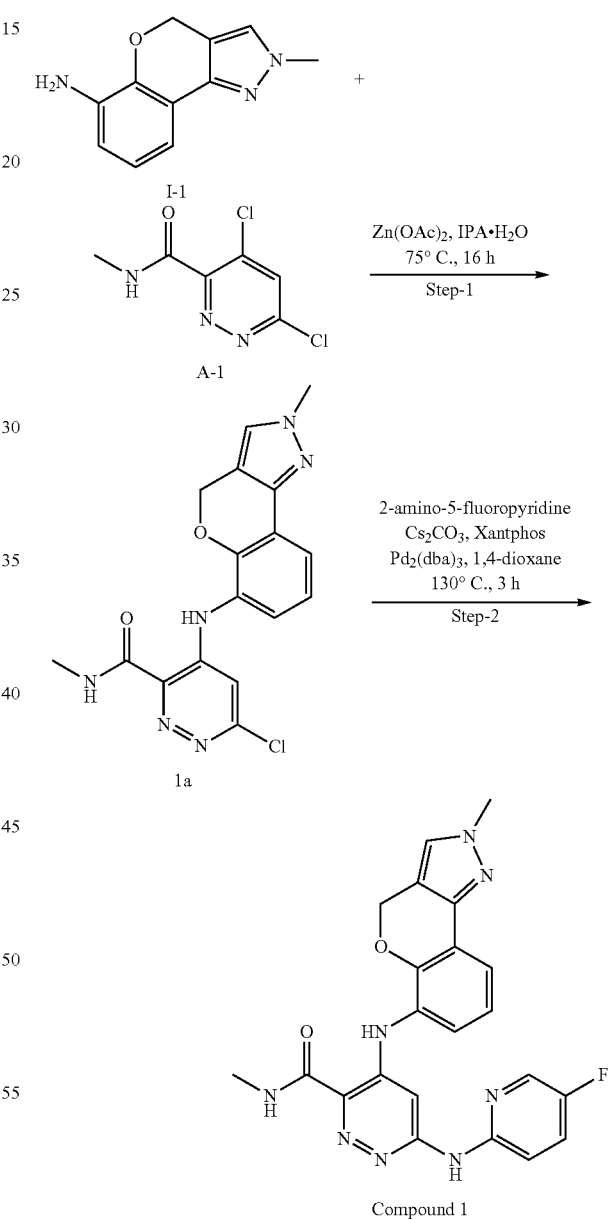

Step-1: 6-chloro-N-methyl-4-({2-methyl-2H,4H-chromeno[4,3-c]pyrazol-6-yl}amino)pyridazine-3-carboxamide (1a): To a stirred solution of I-1 (0.52 g, 2.58 mmol) and A-1 (0.639 g, 3.10 mmol) in propan-2-ol (3.00 mL) and water (2.00 mL) was added Zn(OAc)₂ (0.759 g, 4.13 mmol) at room temperature. The reaction mixture was then stirred at 75° C. for 16 h in a sealed tube. The progress of the reaction was monitored by LCMS. After complete consumption of starting material, it was cooled to room temperature and stirred for 1 h. The obtained solid was filtered, washed with water (5 mL×2) and dried (co-evaporation with toluene). It was further stirred in diethyl ether (20.0 mL), filtered and dried to afford desired compound 6-chloro-N-methyl-4-({2-methyl-2H,4H-chromeno[4,3-c]pyrazol-6-yl}amino)pyridazine-3-carboxamide 1a (0.48 g) as an off white solid. LCMS (ES) m/z; 371.1 [M+H]$^+$. $^1$H NMR (400 MHz, DMSO-d$_6$) δ 10.71 (s, 1H); 9.31-9.30 (m, 1H); 7.58 (s, 1H); 7.49 (d, J=6.4 Hz, 1H); 7.38 (d, J=6.8 Hz, 1H); 7.12-7.05 (m, 2H); 5.30 (s, 2H); 3.87 (s, 3H); 2.83 (d, J=4.8 Hz, 3H).

Step-2: 6-[(5-fluoropyridin-2-yl) amino]-N-methyl-4-({2-methyl-2H,4H-chromeno[4,3-c]pyrazol-6-yl}amino)pyridazine-3-carboxamide (Compound 1): Argon gas was purged through a stirred suspension of 1a (0.4 g, 1.08 mmol), 5-fluoropyridin-2-amine (0.181 g, 1.62 mmol) and Cs$_2$CO$_3$ (0.703 g, 2.16 mmol) in 1,4-dioxane (6.00 mL) for 15 min. To this was then added [5-(diphenylphosphanyl)-9,9-dimethyl-9H-xanthen-4-yl]diphenylphosphane (0.125 g, 0.216 mmol) and Pd$_2$(dba)$_3$ (0.198 g, 0.216 mmol). The reaction mixture was then stirred at 130° C. for 3 h in a sealed tube. The reaction progress was monitored by TLC. After complete consumption of starting material, it was cooled to room temperature and filtered through Celite bed. It was washed with EtOAc (50 mL×2) and the filtrate was concentrated under reduced pressure. The residue was purified by Combi-Flash (using gradient elution of 0-5% MeOH in DCM) to afford desired compound 6-[(5-fluoropyridin-2-yl)amino]-N-methyl-4-({2-methyl-2H,4H-chromeno[4,3-c]pyrazol-6-yl}amino)pyridazine-3-carboxamide (1, 0.280 g) as an off-white solid. LCMS (ES) m/z; 447.2 [M+H]$^+$. $^1$H NMR (400 MHz, DMSO-d$_6$) δ 10.64 (s, 1H); 10.14 (s, 1H); 9.08-9.02 (m, 1H); 8.11 (d, J=2.4 Hz, 1H); 7.83 (s, 1H); 7.75-7.65 (m, 2H); 7.60 (s, 1H); 7.46-7.39 (m, 2H); 7.10 (t, J=8 Hz, 1H); 5.35 (s, 2H); 3.90 (s, 3H); 2.85 (d, J=4.8 Hz, 3H).

Example 30: Preparation of 6-(cyclopropanecarboxamido)-N-methyl-4-((2-methyl-2,4-dihydrochromeno [4,3-c]pyrazol-6-yl)amino)pyridazine-3-carboxamide (Compound 2)

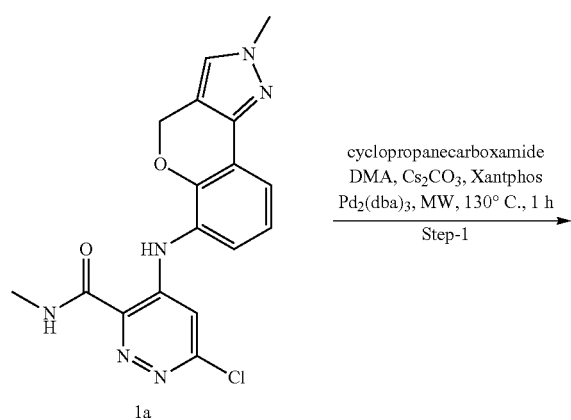

1a cyclopropanecarboxamide
DMA, Cs$_2$CO$_3$, Xantphos
Pd$_2$(dba)$_3$, MW, 130° C., 1 h
——————————→
Step-1

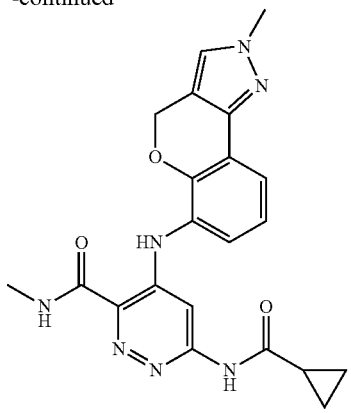

Compound 2

Step-1: 6-(cyclopropanecarboxamido)-N-methyl-4-((2-methyl-2,4-dihydrochromeno[4,3-c]pyrazol-6-yl)amino)pyridazine-3-carboxamide (Compound 2): Argon gas was purged through a stirred suspension of 6-chloro-N-methyl-4-({2-methyl-2H,4H-chromeno[4,3-c]pyrazol-6-yl}amino)pyridazine-3-carboxamide 1a (0.15 g, 0.405 mmol), cyclopropanecarboxamide (0.068 g., 0.809 mmol) and Cs$_2$CO$_3$ (0.264 g, 0.809 mmol) in DMA (2.00 mL) for 15 min. To this was then added [5-(diphenylphosphanyl)-9,9-dimethyl-9H-xanthen-4-yl]diphenylphosphane (0.047 g, 0.081 mmol) and Pd$_2$(dba)$_3$ (0.074 g, 0.081 mmol). The reaction mixture was then irradiated at 130° C. for 1 h in a MW reactor. After completion, it was cooled to room temperature and filtered through Celite bed. It was washed with EtOAc (50 mL×2). The filtrate was concentrated under reduced pressure and the residue was purified by Combi-Flash (using gradient elution of 0-5% MeOH in DCM) to afford 6-(cyclopropanecarboxamido)-N-methyl-4-((2-methyl-2,4-dihydrochromeno[4,3-c]pyrazol-6-yl)amino)pyridazine-3-carboxamide (2, 32 mg) as an off-white solid. LCMS (ES) m/z; 420.3 [M+H]$^+$. $^1$H NMR (400 MHz, DMSO-d$_6$) δ 11.24 (s, 1H); 10.64 (s, 1H); 9.01-9.08 (m, 1H); 7.99 (s, 1H); 7.59 (s, 1H); 7.46-7.44 (m, 1H); 7.28-7.26 (m, 1H); 7.05 (t, J=7.6 Hz, 1H); 5.30 (s, 2H); 3.89 (s, 3H); 2.85 (d, J=4.8 Hz, 3H); 2.08-2.06 (m, 1H); 0.82-0.80 (m, 4H).

Example 31: Preparation of 6-(cyclopropanecarboxamido)-4-((2,5-dimethyl-4,5-dihydro-2H-pyrazolo[4,3-c]quinolin-6-yl)amino)-N-(methyl-d3)nicotinamide (Compound 14)

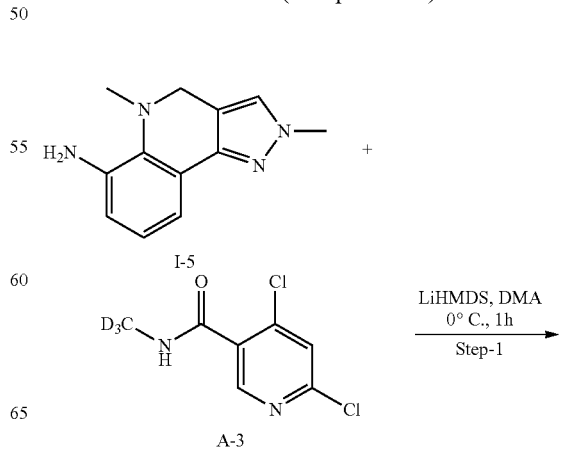

I-5

A-3

LiHMDS, DMA
0° C., 1h
——————————→
Step-1

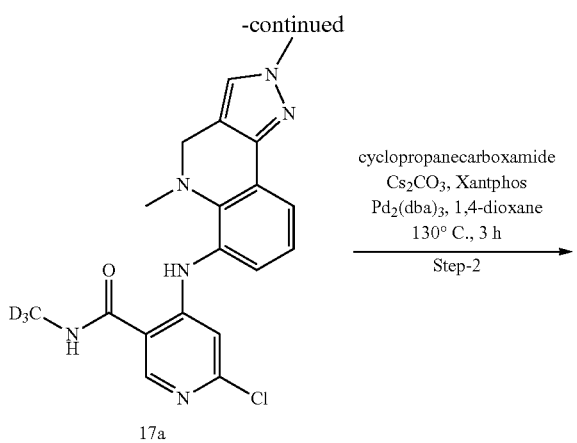

17a

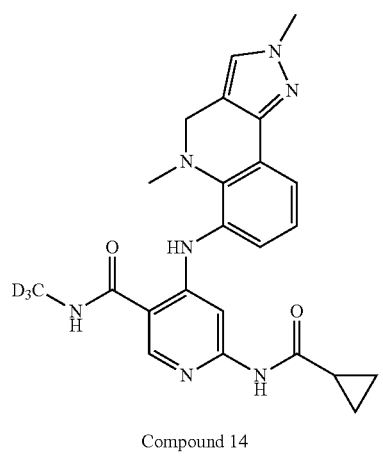

Compound 14

Step-1: 6-chloro-4-((2,5-dimethyl-4,5-dihydro-2H-pyrazolo[4,3-c]quinolin-6-yl)amino)-N-(methyl-d3)nicotinamide (17a): To a stirred solution of I-5 (4.5 g, 21.0 mmol) and A-3 (4.37 g, 21.0 mmol) in anhydrous DMA (10.0 mL) was added a 1M solution of LiHMDS (in THF) (73.5 mL, 73.5 mmol) drop wise at 0° C. The reaction mixture was allowed to stir at the same temperature for 1 h, while monitoring reaction progress by TLC. After completion, it was quenched with addition of water (50 mL) and extraction was carried out using 10% MeOH in DCM (100 mL×3). The combined organic extracts were washed with brine (50 mL), dried over anhydrous Na$_2$SO$_4$, filtered and concentrated under reduced pressure. The resulting crude was purified by Combi-Flash (using gradient elution 0-5% MeOH in DCM) to afford desired compound 6-chloro-4-((2,5-dimethyl-4,5-dihydro-2H-pyrazolo[4,3-c]quinolin-6-yl)amino)-N-(methyl-ds)nicotinamide 17a (6.2 g) as an off-white solid. LCMS (ES) m/z; 386.1 [M+H]$^+$.

Step-2: 6-(cyclopropanecarboxamido)-4-((2,5-dimethyl-4,5-dihydro-2H-pyrazolo[4,3-c]quinolin-6-yl)amino)-N-(methyl-d$_3$)nicotinamide (compound 14): Argon gas was purged through a stirred suspension of 17a (6.0 g, 15.5 mmol), cyclopropanecarboxamide (1.99 g, 23.3 mmol) and Cs$_2$CO$_3$ (10.1 g, 31.1 mmol) in 1,4-dioxane (20 mL) for 15 min. To this was then added [5-(diphenylphosphanyl)-9,9-dimethyl-9H-xanthen-4-yl]diphenylphosphane (0.9 g, 1.55 mmol) and Pd$_2$(dba)$_3$ (1.42 g, 1.55 mmol). The reaction mixture was then stirred at 130° C. for 3 h in a sealed tube. The reaction progress was monitored by TLC. After completion, it was cooled to room temperature, filtered through a pad of celite and washed with EtOAc (200 mL×2). The filtrate was concentrated under reduced pressure and water (200 mL) was added to the residue. Extraction was carried out using EtOAc (3×70 mL); the combined organic extracts were washed brine (100 mL), dried over anhydrous Na$_2$SO$_4$, filtered and concentrated under reduced pressure. The residue was purified by Combi-Flash (using gradient elution of 0-5% MeOH in DCM) to afford 6-(cyclopropanecarboxamido)-4-((2,5-dimethyl-4,5-dihydro-2H-pyrazolo[4,3-c]quinolin-6-yl)amino)-N-(methyl-d3)nicotinamide compound 14 (1.8 g). LCMS (ES) m/z; 435.3 [M+H]$^+$. $^1$H NMR (400 MHz, DMSO-d$_6$) δ 10.71 (s, 1H); 10.48 (s, 1H); 8.51 (s, 1H); 8.45 (s, 1H); 8.10 (s, 1H); 7.55 (s, 1H); 7.36 (d, J=7.6 Hz, 1H); 7.27 (d, J=8.0 Hz, 1H); 7.10 (apparent t, J=8.0 Hz, 1H); 4.05 (s, 2H); 3.87 (s, 3H); 2.41 (s, 3H); 2.00-1.90 (m, 1H); 0.78-0.70 (m, 4H).

Example 32: Preparation of 6-(cyclopropanecarboxamido)-4-((2,5-dimethyl-4,5-dihydro-2H-pyrazolo[4,3-c][1,7]naphthyridin-6-yl)amino)-N-(methyl-d3)pyridazine-3-carboxamide (Compound 65)

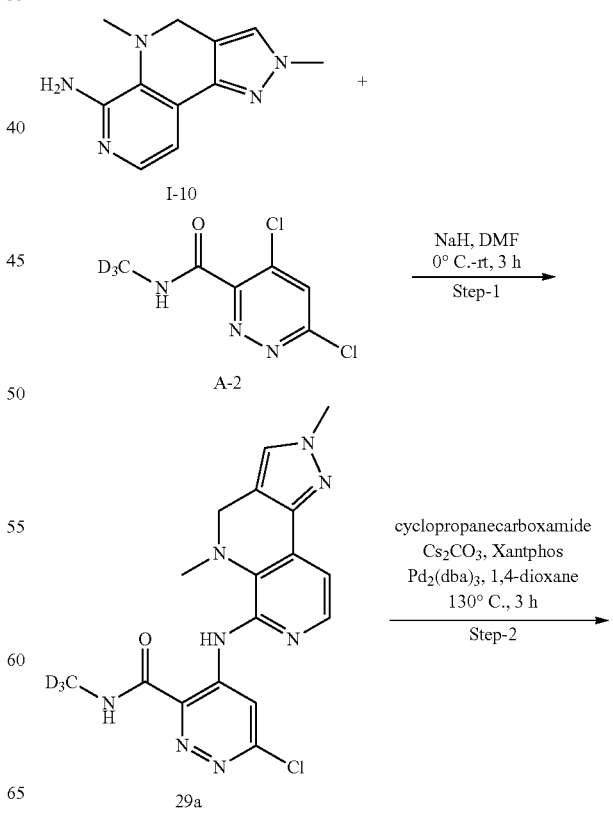

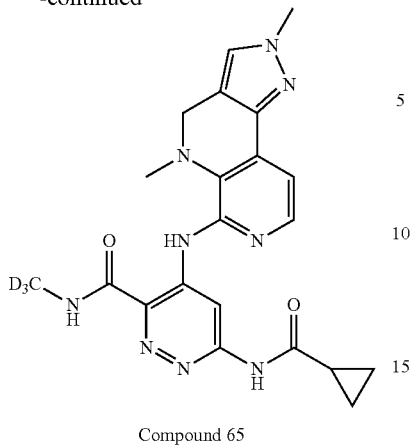

Compound 65

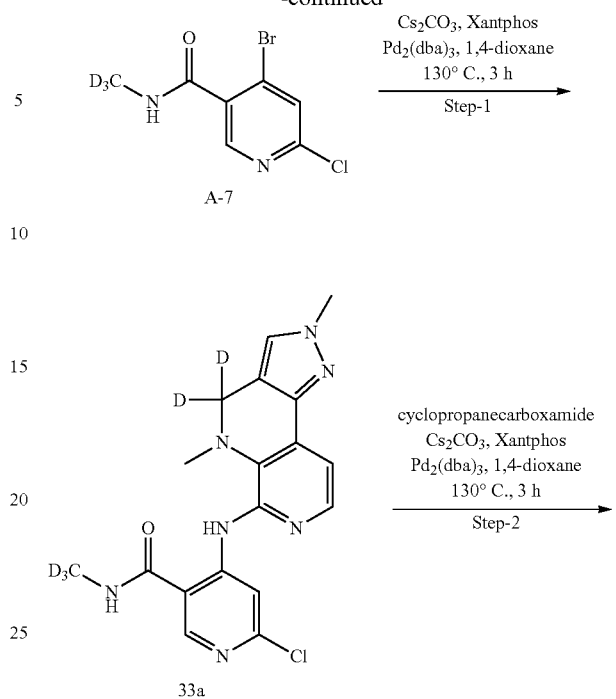

33a

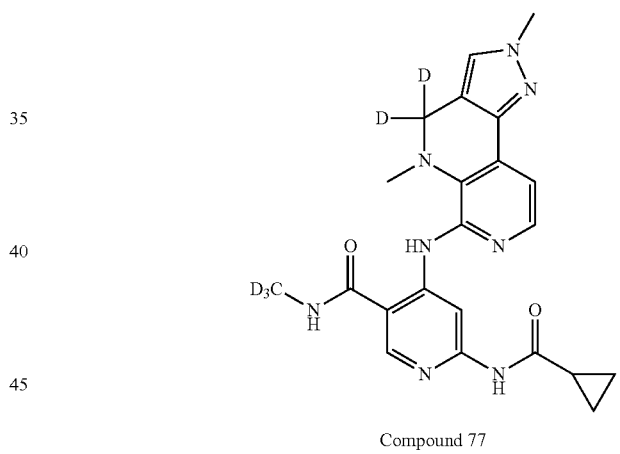

Compound 77

Step-1: 6-chloro-4-((2,5-dimethyl-4,5-dihydro-2H-pyrazolo[4,3-c][1,7]naphthyridin-6-yl)amino)-N-(methyl-d3)pyridazine-3-carboxamide (29a): To a stirred solution of I-10 (0.5 g, 2.32 mmol) and A-2 (0.78 g, 3.72 mmol) in DMF (10.0 mL) was added NaH (60% suspension in mineral oil) (0.56 g, 13.9 mmol) at 0° C. The reaction mixture was then stirred at room temperature for 3 h. After completion, ice-cold water (20 mL) was added to it and extraction was carried out using 10% MeOH in DCM (50 mL×3). The combined organic extracts were washed with water (50 mL), brine (50 mL), dried over anhydrous Na$_2$SO$_4$, filtered and concentrated under vacuum. The resulting crude was purified by Combi-Flash (using gradient elution 0-10% MeOH in DCM) to afford desired compound 6-chloro-4-((2,5-dimethyl-4,5-dihydro-2H-pyrazolo[4,3-c][1,7]naphthyridin-6-yl)amino)-N-(methyl-d3)pyridazine-3-carboxamide 29a (0.35 g) as a pale yellow solid. LCMS (ES) m/z; 388 [M+H]$^+$.

Step-2: 6-(cyclopropanecarboxamido)-4-((2,5-dimethyl-4,5-dihydro-2H-pyrazolo[4,3-c][1,7]naphthyridin-6-yl)amino)-N-(methyl-d3)pyridazine-3-carboxamide (Compound 65): Compound 65 (150 mg) was synthesized by following procedure as described for the synthesis of compound 1 (step-2) using 29a (0.34 g, 0.877 mmol) and cyclopropanecarboxamide (0.097 g, 1.14 mmol) as the starting materials. LCMS (ES) m/z; 437.3 [M+H]$^+$. $^1$H NMR (400 MHz, DMSO-d$_6$) δ 12.10 (s, 1H); 11.26 (s, 1H); 9.85 (s, 1H); 9.14 (s, 1H); 8.07 (d, J=5.2 Hz, 1H); 7.66 (s, 1H); 7.23 (d, J=5.2 Hz, 1H); 4.13 (s, 2H); 3.92 (s, 3H); 2.48 (s, 3H); 2.12-2.06 (m, 1H); 0.90-0.80 (m, 4H).

Example 33: 6-(cyclopropanecarboxamido)-4-((2,5-dimethyl-4,5-dihydro-2H-pyrazolo[4,3-c][1,7]naphthyridin-6-yl-4,4-d2)amino)-N-(methyl-d3)nicotinamide (Compound 77)

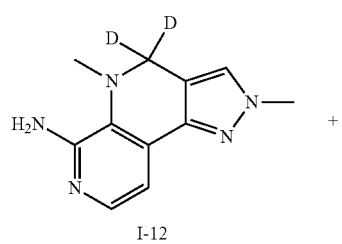

I-12

Step-1: 6-chloro-4-((2,5-dimethyl-4,5-dihydro-2H-pyrazolo[4,3-c][1,7]naphthyridin-6-yl)amino)-N-(methyl-d3)nicotinamide (33a): 33a (0.25 g) was synthesized by following procedure as described for the synthesis of compound 1 (step-2) using I-12 (0.31 g, 1.43 mmol) and A-7 (0.396 g, 1.57 mmol) as the starting materials. LCMS (ES) m/z; 389.2 [M+H]$^+$.

Step-2: 6-(cyclopropanecarboxamido)-4-((2,5-dimethyl-4,5-dihydro-2H-pyrazolo[4,3-c][1,7]naphthyridin-6-yl)amino)-N-(methyl-d3)nicotinamide (Compound 77): Compound 77 (27 mg) was synthesized by following procedure as described for the synthesis of compound 1 (step-2) using 33a (0.25 g, 0.643 mmol) and cyclopropanecarboxamide (0.066 g, 0.771 mmol) as the starting materials. LCMS (ES) m/z; 438.3 [M+H]$^+$. $^1$H NMR (400 MHz, DMSO-d$_6$) δ 11.55 (s, 1H); 10.67 (s, 1H); 9.50 (s, 1H); 8.56 (s, 1H); 8.54 (s, 1H); 8.04 (d, J=4.8 Hz, 1H); 7.66 (s, 1H); 7.20 (d, J=5.2 Hz, 1H); 3.93 (s, 3H); 2.55 (s, 3H); 2.04-2.00 (m, 1H); 0.86-0.78 (m, 4H).

Example 34: 4-((2,5-dimethyl-4,5-dihydro-2H-pyrazolo[4,3-c]quinolin-6-yl)amino)-6-(1-hydroxycyclopropane-1-carboxamido)-N-(methyl-d3)nicotinamide (Compound 21)

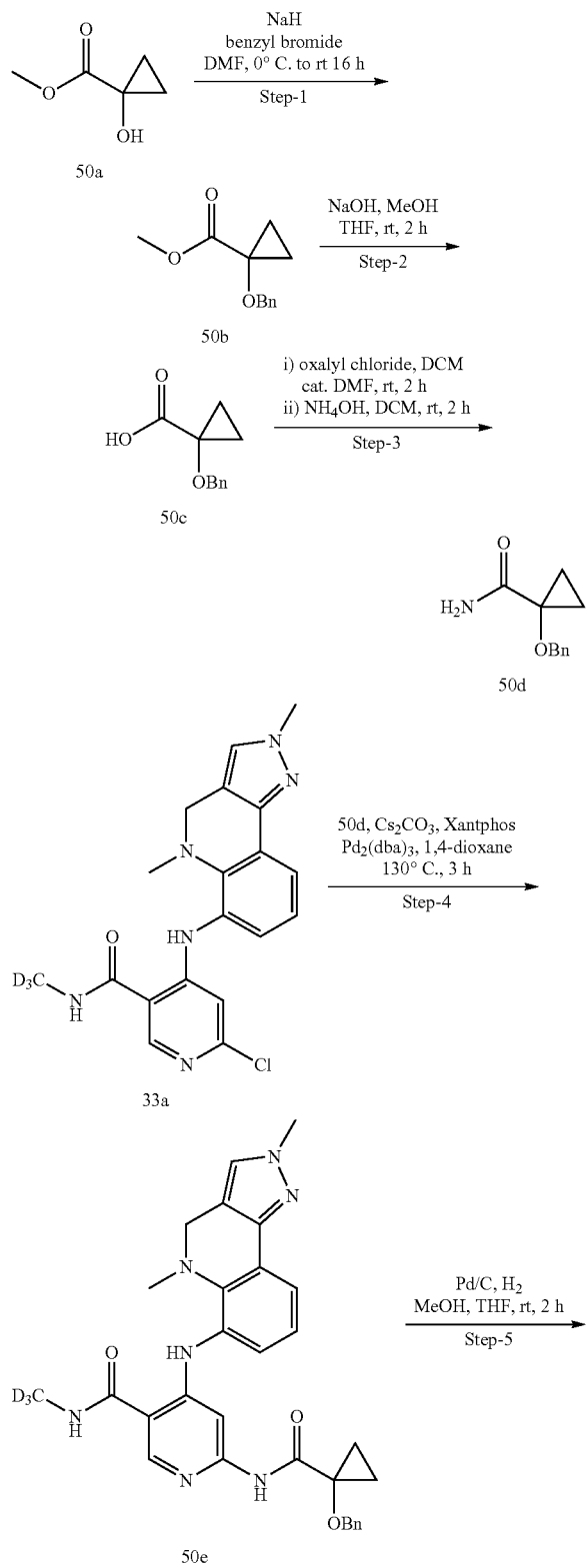

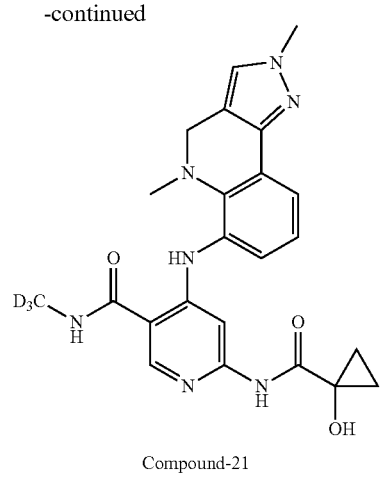

Compound-21

Step-1: methyl 1-(benzyloxy)cyclopropane-1-carboxylate (50b): To a stirred solution of 50a (1.54 mL, 17.2 mmol) in anhydrous DMF (15 mL) was added sodium hydride (60% suspension) (1.32 g, 34.4 mmol) at 0° C. and stirred for 30 min. To this was then added benzyl bromide (2.60 mL, 20.7 mmol 1) dropwise at 0° C. and the reaction mixture was stirred at room temperature for 16 h. It was then quenched with addition of saturated NaHCO$_3$ solution (30 mL) and extraction was carried out using (50 mL×3). The combined organic extracts were washed with brine (50 mL), dried over anhydrous Na$_2$SO$_4$, filtered and concentrated under reduced pressure. The residue was purified by Combi-Flash (using gradient elution of 0-15% EtOAc in hexane) to afford desired compound methyl 1-(benzyloxy)cyclopropane-1-carboxylate 50b (0.7 g) as a pale yellow oil. $^1$H NMR (400 MHz, DMSO-d$_6$) δ 7.35-7.29 (m, 5H); 4.60 (s, 2H); 3.69 (s, 3H); 1.26-1.24 (m, 4H).

Step-2: 1-(benzyloxy)cyclopropane-1-carboxylic acid (50c): To a stirred solution of 50b (1.20 g, 5.82 mmol) in MeOH (10.0 mL) and THF (10 mL) was added 8.0 mL of aqueous solution of sodium hydroxide (0.7 g, 17.46 mmol) and the reaction mixture was stirred at room temperature for 2 h. After completion (as indicated by TLC), volatiles were removed under reduced pressure and diluted with water (15 mL). It was then acidified by slow addition of 2N aqueous HCl solution. The resulting precipitates was filtered, washed with water (3 mL×2) and dried to afford desired compound 1-(benzyloxy)cyclopropane-1-carboxylic acid 50c (0.7 g) as an off white solid. LCMS (ES) m/z; 191.0 [M–H]$^+$. $^1$H NMR (400 MHz, DMSO-d$_6$) δ 12.66 (s, 1H); 7.34-7.25 (m, 5H); 4.61 (s, 2H); 1.24-1.16 (m, 4H).

Step-3: 1-(benzyloxy)cyclopropane-1-carboxamide (50d): To a stirred solution of 50c (0.8 g, 4.16 mmol) in anhydrous DCM (10 mL) was added catalytic amount of DMF (2-3 drops) and oxalyl chloride (0.714 mL, 8.32 mmol) drop wise at 0° C. The reaction mixture was then allowed to warm to room temperature over 2 h. Volatiles were then removed under reduced pressure and the residue was dried. It was then dissolved in anhydrous DCM (8 mL) and an aqueous solution of NH$_4$OH (10 mL) was added to it at 0° C. The reaction mixture was then stirred at room temperature for 16 h. Water (20 mL) was then added to it and extraction was carried out using DCM (25 mL×2). The combined organic extracts were washed with saturated NaHCO$_3$ solution (30 mL), brine (30 mL), dried over anhydrous Na$_2$SO$_4$, filtered and concentrated under reduced pressure. The residue was stirred in diethyl ether (15 mL), filtered and dried to afford desired compound 1-(benzyloxy)cyclopropane-1-carboxamide 50d (0.6 g). ¹H NMR (400 MHz, DMSO-d₆) δ 7.33-7.32 (m, 7H); 4.54 (s, 2H); 1.09-1.03 (m, 4H).

Step-4: 6-(1-(benzyloxy)cyclopropane-1-carboxamido)-4-((2,5-dimethyl-4,5-dihydro-2H-pyrazolo[4,3-c]quinolin-6-yl)amino)-N-(methyl-d3)nicotinamide (50e): 50e (0.2 g) was synthesized by following procedure as described for the synthesis of compound 1 (step-2) using 33a (0.3 g, 0.78 mmol) and 50d (0.18 g, 0.933 mmol) as the starting materials. LCMS (ES) m/z; 541.2 [M+H]⁺.

Step-5: 4-((2,5-dimethyl-4,5-dihydro-2H-pyrazolo[4,3-c]quinolin-6-yl)amino)-6-(1-hydroxycyclopropane-1-carboxamido)-N-(methyl-d3)nicotinamide (compound-21): To a stirred solution of 50e (0.27 g, 0.499 mmol) in MeOH (10.0 mL) and THF (10.0 mL) was added 10% Pd/C (100 mg) at room temperature. The reaction mixture was then stirred under hydrogen atmosphere (balloon) for 16 h. After completion, the catalyst was filtered off through celite bed and washed with MeOH (20 mL×3). The combined filtrate was concentrated under reduced pressure. The residue was purified by preparative HPLC to afford desired compound 4-((2,5-dimethyl-4,5-dihydro-2H-pyrazolo[4,3-c]quinolin-6-yl)amino)-6-(1-hydroxycyclopropane-1-carboxamido)-N-(methyl-d3)nicotinamide compound 21 (0.14 g) as an off white solid. LCMS (ES) m/z; 451.2 [M+H]⁺. ¹H NMR (400 MHz, DMSO-d₆) δ 10.55 (s, 1H); 9.30 (s, 1H); 8.55 (s, 1H); 8.48 (s, 1H); 8.08 (s, 1H); 7.57 (s, 1H); 7.41 (dd, J₁=1.2 Hz, J₂=7.6 Hz, 1H); 7.30 (d, J=7.2 Hz, 1H); 7.14 (apparent t, J=8.0 Hz, 1H); 6.81 (s, 1H); 4.08 (s, 2H); 3.90 (s, 3H); 2.45 (s, 3H); 1.18-1.14 (m, 2H); 1.04-0.98 (m, 2H).

Example 35: Preparation of 2-(cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide (Compound 22)

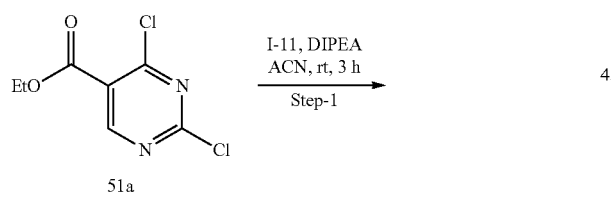

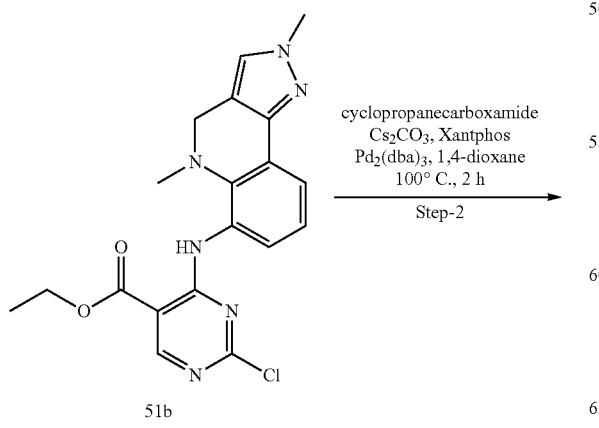

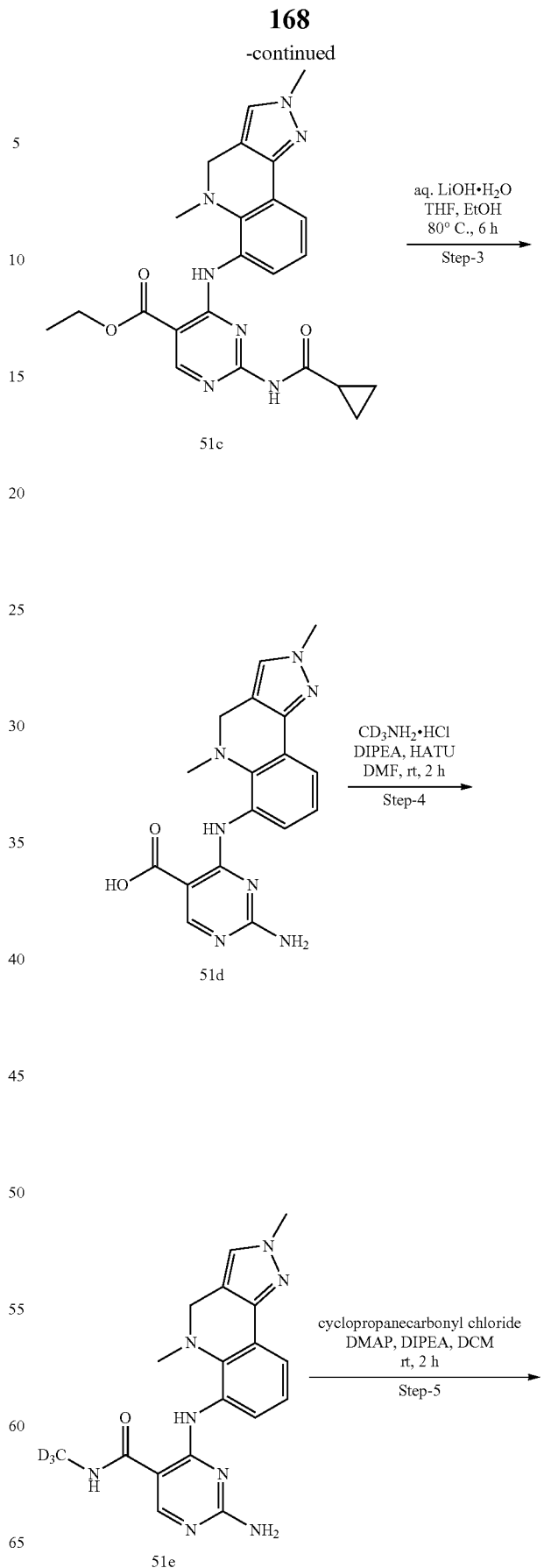

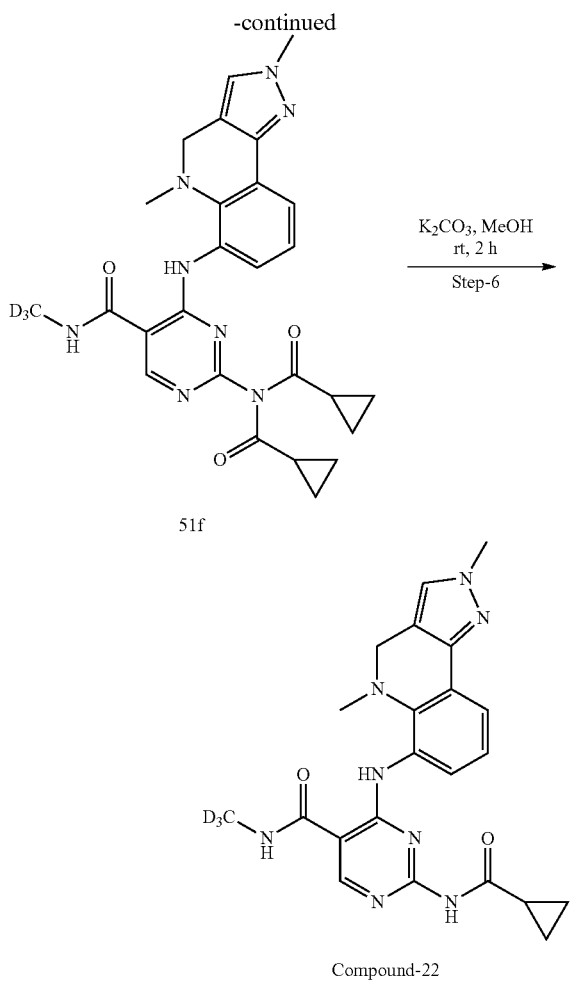

51f

Compound-22

Step-1: ethyl 2-chloro-4-((2,5-dimethyl-4,5-dihydro-2H-pyrazolo[4,3-c]quinolin-6-yl)amino)pyrimidine-5-carboxylate (51b): To a solution of I-11 (0.5 g, 2.33 mmol) and 51a (0.67 g, 3.03 mmol) in ACN (15 mL) was added DIPEA (0.62 mL, 3.50 mmol); and the reaction mixture was stirred for 3 h (reaction progress was monitored by TLC) at room temperature. After complete consumption of starting material, volatiles were removed under reduced pressure and water (20 mL) was added to the residue. The resulting precipitate was filtered, washed with water (10 mL) and dried. It was then stirred in Et$_2$O (10 mL), filtered and dried to afford desired compound ethyl 2-chloro-4-((2,5-dimethyl-4,5-dihydro-2H-pyrazolo[4,3-c]quinolin-6-yl)amino)pyrimidine-5-carboxylate 51b (0.58 g) as a pale yellow solid. LCMS (ES) m/z; 399.1 [M+H]$^+$.

Step-2: ethyl 2-(cyclopropanecarboxamido)-4-((2,5-dimethyl-4,5-dihydro-2H-pyrazolo[4,3-c]quinolin-6-yl)amino)pyrimidine-5-carboxylate (51c): Argon gas was purged through a stirred suspension of 51b (0.5 g, 1.25 mmol), cyclopropanecarboxamide (0.22 g, 2.51 mmol) and Cs$_2$CO$_3$ (1.23 g, 3.76 mmol) in 1,4-dioxane (8.00 mL) for 15 min. To this was then added [5-(diphenylphosphanyl)-9,9-dimethyl-9H-xanthen-4-yl]diphenylphosphane (75 mg, 0.12 mmol) and Pd$_2$(dba)$_3$ (0.12 g, 0.12 mmol). The reaction mixture was then stirred at 100° C. for 2 h in a sealed tube. The reaction progress was monitored by TLC. After complete consumption of starting material, it was cooled to room temperature and filtered through celite bed. It was washed with EtOAc (10 mL×2) and the filtrate was concentrated under reduced pressure. The residue was purified by Combi-Flash (using gradient elution of 0-5% MeOH in DCM) to afford desired compound ethyl 2-(cyclopropanecarboxamido)-4-((2,5-dimethyl-4,5-dihydro-2H-pyrazolo[4,3-c]quinolin-6-yl)amino)pyrimidine-5-carboxylate 51c (0.38 g) as an off-white solid. LCMS (ES) m/z; 448.2 [M+H]$^+$.

Step-3: 2-amino-4-((2,5-dimethyl-4,5-dihydro-2H-pyrazolo[4,3-c]quinolin-6-yl)amino)pyrimidine-5-carboxylic acid (51d): To a stirred solution of 51c (0.38 g, 0.85 mmol) in THF:EtOH (5:5 mL) was added an aqueous solution of LiOH H$_2$O (0.11 g, 2.55 mmol, in 2 mL water) at room temperature. It was then stirred at 80° C. for 6 h, while monitoring reaction progress by LCMS. After complete consumption of starting material, volatiles were removed under reduced pressure and the aqueous layer was washed with diethyl ether (10 mL). The aqueous layer was then diluted with water (20 mL) and pH was adjusted to 4 by using 1N aqueous HCl solution. The resulting precipitate was collected by filtration, washed with water (2 mL×2) and dried to afford desired compound 2-amino-4-((2,5-dimethyl-4,5-dihydro-2H-pyrazolo[4,3-c]quinolin-6-yl)amino)pyrimidine-5-carboxylic acid 51d (0.26 g) as an off white solid. LCMS (ES) m/z; 352.1 [M+H]$^+$.

Step-4: 2-amino-4-((2,5-dimethyl-4,5-dihydro-2H-pyrazolo[4,3-c]quinolin-6-yl)amino)-N-(methyl-d3)pyrimidine-5-carboxamide (51e): To a stirred solution of 51d (0.2 g, 0.57 mmol) and methan-d$_3$-amine hydrochloride (0.08 g, 1.14 mmol) in DMF (3 mL) was added DIPEA (0.5 mL, 2.85 mmol) and HATU (0.43 g, 1.14 mmol). The reaction mixture was stirred at room temperature for 2 h. After complete consumption of starting material, volatiles were removed under reduced pressure and the residue was then purified by Combi-Flash (using gradient elution 0-5% MeOH in DCM) to afford desired 2-amino-4-((2,5-dimethyl-4,5-dihydro-2H-pyrazolo[4,3-c]quinolin-6-yl)amino)-N-(methyl-d3)pyrimidine-5-carboxamide 51e (0.13 g) as an off-white solid. LCMS (ES) m/z; 368.2 [M+H]$^+$.

Step-5: 2-(N-(cyclopropanecarbonyl)cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide (51f): To a stirred solution of 51e (0.13 g, 0.35 mmol) in anhydrous DCM (10 mL) was added DIPEA (0.13 mL, 0.70 mmol), DMAP (5 mg, 0.03 mmol) and cyclopropanecarbonyl chloride (0.04 g, 0.39 mmol) sequentially. The reaction mixture was stirred at room temperature for 2 h, while monitoring reaction progress by LCMS. After completion, water (10 mL) was added to it and extraction was carried out using DCM (3×15 mL). The combined organic extracts were washed with water (10 mL), brine (15 mL), dried over anhydrous Na$_2$SO$_4$, filtered and concentrated under reduced pressure. The resulting crude was purified by Combi-Flash (using gradient elution of 0-3% MeOH in DCM) to afford 2-(N-(cyclopropanecarbonyl)cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide 51f (0.15 g) as a viscous liquid; LCMS (ES) m/z; 504.3 [M+H]$^+$.

Step-6: 2-(cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide (Compound 22): To a stirred solution of 51f (0.15 g, 0.29 mmol) in MeOH (10 mL) was added K$_2$CO$_3$ (50 mg, 0.33 mmol) and the reaction mixture was stirred at room temperature for 2 h. After complete consumption of starting material, K$_2$CO$_3$ was filtered off through celite and washed with MeOH. The filtrate was concentrated under reduced pressure and the residue was purified by Combi-Flash (using gradient elution 0-2% MeOH in DCM) to afford desired compound 2-(cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide compound 22 (0.06 g) as an off-white solid. LCMS (ES) m/z; 436.3 [M+H]⁺. ¹H NMR (400 MHz, DMSO-d₆) δ 11.70 (s, 1H); 10.80 (s, 1H); 9.05 (d, J=8.0 Hz, 1H); 8.69 (s, 1H); 8.54 (s, 1H); 7.56 (s, 1H); 7.32 (d, J=6.4 Hz, 1H); 7.09 (app t, J=8.0 Hz, 1H); 4.05 (s, 2H); 3.87 (s, 3H); 2.44 (s, 3H); 2.19-2.10 (m, 1H); 0.88-0.78 (m, 4H).

Example 36: Preparation of 6-(cyclopropanecarboxamido)-N-(methyl-d3)-4-((5-methyl-4,5-dihydro-2H-pyrazolo[4,3-c]quinolin-6-yl)amino)nicotinamide (Compound 23)

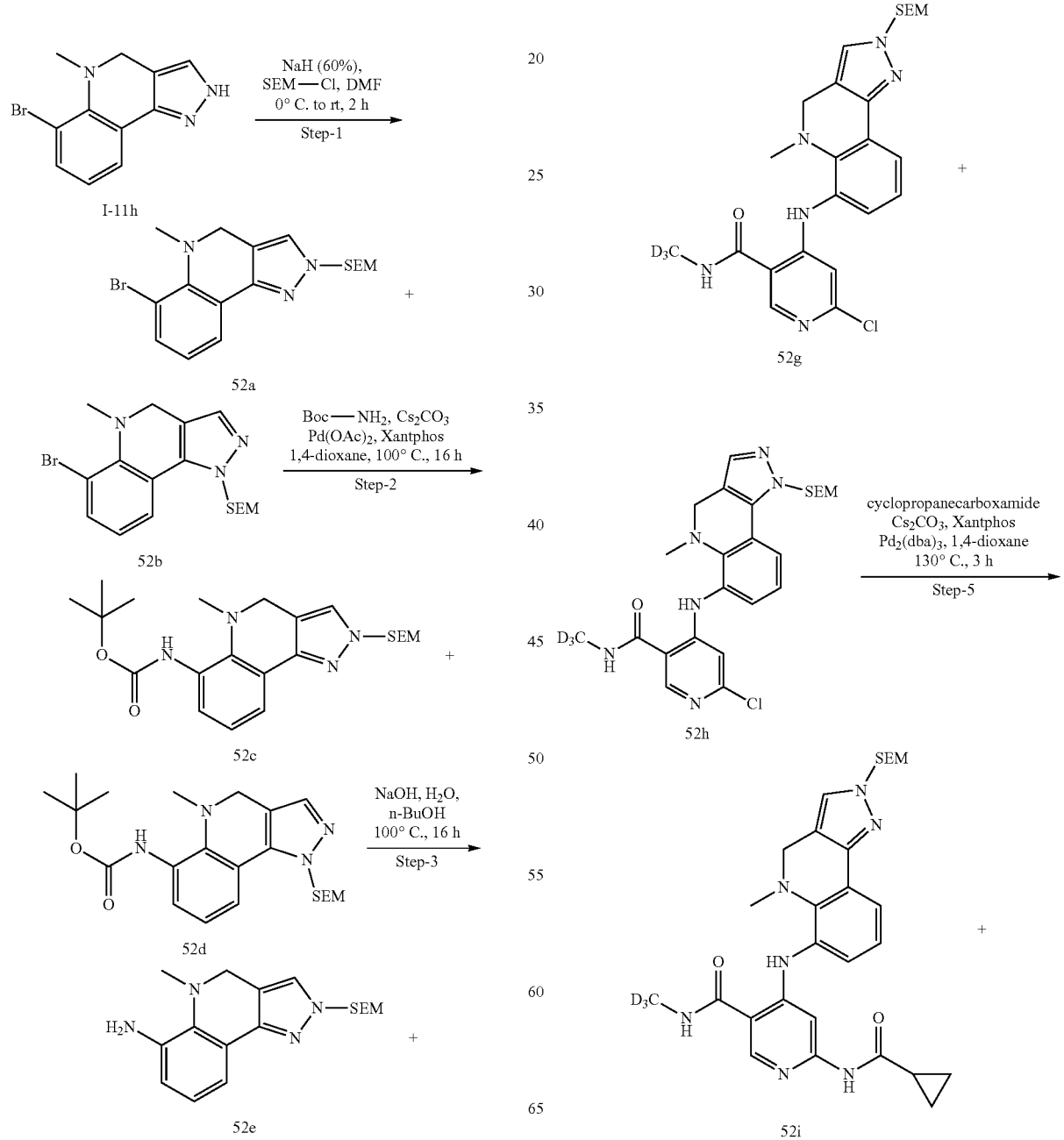

-continued

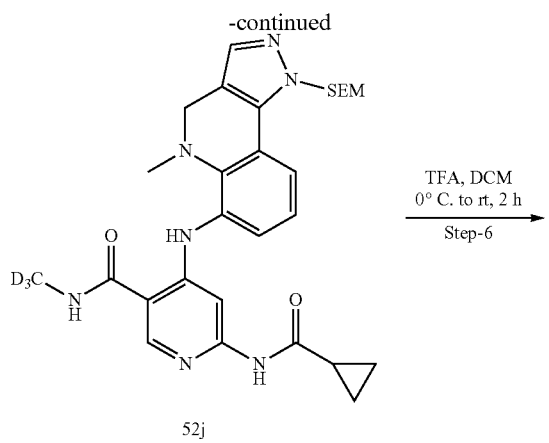

52j

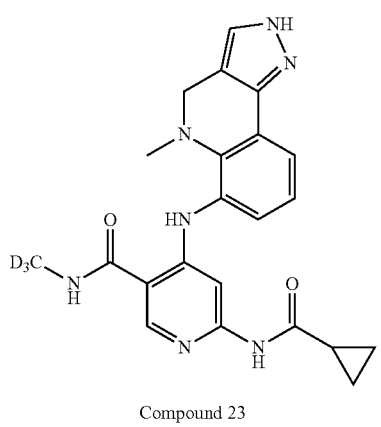

Compound 23

Step-1: 6-bromo-5-methyl-2-((2-(trimethylsilyl)ethoxy)methyl)-4,5-dihydro-2H-pyrazolo[4,3-c]quinolone (52a) & 6-bromo-5-methyl-1-((2-(trimethylsilyl)ethoxy)methyl)-4,5-dihydro-1H-pyrazolo[4,3-c]quinolone (52b): To a stirred solution of I-11h (3.00 g, 11.4 mmol) in DMF (20.0 mL) was added NaH (60% suspension) (0.681 g, 17.0 mmol) at 0° C. and stirred for 20 min. To this was then added [2-(chloromethoxy)ethyl]trimethylsilane (2.84 g, 17.0 mmol) drop wise at 0° C. and stirred at room temperature for 2 h. After completion, ice cold water (50 mL) was added to it and extraction was carried out using EtOAc (30 mL×3). The combined organic extracts were washed with brine (50 mL), dried over anhydrous $Na_2SO_4$, filtered and concentrated under reduced pressure. The residue was purified by Combi-Flash (using gradient elution of 0-25% EtOAc in hexane) to afford 3. g of mixture of 6-bromo-5-methyl-2-((2-(trimethylsilyl)ethoxy)methyl)-4,5-dihydro-2H-pyrazolo[4,3-c]quinolone (52a) and 6-bromo-5-methyl-1-((2-(trimethylsilyl)ethoxy)methyl)-4,5-dihydro-1H-pyrazolo[4,3-c]quinolone (52b) as a yellow viscous liquid. LCMS (ES) m/z; 394.0 [M+H]⁺.

Step-2: tert-butyl (5-methyl-2-((2-(trimethylsilyl)ethoxy)methyl)-4,5-dihydro-2H-pyrazolo[4,3-c]quinolin-6-yl)carbamate (52c) & tert-butyl (5-methyl-1-((2-(trimethylsilyl)ethoxy)methyl)-4,5-dihydro-1H-pyrazolo[4,3-c]quinolin-6-yl)carbamate (52d): 1.05 g of mixture of 52c and 52d was synthesized by following procedure as described for the synthesis of I-11 (step-9) using mixture of 52a and 52b (1.05 g, 2.33 mmol) as the starting material. LCMS (ES) m/z; 431.0 [M+H]⁺.

Step-3: 5-methyl-2-((2-(trimethylsilyl)ethoxy)methyl)-4,5-dihydro-2H-pyrazolo[4,3-c]quinolin-6-amine (52e) & 5-methyl-1-((2-(trimethylsilyl)ethoxy)methyl)-4,5-dihydro-1H-pyrazolo[4,3-c]quinolin-6-amine (52f): To a stirred solution (52c+52d) (0.65 g, 1.51 mmol) in n-BuOH (2.0 mL) were added water (1.0 mL) and sodium hydroxide (1.21 g, 30.2 mmol) at room temperature. It was then stirred at 100° C. for 16 h. After completion (as indicated by TLC), ice cold water (30 mL) was added to it and extraction was carried out using EtOAc (30 mL×3). The combined organic extracts were washed with brine (30 mL), dried over anhydrous $Na_2SO_4$, filtered and concentrated under reduced pressure. The residue was purified by Combi-Flash (using gradient elution of 0-50% EtOAc in hexane) to afford 0.25 g of mixture of 5-methyl-2-((2-(trimethylsilyl)ethoxy)methyl)-4,5-dihydro-2H-pyrazolo[4,3-c]quinolin-6-amine (52e) and 5-methyl-1-((2-(trimethylsilyl)ethoxy)methyl)-4,5-dihydro-1H-pyrazolo[4,3-c]quinolin-6-amine (52f) as a pale yellow solid. LCMS (ES) m/z; 331.2 [M+H]⁺.

Step-4: 6-chloro-N-(methyl-d3)-4-((5-methyl-2-((2-(trimethylsilyl)ethoxy)methyl)-4,5-dihydro-2H-pyrazolo[4,3-c]quinolin-6-yl)amino)nicotinamide (52g) & 6-chloro-N-(methyl-d3)-4-((5-methyl-1-((2-(trimethylsilyl)ethoxy)methyl)-4,5-dihydro-1H-pyrazolo[4,3-c]quinolin-6-yl)amino)nicotinamide (52h): 0.3 g of mixture of 52g and 52h was synthesized by following procedure as described for the synthesis of compound 17 (step-2) using mixture of 52e and 52f (0.21 g, 0.635 mmol) and A-3 (0.132 g, 0.635 mmol) as the starting materials. LCMS (ES) m/z; 502.1 [M+H]⁺.

Step-5: 6-(cyclopropanecarboxamido)-N-(methyl-d3)-4-((5-methyl-2-((2-(trimethylsilyl)ethoxy)methyl)-4,5-dihydro-2H-pyrazolo[4,3-c]quinolin-6-yl)amino)nicotinamide (52i) & 6-(cyclopropanecarboxamido)-N-(methyl-d3)-4-((5-methyl-1-((2-(trimethylsilyl)ethoxy)methyl)-4,5-dihydro-1H-pyrazolo[4,3-c]quinolin-6-yl)amino) nicotinamide (52j): 0.3 g of mixture of 52i and 52j was synthesized by following procedure as described for the synthesis of compound 17 (step-2) using mixture of 52g and 52h (0.25 g, 0.498 mmol) as the starting material. LCMS (ES) m/z; 551.2 [M+H]⁺.

Step-6: 6-(cyclopropanecarboxamido)-N-(methyl-d3)-4-((5-methyl-4,5-dihydro-2H-pyrazolo[4,3-c]quinolin-6-yl)amino)nicotinamide (Compound 23): To a stirred solution of (52i+52j) (250 mg, 0.454 mmol) in DCM (10.0 mL) was added trifluoroacetic acid (2.50 mL) at 0° C. under $N_2$ atmosphere. It was then stirred at room temperature for 2 h. After completion, volatiles were removed under reduced pressure and saturated sodium bicarbonate solution (10 mL) was added to the residue. Extraction was carried out using 5% MeOH in DCM (3×30 mL); the combined organic extracts were washed with water (10 mL), brine (10 mL), dried over anhydrous sodium sulphate, filtered and evaporated under reduced pressure. The residue was purified by preparative HPLC to afford 6-(cyclopropanecarboxamido)-N-(methyl-d3)-4-((5-methyl-4,5-dihydro-2H-pyrazolo[4,3-c]quinolin-6-yl)amino)nicotinamide (23, 28.0 mg) as an off-white solid. LCMS (ES) m/z; 421.2 [M+H]⁺. ¹H NMR (400 MHz, DMSO-$d_6$) δ 12.79 (bs, 1H); 10.70 (s, 1H); 10.48 (s, 1H); 8.50 (s, 1H); 8.45 (s, 1H); 8.09 (s, 1H); 7.60 (s, 1H); 7.48-7.38 (m, 1H); 7.27 (d, J=8.0 Hz, 1H); 7.12 (apparent t, J=8.0 Hz, 1H); 4.08 (s, 2H); 2.41 (s, 3H); 2.00-1.92 (m, 1H); 0.77-0.71 (m, 4H).

Example 37: Preparation of methyl 6-(cyclopropanecarboxamido)-4-((2,5-dimethyl-4,5-dihydro-2H-pyrazolo[4,3-c]quinolin-6-yl)amino)nicotinate (Compound 60)

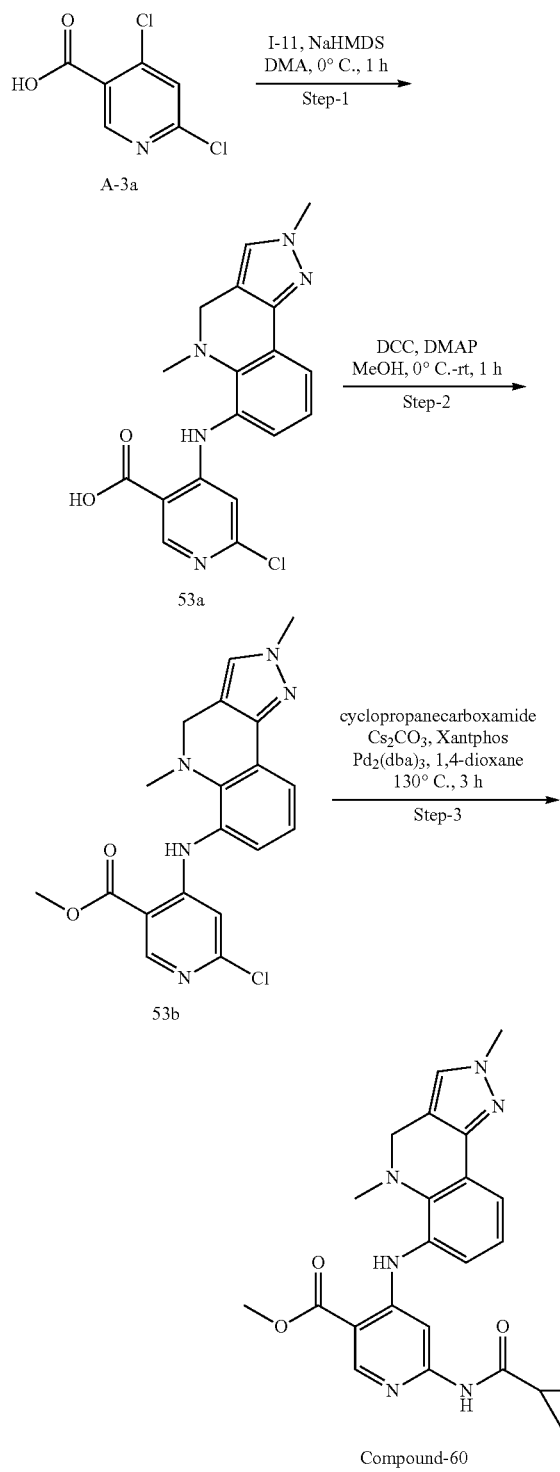

Step-1: 6-chloro-4-((2,5-dimethyl-4,5-dihydro-2H-pyrazolo[4,3-c]quinolin-6-yl)amino)nicotinic acid (53a): To a stirred solution of I-11 (0.3 g, 1.4 mmol) and A-3a (0.4 g, 2.1 mmol) in anhydrous DMA (6.0 mL) was added a 1M solution of NaHMDS (in THF) (11.2 mL, 11.2 mmol) drop wise at 0° C. The reaction mixture was allowed to stir at the same temperature for 1 h, while monitoring reaction progress by TLC. After completion, it was quenched with addition of 0.5N aqueous HCl solution and extraction was carried out using 10% MeOH in DCM (50 mL×2). The combined organic extracts were washed with brine (30 mL), dried over anhydrous $Na_2SO_4$, filtered and concentrated under reduced pressure to get 6-chloro-4-((2,5-dimethyl-4,5-dihydro-2H-pyrazolo[4,3-c]quinolin-6-yl)amino)nicotinic acid 53a (0.25 g) as a pale brown solid. LCMS (ES) m/z; 369.9 [M+H]⁺.

Step-2: methyl 6-chloro-4-((2,5-dimethyl-4,5-dihydro-2H-pyrazolo[4,3-c]quinolin-6-yl)amino)nicotinate (53b): To the solution of 53a (0.125 g, 0.338 mmol) in DCM (10.0 mL) was added N,N'-dicyclohexylmethanediimine (0.209 g, 1.01 mmol), DMAP (4.13 mg, 0.033 mmol) and MeOH (0.14 mL, 3.38 mmol). It was then stirred at room temperature for 16 h. Water (20 mL) was added to it and extraction was carried out using 10% MeOH in DCM (50 mL×2). The combined organic extracts were washed with brine (50 mL), dried over anhydrous $Na_2SO_4$, filtered and concentrated under reduced pressure. The residue was purified by Combi-Flash (using gradient elution of 0-50% EtOAc in hexane) to afford desired compound methyl 6-chloro-4-((2,5-dimethyl-4,5-dihydro-2H-pyrazolo[4,3-c]quinolin-6-yl)amino)nicotinate 53b (90.0 mg) as an off white solid. LCMS (ES) m/z; 384.2 [M+H]⁺.

Step-3: methyl 6-(cyclopropanecarboxamido)-4-((2,5-dimethyl-4,5-dihydro-2H-pyrazolo[4,3-c]quinolin-6-yl)amino)nicotinate (Compound 60): Compound 60 (15 mg) was synthesized by following procedure as described for the synthesis of compound 1 (step-2) using 53b (90 mg, 0.234 mmol) as the starting material. LCMS (ES) m/z; 433.2 [M+H]⁺. ¹H NMR (400 MHz, DMSO-d₆) δ 10.88 (s, 1H); 10.04 (s, 1H); 8.69 (s, 1H); 8.13 (s, 1H); 7.57 (s, 1H); 7.43 (d, J=7.6 Hz, 1H); 7.33 (d, J=8.0 Hz, 1H); 7.15 (apparent t, J=7.6 Hz, 1H); 4.07 (s, 2H); 3.87 (s, 3H); 3.30 (s, 3H); 2.38 (s, 3H); 2.00-1.94 (m, 1H); 0.78-0.72 (m, 4H).

Example 38: 6-chloro-N-(methyl-d3)-4-((2,4,5-trimethyl-4,5-dihydro-2H-pyrazolo[4,3-c]quinolin-6-yl)amino)nicotinamide (34a)

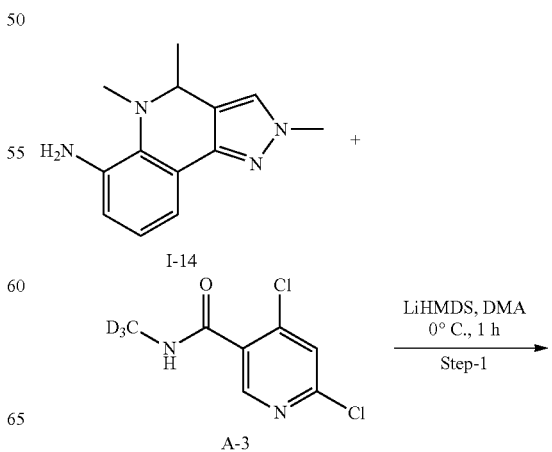

-continued

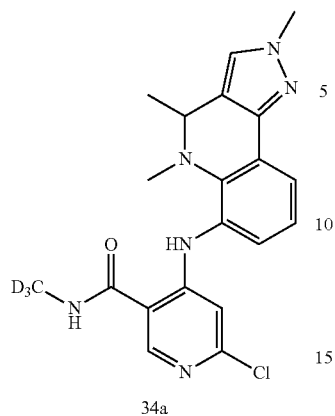

34a

Step-1: 6-chloro-N-(methyl-d3)-4-((2,4,5-trimethyl-4,5-dihydro-2H-pyrazolo[4,3-c]quinolin-6-yl)amino)nicotinamide (34a): 34a (1.3 g) was synthesized by following procedure as described for the synthesis of compound 14 (step-1) using I-14 (1.0 g, 4.38 mmol) and A-3 (1.37 g, 6.57 mmol) as the starting material. LCMS (ES) m/z; 400.2 [M+H]$^+$.

Racemate 34a (1.3 g) was resolved by chiral HPLC [(Column: CHIRALPAK IC (250 mm×30 mm×5 m); Mobile phase: n-Hexane:IPA with 0.1% DEA (50:50); Flow rate: 40 mL/min)] to afford two enantiomers {34B (0.49 g): peak-1; Rt: 6.96 min and 34C (0.5 g): peak-2; Rt: 8.54 min} which were carried forward without their absolute configuration determination.

Example 39: Preparation of 6-(cyclopropanecarboxamido)-4-((2,5-dimethyl-4,5-dihydropyrazolo[1,5-a]quinoxalin-6-yl)amino)-N-(methyl-d3)pyridazine-3-carboxamide (Compound 52)

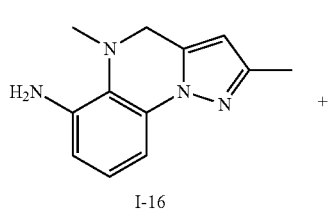

I-16

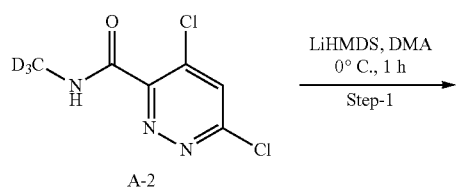

A-2

LiHMDS, DMA
0° C., 1 h
Step-1

-continued

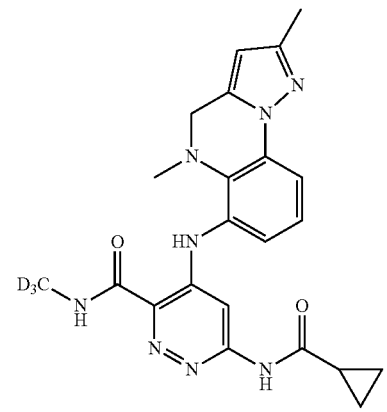

59a cyclopropanecarboxamide
Cs$_2$CO$_3$, Xantphos
Pd$_2$(dba)$_3$, 1,4-dioxane
130° C., 3 h
Step-2

Compound 52

Step-1: 6-chloro-4-((2,5-dimethyl-4,5-dihydropyrazolo[1,5-a]quinoxalin-6-yl)amino)-N-(methyl-d3)pyridazine-3-carboxamide (59a): 59a (0.36 g) was synthesized by following procedure as described for the synthesis of compound 14 (step-1) using I-16 (0.25 g, 1.17 mmol) and A-2 (0.37 g, 1.75 mmol) as the starting material. LCMS (ES) m/z; 387.0 [M+H]$^+$.

Step-2: 6-(cyclopropanecarboxamido)-4-((2,5-dimethyl-4,5-dihydropyrazolo[1,5-a]quinoxalin-6-yl)amino)-N-(methyl-d3)pyridazine-3-carboxamide (Compound 52): Compound 52 (0.22 g) was synthesized by following procedure as described for the synthesis of compound 1 (step-2) using 59a (0.35 g, 0.95 mmol) and cyclopropanecarboxamide (0.1 g, 1.18 mmol) as the starting materials. LCMS (ES) m/z; 436.3 [M+H]$^+$. $^1$H NMR (400 MHz, DMSO-d$_6$) δ 11.30 (s, 1H); 10.93 (s, 1H); 9.09 (s, 1H); 8.21 (s, 1H); 7.55 (t, J=4.8 Hz, 1H); 7.25 (d, J=4.8 Hz, 2H); 6.14 (s, 1H); 4.24 (s, 2H); 2.48 (s, 3H); 2.29 (s, 3H); 2.12-2.07 (m, 1H); 0.84-0.80 (m, 4H).

Example 40: Preparation of 6-(cyclopropanecarboxamido)-4-((2,5-dimethyl-4,5-dihydropyrazolo[1,5-a]pyrido[3,4-e]pyrazin-6-yl)amino)-N-(methyl-d3) pyridazine-3-carboxamide (Compound 68)

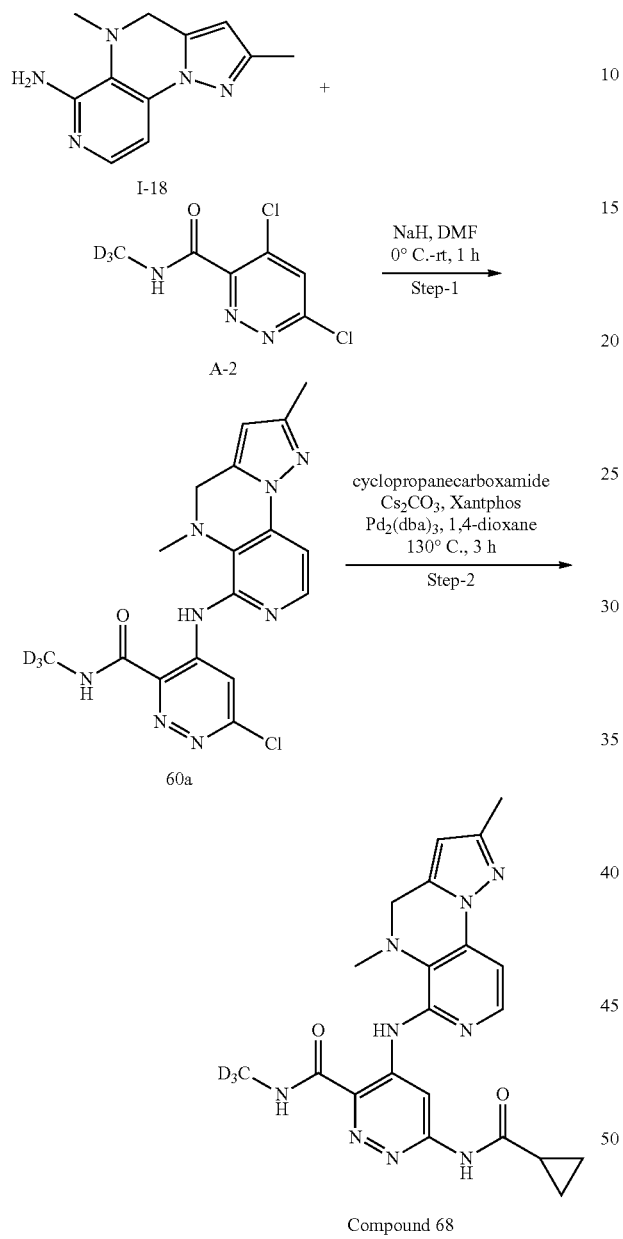

Compound 68

Step-1: 6-chloro-4-((2,5-dimethyl-4,5-dihydropyrazolo[1,5-a]pyrido[3,4-e]pyrazin-6-yl)amino)-N-(methyl-d3) pyridazine-3-carboxamide (60a): 60a (0.18 g) was synthesized by following procedure as described for the synthesis of compound 65 (step-1) using I-18 (0.21 g, 0.976 mmol) and A-2 (0.408 g, 1.15 mmol) as the starting materials. LCMS (ES) m/z; 388.0 [M+H]⁺.

Step-2: 6-(cyclopropanecarboxamido)-4-((2,5-dimethyl-4,5-dihydropyrazolo[1,5-a]pyrido[3,4-e]pyrazin-6-yl) amino)-N-(methyl-d3)pyridazine-3-carboxamide (Compound 68): Compound 68 (45 mg) was synthesized by following procedure as described for the synthesis of compound 1 (step-2) using 60a (0.18 g, 0.464 mmol) and cyclopropanecarboxamide (0.059 g, 0.70 mmol) as the starting materials. LCMS (ES) m/z; 437.3 [M+H]⁺. ¹H NMR (400 MHz, DMSO-d₆) δ 12.16 (s, 1H); 11.29 (s, 1H); 9.86 (s, 1H); 9.18 (s, 1H); 8.14 (d, J=5.2 Hz, 1H); 7.34 (d, J=5.6 Hz, 1H); 6.26 (s, 1H); 4.32 (s, 2H); 2.57 (s, 3H); 2.31 (s, 3H); 2.15-2.10 (m, 1H); 0.92-0.84 (m, 4H).

Example 41: Preparation of 6-(cyclopropanecarboxamido)-4-((2,5-dimethyl-4,5-dihydropyrazolo[1,5-a]pyrido[3,4-e]pyrazin-6-yl)amino)-N-(methyl-d3) nicotinamide (Compound 71)

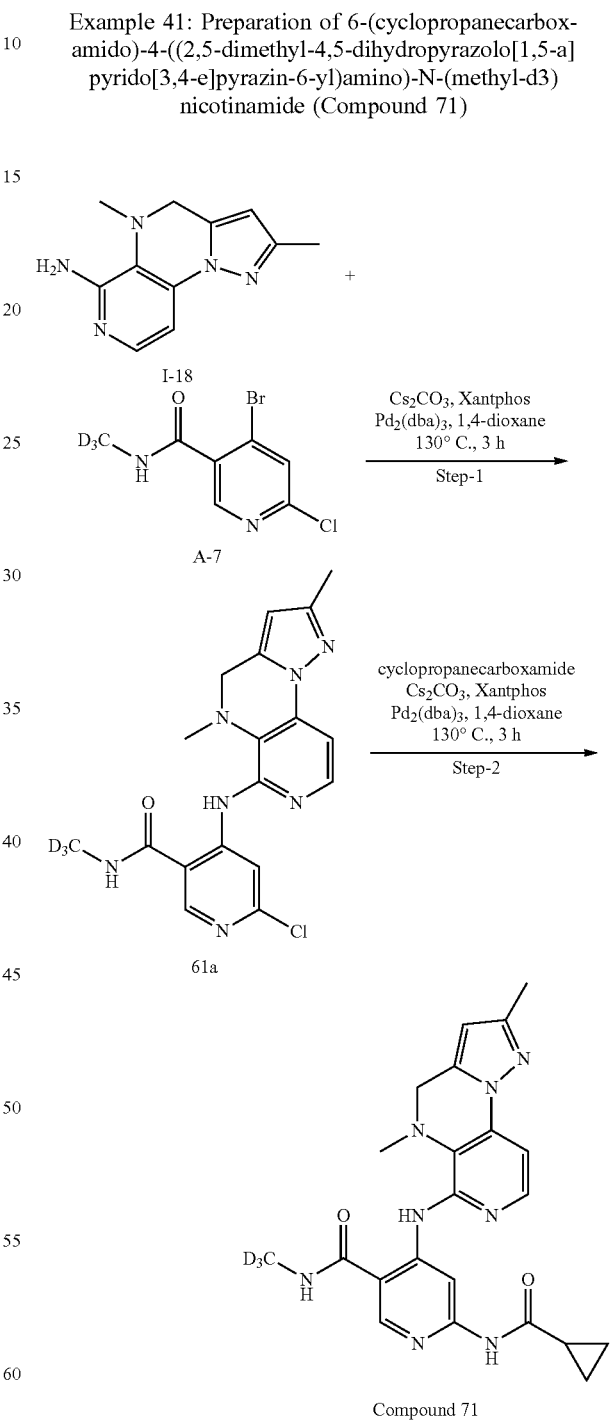

Compound 71

Step-1: 6-chloro-4-((2,5-dimethyl-4,5-dihydropyrazolo[1,5-a]pyrido[3,4-e]pyrazin-6-yl)amino)-N-(methyl-d3) nicotinamide (61a): 61a (0.16 g) was synthesized by following procedure as described for the synthesis of compound 1 (step-2) using I-18 (0.25 g, 1.16 mmol) and A-7 (0.352 g, 1.39 mmol) as the starting materials. LCMS (ES) m/z; 387.1 [M+H]$^+$.

Step-2: 6-(cyclopropanecarboxamido)-4-((2,5-dimethyl-4,5-dihydropyrazolo[1,5-a]pyrido[3,4-e]pyrazin-6-yl)amino)-N-(methyl-d3)nicotinamide (Compound 71): Compound 71 (90 mg) was synthesized by following procedure as described for the synthesis of compound 1 (step-2) using 61a (0.16 g, 0.414 mmol) and cyclopropanecarboxamide (0.046 g, 0.538 mmol) as the starting materials. LCMS (ES) m/z; 436.4 [M+H]$^+$. $^1$H NMR (400 MHz, DMSO-d$_6$) δ 10.98 (s, 1H); 10.95 (s, 1H); 8.66 (s, 1H); 8.57 (s, 1H); 8.31 (s, 1H); 8.08 (d, J=5.6 Hz, 1H); 7.28 (d, J=6.0 Hz, 1H); 6.17 (s, 1H); 4.23 (s, 2H); 2.48 (s, 3H); 2.27 (s, 3H); 2.03-1.97 (m, 1H); 0.84-0.80 (m, 4H).

Example 42: Preparation of 6-[(5-fluoropyridin-2-yl)amino]-N-methyl-4-{[2-(oxetan-3-yl)-2H,4H-chromeno[4,3-c]pyrazol-6-yl]amino}pyridazine-3-carboxamide (Compound 3)

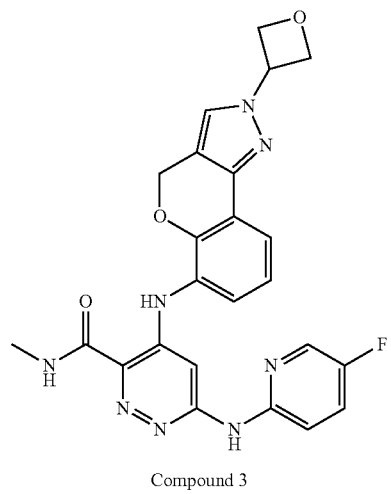

Compound 3

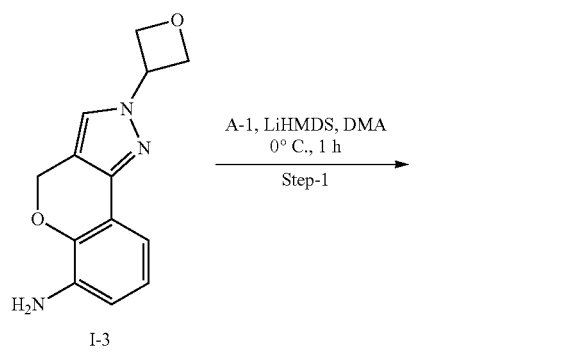

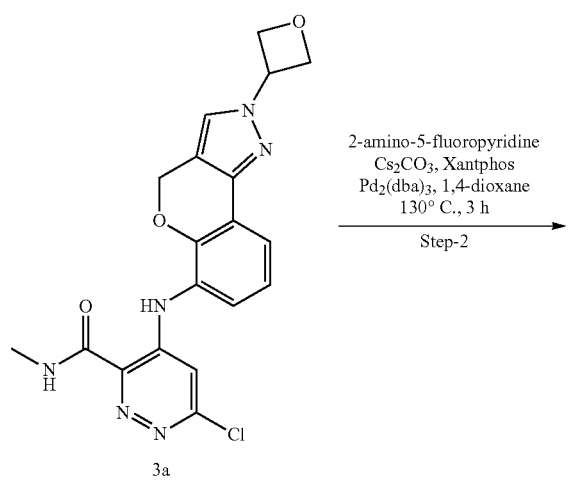

Step-1: 6-chloro-N-methyl-4-{[2-(oxetan-3-yl)-2H,4H-chromeno[4,3-c]pyrazol-6-yl]amino}pyridazine-3-carboxamide (3a): To a stirred solution of I-3 (0.5 g, 2.06 mmol) and A-1 (0.551 g, 2.67 mmol) in anhydrous DMA (6.00 mL) was added a 1M solution of LiHMDS (in THF) (10.7 mL, 10.68 mmol) drop wise at 0° C. The reaction mixture was allowed to stir at the same temperature for 1 h, while monitoring reaction progress by TLC. After completion, it was quenched with addition of water (10 mL) and extraction was carried out using 10% MeOH in DCM (30 mL×3). The combined organic extracts were washed with brine (30 mL), dried over anhydrous Na$_2$SO$_4$, filtered and concentrated under reduced pressure. The resulting crude was purified by Combi-Flash (using gradient elution 0-5% MeOH in DCM) to afford desired compound 6-chloro-N-methyl-4-{[2-(oxetan-3-yl)-2H,4H-chromeno[4,3-c]pyrazol-6-yl]amino}pyridazine-3-carboxamide 3a (0.57 g) as an off-white solid. LCMS (ES) m/z; 413.2 [M+H]$^+$. $^1$H NMR (400 MHz, DMSO-d$_6$) δ 10.81 (s, 1H); 9.35-9.34 (m, 1H); 7.79 (s, 1H); 7.56 (d, J=6.4 Hz, 1H); 7.38 (d, J=6.8 Hz, 1H); 7.12-7.05 (m, 2H); 5.65-5.58 (m, 1H); 5.32 (s, 2H); 4.92 (d, J=7.2 Hz, 4H); 2.83 (d, J=4.8 Hz, 3H).

Step-2: 6-[(5-fluoropyridin-2-yl)amino]-N-methyl-4-{[2-(oxetan-3-yl)-2H,4H-chromeno[4,3-c]pyrazol-6-yl]amino}pyridazine-3-carboxamide (Compound 3): Compound 3 (60 mg) was synthesized by following procedure as described for the synthesis of Compound 1 (step-2) using 3a (0.2 g, 0.484 mmol) and 5-fluoropyridin-2-amine (0.082 g, 0.727 mmol) as the starting materials. LCMS (ES) m/z; 489.2 [M+H]$^+$. $^1$H NMR (400 MHz, DMSO-d$_6$) δ 10.66 (s, 1H); 10.15 (s, 1H); 9.10-9.04 (m, 1H); 8.11 (d, J=2.8 Hz, 1H); 7.82-7.80 (m, 2H); 7.78-7.66 (m, 2H); 7.53 (d, J=6.8 Hz, 1H); 7.43 (d, J=7.6 Hz, 1H); 7.13 (t, J=8.0 Hz, 1H); 5.62-5.70 (m, 1H); 5.37 (s, 2H); 4.97 (s, 2H); 4.95 (s, 2H); 2.86 (d, J=4.8 Hz, 3H).

Example 43: Preparation of 6-(cyclopropanecarbox-amido)-N-methyl-4-((2-(oxetan-3-yl)-2,4-dihydro-chromeno[4,3-c]pyrazol-6-yl)amino)pyridazine-3-carboxamide (Compound 4)

Example 44: Preparation of 6-((5-fluoropyridin-2-yl)amino)-N-(methyl-d3)-4-((2-methyl-2,4-dihydro-chromeno[4,3-c]pyrazol-6-yl)amino)pyridazine-3-carboxamide (Compound 5)

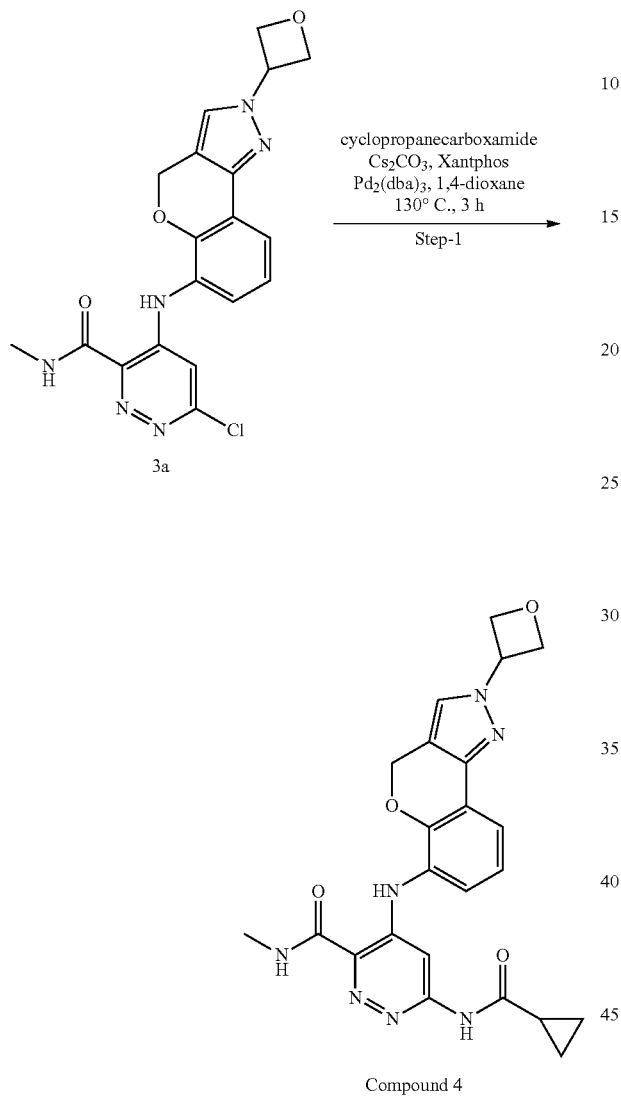

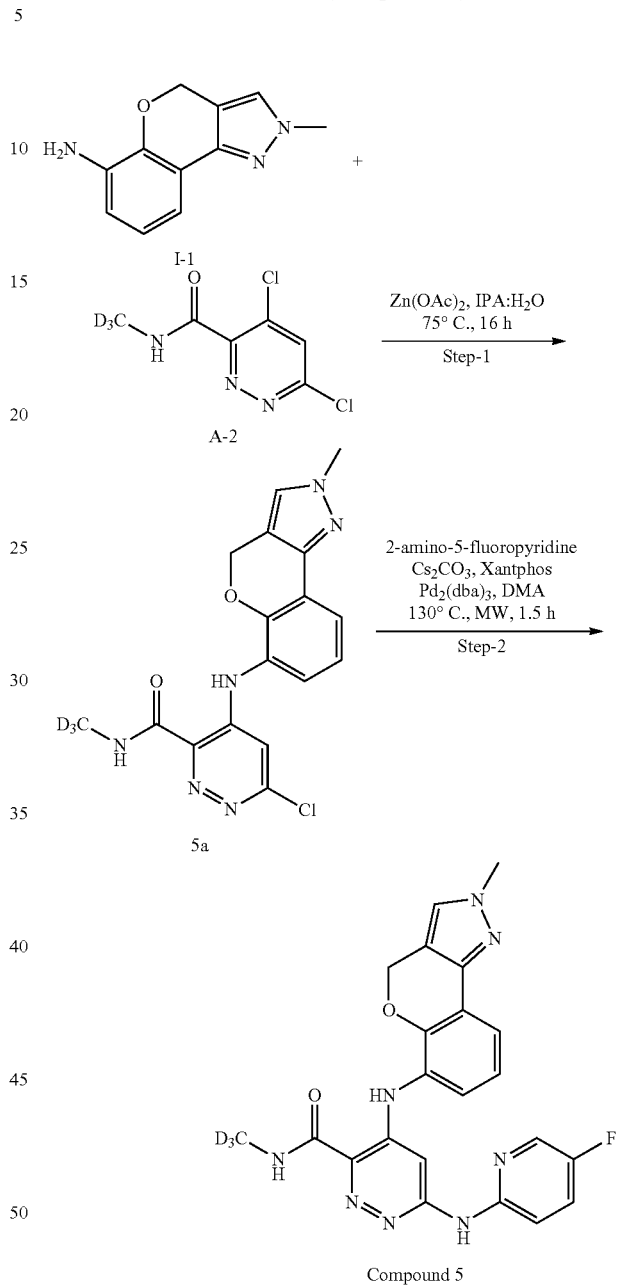

Step-1: 6-(cyclopropanecarboxamido)-N-methyl-4-((2-(oxetan-3-yl)-2,4-dihydrochromeno [4,3-c]pyrazol-6-yl)amino)pyridazine-3-carboxamide (Compound 4): Compound 4 (55 mg) was synthesized by following procedure as described for the synthesis of Compound 1 (step-2) using 3a (0.25 g, 0.606 mmol) and cyclopropanecarboxamide (0.077 g, 0.91 mmol) as the starting materials. LCMS (ES) m/z; 462.2 [M+H]$^+$. $^1$H NMR (400 MHz, DMSO-d$_6$) δ 11.26 (s, 1H); 10.65 (s, 1H); 9.14-9.08 (m, 1H); 7.99 (s, 1H); 7.80 (s, 1H); 7.55 (d, J=6.8 Hz, 1H); 7.31 (d, J=7.6 Hz, 1H); 7.08 (t, J=8.0 Hz, 1H); 5.68-5.60 (m, 1H); 5.38 (s, 2H); 4.96 (s, 2H); 4.94 (s, 2H); 2.86 (d, J=4.4 Hz, 3H); 2.12-2.02 (m, 1H); 0.82-0.78 (m, 4H).

Step-1: 6-chloro-N-(methyl-d3)-4-((2-methyl-2,4-dihydrochromeno[4,3-c]pyrazol-6-yl)amino)pyridazine-3-carboxamide (Compound 5a): To a stirred solution of I-1 (0.21 g, 1.04 mmol) and A-2 (0.262 g, 1.04 mmol) in propan-2-ol (2.00 mL) and water (2.00 mL) was added Zn(OAc)$_2$ (0.287 g, 1.57 mmol) at room temperature. The reaction mixture was then stirred at 75° C. for 16 h in a sealed tube. The progress of the reaction was monitored by LCMS. After complete consumption of starting material, it was cooled to room temperature and stirred for 1 h. The obtained solid was filtered, washed with water (5 mL×2) and dried (co-evaporation with toluene). It was further stirred in diethyl ether (20.0 mL), filtered and dried to afford desired compound 6-chloro-N-(methyl-d3)-4-((2-methyl-2,4-dihydrochromeno[4,3-c]pyrazol-6-yl)amino)pyridazine-3-carboxamide 5a (0.32 g) as an off-white solid. LCMS (ES) m/z; 374.1 [M+H]$^+$. $^1$H NMR (400 MHz, DMSO-d$_6$) δ 10.81 (s, 1H); 9.30 (s, 1H); 7.60 (s, 1H); 7.50 (d, J=6.8 Hz, 1H); 7.36 (d, J=6.8 Hz, 1H); 7.10 (s, 1H); 7.07 (t, J=8.0 Hz, 1H); 5.32 (s, 2H); 3.90 (s, 3H).

Step-2: 6-((5-fluoropyridin-2-yl)amino)-N-(methyl-d3)-4-((2-methyl-2,4-dihydrochromeno[4,3-c]pyrazol-6-yl)amino)pyridazine-3-carboxamide (Compound 5): Argon gas was purged through a stirred suspension of 5a (0.35 g, 0.936 mmol), 5-fluoropyridin-2-amine (0.157 g, 1.40 mmol) and Cs$_2$CO$_3$ (0.61 g, 1.87 mmol) in DMA (3.00 mL) for 15 min. To this was then added [5-(diphenylphosphanyl)-9,9-dimethyl-9H-xanthen-4-yl]diphenylphosphane (0.108 g, 0.187 mmol) and Pd$_2$(dba)$_3$ (0.171 g, 0.187 mmol). The reaction mixture was then irradiated at 130° C. for 1.5 h in a MW reactor. The reaction progress was monitored by TLC. After complete consumption of starting material, it was cooled to room temperature and filtered through Celite bed. It was washed with EtOAc (50 mL×2) and the filtrate was concentrated under reduced pressure. The residue was purified by preparative HPLC to afford desired compound 6-((5-fluoropyridin-2-yl)amino)-N-(methyl-d3)-4-((2-methyl-2,4-dihydrochromeno[4,3-c]pyrazol-6-yl)amino) pyridazine-3-carboxamide Compound 5 (45 mg, TFA salt) as an off-white solid. LCMS (ES) m/z; 450.2 [M+H]$^+$. $^1$H NMR (400 MHz, DMSO-d$_6$) δ 10.71 (s, 1H); 10.38 (br s, 1H); 9.05 (s, 1H); 8.14 (s, 1H); 7.74-7.58 (m, 3H); 7.44 (d, J=8.0 Hz, 1H); 7.36 (d, J=7.7 Hz, 1H); 7.09 (t, J=8.0 Hz, 1H); 5.33 (s, 2H); 3.88 (s, 3H).

Example 45: Preparation of 6-(cyclopropanecarboxamido)-N-(methyl-d3)-4-((2-methyl-2,4-dihydrochromeno[4,3-c]pyrazol-6-yl)amino)nicotinamide (Compound 6)

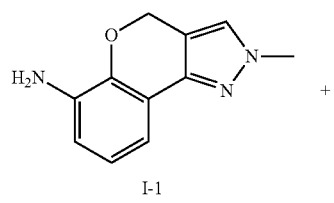

I-1

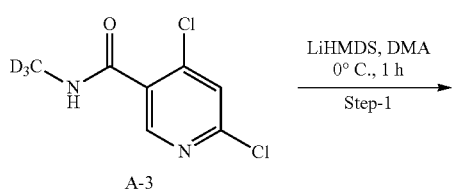

A-3

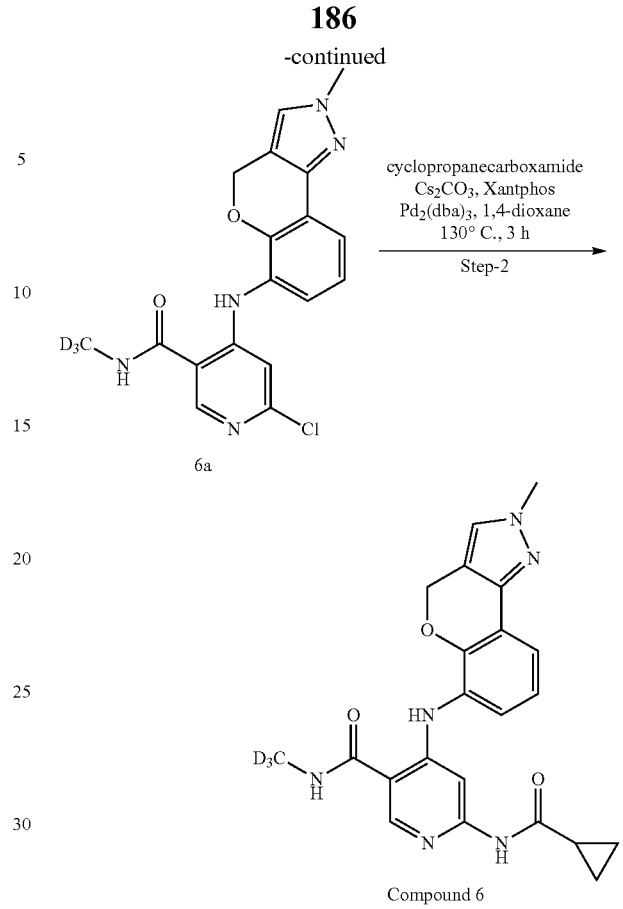

Compound 6

Step-1: 6-chloro-N-(methyl-d3)-4-((2-methyl-2,4-dihydrochromeno[4,3-c]pyrazol-6-yl)amino)nicotinamide (6a): To a stirred solution of I-1 (0.5 g, 2.48 mmol) and A-3 (0.57 g, 2.48 mmol) in anhydrous DMA (8.00 mL) was added a 1M solution of LiHMDS (in THF) (10.0 mL, 10.0 mmol) drop wise at 0° C. The reaction mixture was allowed to stir at the same temperature for 1 h, while monitoring reaction progress by TLC. After completion, it was quenched with addition of water (30 mL) and extraction was carried out using 10% MeOH in DCM (30 mL×3). The combined organic extracts were washed with brine (30 mL), dried over anhydrous Na$_2$SO$_4$, filtered and concentrated under reduced pressure. The resulting crude was purified by Combi-Flash (using gradient elution 0-5% MeOH in DCM) to afford desired compound 6-chloro-N-(methyl-d3)-4-((2-methyl-2,4-dihydrochromeno[4,3-c]pyrazol-6-yl)amino)nicotinamide 6a (0.65 g) as an off-white solid. LCMS (ES) m/z; 372.9 [M+H]$^+$. $^1$H NMR (400 MHz, DMSO-d$_6$) δ 10.30 (s, 1H); 8.72 (s, 1H); 8.46 (s, 1H); 7.58 (s, 1H); 7.43 (d, J=7.2 Hz, 1H); 7.27 (d, J=7.2 Hz, 1H); 7.02 (t, J=8.0 Hz, 1H); 6.81 (s, 1H); 5.28 (s, 2H); 3.87 (s, 3H).

Step-2: 6-(cyclopropanecarboxamido)-N-(methyl-d3)-4-((2-methyl-2,4-dihydrochromeno[4,3-c]pyrazol-6-yl)amino)nicotinamide (Compound 6): Argon gas was purged through a stirred suspension of 6a (0.25 g, 0.671 mmol), cyclopropanecarboxamide (0.086 g, 1.01 mmol) and Cs$_2$CO$_3$ (0.437 g, 1.34 mmol) in 1,4-dioxane (6.00 mL) for 15 min. To this was then added [5-(diphenylphosphanyl)-9,9-dimethyl-9H-xanthen-4-yl]diphenylphosphane (0.039 g, 0.067 mmol) and Pd$_2$(dba)$_3$ (0.061 g, 0.067 mmol). The reaction mixture was then stirred at 130° C. for 3 h in a sealed tube. The reaction progress was monitored by TLC.

After complete consumption of starting material, it was cooled to room temperature and filtered through Celite bed. It was washed with EtOAc (50 mL×2) and the filtrate was concentrated under reduced pressure. The residue was purified by Combi-Flash (using gradient elution of 0-5% MeOH in DCM) to afford desired compound 6-[(5-fluoropyridin-2-yl)amino]-N-methyl-4-({2-methyl-2H,4H-chromeno[4,3-c]pyrazol-6-yl}amino)pyridazine-3-carboxamide Compound 6 (90 mg) as an off-white solid. LCMS (ES) m/z; 422.2 [M+H]⁺. ¹H NMR (400 MHz, DMSO-d₆) δ 10.69 (s, 1H); 10.35 (s, 1H); 8.51 (s, 1H); 8.46 (s, 1H); 7.89 (s, 1H); 7.57 (s, 1H); 7.34 (dd, J₁=1.2 Hz, J₂=8.0 Hz, 1H); 7.23 (dd, J₁=1.2 Hz, J₂=8.0 Hz, 1H); 6.97 (t, J=8.0 Hz, 1H); 5.27 (s, 2H); 3.87 (s, 3H); 1.99-1.90 (m, 1H); 0.74-0.70 (m, 4H).

Example 46: Preparation of 6-(cyclopropanecarboxamido)-4-((1,5-dimethyl-4,5-dihydro-1H-pyrazolo[4,3-c]quinolin-6-yl)amino)-N-(methyl-d3)nicotinamide (Compound 51)

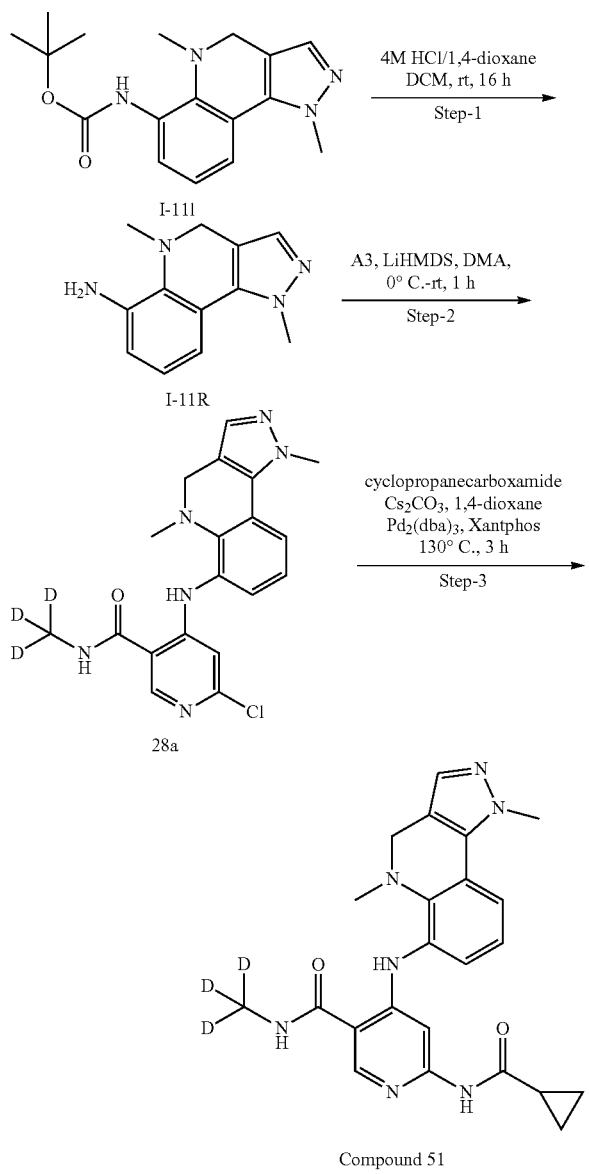

Step-1: 1,5-dimethyl-4,5-dihydro-1H-pyrazolo[4,3-c]quinolin-6-amine (I-11R): To a stirred solution of I-111 (contaminated with I-11k) (0.8 g, 2.54 mmol) in DCM (10.0 mL) was added a 4M solution of HCl in 1,4-dioxane (5.00 mL) at 0° C. The reaction mixture was stirred at room temperature for 16 h. After completion, volatiles were removed under reduced pressure and saturated NaHCO₃ solution (20 mL) was added to the residue. Extraction was carried out using EtOAc (3×30 mL); the combined organic extracts were washed with water (30 mL), brine (30 mL), dried over anhydrous Na₂SO₄, filtered and concentrated under reduced pressure. The residue was purified by Combi-Flash (using gradient elution of 0-80% EtOAc in hexane) to afford desired compound 1,5-dimethyl-4,5-dihydro-1H-pyrazolo[4,3-c]quinolin-6-amine I-11R (contaminated with I-11) (0.5 g) as a semi-solid (mixture of regioisomers was carried forward for the next step). LCMS (ES) m/z; 214.9 [M+H]⁺.

Step-2: 6-chloro-4-((1,5-dimethyl-4,5-dihydro-1H-pyrazolo[4,3-c]quinolin-6-yl)amino)-N-(methyl-d3)nicotinamide (28a): To a stirred solution of I-11R (0.5 g, 2.33 mmol) in anhydrous DMA (8.00 mL) was added A-3 (0.486 g, 2.33 mmol) and the reaction mixture was cooled to 0° C. To this was then added 1M solution of LiHMDS in THF (10 mL, 10.0 mmol) and the reaction mixture was allowed to warm to room temperature over 1 h. The progress of the reaction was monitored by TLC. After completion, it was quenched with addition of ice-cold water (10 mL) and extraction was carried out using 10% MeOH in DCM (30 mL×3). The combined organic extracts were washed with brine (50 mL), dried over anhydrous Na₂SO₄, filtered and concentrated under reduced pressure. The residue was purified by silica gel column chromatography (using gradient elution of 0-3% MeOH in DCM) to afford desired compound a 6-chloro-4-((1,5-dimethyl-4,5-dihydro-1H-pyrazolo[4,3-c]quinolin-6-yl)amino)-N-(methyl-d3)nicotinamide 28a (500 mg) as a brown solid. LCMS (ES) m/z; 384.1 [M−H]⁺.

Step-3: 6-(cyclopropanecarboxamido)-4-((1,5-dimethyl-4,5-dihydro-1H-pyrazolo[4,3-c]quinolin-6-yl)amino)-N-(methyl-d3)nicotinamide (Compound 51): Argon gas was purged through a stirred suspension of 28a (0.5 g, 1.30 mmol), cyclopropanecarboxamide (0.121 g, 1.43 mmol) and Cs₂CO₃ (0.844 g, 2.59 mmol) in 1,4-dioxane (10 mL) for 15 min. To this was then added [5-(diphenylphosphanyl)-9,9-dimethyl-9H-xanthen-4-yl]diphenylphosphane (0.075 g, 130 μmol) and tris(1,5-diphenylpenta-1,4-dien-3-one) dipalladium (0.119 g, 130 μmol)). The reaction mixture was then stirred at 130° C. for 3 h in a sealed tube. It was then cooled to room temperature, filtered through a pad of Celite and washed with EtOAc (20 mL×2). The filtrate was concentrated under reduced pressure and the residue was purified by Combi-Flash (using gradient elution of 0-5% MeOH in DCM). The residue obtained was further purified by preparative HPLC (separation of regioisomers) to afford desired compound 6-(cyclopropanecarboxamido)-4-((1,5-dimethyl-4,5-dihydro-1H-pyrazolo[4,3-c]quinolin-6-yl)amino)-N-(methyl-d3)nicotinamide Compound 51 (75 mg) as an off-white solid. LCMS (ES) m/z; 435.3 [M+H]⁺. ¹H NMR (400 MHz, DMSO-d₆) b 10.73 (s, 1H); 10.50 (s, 1H); 8.52 (s, 1H); 8.46 (s, 1H); 8.10 (s, 1H); 7.46 (d, J=6.8 Hz, 1H); 7.36-7.32 (m, 2H); 7.20 (apparent t, J=8.0 Hz, 1H); 4.09 (s, 3H); 4.03 (s, 2H); 2.38 (s, 3H); 2.00-1.90 (m, 1H); 0.78-0.70 (m, 4H).

The following compounds were synthesized by following the procedures described in the previous examples using appropriate intermediates. For final Buchwald coupling, corresponding amine coupling partners (e.g., 2-amino-5- fluoropyridine or 2-amino-4,6-dimethylpyrimidine) or amide coupling partner (e.g., cyclopropanecarboxamide) were used, as appropriate.

| Compound No. | Structure | Analytical Data |
|---|---|---|
| 7 | 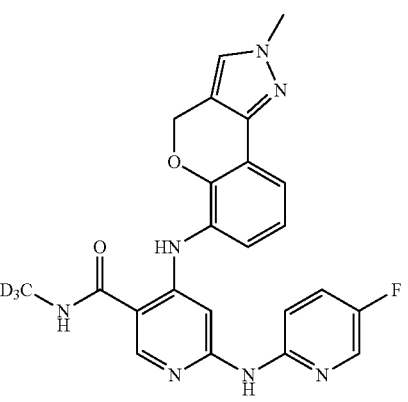 [SMILES: [2H]C([2H])([2H])NC(=O)c1cnc(Nc2ccc(F)cn2)cc1Nc1cccc2c1OCc1cn(C)nc1-2] | LCMS (ES) m/z; 449.2 [M + H]+. ¹NMR (400 MHz, DMSO-d₆) δ 10.36 (s, 1H); 9.75 (s, 1H); 8.42-8.40 (m, 2H); 8.07 (d, J = 6.4 Hz, 1H); 7.70 (dd, J₁ = 4.0 Hz, J₂ = 9.2 Hz, 1H); 7.64-7.54 (m, 3H); 7.38-7.30 (m, 2H); 7.04 (apparent t, J = 8.0 Hz, 1H); 5.31 (s, 2H); 3.87 (s, 3H). |
| 8 | 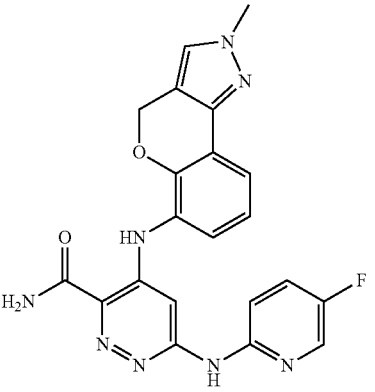 [SMILES: Cn1cc2c(n1)-c1cccc(Nc3cc(Nc4ccc(F)cn4)nnc3C(N)=O)c1OC2] | LCMS (ES) m/z; 433.2 [M + H]+. ¹H NMR (400 MHz, DMSO-d₆) δ 10.72 (s, 1H); 10.46 (br s, 1H); 8.43 (s, 1H); 8.16 (s, 1H); 7.85 (br s, 1H); 7.74-7.70 (m, 1H); 7.60-7.47 (m, 3H); 7.46 (d, J = 6.8 Hz, 1H); 7.35 (d, J = 8.0 Hz, 1H); 7,00 (apparent t, J = 8.0 Hz, 1H); 5.32 (s, 2H); 3.88 (s, 3H). |
| 9 | 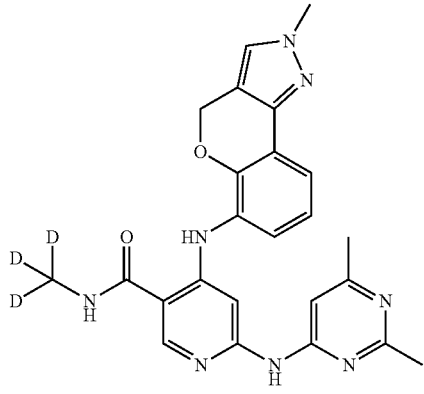 [SMILES: [2H]C([2H])([2H])NC(=O)c1cnc(Nc2cc(C)nc(C)n2)cc1Nc1cccc2c1OCc1cn(C)nc1-2] | LCMS (ES) m/z; 460.2 [M + H]+. ¹H NMR (400 MHz, DMSO-d₆) δ 11.24 (hr s, 1H); 10.45 (s, 1H); 8.64 (s, 1H); 8.55 (s, 1H); 7.62-7.58 (m, 2H); 7.43 (d, J = 7.6 Hz, 1H); 7.33 (d, J = 7.6 Hz, 1H); 7.03 (t, J = 7.2 Hz, 1H); 5.30 (s, 2H); 3.87 (s, 3H); 2.43 (s, 6H). |

-continued

| Compound No. | Structure | Analytical Data |
|---|---|---|
| 10 | 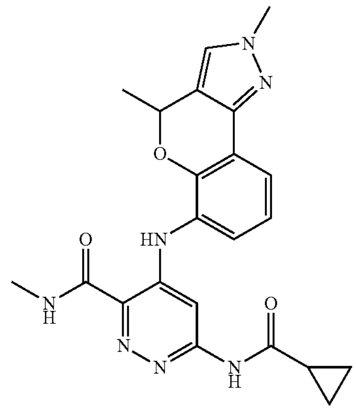 [SMILES: CNC(=O)c1nnc(NC(=O)C2CC2)cc1Nc1cccc2c1OC(C)c1cn(C)nc1-2] | LCMS (ES) m/z; 434.2 [M + H]⁺. ¹H NMR (400 MHz, DMSO-d$_6$) δ 11.25 (s, 1H); 10.73 (s, 1H); 9.09 (d, J = 4.8 Hz, 1H); 8.04 (s, 1H); 7.64 (s, 1H); 7.43 (dd, J$_1$ = 1.2 Hz, J$_2$ = 7.6 Hz, 1H); 7.28 (dd, J$_1$ = 1.2 Hz. J$_2$ = 8.0 Hz, 1H); 7.03 (app t, J = 7.6 Hz, 1H); 5.54 (q, J = 6.0 Hz, 1H); 3.89 (s, 3H); 2.86 (d, J = 4.8 Hz, 3H); 2.09-2.02 (m, 1H); 1.51 (d, J = 6.4 Hz, 3H); 0.82-0.79 (m, 4H). |
| 11 | 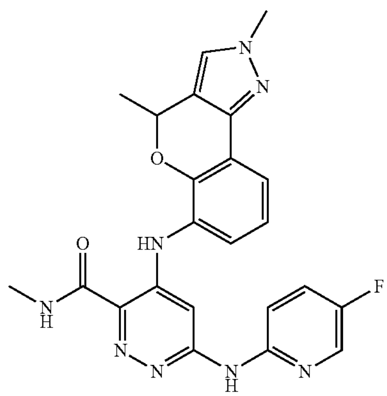 [SMILES: CNC(=O)c1nnc(Nc2ccc(F)cn2)cc1Nc1cccc2c1OC(C)c1cn(C)nc1-2] | LCMS (ES) m/z; 461.2 [M + H]⁺. ¹H NMR (400 MHz, DMSO-d$_6$) δ 10.74 (s, 1H); 10.15 (s, 1H); 9.06 (d, J = 4.8 Hz, 1H); 8.11 (d, J = 2.4 Hz, 1H); 7.87 (s, 1H); 7.72-7.63 (m, 2H); 7.63 (s, 1H); 7.38 (d, J = 7.6 Hz, 2H); 7.07 (app t, J = 7.6 Hz, 1H); 5.54 (q, J = 6.4 Hz, 1H); 3.87 (s, 3H); 2.83 (d, J = 4.8 Hz, 3H); 1,53 (d, J = 6.0 Hz, 3H). |
| 12 | 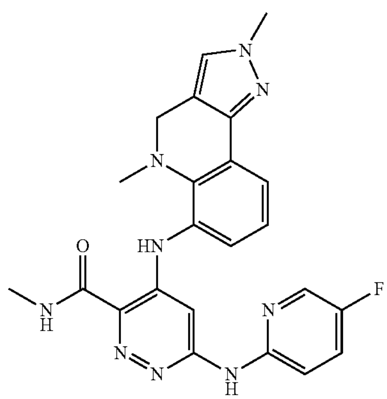 [SMILES: CNC(=O)c1nnc(Nc2ccc(F)cn2)cc1Nc1cccc2c1N(C)Cc1cn(C)nc1-2] | LCMS (ES) m/z: 460.2 [M + H]⁺. ¹H NMR (400 MHz, DMSO-d$_6$) δ 10.86 (s, 1H); 10.16 (s, 1H); 9.10-9.00 (m, 1H); 8.16 (s, 1H); 8.04 (s, 1H); 7.70-7.64 (m, 2H); 7.57 (s, 1H); 7.43 (apparent t, J = 8.0 Hz, 2H); 7.22 (apparent t, J = 8.0 Hz, 1H); 4.08 (s, 2H); 3.88 (s, 3H); 2.84 (d, J = 5.2 Hz, 3H); 2.44 (s, 3H). |
| 13 | 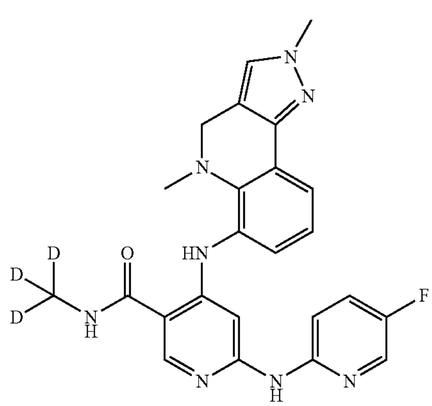 [SMILES: [2H]C([2H])([2H])NC(=O)c1cnc(Nc2ccc(F)cn2)cc1Nc1cccc2c1N(C)Cc1cn(C)nc1-2] | LCMS (ES) m/z: 462.2 [M + H]⁺. ¹H NMR (400 MHz, DMSO-d$_6$) δ 10.49 (s, 1H); 9.75 (s, 1H); 8.41-8.38 (m, 2H); 8.13 (d, J = 2.4 Hz, 1H); 7.76 (s, 1H); 7.70-7.58 (m, 2H); 7.56 (s, 1H); 7.41 (d, J = 7.6 Hz, 1H), 7.36 (d, J = 7.6 Hz, 1H); 7.19 (apparent J = 8.0 Hz, 1H); 4.10 (s, 2H); 3.88 (s, 3H); 2.43 (s, 3H). |

-continued

| Compound No. | Structure | Analytical Data |
| --- | --- | --- |
| 15 | 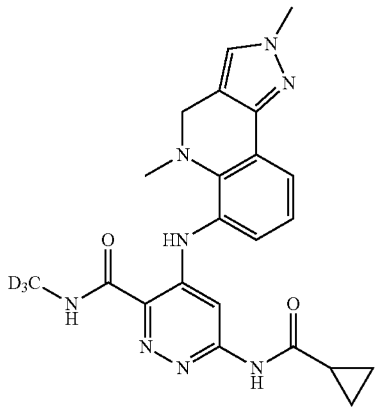 [SMILES: [2H]C([2H])([2H])NC(=O)c1nnc(NC(=O)C2CC2)cc1Nc1cccc2c1N(C)Cc1cn(C)nc1-2] | LCMS (ES) m/z: 436.2 [M + H]⁺. ¹H NMR (400 MHz, DMSO-d₆) δ 11.27 (s, 1H); 10.88 (s, 1H); 9.07 (s, 1H); 8.22 (s, 1H); 7.58 (s, 1H); 7.47 (dd, $J_1$ = 0.8 Hz, $J_2$ = 7.6 Hz, 1H); 7.31 (dd, $J_1$ = 0.8 Hz, $J_2$ = 8.0 Hz, 1H); 7.17 (app t, J = 7.6 Hz, 1H); 4.08 (s, 2H); 3.90 (s, 3H); 2.44 (s, 3H); 2.11-2.05 (m, 1H); 0.84-0.80 (m, 4H). |
| 16 | 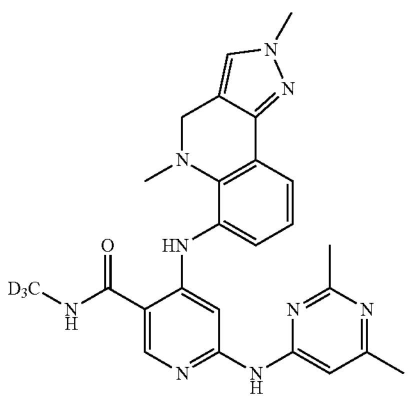 [SMILES: [2H]C([2H])([2H])NC(=O)c1cnc(Nc2cc(C)nc(C)n2)cc1Nc1cccc2c1N(C)Cc1cn(C)nc1-2] | LCMS (ES) m/z; 473.2 [M + H]⁺. ¹H NMR (400 MHz, DMSO-d₆) δ 10.57 (s, 1H); 9.98 (s, 1H); 8.45 (s, 2H); 8.14 (s, 1H); 7.56 (s, 1H); 7.45 (d, J = 8.0 Hz, 1H); 7.38 (d, J = 6.8 Hz, 1H); 7.18 (apparent t, J = 8.0 Hz, 1H); 7.07 (s, 1H); 4.06 (s, 2H); 3.88 (s, 3H); 2.44 (s, 3H); 2.37 (s, 3H); 2.26 (s, 3H). |
| 17 | 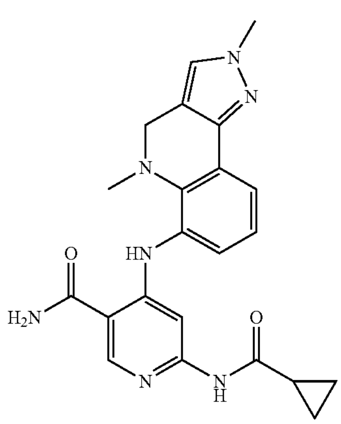 [SMILES: CN1Cc2cn(C)nc2-c2cccc(Nc3cc(NC(=O)C4CC4)ncc3C(N)=O)c21] | LCMS (ES) m/z; 418.2 [M + H]⁺. ¹H NMR (400 MHz, DMSO-d₆) δ 10.70 (s, 1H); 10.69 (s, 1H); 8.53 (s, 1H); 8.07 (s, 1H); 7.55 (s, 1H); 7.40-7.20 (m, 2H); 7.37 (d, J = 7.2 Hz, 1H); 7.27 (d, J = 8.0 Hz, 1H); 7,11 (apparent t, J = 7.6 Hz, 1H); 4.03 (s, 2H); 3.87 (s, 3H); 2.41 (s, 3H); 2.00-1.92 (m, 1H); 0.70-0.72 (m, 4H). |

| Compound No. | Structure | Analytical Data |
|---|---|---|
| 18 | 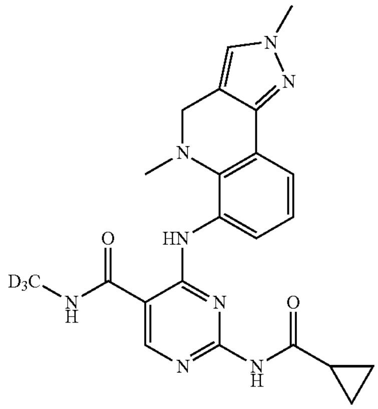 | LCMS (ES) m/z; 432.2 [M + H]⁺. ¹H NMR (400 MHz, DMSO-d₆) δ 10.71 (s, 1H); 10.49 (s, 1H); 8.57-8.52 (m, 1H); 8.48 (s, 1H); 8.12 (s, 1H); 7.57 (s, 1H); 7.39 (dd, J₁ = 1.2 Hz, J₂ = 7.6 Hz, 1H); 7,29 (dd, J₁ = 0.8 Hz, J₂ = 8.0 Hz, 1H); 7.13 (apparent t, J = 8.0 Hz, 1H); 4.08 (s, 2H); 3.90 (s, 3H); 2.80 (d, J = 4.8 Hz, 3H); 2.44 (s, 3H); 2.01-1.94 (m, 1H); 0.80-0.75 (m, 4H). |
| 19 | 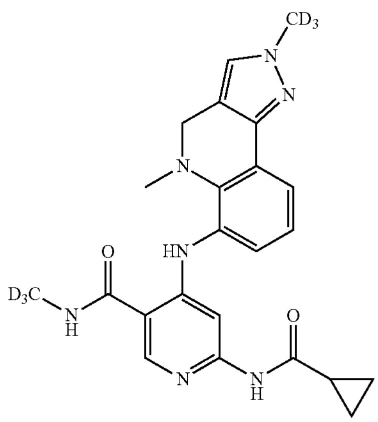 | LCMS (ES) m/z; 438.3 [M + H]⁺. ¹H NMR (400 MHz, DMSO-d₆) δ 10.70 (s, 1H); 10.48 (s, 1H); 8.50 (s, 1H); 8.45 (s, 1H); 8.10 (s, 1H); 7.55 (s, 1H); 7.36 (d, J = 7.6 Hz, 1H); 7.26 (d, J = 8.0 Hz, 1H); 7.10 (apparent t, J = 8.0 Hz, 1H); 4.05 (s, 2H); 2.41 (s, 3H); 1.98-1.92 (m, 1H); 0.75-0.71 (m, 4H). |
| 20 | 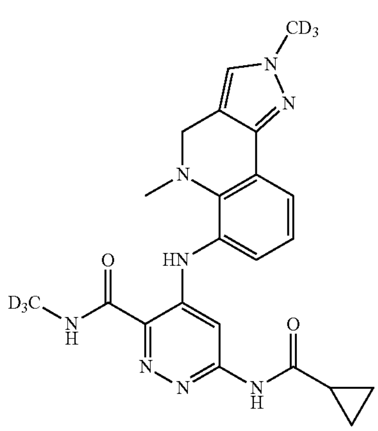 [SMILES: [2H]C([2H])([2H])NC(=O)c1nnc(NC(=O)C2CC2)cc1Nc1cccc2c1N(C)Cc1cn(C([2H])([2H])[2H])nc1-2] | LCMS (ES) m/z; 439.3 [M + H]⁺. ¹H NMR (400 MHz, DMSO-d₆) δ 11.26 (s, 1H); 10.87 (s, 1H); 9.06 (s, 1H); 8,21 (s, 1H); 7.58 (s, 1H); 7.48 (dd, J₁ = 1.2 Hz, J₂ = 7.6 Hz, 1H); 7.30 (d, J = 7.2 Hz, 1H); 7.16 (app t, J = 7.6 Hz, 1H); 4.09 (s, 2H); 2.45 (s, 3H); 2.10-2.06 (m, 1H); 0.84-0.80 (m, 4H). |

| Compound No. | Structure | Analytical Data |
| --- | --- | --- |
| 24 | 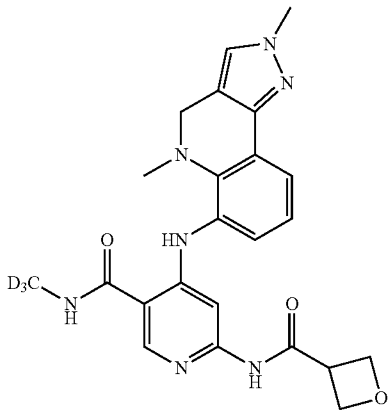 [SMILES: [2H]C([2H])([2H])NC(=O)c1cnc(NC(=O)C2COC2)cc1Nc1cccc2c1N(C)Cc1cn(C)nc1-2] | LCMS (ES) m/z, 451.3 [M + H]⁺. ¹H NMR (400 MHz, DMSO-d$_6$) δ 10.53 (s, 1H); 10.42 (s, 1H); 8.52 (s, 1H); 8.47 (s, 1H); 8.18 (s, 1H); 7.58 (s, 1H); 7.43 (d, J = 7.6 Hz, 1H); 7.35 (d, J = 7.2 Hz, 1H); 7.18 (t, J = 7.6 Hz, 1H); 4.67-4.61 (m, 4H); 4.09 (s, 2H); 4.06-4.03 (m, 1H); 3.91 (s, 3H); 2.46 (s, 3H). |
| 25 | 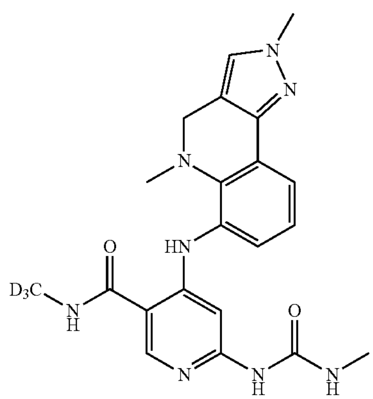 [SMILES: [2H]C([2H])([2H])NC(=O)c1cnc(NC(=O)NC)cc1Nc1cccc2c1N(C)Cc1cn(C)nc1-2] | LCMS (ES) m/z; 424.3 [M + H]⁺. ¹H NMR (400 MHz, DMSO-d$_6$) δ 10.43 (s, 1H); 9.09 (s, 1H); 8.43 (s, 1H); 8.36 (s, 1H); 7.89 (bs, 1H); 7.57 (s, 1H); 7.39 (dd, J$_1$ = 1.2 Hz, J$_2$ = 7.6 Hz, 1H); 7.37 (s, 1H); 7.30 (dd, J$_1$ = 1.2 Hz, J$_2$ = 7.6 Hz, 1H); 7.13 (t, J = 8.0 Hz, 1H); 4.08 (s, 2H); 3.90 (s, 3H); 2.69 (d, J = 4.8 Hz, 3H); 2.44 (s, 3H). |
| 26 | 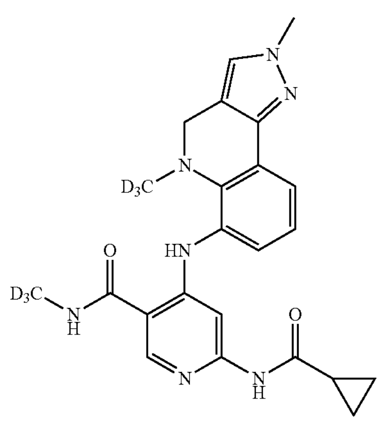 [SMILES: [2H]C([2H])([2H])NC(=O)c1cnc(NC(=O)C2CC2)cc1Nc1cccc2c1N(C([2H])([2H])[2H])Cc1cn(C)nc1-2] | LCMS (ES) m/z; 438.3 [M + H]⁺. ¹H NMR (400 MHz, DMSO-d$_6$) δ 10.71 (s, 1H); 10.49 (s, 1H); 8.51 (s, 1H); 8.47 (s, 1H); 8.12 (s, 1H); 7.57 (s, 1H); 7.39 (dd, J$_1$ = 1.2 Hz, J$_2$ = 7.6 Hz, 1H); 7.29 (dd, J$_1$ = 1.2 Hz, J$_2$ = 7.6 Hz, 1H); 7.12 (t, J = 7.6 Hz, 1H); 4.07 (s, 2H); 3.90 (s, 3H); 2.00-1.95 (m, 1H); 0.80-0.76 (m, 4H). |

-continued
| Compound No. | Structure | Analytical Data |
|---|---|---|
| 27 | 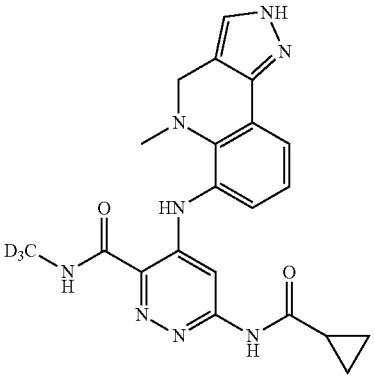 [SMILES: [2H]C([2H])([2H])NC(=O)c1nnc(NC(=O)C2CC2)cc1Nc1cccc2c1N(C)Cc1c[nH]nc1-2] | LCMS (ES) m/z; 422.3 [M + H]$^+$. $^1$H NMR (400 MHz, DMSO-d$_6$) δ 12.82 (s, 1H); 11.25 (s, 1H); 10.86 (s, 1H); 9.05 (s, 1H); 8.19 (s, 1H); 7.60 (s, 1H); 7.52-7.40 (m, 1H); 7.28 (d, J = 8.0 Hz, 1H); 7.15 (t, J = 8.0 Hz, 1H); 4.09 (s, 2H); 2.42 (s, 3H); 2.10-2.02 (m, 1H); 0.82-0.72 (m, 4H). |
| 28 | 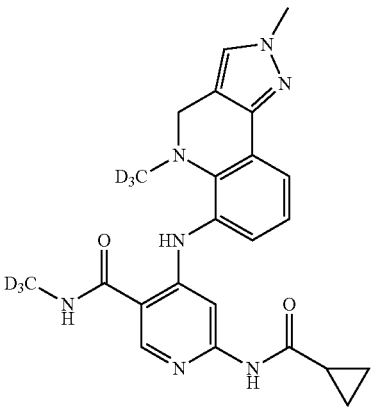 [SMILES: [2H]C([2H])([2H])NC(=O)c1cnc(NC(=O)C2CC2)cc1Nc1cccc2c1N(C([2H])([2H])[2H])Cc1cn(C)nc1-2] | LCMS (ES) m/z; 438.3 [M + H]$^+$. $^1$H NMR (400 MHz, DMSO-d$_6$) δ 11.28 (s, 1H); 10.88 (s, 1H); 9.07 (s, 1H); 8.22 (s, 1H); 7.58 (s, 1H); 7.47 (dd, J$_1$ = 1.2 Hz, J$_2$ = 7.6 Hz, 1H); 7.31 (dd, J$_1$ = 1.2 Hz, J$_2$ = 7.6 Hz, 1H); 7.16 (t, J = 7.6 Hz; 1H); 4.08 (s, 2H); 3.90 (s, 3H); 2.11-2.05 (m, 1H); 0.83-0.80 (m, 4H). |
| 29 | 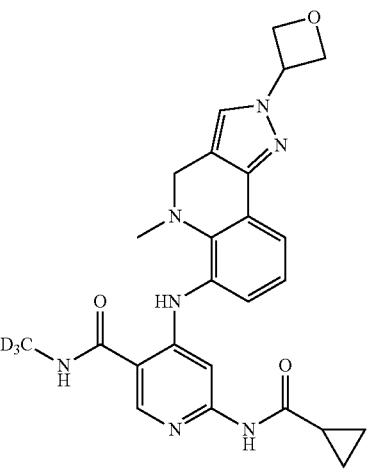 [SMILES: [2H]C([2H])([2H])NC(=O)c1cnc(NC(=O)C2CC2)cc1Nc1cccc2c1N(C)Cc1cn(C3COC3)nc1-2] | LCMS (ES) m/z; 477.3 [M + H]$^+$. $^1$H NMR (400 MHz, DMSO-d$_6$) δ 10.69 (s, 1H); 10.50 (s, 1H); 8.51 (s, 1H); 8.48 (s, 1H); 8.10 (s, 1H); 7.80 (s, 1H); 7.48 (d, J = 7.6 Hz, 1H); 7.32 (d, J = 7.2 Hz, 1H); 7.15 (t, J = 7.6 Hz, 1H); 5.63-5.59 (m, 1H); 4.98-4.93 (m, 4H); 4,10 (s, 2H); 2.46 (s, 3H); 2.00-1.94 (m, 1H); 0.78-0.72 (m, 4H). |

| Compound No. | Structure | Analytical Data |
|---|---|---|
| 30 | 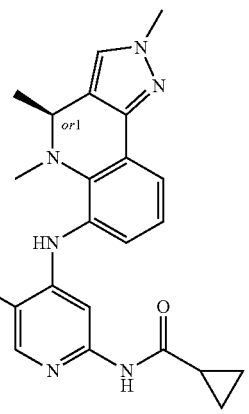<br>absolute configuration not determined | LCMS (ES) m/z; 449.3 [M + H]$^+$. $^1$H NMR (400 MHz, DMSO-d$_6$) δ 10.69 (s, 1H); 10.55 (s, 1H); 8.47 (s, 2H); 8.11 (s, 1H); 7.57 (s, 1H); 7.39 (dd, J$_1$ = 1.2 Hz, J$_2$ = 7.6 Hz, 1H); 7.30 (dd, J$_1$ = 1.2 Hz, J$_2$ = 7.6 Hz, 1H); 7.12 (t, J = 8.0 Hz, 1H); 4.22 (q, J = 6.8 Hz, 1H); 3.94 (s, 3H); 2.37 (s, 3H); 2.01-1.95 (m, 1H); 1.10 (d, J = 6.8 Hz, 3H); 0.81-0.74 (m, 4H).<br>{34B (0.49 g): peak-1; R$_t$: 6.96 min and 34C (0.5 g): peak-2; R$_t$: 8.54 min.}, |
| 31 | 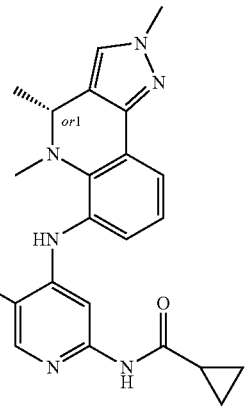<br>absolute configuration not determined | LCMS (ES) m/z; 449.3 [M + H]$^+$. $^1$H NMR (400 MHz, DMSO-d$_6$) δ 10.69 (s, 1H); 10.54 (s, 1H); 8.47 (s, 2H); 8.11 (s, 1H); 7.57 (s, 1H); 7.39 (dd, J$_1$ = 1.2 Hz, J$_2$ = 7.6 Hz, 1H); 7.30 (dd, J$_1$ = 1.2 Hz, J$_2$ = 7.6 Hz, 1H); 7.12 (t, J = 8.0 Hz, 1H); 4.22 (q, J = 6.8 Hz, 1H); 3.89 (s, 3H); 2.34 (s, 3H); 2.01-1.97 (m, 1H); 1.10 (d, J = 6.8 Hz, 3H); 0.80-0.76 (m, 4H).<br>Chiral MD: Column: CHIRALPAK IA (100 mm × 4.6 mm × 3 μm); Mobile phase: n-Hexane: IPA with 0.1% DEA (60:40); Flow rate: 1.0 mL/min; peak-2; R$_t$: 5.83 min. |
| 32 | 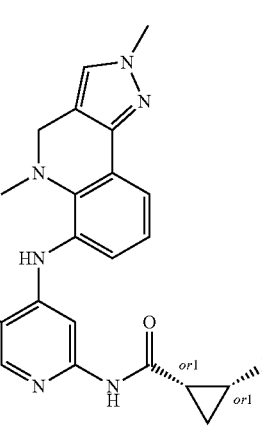<br>(cis or trans) absolute configuration not determined | LCMS (ES) m/z; 453.3 [M + H]$^+$. $^1$H NMR (400 MHz, DMSO-d$_6$) δ 10.73 (s, 1H); 10.49 (s, 1H); 8.51 (s, 1H); 8.46 (s, 1H); 8.08 (s, 1H); 7.55 (s, 1H); 7.37 (d, J = 7.6 Hz, 1H); 7.27 (d, J = 7.2 Hz, 1H); 7.12 (t, J = 8.0 Hz, 1H); 4.96-4.75 (m, 1H); 4.05 (s, 2H); 3.87 (s, 3H); 2.42 (s, 3H); 2.20-2.10 (m, 1H); 1.64-1.52 (m, 1H); 1.14-1.06 (m, 1H). |

| Compound No. | Structure | Analytical Data |
| --- | --- | --- |
| 33 | 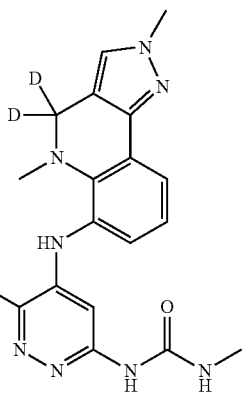 | LCMS (ES) m/z; 427.3 [M + H]⁺. ¹H NMR (400 MHz, DMSO-d₆) δ 10.85 (s, 1H); 9.48 (s, 1H); 9.04 (s, 1H); 7.79 (s, 1H); 7.58 (s, 1H); 7.47 (dd, $J_1$ = 1.2 Hz, $J_2$ = 7.6 Hz, 1H); 7.34-7.29 (m, 2H); 7.17 (t, J = 8.0 Hz, 1H); 3.90 (s, 3H); 2.69 (d, J = 4.4 Hz, 3H); 2.40 (s, 3H). |
| 34 | 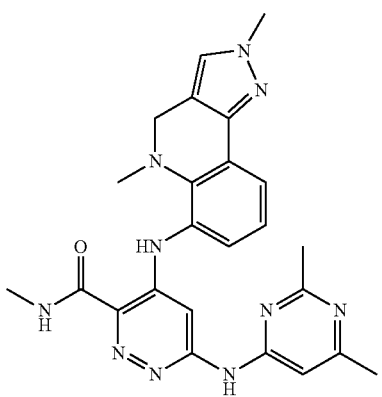 | LCMS (ES) m/z; 471.3 [M + H]⁺. ¹H NMR (400 MHz, DMSO-d₆) δ 10.95 (s, 1H); 10.46 (s, 1H); 9.11 (q, J = 4.4 Hz, 1H); 8.42 (s, 1H); 7.58 (s, 1H); 7.48 (d, J = 6.8 Hz, 2H); 7.21 (t, J = 8.0 Hz, 1H); 7.13 (s, 1H); 4.09 (s, 2H); 3.90 (s, 3H); 2.86 (d, J = 4.4 Hz, 3H); 2.46 (s, 3H); 2.39 (s, 3H); 2.30 (s, 3H). |
| 35 | 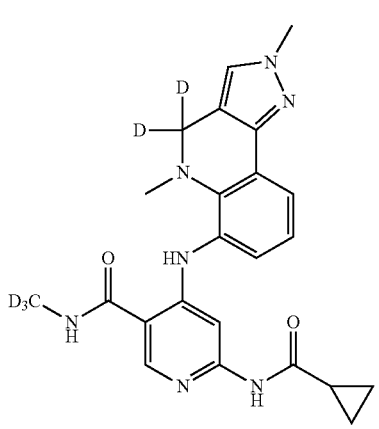 [SMILES: [2H]C([2H])([2H])NC(=O)c1cnc(NC(=O)C2CC2)cc1Nc1cccc2c1N(C)C([2H])([2H])c1cn(C)nc1-2] | LCMS (ES) m/z; 437.3 [M + H]⁺. ¹H NMR (400 MHz, DMSO-d₆) δ 10.70 (s, 1H); 10.48 (s, 1H); 8.50 (s, 1H); 8.45 (s, 1H); 8.10 (s, 1H); 7.55 (s, 1H); 7.36 (d, J = 8.0 Hz, 1H); 7.26 (d, J = 7.2 Hz, 1H); 7.10 (t, J = 8.0 Hz, 1H); 3.87 (s, 3H); 2.41 (s, 3H); 1.99-1.93 (m, 1H); 0.76-0.74 (m, 4H). |

-continued

| Compound No. | Structure | Analytical Data |
|---|---|---|
| 36 | (cis or trans) absolute configuration not determined | LCMS (ES) m/z; 453.3 [M + H]$^+$. $^1$H NMR (400 MHz, DMSO-d$_6$) δ 10.85 (s, 1H); 10.49 (s, 1H); 8.52 (s, 1H); 8.48 (s, 1H); 8.05 (s, 1H); 7.57 (s, 1H); 7.40 (dd, J$_1$ = 1.2 Hz, J$_2$ = 7.6 Hz, 1H); 7.28 (dd, J$_1$ = 1.2 Hz, J$_2$ = 7.6 Hz, 1H); 7.11 (t, J = 8.0 Hz, 1H); 4.94-4.76 (m, 1H); 4.07 (s, 2H); 3.89 (s, 3H); 2.44 (s, 3H); 2.08-2.06 (m, 1H); 1.52-1.40 (m, 1H); 1.24-1.16 (m, 1H). |
| 49 | 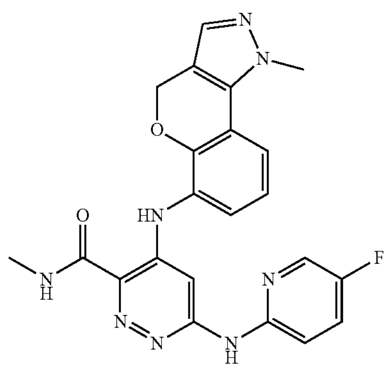 [SMILES: CNC(=O)c1nnc(Nc2ccc(F)cn2)cc1Nc1cccc2c1OCc1cnn(C)c1-2] | LCMS (ES) m/z; 447.3 [M + H]$^+$. $^1$H NMR (400 MHz, DMSO-d$_6$) δ 10.69 (s, 1H); 10.18 (s, 1H); 9.09 (d, J = 4.8 Hz, 1H); 8.11 (s, 1H); 7.86 (s, 1H); 7.68 (d, J = 5.6 Hz, 2H); 7.54 (d, J = 8.0 Hz, 1H); 7.47 (d, J = 8.0 Hz, 1H); 7.34 (s, 1H); 7.18 (t, J = 8.0 Hz, 1H); 5.30 (s, 2H); 4.11 (s, 3H); 2.83 (d, J = 4.4 Hz, 3H). |
| 50 | 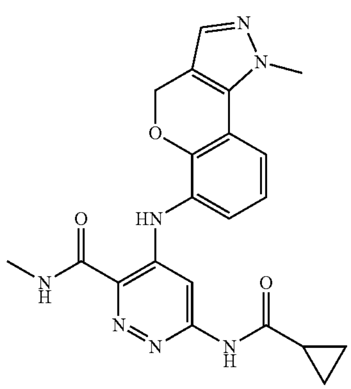 [SMILES: CNC(=O)c1nnc(NC(=O)C2CC2)cc1Nc1cccc2c1OCc1cnn(C)c1-2] | LCMS (ES) m/z; 420.2 [M + H]$^+$. $^1$H NMR (400 MHz, DMSO-d$_6$) δ 11.30 (s, 1H); 10.67 (s, 1H); 9.12 (d, J = 4.4 Hz, 1H); 7.99 (s, 1H); 7.56 (d, J = 7.6 Hz, 1H); 7.30-7.38 (m, 2H); 7.12 (apparent t, = 8.0 Hz, 1H); 5.26 (s, 2H); 4.10 (s, 3H); 2.83 (d, J = 4.4 Hz, 3H); 2.10-2.02 (m, 1H); 0.82-0.72 (m, 4H). |

| Compound No. | Structure | Analytical Data |
|---|---|---|
| 53 | 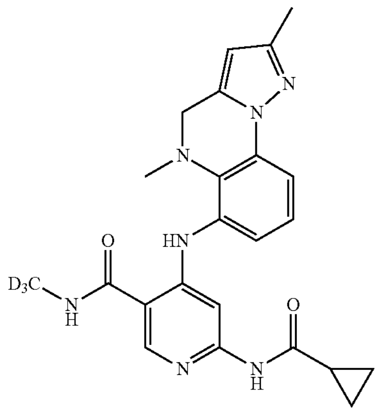 [SMILES: [2H]C([2H])([2H])NC(=O)c1cnc(NC(=O)C2CC2)cc1Nc1cccc2c1N(C)Cc1cc(C)nn1-2] | LCMS (ES) m/z; 435.3 [M + H]⁺. ¹H NMR (400 MHz, DMSO-d₆) δ 10.74 (s, 1H); 10.58 (s, 1H); 8.55 (s, 1H); 8.51 (s, 1H); 8.12 (s, 1H); 7.47 (dd, J₁ = 2.0 Hz, J₂ = 7.2 Hz, 1H); 7.24-7.18 (m, 2H); 6.14 (s, 1H); 4.23 (s, 2H); 2.46 (s, 3H); 2.29 (s, 3H); 2.01-1.97 (m, 1H); 0.80-0.76 (m, 4H). |
| 54 | 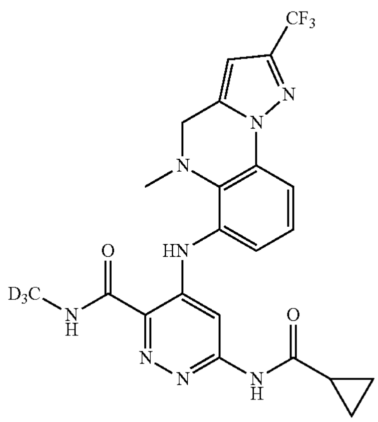 [SMILES: [2H]C([2H])([2H])NC(=O)c1nnc(NC(=O)C2CC2)cc1Nc1cccc2c1N(C)Cc1cc(C(F)(F)F)nn1-2] | LCMS (ES) m/z; 490.3 [M + H]⁺. ¹H NMR (400 MHz, DMSO-d₆) δ 11.33 (s, 1H); 10.99 (s, 1H); 9.12 (s, 1H); 8.22 (s, 1H); 7.67 (dd, J₁ = 0.8 Hz, J₂ = 8.0 Hz, 1H); 7.40 (d, J = 8.0 Hz, 1H); 7.33 (t, J = 8.0 Hz, 1H) 6.84 (s, 1H); 4.40 (s, 2H); 2.53 (s, 3H); 2.12-2.06 (m, 1H); 0.84-0.82 (m, 4H). |
| 55 | 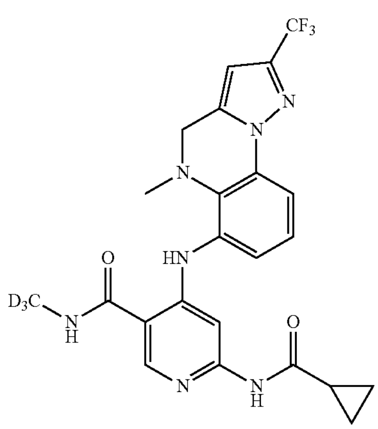 | LCMS (ES) m/z; 489.3 [M + H]⁺. ¹H NMR (400 MHz, DMSO-d₆) δ 10.77 (s, 1H); 10.65 (s, 1H); 8.58 (s, 1H); 8.53 (s, 1H); 8.12 (s, 1H); 7.58 (dd, J₁ = 1.2 Hz, J₂ = 8.0 Hz, 1H); 7.39 (d, J = 8.0 Hz, 1H); 7.29 (t, J = 8.0 Hz, 1H); 6.84 (s, 1H); 4.39 (s, 2H); 2.51 (s, 3H); 2.01-1.97 (m, 1H); 0.80-0.76 (m, 4H). |

| Compound No. | Structure | Analytical Data |
|---|---|---|
| 56 | 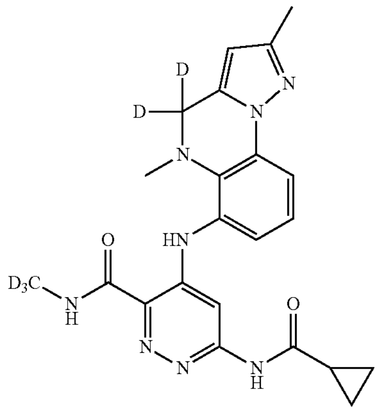 | LCMS (ES) m/z; 438.4 [M + H]⁺. ¹H NMR (400 MHz, DMSO-d₆) δ 11.30 (s, 1H); 10.93 (s, 1H); 9.10 (s, 1H); 8.21 (s, 1H); 7.56-7.53 (m, 1H); 7.25 (d, J = 4.8 Hz, 2H); 6.15 (s, 1H); 2.46 (s, 3H); 2.29 (s, 3H); 2.11-2.07 (m, 1H); 0.84-0.80 (m, 4H). |
| 57 | 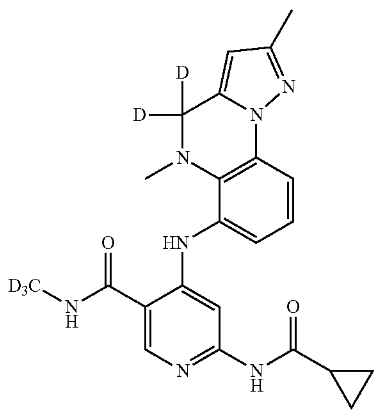 [SMILES: [2H]C([2H])([2H])NC(=O)c1cnc(NC(=O)C2CC2)cc1Nc1cccc2c1N(C)C([2H])([2H])c1cc(C)nn1-2] | LCMS (ES) m/z; 437.3 [M + H]⁺. ¹H NMR (400 MHz, DMSO-d₆) δ 10.75 (s, 1H); 10.57 (s, 1H); 8.55 (s, 1H); 8.48 (s, 1H); 8.10 (s, 1H); 7.43 (dd, J₁ = 2.0 Hz, J₂ = 7.2 Hz, 1H); 7.22-7.16 (m, 2H); 6.12 (s, 1H); 2.44 (s, 3H); 2.26 (s, 3H); 1.99-1.92 (m, 1H); 0.76-0.72 (m, 4H). |
| 58 | 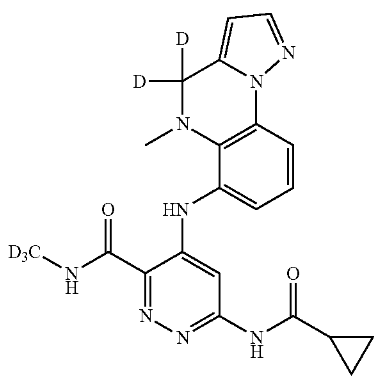 [SMILES: [2H]C([2H])([2H])NC(=O)c1nnc(NC(=O)C2CC2)cc1Nc1cccc2c1N(C)C([2H])([2H])c1ccnn1-2] | LCMS (ES) m/z; 424.3 [M + H]⁺. ¹H NMR (400 MHz, DMSO-d₆) δ 11.33 (s, 1H); 10.97 (s, 1H); 9.12 (s, 1H); 8.23 (s, 1H); 7.76 (d, J = 2.0 Hz, 1H); 7.62 (dd, J₁ = 3.2 Hz, J₂ = 6.4 Hz, 1H); 7.31-7.26 (m, 2H); 6.35 (d, J = 1.6 Hz, 1H); 2.48 (s, 3H); 2.11-2.07 (m, 1H); 0.84-0.80 (m, 4H). |
| 59 | 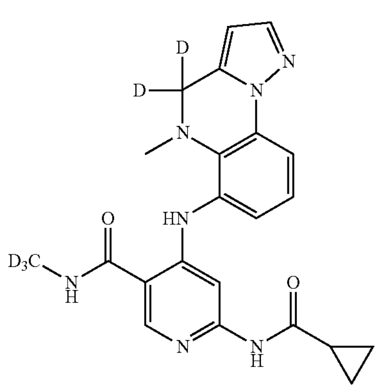 [SMILES: [2H]C([2H])([2H])NC(=O)c1cnc(NC(=O)C2CC2)cc1Nc1cccc2c1N(C)C([2H])([2H])c1ccnn1-2] | LCMS (ES) m/z; 423.3 [M + H]⁺. ¹H NMR (400 MHz, DMSO-d₆) δ 10.75 (s, 1H); 10.59 (s, 1H); 8.55 (s, 1H); 8.49 (s, 1H); 8.11 (s, 1H); 7.73 (d, J = 1.6 Hz, 1H); 7.51 (dd, J₁ = 2.0 Hz, J₂ = 7.6 Hz, 1H); 7.27-7.20 (m, 2H); 6.33 (d, J = 1.2 Hz, 1H); 2.45 (s, 3H); 1.99-1.91 (m, 1H); 0.76-0.72 (m, 4H). |

-continued
| Compound No. | Structure | Analytical Data |
|---|---|---|
| 61 | 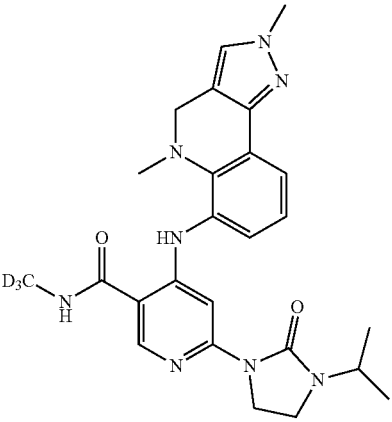 [SMILES: [2H]C([2H])([2H])NC(=O)c1cnc(N2CCN(C(C)C)C2=O)cc1Nc1cccc2c1N(C)Cc1cn(C)nc1-2] | LCMS (ES) m/z; 478.3 [M + H]$^+$. $^1$H NMR (400 MHz, DMSO-d$_6$) δ 10.39 (s, 1H); 8.45 (s, 1H); 8.44 (s, 1H); 8.22 (s, 1H); 7.57 (s, 1H); 7.38 (dd, J$_1$ = 0.8 Hz, J$_2$ = 7.6 Hz, 1H);); 7.34 (dd, J$_1$ = 0.8 Hz, J$_2$ = 8.0 Hz, 1H); 7.13 (t, J = 8.0 Hz, 1H); 4.08 (s, 2H); 4.06-4.00 (m, 1H); 3.94-3.92 (m, 2H); 3.91 (s, 3H); 3.40-3.36 (m, 2H); 2.40 (s, 3H); 1.05 (d, J = 6.8 Hz, 6H). |
| 62 | 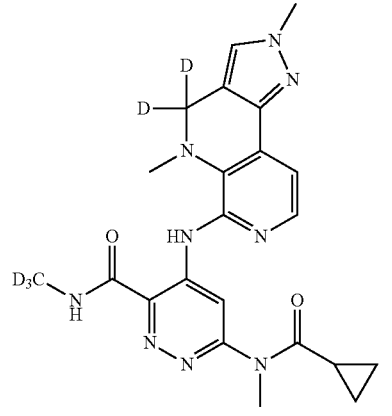 [SMILES: [2H]C([2H])([2H])NC(=O)c1nnc(N(C)C(=O)C2CC2)cc1Nc1nccc2c1N(C)C([2H])([2H])c1cn(C)nc1-2] | LCMS (ES) m/z; 453.3 [M + H]$^+$. $^1$H NMR (400 MHz, DMSO-d$_6$) δ 12.23 (s, 1H); 9.38 (s, 2H); 8.15 (d, J = 5.2 Hz, 1H); 7.69 (s, 1H); 7.30 (d, J = 5.2 Hz, 1H); 3.94 (s, 3H); 3.43 (s, 3H); 2.56 (s, 3H); 1.87-1.83 (m, 1H); 0.98-0.94 (m, 2H); 0.82-0.78 (m, 2H). |
| 63 | 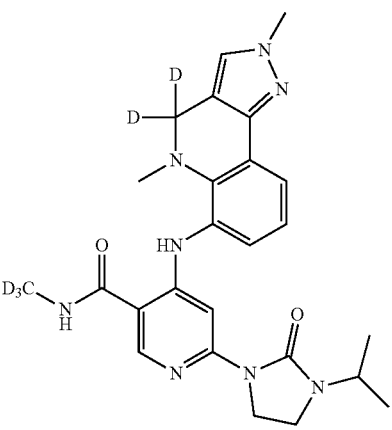 [SMILES: [2H]C([2H])([2H])NC(=O)c1cnc(N2CCN(C(C)C)C2=O)cc1Nc1cccc2c1N(C)C([2H])([2H])c1cn(C)nc1-2] | LCMS (ES) m/z; 480.4 [M + H]$^+$. $^1$H NMR (400 MHz, DMSO-d$_6$) δ 10.40 (s, 1H); 8.44 (s, 2H); 8.22 (s, 1H); 7.57 (s, 1H); 7.38 (d, J = 8.0 Hz, 1H); 7.33 (d, J = 8.0 Hz, 1H); 7.13 (t, J = 8.0 Hz, 1H); 4.09-4.00 (m, 1H); 3.93 (t, J = 8.8 Hz, 2H); 3.90 (s, 3H); 3.37 (t, J = 8.4 Hz, 2H); 2.44 (s, 3H); 1.11 (d, J = 6.8 Hz, 6H). |

| Compound No. | Structure | Analytical Data |
|---|---|---|
| 64 | 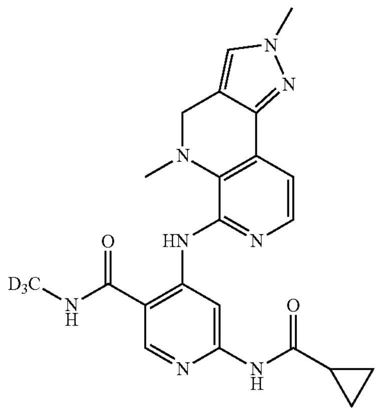 [SMILES: [2H]C([2H])([2H])NC(=O)c1cnc(NC(=O)C2CC2)cc1Nc1nccc2c1N(C)Cc1cn(C)nc1-2] | LCMS (ES) m/z; 436.1 [M + H]⁺. $^1$H NMR (400 MHz, DMSO-$d_6$) δ 11.55 (s, 1H); 10.67 (s, 1H); 9.50 (s, 1H); 8.56 (s, 1H); 8.54 (s, 1H); 8.04 (d, J = 5.2 Hz, 1H); 7,66 (s, 1H); 7.20 (d, J = 5.2 Hz, 1H); 4.13 (s, 2H); 3.93 (s, 3H); 2.55 (s, 3H); 2.04-1.99 (m, 1H); 0.84-0.78 (m, 4H). |
| 66 | 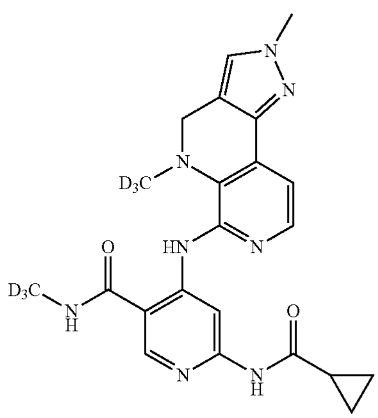 | LCMS (ES) m/z; 439.3 [M + H]⁺. $^1$H NMR (400 MHz, DMSO-$d_6$) δ 11.54 (s, 1H); 10.67 (s, 1H); 9.49 (s, 1H); 8.56 (s, 1H); 8.52 (s, 1H); 8.02 (d, J = 5.2 Hz, 1H); 7.64 (s, 1H); 7.17 (d, J = 4.8 Hz, 1H); 4.07 (s, 2H); 3.91 (s, 3H); 2.03-1.97 (m, 1H); 0.84-0.75 (m, 4H). |
| 67 | 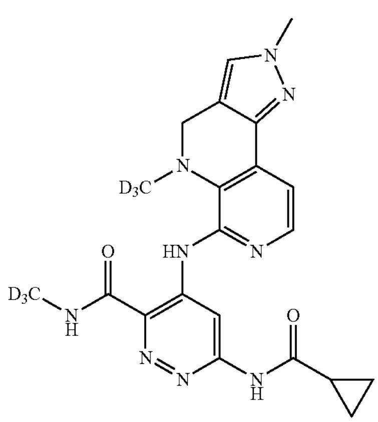 [SMILES: [2H]C([2H])([2H])NC(=O)c1nnc(NC(=O)C2CC2)cc1Nc1nccc2c1N(C([2H])([2H])[2H])Cc1cn(C)nc1-2] | LCMS (ES) m/z; 440.3 [M + H]⁺. $^1$H NMR (400 MHz, DMSO-$d_6$) δ 12.1 (s, 1H); 11.26 (s, 1H); 9.87 (s, 1H); 9.14 (s, 1H); 8.09 (d, J = 5.2 Hz, 1H); 7.67 (s, 1H); 7.26 (d, J = 4.8 Hz, 1H); 4.15 (s, 2H); 3.94 (s, 3H); 2.15-2.11 (m, 1H); 0.90-0.86 (m, 4H). |

-continued

| Compound No. | Structure | Analytical Data |
| --- | --- | --- |
| 69 | 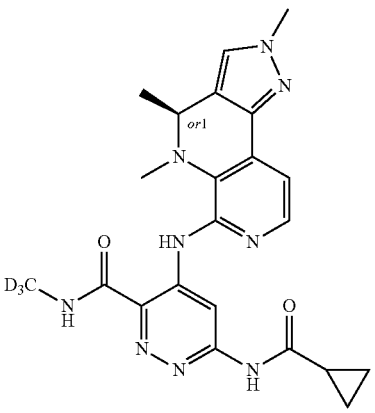<br>absolute configuration not determined | LCMS (ES) m/z, 451.3 [M + H]$^+$. $^1$H NMR (400 MHz, DMSO-d$_6$) δ 12.13 (s, 1H); 11.25 (s, 1H); 9.84 (s, 1H); 9.12 (s, 1H); 8.09 (d, J = 5.2 Hz, 1H); 7.68 (s, 1H); 7.26 (d, J = 4.8 Hz, 1H); 4.33 (q, J = 6.8 Hz, 1H); 3.93 (s, 3H); 2.50 (s, 3H); 2.16-2.10 (m, 1H); 1.13 (d, J = 7.2 Hz, 3H); 0.91-0.85 (m, 4H). |
| 70 | 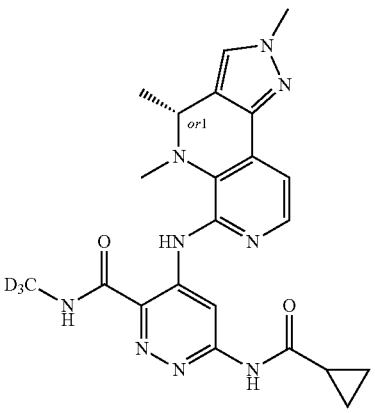<br>absolute configuration not determined | LCMS (ES) m/z; 451.3 [M + H]$^+$. $^1$H NMR (400 MHz, DMSO-d$_6$) δ 12.12 (s, 1H); 11.26 (s, 1H); 9.82 (s, 1H); 9.12 (s, 1H); 8.06 (d, J = 5.2 Hz, 1H); 7.66 (s, 1H); 7.24 (d, J = 4.8 Hz, 1H); 4.32 (q, J = 6.8 Hz, 1H); 3.91 (s, 3H); 2.50 (s, 3H); 2.14-2.08 (m, 1H); 1.10 (d, J = 6.8 Hz, 3H); 0.90-0.80 (m, 4H). |
| 72 | 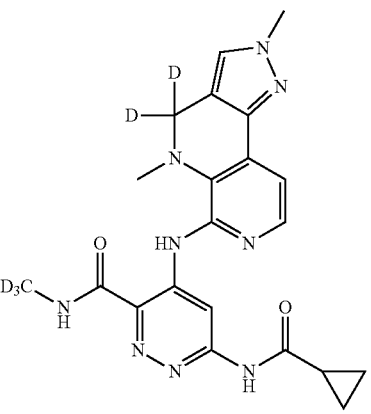 [SMILES: [2H]C([2H])([2H])NC(=O)c1nnc(NC(=O)C2CC2)cc1Nc1nccc2c1N(C)C([2H])([2H])c1cn(C)nc1-2] | LCMS (ES) m/z; 439.4 [M + H]$^+$. $^1$H NMR (400 MHz, DMSO-d$_6$) δ 12.11 (s, 1H); 11.26 (s, 1H); 9.86 (s, 1H); 9.14 (s, 1H); 8.09 (d, J = 5.2 Hz, 1H); 7.67 (s, 1H); 7.26 (d, J = 5.2 Hz, 1H); 3.94 (s, 3H); 2.53 (s, 3H); 2.15-2.10 (m, 1H); 0.90-0.86 (m, 4H). |

| Compound No. | Structure | Analytical Data |
|---|---|---|
| 73 | 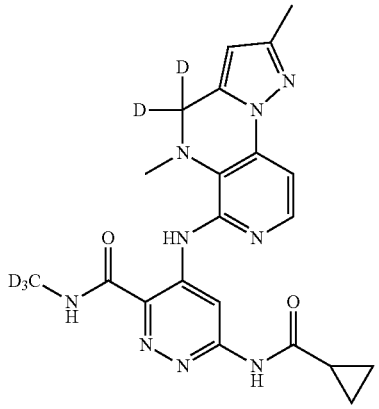 [SMILES: [2H]C([2H])([2H])NC(=O)c1nnc(NC(=O)C2CC2)cc1Nc1nccc2c1N(C)C([2H])([2H])c1cc(C)nn1-2] | LCMS (ES) m/z; 439.3 [M + H]⁺. ¹H NMR (400 MHz, DMSO-$d_6$) δ 12.16 (s, 1H); 11.29 (s, 1H); 9.86 (s, 1H); 9.18 (s, 1H); 8.14 (d, J = 5.2 Hz, 1H); 7.34 (d, J = 5.2 Hz, 1H); 6.26 (s, 1H); 2.56 (s, 3H); 2.31 (s, 3H); 2.16-2.10 (m, 1H); 0.91-0.83 (m, 4H). |
| 74 | 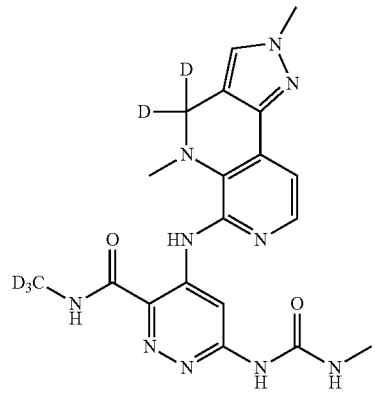 [SMILES: [2H]C([2H])([2H])NC(=O)c1nnc(NC(=O)NC)cc1Nc1nccc2c1N(C)C([2H])([2H])c1cn(C)nc1-2] | LCMS (ES) m/z; 428.3 [M + H]⁺. ¹H NMR (400 MHz, DMSO-$d_6$) δ 12.06 (s, 1H); 9.63 (s, 1H); 9.35 (s, 1H); 9.11 (s, 1H); 8.11 (d, J = 5.2 Hz, 1H); 7.69-7.62 (m, 2H); 7.27 (d, J = 5.2 Hz, 1H); 3.94 (s, 3H); 2.76 (d, J = 4.8 Hz, 3H); 2.53 (s, 3H). |
| 75 | 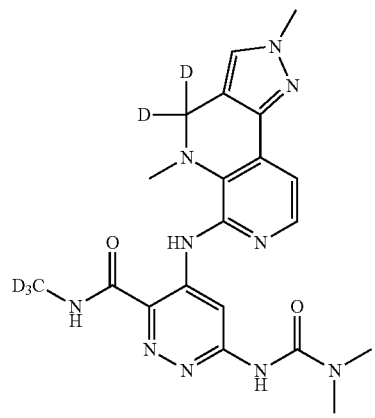 [SMILES: [2H]C([2H])([2H])NC(=O)c1nnc(NC(=O)N(C)C)cc1Nc1nccc2c1N(C)C([2H])([2H])c1cn(C)nc1-2] | LCMS (ES) m/z, 442.4 [M + H]⁺. ¹H NMR (400 MHz, DMSO-$d_6$) δ 12.12 (s, 1H); 9.50 (s, 1H); 9.40 (s, 1H); 9.05 (s, 1H); 8.09 (d, J = 5.2 Hz, 1H); 7.68 (s, 1H); 7.26 (d, J = 5.2 Hz, 1H); 3.94 (s, 3H); 3.00 (s, 6H); 2.53 (s, 3H). |

| Compound No. | Structure | Analytical Data |
|---|---|---|
| 76 | 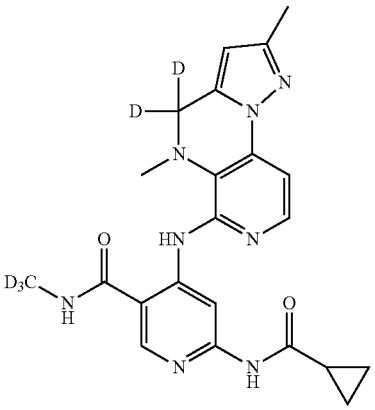 [SMILES: [2H]C([2H])([2H])NC(=O)c1cnc(NC(=O)C2CC2)cc1Nc1nccc2c1N(C)C([2H])([2H])c1cc(C)nn1-2] | LCMS (ES) m/z; 438.3 [M + H]⁺. ¹H NMR (400 MHz, DMSO-d₆) δ 11.62 (s, 1H); 10.70 (s, 1H); 9.50 (s, 1H); 8.60 (s, 1H); 8.53 (s, 1H); 8.07 (d, J = 5.2 Hz, 1H); 7.26 (d, J = 5.2 Hz, 1H); 6.21 (s, 1H); 2.48 (s, 3H); 2.27 (s, 3H); 2.01-1.97 (m, 1H); 0.82-0.74 (m, 4H). |
| 78 | 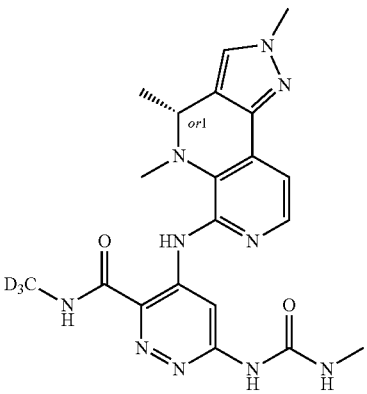<br>absolute configuration not determined | LCMS (ES) m/z; 440.3 [M + H]⁺. ¹H NMR (400 MHz, DMSO-d₆) δ 12.08 (s, 1H); 9.63 (s, 1H); 9.31 (s, 1H); 9.09 (s, 1H); 8.08 (d, J = 4.8 Hz, 1H); 7.68-7.65 (m, 2H); 7.25 (d, J = 4.8 Hz, 1H); 4.30 (q, J = 6.8 Hz, 1H); 3.91 (s, 3H); 2.73 (d, J = 4.4 Hz, 3H); 2.48 (s, 3H); 1.09 (d, J = 6.4 Hz, 3H). |
| 79 | 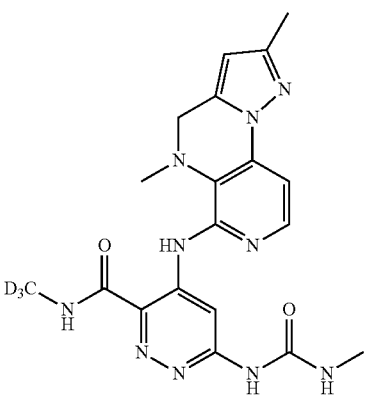 [SMILES: [2H]C([2H])([2H])NC(=O)c1nnc(NC(=O)NC)cc1Nc1nccc2c1N(C)Cc1cc(C)nn1-2] | LCMS (ES) m/z; 426.4 [M + H]⁺. ¹H NMR (400 MHz, DMSO-d₆) δ 12.12 (s, 1H); 9.66 (s, 1H); 9.36 (s, 1H); 9.15 (s, 1H); 8.16 (d, J = 5.6 Hz, 1H); 7.62-7.58 (m, 1H); 7.36 (d, J = 5.6 Hz, 1H); 6.26 (s, 1H); 4.32 (s, 2H); 2.79 (d, J = 4.4 Hz, 3H); 2.57 (s, 3H); 2.30 (s, 3H). |

| Compound No. | Structure | Analytical Data |
|---|---|---|
| 80 | 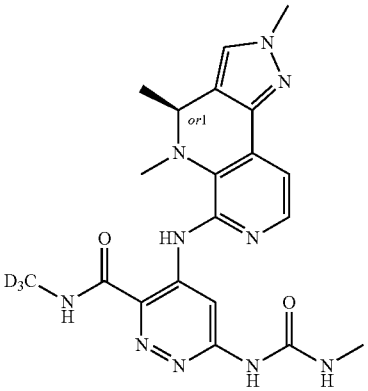<br>absolute configuration not determined | LCMS (ES) m/z; 440.4 [M + H]⁺. ¹H NMR (400 MHz, DMSO-d₆) δ 12.08 (s, 1H); 9.63 (s, 1H); 9.31 (s, 1H); 9.10 (s, 1H); 8.08 (d, J = 4.8 Hz, 1H); 7.66-7.64 (m, 2H); 7.25 (d, J = 5.2 Hz, 1H); 4.31 (q, J = 6.8 Hz, 1H); 3.91 (s, 3H); 2.73 (d, J = 4.4 Hz, 3H); 2.48 (s, 3H); 1.09 (d, J = 7.2 Hz, 3H). |

Example 47: Preparation of N-(2-methyl-4-((2-methyl-2,4-dihydrochromeno[4,3-c]pyrazol-6-yl)amino)-3-oxo-2,3-dihydro-1H-pyrazolo[3,4-b]pyridin-6-yl)cyclopropanecarboxamide (Compound 88)

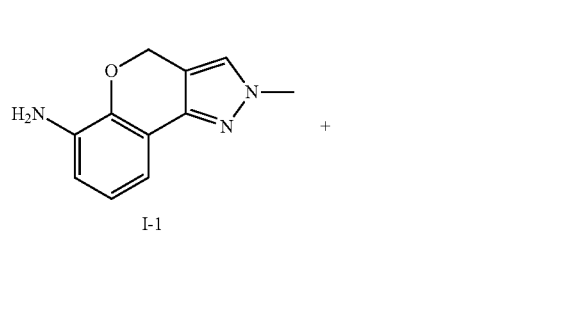

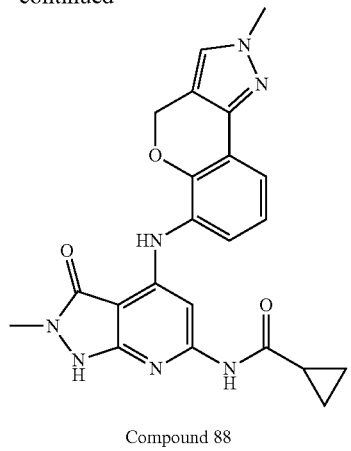

Compound 88

Step-1: 6-chloro-2-methyl-4-((2-methyl-2,4-dihydrochromeno[4,3-c]pyrazol-6-yl)amino)-1,2-dihydro-3H-pyrazolo[3,4-b]pyridin-3-one (54b): To a stirred solution of I-1 (0.25 g, 1.24 mmol) and 54a (0.298 g, 1.37 mmol) in anhydrous THF (6.00 mL) was added a 1M solution of LiHMDS (in THF) (2.48 mL, 4.97 mmol) drop wise at 0° C. The reaction mixture was allowed to stir at room temperature for 16 h, while monitoring reaction progress by TLC. After completion, it was quenched with addition of water (30 mL) and extraction was carried out using 5% MeOH in DCM (30 mL×3). The combined organic extracts were washed with brine (30 mL), dried over anhydrous Na₂SO₄, filtered and concentrated under reduced pressure. The resulting crude was purified by Combi-Flash (using gradient elution 0-3% MeOH in DCM) to afford desired compound 6-chloro-2-methyl-4-((2-methyl-2,4-dihydrochromeno[4,3-c]pyrazol-6-yl)amino)-1,2-dihydro-3H-pyrazolo[3,4-b]pyridin-3-one 54b (0.16 g) as an off-white solid. LCMS (ES) m/z; 383.1 [M+H]⁺.

Step-2: N-(2-methyl-4-((2-methyl-2,4-dihydrochromeno[4,3-c]pyrazol-6-yl)amino)-3-oxo-2,3-dihydro-1H-pyrazolo[3,4-b]pyridin-6-yl)cyclopropanecarboxamide (Compound 88): Argon gas was purged through a stirred suspension of 54b (0.12 g, 0.313 mmol), cyclopropanecarboxamide (0.032 g., 0.376 mmol) and $Cs_2CO_3$ (0.204 g, 0.627 mmol) in DMA (2.00 mL) for 15 min. To this was then added [5-(diphenylphosphanyl)-9,9-dimethyl-9H-xanthen-4-yl]diphenylphosphane (0.018 g, 0.031 mmol) and tris(1,5-diphenylpenta-1,4-dien-3-one) dipalladium (0.028 g, 0.031 mmol). The reaction mixture was then irradiated at 130° C. for 1 h in a MW reactor. After completion, it was cooled to room temperature and filtered through Celite bed. It was washed with EtOAc (10 mL×2) and the filtrate was concentrated under reduced pressure. The residue was purified by preparative HPLC to afford desired compound N-(2-methyl-4-((2-methyl-2,4-dihydrochromeno[4,3-c]pyrazol-6-yl)amino)-3-oxo-2,3-dihydro-1H-pyrazolo[3,4-b]pyridin-6-yl)cyclopropanecarboxamide Compound 88 (40 mg) as an off-white solid. LCMS (ES) m/z; 432.3 $[M+H]^+$. $^1$H NMR (400 MHz, DMSO-$d_6$) δ 10.71 (s, 1H); 8.53 (s, 1H); 7.62-7.54 (m, 2H); 7.38-7.30 (m, 2H); 7.02 (apparent t, J=8.0 Hz, 1H); 5.31 (s, 2H); 3.87 (s, 3H); 3.28 (s, 3H); 2.01-1.92 (m, 1H); 0.82-0.72 (m, 4H).

Example A-1: Oral Tablet

A tablet is prepared by mixing 20-50% by weight of a compound of Formula (A1), or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-2: Topical Cream

A topical cream (or an ointment, gel, oil, or the like) is prepared by mixing a compound of Formula (A1) with a non-toxic vehicle such as an oil and water emulsion, optionally diluted with additional buffering agents, stabilizing agents, scent ingredients, emulsifiers, oils, alcohols, or other excipients. A cream, for purposes of the present disclosure, encompasses topical compositions of various viscosities (e.g., lotions, ointments, pastes, gels, tinctures, and the like).

Example A-3: Eye Drops

Eye drops comprising a compound of Formula (A1) are prepared by dissolving an appropriate amount of the compound in water or a buffered solution (e.g., buffered for salinity and/or pH), and optionally diluted with additional excipients or vehicles. An eye drop may be further compounded with stabilizers, time-release polymers, or other diluents to enhance the therapeutic effect or duration of action at the treated site (e.g., ocular tissues or surrounding areas). Viscous liquids and gels are also included within the definition of eye drops.

Example A-4: Metered-Dose Inhaler (MDI)

A compound of Formula (A1) is dissolved in a liquid or liquified gas propellant, optionally in combination with stabilizing or flavor excipients, to be administered via an aerosol spray in a metered dose to a patient's lungs or respiratory tract. The aerosol may optionally be further compounded with a bronchodilator, a corticosteroid, or a combination of the two. An MDI for use with a compound of Formula (A1) may be self-administered, or in the case of critical host-mediated lung inflammation requiring artificial ventilation (e.g., Covid-19 associated respiratory inflammation), the inhalant may be administered via tracheal intubation, nasopharyngeal catheterization, or similar devices in accordance with advanced airway management procedures.

Example B-1: HEK-Blue™ IL-23 and IFNα/β Reporter Assays for Profiling TYK2 Pseudokinase (JH2) Inhibition HEK-Blue™ IL-23 and IFNα/β cells with a stably-integrated cytokine receptor and STAT3 or STAT1 express STAT-inducible secreted embryonic alkaline phosphatase (SEAP) reporter gene upon cytokine stimulation. These cells are plated in DMEM (Gibco) containing 10% heat-inactivated FBS (Gibco) and 100 U/mL PenStrep (Gibco) at 37° C. under 5% $CO_2$ conditions for 20-22 hours. The cells are then pretreated with serially diluted test compounds for 60 min prior to stimulation with either 10 ng/mL human recombinant IL-23 (Miltenyi Biotech) or 1 ng/mL human recombinant IFNα (InvivoGen) for 22-24 hours for IL-23 or 16-18 h for IFNα. SEAP induction is measured using the QUANTI Blue™ Solution (InvivoGen) according to the manufacturer's instructions. Inhibition data are calculated by comparison to no inhibitor control wells for 0% inhibition and non-stimulated control wells for 100% inhibition. Dose response curves are generated to determine the concentration required to inhibit 50% of cellular response ($IC_{50}$) as derived by non-linear regression analysis.

Table B-1 provides TYK2 inhibitory activity of illustrative compounds, where A means $IC_{50}$<30 nM; B means $IC_{50}$ is between 30 and 300 nM; C means ICso is between 300 and 1000 nM; D means $IC_{50}$>1000 nM; n/a means no observed activity at 1000 nM; and n.d. means not determined.

TABLE B-1

Representative TYK2 Inhibitory Activity

| Compound No. | IL23 | IFNα | Compound No. | IL23 | IFNα |
|---|---|---|---|---|---|
| 1 | B | B | 14 | A | A |
| 2 | B | C | 15 | A | A |
| 3 | B | D | 16 | A | A |
| 4 | B | D | 17 | A | A |
| 5 | A | B | 18 | A | A |
| 6 | B | B | 19 | A | A |
| 7 | B | C | 20 | A | A |
| 8 | A | B | 21 | B | B |
| 9 | A | B | 22 | A | A |
| 10 | B | D | 23 | A | A |
| 11 | B | D | 24 | B | B |
| 12 | A | A | 25 | A | A |
| 13 | A | A | 26 | A | A |
| 27 | A | A | 62 | A | B |
| 28 | A | A | 63 | A | B |
| 29 | A | A | 64 | A | A |
| 30 | A | A | 65 | A | A |
| 31 | A | B | 66 | A | A |
| 32 | A | A | 67 | A | A |
| 33 | A | A | 68 | A | A |
| 34 | A | A | 69 | B | B |
| 35 | A | A | 70 | A | A |
| 37 | A | B | 71 | A | A |
| 49 | B | D | 72 | A | n.d. |
| 50 | C | C | 73 | A | A |
| 51 | A | B | 74 | A | A |
| 52 | A | A | 75 | A | B |
| 53 | A | A | 76 | A | A |
| 54 | B | C | 77 | A | A |
| 55 | B | C | 78 | B | C |
| 56 | A | A | 79 | A | B |
| 57 | A | A | 80 | A | A |

TABLE B-1-continued

Representative TYK2 Inhibitory Activity

| Compound No. | IL23 | IFNα | Compound No. | IL23 | IFNα |
|---|---|---|---|---|---|
| 58 | A | A | 81 | A | A |
| 59 | A | A | 88 | C | D |
| 60 | A | A | 89 | A | B |
| 61 | A | B | 91 | A | B |

Example B-2: HTRF-Based Selectivity Assay

The ability of compounds to inhibit the activity of JAK1, JAK2, JAK3 and TYK2 is measured using a recombinant purified His or GST-tagged catalytic domain for each enzyme (JAK1, JAK2 and TYK2 are generated in-house; JAK3 was purchased from Carna biosciences, Cat #08-046) in an HTRF format biochemical assay. The reactions employs a commercial peptide substrate from Cisbio (Cat #62TK0PEC). The basic assay protocol is as follows: first, 2.5 μL of diluted compounds (4×) in DMSO are dispensed into a 384-well Optiplate. Next, 2.5 μL of enzyme (final concentrations for enzymes are: TYK2—700 ng/mL, JAK1—80.6 ng/mL, JAK2—2.1 ng/mL and JAK3—171.8 ng/mL) is added and incubated at RT for 5-20 min. Finally, 5 μl of mixture of 2×ATP [Final concentration 20 μM for TYK2, 21.43 μM for JAK1, 14.7 μM for JAK2 and 2.12 μM for JAK3]+2× Substrate [Final concentration 217 nM for TYK2, 454.7 nM for JAK1, 200 nM for JAK2 and 257.4 nM for JAK3] is added to 384 well Optiplate. Composition of Kinase assay buffer used in the assay is as follows: HEPES 50 mM, EGTA 1 mM, $MgCl_2$ 10 mM, DTT 2 mM, Tween-20 0.01% and water. Then the plates are shaken and then incubated at 26.5° C. for 60 min. At the end of the incubation, 10 μL of mixture of 2× detection mix [(EU3+Cryptate (1×)+Streptavidin-XL665 (final concentration: 62.5 nM) (HTRF KinEASE-TK kit Cat #62TK0PEC)] is added to the assay plate, shaken and incubated at 26.5° C. for 60 min. Plates are then read on a Perkin Elmer Envision for HTRF signal (665 nm reading/615 nm reading). After normalization to untreated controls, the percent inhibition of the HTRF signal at each compound concentration is calculated. The plot of percent inhibition versus the log of compound concentration is fit with a 4-parameter dose response equation to calculate $IC_{50}$ values.

Table B-2 provides selectivity data of illustrative compounds across the JAK family (TYK2, JAK1, JAK2, and JAK3) at the kinase domain (JH1), where A means $IC_{50}$<30 nM; B means $IC_{50}$ is between 30 and 300 nM; C means $IC_{50}$ is between 300 and 1000 nM; D means $IC_{50}$>1000 nM; n/a means no observed activity at 1000 nM; and n.d. means not determined.

TABLE B-2

HTRF-Based TYK2 Selectivity Data

| Cmpd No. | TYK2-JH1 | JAK-JH1 | JAK2-JH1 | JAK3-JH1 |
|---|---|---|---|---|
| 1 | C | D | D | D |
| 2 | D | D | D | D |
| 5 | D | D | D | D |
| 6 | D | D | D | D |
| 7 | D | D | D | D |
| 8 | D | D | C | D |
| 9 | D | D | D | D |
| 12 | D | D | D | D |
| 13 | D | D | D | D |
| 14 | D | D | D | D |
| 15 | D | D | D | D |
| 16 | D | D | D | D |
| 17 | B | A | A | A |
| 18 | D | D | D | B |
| 19 | D | D | D | D |
| 20 | D | D | D | D |
| 21 | D | D | D | D |
| 22 | D | D | D | D |
| 23 | D | D | D | D |
| 25 | D | D | D | n.d. |
| 26 | D | D | D | D |
| 27 | D | D | D | D |
| 28 | n.d. | D | D | D |
| 29 | D | D | D | n.d. |
| 30 | D | D | D | D |
| 32 | D | D | D | D |
| 35 | D | D | D | D |
| 49 | D | D | D | D |
| 50 | D | D | D | D |
| 51 | D | D | D | D |
| 60 | D | D | D | D |
| 61 | D | D | D | D |
| 64 | D | D | D | n.d. |
| 65 | D | D | D | D |
| 66 | D | D | D | D |
| 67 | D | D | D | n.d. |
| 68 | D | D | D | D |
| 70 | D | D | B | C |
| 88 | D | D | D | D |
| 89 | D | D | D | D |

Example B-3: HEK-Blue™ IL-2 and IFNγ Reporter Assays for Determining Selectivity HEK-Blue™ IL-2 and IFNγ reporter cells with a stably-integrated cytokine receptor and STAT5 or STAT1 express STAT-inducible secreted embryonic alkaline phosphatase (SEAP) reporter gene upon cytokine stimulation. These cells were plated in DMEM (Gibco) containing 10% heat-inactivated FBS (Gibco) and 100 U/mL PenStrep (Gibco) at 37° C. under 5% $CO_2$ conditions for 20-22 hours. The cells were then pretreated with serially diluted test compounds for 60 min prior to stimulation with either 4 ng/mL human recombinant IL-2 (Miltenyi Biotech) or 50 ng/mL human recombinant IFNγ (InvivoGen) for 24 hours. SEAP induction was measured using the QUANTI-Blue™ Solution (InvivoGen) according to the manufacturer's instructions. Inhibition data were calculated by comparison to no inhibitor control wells for 0% inhibition and non-stimulated control wells for 100% inhibition. Dose response curves were generated to determine the concentration required to inhibit 50% of cellular response (IC50) as derived by non-linear regression analysis.

Table B-3 provides selectivity data (SEAP) of illustrative compounds for IL-2 and IFN-γ, where A means $IC_{50}$<30 nM; B means $IC_{50}$ is between 30 and 300 nM; C means $IC_{50}$ is between 300 and 1000 nM; D means $IC_{50}$>1000 nM; n/a means no observed activity at 1000 nM; and n.d. means not determined.

TABLE B-3

SEAP Selectivity Assay Data at IL-2 and IFN-γ

| Compound No. | IL-2 | IFN-γ | Compound No. | IL-2 | IFN-γ |
|---|---|---|---|---|---|
| 1 | C | C | 21 | D | D |
| 2 | D | C | 22 | D | D |
| 3 | C | C | 23 | D | D |
| 4 | C | D | 25 | n/a | D |
| 5 | D | D | 26 | D | B |
| 6 | D | D | 27 | D | B |
| 7 | D | C | 28 | C | B |
| 8 | C | A | 29 | D | D |
| 9 | D | C | 32 | D | n.d. |
| 12 | D | B | 33 | D | C |
| 13 | D | C | 34 | B | B |
| 14 | D | C | 35 | D | n.d |
| 15 | D | D | 49 | C | A |
| 16 | C | B | 50 | B | C |
| 17 | A | A | 51 | D | D |
| 18 | D | D | 52 | D | C |
| 19 | D | D | 53 | D | B |
| 20 | C | B | 56 | D | B |
| 57 | D | B | 71 | D | D |
| 58 | D | C | 72 | C | n.d. |
| 59 | D | B | 73 | D | B |
| 60 | D | D | 74 | n/a | B |
| 61 | D | D | 75 | D | D |
| 63 | D | D | 76 | D | C |
| 64 | D | C | 77 | D | C |
| 65 | D | B | 79 | D | D |
| 66 | D | C | 80 | D | D |
| 68 | D | n.d. | 88 | D | D |
| 70 | D | n.d. | 89 | D | D |

The examples and embodiments described herein are for illustrative purposes only and various modifications or changes suggested to persons skilled in the art are to be included within the spirit and purview of this application and scope of the appended claims.

What is claimed is:

1. A compound of Formula (I):

Formula (I)

or a pharmaceutically acceptable salt, tautomer, or solvate thereof,
wherein:

$Z$ is $-NR^{10}-$, $-O-$, $-S-$, $-S(=O)-$, or $-S(=O)_2-$;

$X^1$ is $CR^{11}$ or N;
$X^2$ is $CR^{11}$ or N;
$X^3$ is $CR^{11}$ or N;
$B^1$ is N or $CR^{12a}$;
$B^2$ is N or $CR^{12b}$;
$W$ is $-NR^3-$ or $-O-$;
$R^1$ is hydrogen, $C_1$-$C_6$ alkyl, or $C_1$-$C_6$ fluoroalkyl;
$R^2$ is a Ring B that is an unsubstituted or substituted heterocyclyl or unsubstituted or substituted carbocyclyl, wherein if Ring B is substituted then Ring B is substituted with q instances of $R^{13}$;
or $R^2$ is $-C(=O)R^{14}$, $-C(=O)NR^{14}R^{15}$, or $-C(=O)OR^{14}$;
$R^3$ is hydrogen, $C_1$-$C_6$ alkyl, $C_1$-$C_6$ deuteroalkyl, $C_1$-$C_6$ fluoroalkyl, $C_3$-$C_6$ cycloalkyl, or a monocyclic heterocyclyl;
$R^4$ is hydrogen, $C_1$-$C_6$ alkyl, $C_1$-$C_6$ deuteroalkyl, $C_1$-$C_6$ fluoroalkyl, $C_3$-$C_6$ cycloalkyl, or a monocyclic heterocyclyl;
or $R^3$ and $R^4$ are taken together with the nitrogen atom to which they are attached to form an unsubstituted or substituted heterocyclyl, wherein the substituted heterocyclyl is substituted with one or two groups independently selected from the group consisting of halogen, $-CN$, $-NH_2$, $-NH(CH_3)$, $-N(CH_3)_2$, $-OH$, $-C(=O)OH$, $-C(=O)O(C_1$-$C_4$alkyl), $-C(=O)NH_2$, $-C(=O)NH(C_1$-$C_4$alkyl), $-C(=O)N(C_1$-$C_4$alkyl)$_2$, $-S(=O)_2NH_2$, $-S(=O)_2NH(C_1$-$C_4$alkyl), $-S(=O)_2N(C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, $-S(C_1$-$C_4$alkyl), $-S(=O)(C_1$-$C_4$alkyl)$, and $-S(=O)_2(C_1$-$C_4$alkyl);
$R^5$ is hydrogen, $C_1$-$C_6$ alkyl, $C_1$-$C_6$ fluoroalkyl, $C_3$-$C_6$ cycloalkyl, or a monocyclic heterocyclyl;
each $R^6$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, a monocyclic heterocyclyl, $-CN$, $-OH$, $-OR^{17}$, $-C(=O)R^{16}$, $-C(=O)OR^{16}$, $-C(=O)N(R^{16})_2$, $-N(R^{16})_2$, $-NR^{16}C(=O)R^{17}$, $-SR^{16}$, $-S(=O)R^{17}$, $-S(=O)_2R^{17}$, or $-S(=O)_2N(R^{16})_2$;
each $R^7$ is independently hydrogen, deuterium, halogen, $C_1$-$C_6$ alkyl, $C_1$-$C_6$ deuteroalkyl, $C_1$-$C_6$ fluoroalkyl, $C_3$-$C_6$ cycloalkyl, a monocyclic heterocyclyl, $-CN$, $-OH$, $-OR^{17}$, $-C(=O)R^{16}$, $-C(=O)OR^{16}$, $-C(=O)N(R^{16})_2$, $-N(R^{16})_2$, $-NR^{16}C(=O)R^{17}$, $-SR^{16}$, $-S(=O)R^{17}$, $-S(=O)_2R^{17}$, or $-S(=O)_2N(R^{16})_2$;
or one $R^6$ and one $R^7$ attached to the same carbon atom are taken together with the carbon atom to which they are attached to form a $-C(=O)-$ or $C_3$-$C_4$ cycloalkyl;
each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocyclyl, unsubstituted or substituted heterocyclyl, —CN, —OH, —OR$^{17}$, —C(=O)R$^{16}$, —C(=O)OR$^{16}$, —C(=O)N(R$^{16}$)$_2$, —N(R$^{16}$)$_2$, —NR$^{16}$C(=O)R$^7$, —SR$^{16}$, —S(=O)R$^{17}$, —S(=O)$_2$R$^{17}$, or —S(=O)$_2$N(R$^{16}$)$_2$;

$R^{10}$ is hydrogen, $C_1$-$C_6$ alkyl, $C_1$-$C_6$ deuteroalkyl, $C_1$-$C_6$ fluoroalkyl, $C_3$-$C_6$ cycloalkyl, or a monocyclic heterocyclyl;

each $R^{11}$ is independently hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocyclyl, unsubstituted or substituted heterocyclyl, —CN, —OH, —OR$^{17}$, —C(=O)R$^{16}$, —C(=O)OR$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —S(=O)$_2$R$^{17}$, or —S(=O)$_2$N(R$^{16}$)$_2$;

$R^{12a}$ is hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocyclyl, unsubstituted or substituted heterocyclyl, —CN, —OH, —OR$^{17}$, —C(=O)R$^{16}$, —C(=O)OR$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —S(=O)$_2$R$^{17}$, or —S(=O)$_2$N(R$^{16}$)$_2$;

$R^{12b}$ is hydrogen, halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocyclyl, unsubstituted or substituted heterocyclyl, —CN, —OH, —OR$^{17}$, —C(=O)R$^{16}$, —C(=O)OR$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —S(=O)$_2$R$^{17}$, or —S(=O)$_2$N(R$^{16}$)$_2$;

each $R^{13}$ is independently halogen, unsubstituted or substituted $C_1$-$C_6$ alkyl, unsubstituted or substituted $C_2$-$C_6$ alkenyl, unsubstituted or substituted $C_2$-$C_6$ alkynyl, unsubstituted or substituted $C_1$-$C_6$ fluoroalkyl, unsubstituted or substituted $C_1$-$C_6$ heteroalkyl, unsubstituted or substituted carbocyclyl, unsubstituted or substituted heterocyclyl, —CN, —OH, —OR$^{17}$, —C(=O)R$^{16}$, —C(=O)OR$^{16}$, —C(=O)N(R$^{16}$)$_2$, —N(R$^{16}$)$_2$, —NR$^{16}$C(=O)R$^{17}$, —SR$^{16}$, —S(=O)R$^{17}$, —S(=O)$_2$R$^{17}$, or —S(=O)$_2$N(R$^{16}$)$_2$;

$R^{14}$ is hydrogen, unsubstituted or substituted $C_1$-$C_6$ alkyl, $C_1$-$C_6$ deuteroalkyl, unsubstituted or substituted $C_2$-$C_6$ alkenyl, unsubstituted or substituted $C_2$-$C_6$ alkynyl, unsubstituted or substituted $C_1$-$C_6$ heteroalkyl, unsubstituted or substituted monocyclic carbocyclyl, unsubstituted or substituted bicyclic carbocyclyl, unsubstituted or substituted monocyclic heterocyclyl, or unsubstituted or substituted bicyclic heterocyclyl;

$R^{15}$ is hydrogen, $C_1$-$C_6$ alkyl, or $C_1$-$C_6$ fluoroalkyl;

or $R^{14}$ and $R^{15}$ are taken together with the nitrogen atom to which they are attached to form an unsubstituted or substituted 5- or 6-membered monocyclic heterocyclyl, wherein the substituted heterocyclyl is substituted with one or two groups independently selected from the group consisting of halogen, —CN, —NH$_2$, —NH(CH$_3$), —N(CH$_3$)$_2$, —OH, —C(=O)OH, —C(=O)O(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —S(C$_1$-C$_4$alkyl), —S(=O)(C$_1$-C$_4$alkyl), and —S(=O)$_2$(C$_1$-C$_4$alkyl);

or $R^1$ and $R^{15}$ are taken together with the intervening atoms to which they are attached to form an unsubstituted or substituted 5- or 6-membered monocyclic heterocyclyl, wherein the substituted heterocyclyl is substituted with one or two groups independently selected from the group consisting of halogen, —CN, —NH$_2$, —NH(CH$_3$), —N(CH$_3$)$_2$, —OH, —C(=O)OH, —C(=O)O(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —S(C$_1$-C$_4$alkyl), —S(=O)(C$_1$-C$_4$alkyl), and —S(=O)$_2$(C$_1$-C$_4$alkyl);

each $R^{16}$ is independently hydrogen, substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, a substituted or unsubstituted monocyclic 3- to 8-membered heterocycloalkyl, substituted or unsubstituted phenyl, or a substituted or unsubstituted monocyclic heteroaryl;

or two $R^{16}$ are taken together with the nitrogen atom to which they are attached to form an unsubstituted or substituted heterocyclyl, wherein the substituted heterocyclyl is substituted with one or two groups independently selected from the group consisting of halogen, —CN, —NH$_2$, —NH(CH$_3$), —N(CH$_3$)$_2$, —OH, —C(=O)OH, —C(=O)O(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —S(C$_1$-C$_4$alkyl), —S(=O)(C$_1$-C$_4$alkyl), and —S(=O)$_2$(C$_1$-C$_4$alkyl); and each $R^{17}$ is independently substituted or unsubstituted $C_1$-$C_6$ alkyl, substituted or unsubstituted $C_1$-$C_6$ fluoroalkyl, substituted or unsubstituted $C_1$-$C_6$ heteroalkyl, substituted or unsubstituted $C_3$-$C_7$ cycloalkyl, a substituted or unsubstituted monocyclic 3- to 8-membered heterocycloalkyl, substituted or unsubstituted phenyl, or a substituted or unsubstituted monocyclic heteroaryl;

wherein when any $R^8$, $R^{11}$, $R^{12a}$, $R^{12b}$, $R^{13}$, $R^{14}$, $R^{16}$, or $R^{17}$ is substituted:

each substituted $C_1$-$C_6$ alkyl, substituted $C_1$-$C_6$ deuteroalkyl, substituted $C_2$-$C_6$ alkenyl, substituted $C_2$-$C_6$ alkynyl, or substituted $C_1$-$C_6$ heteroalkyl is independently substituted with one or two groups independently selected from the group consisting of halogen, —CN, —NH$_2$, —NH(CH$_3$), —N(CH$_3$)$_2$, —OH, —C(=O)OH, —C(=O)O(C$_1$-C$_4$alkyl), —C(=O)NH$_2$, —C(=O)NH(C$_1$-C$_4$alkyl), —C(=O)N(C$_1$-C$_4$alkyl)$_2$, —S(=O)$_2$NH$_2$, —S(=O)$_2$NH(C$_1$-C$_4$alkyl), —S(=O)$_2$N(C$_1$-C$_4$alkyl)$_2$, C$_3$-C$_6$cycloalkyl, C$_1$-C$_4$alkoxy, C$_1$-C$_4$fluoroalkoxy, —S(C$_1$-C$_4$alkyl), —S(=O)(C$_1$-C$_4$alkyl), and —S(=O)$_2$(C$_1$-C$_4$alkyl);

each substituted $C_1$-$C_6$ fluoroalkyl is independently substituted with one or two groups independently selected from the group consisting of —CN, —NH$_2$, —NH(CH$_3$), —N(CH$_3$)$_2$, —OH, —C(═O)OH, —C(═O)O(C$_1$-C$_4$alkyl), —C(═O)NH$_2$, —C(═O)NH(C$_1$-C$_4$alkyl), —C(═O)N(C$_1$-C$_4$alkyl)$_2$, —S(═O)$_2$NH$_2$, —S(═O)$_2$NH(C$_1$-C$_4$alkyl), —S(═O)$_2$N(C$_1$-C$_4$alkyl)$_2$, C$_3$-C$_6$cycloalkyl, C$_1$-C$_4$alkoxy, C$_1$-C$_4$fluoroalkoxy, —S(C$_1$-C$_4$alkyl), —S(═O)(C$_1$-C$_4$alkyl), and —S(═O)$_2$(C$_1$-C$_4$alkyl);

each substituted carbocyclyl, substituted cycloalkyl, substituted phenyl, substituted heterocyclyl, substituted heterocycloalkyl, and substituted heterocyclyl is independently substituted with one or two groups independently selected from the group consisting of halogen, —CN, —NH$_2$, —NH(CH$_3$), —N(CH$_3$)$_2$, —OH, —C(═O)OH, —C(═O)O(C$_1$-C$_4$alkyl, —C(═O)NH$_2$, —C(═O)NH(C$_1$-C$_4$alkyl), —C(═O)N(C$_1$-C$_4$alkyl)$_2$, —S(═O)$_2$NH$_2$, —S(═O)$_2$NH(C$_1$-C$_4$alkyl), —S(═O)$_2$N(C$_1$-C$_4$alkyl)$_2$, C$_1$-C$_4$alkyl, C$_3$-C$_6$cycloalkyl, C$_1$-C$_4$fluoroalkyl, C$_1$-C$_4$heteroalkyl, C$_1$-C$_4$alkoxy, C$_1$-C$_4$fluoroalkoxy, —S(C$_1$-C$_4$alkyl), —S(═O)(C$_1$-C$_4$alkyl), and —S(═O)$_2$(C$_1$-C$_4$alkyl);

n is 1, 2, or 3; and q is 1, 2, 3, or 4;

with the provisos that:

(i) if $R^8$ is attached to a nitrogen atom, then $R^8$ is hydrogen, unsubstituted or substituted C$_1$-C$_6$ alkyl, unsubstituted or substituted C$_1$-C$_6$ deuteroalkyl, unsubstituted or substituted C$_2$-C$_6$ alkenyl, unsubstituted or substituted C$_2$-C$_6$ alkynyl, unsubstituted or substituted C$_1$-C$_6$ fluoroalkyl, unsubstituted or substituted C$_1$-C$_6$ heteroalkyl, unsubstituted or substituted carbocyclyl, unsubstituted or substituted heterocyclyl, —C(═O)R$^{16}$, —C(═O)OR$^{16}$, —C(═O)N(R$^{16}$)$_2$, —S(═O)R$^{17}$, —S(═O)$_2$R$^{17}$, or —S(═O)$_2$N(R$^{16}$)$_2$;

(ii) the compound of Formula (I) is not selected from the group consisting of: 6-(cyclopropanecarboxamido)-4-((2,5-dimethyl-4,5-dihydro-2H-pyrazolo[4,3-c]quinolin-6-yl)amino)-N-methylpyridazine-3-carboxamide, 4-((2,5-dimethyl-4,5-dihydro-2H-pyrazolo[4,3-c]quinolin-6-yl)amino)-6-((5-fluoropyridin-2-yl)amino)-N-methylnicotinamide, 4-((2,5-dimethyl-4,5-dihydro-2H-pyrazolo[4,3-c]quinolin-6-yl)amino)-6-((2,6-dimethylpyrimidin-4-yl)amino)-N-methylnicotinamide, and 6-(cyclopropanecarboxamido)-4-((2,5-dimethyl-4,5-dihydropyrazolo[1,5-a]quinoxalin-6-yl)amino)-N-methylpyridazine-3-carboxamide.

2. The compound of claim 1, or a pharmaceutically acceptable salt, tautomer, or solvate thereof, wherein;

Z is —NR$^{10}$— or —O—;

each $R^6$ is independently hydrogen, deuterium, halogen, C$_1$-C$_4$ alkyl, or C$_1$-C$_4$ deuteroalkyl; and each $R^7$ is independently hydrogen, deuterium, halogen, C$_1$-C$_4$ alkyl, or C$_1$-C$_4$ deuteroalkyl;

or one $R^6$ and one $R^7$ attached to the same carbon atom are taken together with the carbon atom to which they are attached to form a —C(═O)— or C$_3$-C$_4$ cycloalkyl.

3. The compound of claim 1, wherein the compound is a compound of Formula (II):

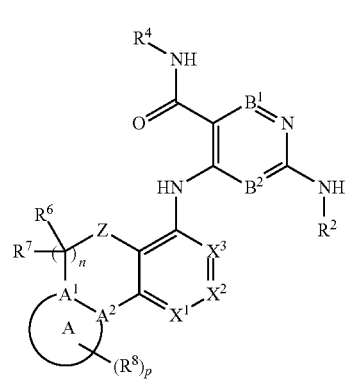

Formula (II)

or a pharmaceutically acceptable salt, tautomer, or solvate thereof.

4. The compound of claim 1, or a pharmaceutically acceptable salt, tautomer, or solvate thereof, wherein:

(i) $X^1$ is CR$^{11}$;
  $X^2$ is CR$^{11}$; and
  $X^3$ is CR$^{11}$; or
(ii) $X^1$ is CR$^{11}$;
  $X^2$ is CR$^{11}$; and
  $X^3$ is N; or
(iii) $X^1$ is CR$^{11}$;
  $X^2$ is N; and
  $X^3$ is CR$^{11}$; or
(iv) $X^1$ is N;
  $X^2$ is CR$^{11}$; and
  $X^3$ is CR$^{11}$; and
  each $R^{11}$ is independently hydrogen, halogen, unsubstituted C$_1$-C$_6$ alkyl, unsubstituted C$_1$-C$_6$ fluoroalkyl, —CN, —OH, —OR$^{17}$, or —N(R$^{16}$)$_2$.

5. The compound of claim 1, wherein the compound is a compound of Formula (IV):

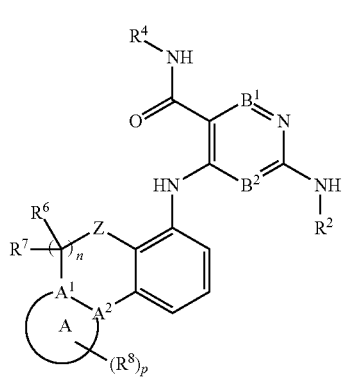

Formula (IV)

or a pharmaceutically acceptable salt, tautomer, or solvate thereof.

6. The compound of claim 1, wherein the compound is a compound of Formula (VIa-1), Formula (VIc-1), or Formula (VIf-1):

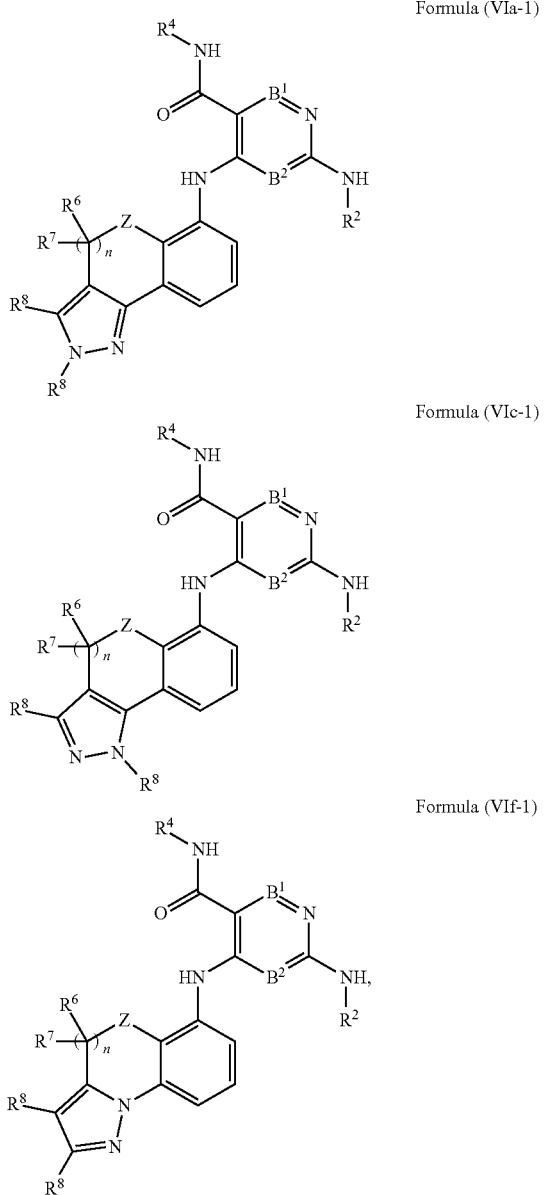

Formula (VIa-1)

Formula (VIc-1)

Formula (VIf-1)

or or a pharmaceutically acceptable salt, tautomer, or solvate thereof.

7. The compound of claim 1, or a pharmaceutically acceptable salt, tautomer, or solvate thereof, wherein:
(i) $B^1$ is $CR^{12a}$; and
$B^2$ is $CR^{12b}$; or
(ii) $B^1$ is N; and
$B^2$ is $CR^{12b}$;
$R^{12a}$ is hydrogen, halogen, unsubstituted $C_1$-$C_4$ alkyl, unsubstituted $C_1$-$C_4$ fluoroalkyl, or —CN; and
$R^{12b}$ is hydrogen, halogen, unsubstituted $C_1$-$C_4$ alkyl, unsubstituted $C_1$-$C_4$ fluoroalkyl, or —CN.

8. The compound of claim 1, or a pharmaceutically acceptable salt, tautomer, or solvate thereof, wherein:
W is —$NR^3$—;
$R^1$ is hydrogen or $C_1$-$C_4$ alkyl;
$R^3$ is hydrogen, $C_1$-$C_4$ alkyl, or $C_1$-$C_4$ deuteroalkyl;
$R^4$ is hydrogen, $C_1$-$C_4$ alkyl, or $C_1$-$C_4$ deuteroalkyl; and
$R^5$ is hydrogen or $C_1$-$C_4$ alkyl.

9. The compound of claim 1, or a pharmaceutically acceptable salt, tautomer, or solvate thereof, wherein:
$R^2$ is a Ring B that is an unsubstituted or substituted monocyclic carbocyclyl, unsubstituted or substituted bicyclic carbocyclyl, unsubstituted or substituted monocyclic heterocyclyl, or unsubstituted or substituted bicyclic heterocyclyl, wherein if Ring B is substituted then Ring B is substituted with q instances of $R^{13}$.

10. The compound of claim 1, or a pharmaceutically acceptable salt, tautomer, or solvate thereof, wherein:
$R^2$ is a Ring B that is an unsubstituted or substituted phenyl, unsubstituted or substituted monocyclic 6-membered heteroaryl, or unsubstituted or substituted monocyclic 5-membered heteroaryl, wherein if Ring B is substituted then Ring B is substituted with q instances of $R^{13}$; and
each $R^{13}$ is independently halogen, unsubstituted or substituted $C_1$-$C_6$ alkyl, unsubstituted or substituted $C_1$-$C_6$ fluoroalkyl, unsubstituted or substituted carbocyclyl, unsubstituted or substituted heterocyclyl, —CN, —OH, —$OR^{17}$, —C(=O)$R^{16}$, —C(=O)$OR^{16}$, —C(=O)N($R^{16}$)$_2$, —N($R^{16}$)$_2$, —$NR^{16}$C(=O)$R^{17}$, —S(=O)$_2R^{17}$, or —S(=O)$_2$N($R^{16}$)$_2$.

11. The compound of claim 1, or a pharmaceutically acceptable salt, tautomer, or solvate thereof, wherein:
$R^2$ is —C(=O)$R^{14}$, —C(=O)$NR^{14}R^{15}$, or —C(=O)$OR^{14}$;
$R^{14}$ is unsubstituted or substituted $C_1$-$C_6$ alkyl, $C_1$-$C_6$ deuteroalkyl, unsubstituted or substituted $C_3$-$C_6$ cycloalkyl, or unsubstituted or substituted 4- to 6-membered heterocycloalkyl and
$R^{15}$ is hydrogen, $C_1$-$C_6$ alkyl, or $C_1$-$C_6$ fluoroalkyl;
or $R^{14}$ and $R^{15}$ are taken together with the intervening atoms to which they are attached to form an unsubstituted or substituted 5- or 6-membered monocyclic heterocyclyl.

12. The compound of claim 11, or a pharmaceutically acceptable salt, tautomer, or solvate thereof, wherein:
$R^2$ is C(=O)$R^{14}$; and
$R^{14}$ is unsubstituted or substituted $C_1$-$C_6$ alkyl, $C_1$-$C_6$ deuteroalkyl, unsubstituted or substituted $C_3$-$C_4$ cycloalkyl, or unsubstituted or substituted 4-membered heterocycloalkyl;
wherein the substituted $C_1$-$C_6$ alkyl is substituted with one or two groups independently selected from the group consisting of halogen, —CN, —$NH_2$, —OH, —NH($CH_3$), —N($CH_3$)$_2$, —$OCH_3$, —$OCHF_2$, and —$OCF_3$; and
wherein the substituted $C_3$-$C_4$ cycloalkyl or substituted 4-membered heterocycloalkyl is substituted with one or two groups independently selected from the group consisting of halogen, —CN, —$NH_2$, —OH, —NH($CH_3$), —N($CH_3$)$_2$, —$CH_3$, —$CH_2CH_3$, —$CHF_2$, —$CF_3$, —$OCH_3$, —$OCHF_2$, and —$OCF_3$.

13. The compound of claim 1, or a pharmaceutically acceptable salt, tautomer, or solvate thereof, wherein each $R^1$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocyclyl, unsubstituted or substituted heterocyclyl, —CN, —OH, —$OR^{17}$, —C(=O)$R^{16}$, —C(=O)$OR^{16}$, or —C(=O)N($R^{16}$)$_2$; with the proviso that if $R^1$ is attached to a nitrogen atom, then $R^1$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, carbocyclyl, unsubstituted or substituted heterocyclyl, —C(=O)$R^{16}$, —C(=O)O$R^{16}$, or —C(=O)N($R^{16}$)$_2$.

14. The compound of claim 1, or a pharmaceutically acceptable salt, tautomer, or solvate thereof, wherein each $R^1$ is independently hydrogen, —Cl, —F, methyl, ethyl, isopropyl, -CD$_3$, —CH$_2$OH, —CF$_3$, cyclopropyl, oxetanyl, azetidinyl, —CN, —OH, —C(=O)OH, or —C(=O)OCH$_3$; with the proviso that if $R^1$ is attached to a nitrogen atom, then $R^1$ is hydrogen, methyl, ethyl, isopropyl, -CD$_3$, —CH$_2$OH, —CF$_3$, cyclopropyl, oxetanyl, azetidinyl, —C(=O)OH, or —C(=O)OCH$_3$.

15. The compound of claim 1, or a pharmaceutically acceptable salt, tautomer, or solvate thereof, wherein:

Z is —N$R^{10}$— or —O—;
$X^1$ is C$R^{11}$ or N;
$X^2$ is C$R^{11}$ or N;
$X^3$ is C$R^{11}$ or N;
$B^1$ is N or C$R^{12a}$;
$B^2$ is N or C$R^{12b}$;
W is —N$R^3$—;
$R^1$ is hydrogen or $C_1$-$C_4$ alkyl;
$R^2$ is a Ring B that is an unsubstituted or substituted phenyl, unsubstituted or substituted monocyclic 5-membered heteroaryl, or unsubstituted or substituted monocyclic 6-membered heteroaryl, wherein if Ring B is substituted, then Ring B is substituted with q instances of $R^{13}$; or
$R^2$ is C(=O)$R^{14}$;
$R^3$ is hydrogen, $C_1$-$C_4$ alkyl, or $C_1$-$C_4$ deuteroalkyl;
$R^4$ is hydrogen, $C_1$-$C_4$ alkyl, or $C_1$-$C_4$ deuteroalkyl;
$R^5$ is hydrogen or $C_1$-$C_4$ alkyl;
each $R^6$ is independently hydrogen, deuterium, halogen, $C_1$-$C_4$ alkyl, or $C_1$-$C_4$ deuteroalkyl;
each $R^7$ is independently hydrogen, deuterium, halogen, $C_1$-$C_4$ alkyl, or $C_1$-$C_4$ deuteroalkyl; or
or one $R^6$ and one $R^7$ attached to the same carbon atom are taken together with the carbon atom to which they are attached to form a —C(=O)— or $C_3$-$C_4$ cycloalkyl;
each $R^8$ is independently hydrogen, halogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocyclyl, unsubstituted or substituted heterocyclyl, —CN, —OH, —O$R^{17}$, C(=O)$R^{16}$, C(=O)O$R^{16}$, or C(=O)N($R^{16}$)$_2$;
$R^{10}$ is hydrogen, $C_1$-$C_4$ alkyl, $C_1$-$C_4$ deuteroalkyl, or cyclopropyl;
each $R^{11}$ is independently hydrogen, halogen, unsubstituted $C_1$-$C_6$ alkyl, unsubstituted $C_1$-$C_6$ fluoroalkyl, —CN, —OH, —O$R^{17}$, or —N($R^{16}$)$_2$;
$R^{12a}$ is hydrogen, halogen, unsubstituted $C_1$-$C_4$ alkyl, unsubstituted $C_1$-$C_4$ fluoroalkyl, or —CN;
$R^{12b}$ is hydrogen, halogen, unsubstituted $C_1$-$C_4$ alkyl, unsubstituted $C_1$-$C_4$ fluoroalkyl, or —CN;
each $R^{13}$ is independently halogen, unsubstituted or substituted $C_1$-$C_6$ alkyl, unsubstituted or substituted $C_1$-$C_6$ fluoroalkyl, unsubstituted or substituted carbocyclyl, or unsubstituted or substituted heterocyclyl, —CN, —OH, —O$R^{17}$, —C(=O)$R^{16}$, —C(=O)O$R^{16}$, —C(=O)N($R^{16}$)$_2$, —N($R^{16}$)$_2$, —N$R^{16}$C(=O)$R^{17}$, —S(=O)$_2$$R^{17}$, —S(=O)$_2$N($R^{16}$)$_2$;
$R^{14}$ is unsubstituted or substituted $C_1$-$C_6$ alkyl, $C_1$-$C_6$ deuteroalkyl, unsubstituted or substituted $C_3$-$C_4$ cycloalkyl, or unsubstituted or substituted 4-membered heterocycloalkyl;

wherein the substituted $C_1$-$C_6$ alkyl is substituted with one or two groups independently selected from the group consisting of halogen, —CN, —NH$_2$, —OH, —NH(CH$_3$), —N(CH$_3$)$_2$, —OCH$_3$, —OCHF$_2$, and —OCF$_3$; and wherein the substituted $C_3$-$C_4$ cycloalkyl or substituted 4-membered heterocycloalkyl is substituted with one or two groups independently selected from the group consisting of halogen, —CN, —NH$_2$, —OH, —NH(CH$_3$), —N(CH$_3$)$_2$, —CH$_3$, —CH$_2$CH$_3$, —CHF$_2$, —CF$_3$, —OCH$_3$, —OCHF$_2$, and —OCF$_3$;

each $R^{16}$ is independently hydrogen, unsubstituted $C_1$-$C_6$ alkyl, unsubstituted $C_1$-$C_6$ fluoroalkyl, unsubstituted $C_1$-$C_6$ heteroalkyl, unsubstituted $C_3$-$C_7$ cycloalkyl, or an unsubstituted monocyclic 3- to 8-membered heterocycloalkyl; or two $R^{16}$ are taken together with the nitrogen atom to which they are attached to form an unsubstituted 4- to 6-membered heterocycloalkyl; and each $R^{17}$ is independently unsubstituted $C_1$-$C_6$ alkyl, unsubstituted $C_1$-$C_6$ fluoroalkyl, unsubstituted $C_1$-$C_6$ heteroalkyl, unsubstituted $C_3$-$C_7$ cycloalkyl, or an unsubstituted monocyclic 3- to 8-membered heterocycloalkyl;

with the proviso that if $R^8$ is attached to a nitrogen atom, then $R^1$ is hydrogen, unsubstituted or substituted $C_1$-$C_6$ alkyl, unsubstituted or substituted $C_1$-$C_6$ deuteroalkyl, unsubstituted or substituted $C_1$-$C_6$ fluoroalkyl, unsubstituted or substituted carbocyclyl, unsubstituted or substituted heterocyclyl, —C(=O)$R^{16}$, —C(=O)O$R^{16}$, or —C(=O)N($R^{16}$)$_2$.

16. The compound of claim 1, wherein the compound is selected from the group consisting of:

1: 6-((5-fluoropyridin-2-yl)amino)-N-methyl-4-((2-methyl-2,4-dihydrochromeno[4,3-c]pyrazol-6-yl)amino)pyridazine-3-carboxamide;

2: 6-(cyclopropanecarboxamido) -N-methyl-4-((2-methyl-2,4-dihydrochromeno[4,3-c]pyrazol-6-yl)amino)pyridazine-3-carboxamide;

3: 6-[(5-fluoropyridin-2-yl)amino]-N-methyl-4-{[2-(oxetan-3-yl)-2H,4H-chromeno[4,3-c]pyrazol-6-yl]amino}pyridazine-3-carboxamide;

4: 6-(cyclopropanecarboxamido)-N-methyl-4-((2-(oxetan-3-yl)-2,4-dihydrochromeno[4,3-c]pyrazol-6-yl)amino)pyridazine-3-carboxamide;

5: 6-((5-fluoropyridin-2-yl)amino)-N-(methyl-d3)-4-((2-methyl-2,4-dihydrochromeno[4,3-c]pyrazol-6-yl)amino)pyridazine-3-carboxamide;

6: 6-(cyclopropanecarboxamido)-N-(methyl-d3)-4-((2-methyl-2,4-dihydrochromeno[4,3-c]pyrazol-6-yl)amino)nicotinamide;

7: 6-((5-fluoropyridin-2-yl)amino)-N-(methyl-d3)-4-((2-methyl-2,4-dihydrochromeno[4,3-c]pyrazol-6-yl)amino)nicotinamide;

8: 6-((5-fluoropyridin-2-yl)amino)-4-((2-methyl-2,4-dihydrochromeno[4,3-c]pyrazol-6-yl)amino)pyridazine-3-carboxamide;

9: 6-((2, 6-dimethylpyrimidin-4-yl)amino)-N-(methyl-d3)-4-((2-methyl-2,4-dihydrochromeno[4,3-c]pyrazol-6-yl)amino)nicotinamide;

10: 6-(cyclopropanecarboxamido)-4-((2,4-dimethyl-2,4-dihydrochromeno[4,3-c]pyrazol-6-yl)amino)-N-methylpyridazine-3-carboxamide;

11: 4-((2,4-dimethyl-2,4-dihydrochromeno[4,3-c]pyrazol-6-yl)amino)-6-((5-fluoropyridin-2-yl)amino)-N-methylpyridazine-3-carboxamide;

12: (4-((2,5-dimethyl-4,5-dihydro-2H-pyrazolo[4,3-c]quinolin-6-yl)amino)-6-((5-fluoropyridin-2-yl)amino)-N-methylpyridazine-3-carboxamide);

13: 4-((2,5-dimethyl-4,5-dihydro-2H-pyrazolo[4,3-c]quinolin-6-yl)amino)-6-((5-fluoropyridin-2-yl)amino)-N-(methyl-d3)nicotinamide;

14: [6-(cyclopropanecarboxamido)-4-((2,5-dimethyl-4,5-dihydro-2H-pyrazolo[4,3-c]quinolin-6-yl)amino)-N-(methyl-d3)nicotinamide];

15: 6-(cyclopropanecarboxamido)-4-((2,5-dimethyl-4,5-dihydro-2H-pyrazolo[4,3-c]quinolin-6-yl)amino)-N-(methyl-d3)pyridazine-3-carboxamide;

16: 4-((2,5-dimethyl-4,5-dihydro-2H-pyrazolo[4,3-c]quinolin-6-yl)amino)-6-((2,6-dimethylpyrimidin-4-yl)amino)-N-(methyl-d3)nicotinamide;

17: 6-(cyclopropanecarboxamido)-4-((2,5-dimethyl-4,5-dihydro-2H-pyrazolo[4,3-c]quinolin-6-yl)amino)nicotinamide;

18: 6-(cyclopropanecarboxamido)-4-((2,5-dimethyl-4,5-dihydro-2H-pyrazolo[4,3-c]quinolin-6-yl)amino)-N-methylnicotinamide;

19: 6-(cyclopropanecarboxamido)-N-(methyl-d3)-4-((5-methyl-2-(methyl-d3)-4,5-dihydro-2H-pyrazolo[4,3-c]quinolin-6-yl)amino)nicotinamide;

20: 6-(cyclopropanecarboxamido)-N-(methyl-d3)-4-((5-methyl-2-(methyl-d3)-4,5-dihydro-2H-pyrazolo[4,3-c]quinolin-6-yl)amino)pyridazine-3-carboxamide;

21: 4-((2,5-dimethyl-4,5-dihydro-2H-pyrazolo[4,3-c]quinolin-6-yl)amino)-6-(1-hydroxycyclopropane-1-carboxamido)-N-(methyl-d3)nicotinamide;

22: 2-(cyclopropanecarboxamido)-4-((2,5-dimethyl-4,5-dihydro-2H-pyrazolo[4,3-c]quinolin-6-yl)amino)-N-(methyl-d3)pyrimidine-5-carboxamide;

23: 6-(cyclopropanecarboxamido)-N-(methyl-d3)-4-((5-methyl-4,5-dihydro-2H-pyrazolo[4,3-c]quinolin-6-yl)amino)nicotinamide;

24: 4-((2,5-dimethyl-4,5-dihydro-2H-pyrazolo[4,3-c]quinolin-6-yl)amino)-N-(methyl-d3)-6-(oxetane-3-carboxamido)nicotinamide;

25: 4-((2,5-dimethyl-4,5-dihydro-2H-pyrazolo[4,3-c]quinolin-6-yl)amino)-N-(methyl-d3)-6-(3-methylureido)nicotinamide;

26: 6-(cyclopropanecarboxamido)-N-(methyl-d3)-4-((2-methyl-5-(methyl-d3)-4,5-dihydro-2H-pyrazolo[4,3-c]quinolin-6-yl)amino)nicotinamide;

27: 6-(cyclopropanecarboxamido)-N-(methyl-d3)-4-((5-methyl-4,5-dihydro-2H-pyrazolo[4,3-c]quinolin-6-yl)amino)pyridazine-3-carboxamide;

28: 6-(cyclopropanecarboxamido)-N-(methyl-d3)-4-((2-methyl-5-(methyl-d3)-4,5-dihydro-2H-pyrazolo[4,3-c]quinolin-6-yl)amino)pyridazine-3-carboxamide;

29: 6-(cyclopropanecarboxamido)-N-(methyl-d3)-4-((5-methyl-2-(oxetan-3-yl)-4,5-dihydro-2H-pyrazolo[4,3-c]quinolin-6-yl)amino)nicotinamide;

30: (S)-6-(cyclopropanecarboxamido)-N-(methyl-d3)-4-((2,4,5-trimethyl-4,5-dihydro-2H-pyrazolo[4,3-c]quinolin-6-yl)amino)nicotinamide;

31: (R)-6-(cyclopropanecarboxamido)-N-(methyl-d3)-4-((2,4,5-trimethyl-4,5-dihydro-2H-pyrazolo[4,3-c]quinolin-6-yl)amino)nicotinamide;

32: 4-((2,5-dimethyl-4,5-dihydro-2H-pyrazolo[4,3-c]quinolin-6-yl)amino)-6-(((2R)-2-fluorocyclopropane-1-carboxamido)-N-(methyl-d3)nicotinamide;

33: 4-((2,5-dimethyl-4,5-dihydro-2H-pyrazolo[4,3-c]quinolin-6-yl-4,4-d2)amino)-N-(methyl-d3)-6-(3-methylureido)pyridazine-3-carboxamide;

34: 4-((2,5-dimethyl-4,5-dihydro-2H-pyrazolo[4,3-c]quinolin-6-yl)amino)-6-((2,6-dimethylpyrimidin-4-yl)amino)-N-methylpyridazine-3-carboxamide;

35: 6-(cyclopropanecarboxamido)-4-((2,5-dimethyl-4,5-dihydro-2H-pyrazolo[4,3-c]quinolin-6-yl-4,4-d2)amino)-N-(methyl-d3)nicotinamide;

36: rel-4-((2,5-dimethyl-4,5-dihydro-2H-pyrazolo[4,3-c]quinolin-6-yl)amino)-6-((1R,2S)-2-fluorocyclopropane-1-carboxamido)-N-(methyl-d3)nicotinamide;

37: 6-(cyclopropanecarboxamido)-4-((2-isopropyl-5-methyl-4,5-dihydro-2H-pyrazolo[4,3-c]quinolin-6-yl)amino)-N-(methyl-d3)nicotinamide;

38: 6-((5-fluoropyridin-2-yl)amino)-N-methyl-4-((2-methyl-4,5-dihydro-2H-benzo[2,3]oxepino[4,5-c]pyrazol-7-yl)amino)pyridazine-3-carboxamide;

39: 4-((2,5-dimethyl-4,5-dihydro-2H-pyrazolo[4,3-c]quinolin-6-yl)amino)-6-(2-hydroxy-2-methylpropanamido)-N-(methyl-d3)nicotinamide;

40: 4-((2,5-dimethyl-4,5-dihydro-2H-pyrazolo[4,3-c]quinolin-6-yl)amino)-N-(methyl-d3)-6-(1-methylazetidine-3-carboxamido)nicotinamide;

41: methyl(4-((2,5-dimethyl-4,5-dihydro-2H-pyrazolo[4,3-c]quinolin-6-yl)amino)-5-((methyl-d3)carbamoyl)pyridin-2-yl)carbamate;

42: 3-(cyclopropanecarboxamido)-5-((2,5-dimethyl-4,5-dihydro-2H-pyrazolo[4,3-c]quinolin-6-yl)amino)-N-(methyl-d3)-1,2,4-triazine-6-carboxamide;

43: 6-(cyclopropanecarboxamido)-N-(methyl-d3)-4-((2,4,5-trimethyl-4,5-dihydro-2H-pyrazolo[4,3-c]quinolin-6-yl)amino)nicotinamide;

44: 6-(cyclopropanecarboxamido)-4-((4,5-dimethyl-2-(methyl-d3)-4,5-dihydro-2H-pyrazolo[4,3-c]quinolin-6-yl)amino)-N-(methyl-d3)nicotinamide;

45: 4-((2,5-bis(methyl-d3)-4,5-dihydro-2H-pyrazolo[4,3-c]quinolin-6-yl)amino)-6-(cyclopropanecarboxamido)-N-(methyl-d3)nicotinamide;

46: 6-(cyclopropanecarboxamido)-N-(methyl-d3)-4-((5-methyl-2-(methyl-d3)-4,5-dihydro-2H-pyrazolo[4,3-c]quinolin-6-yl-4,4-d2)amino)nicotinamide;

47: 6-(cyclopropanecarboxamido)-4-((4,4-difluoro-2,5-dimethyl-4,5-dihydro-2H-pyrazolo[4,3-c]quinolin-6-yl)amino)-N-(methyl-d3)nicotinamide;

48: 6-(cyclopropanecarboxamido)-4-((4,4-difluoro-5-methyl-2-(methyl-d3)-4,5-dihydro-2H-pyrazolo[4,3-c]quinolin-6-yl)amino)-N-(methyl-d3)nicotinamide;

49: 6-((5-fluoropyridin-2-yl)amino)-N-methyl-4-((1-methyl-1,4-dihydrochromeno[4,3-c]pyrazol-6-yl)amino)pyridazine-3-carboxamide;

50: 6-(cyclopropanecarboxamido)-N-methyl-4-((1-methyl-1,4-dihydro chromeno[4,3-c]pyrazol-6-yl)amino)pyridazine-3-carboxamide;

51: 6-(cyclopropanecarboxamido)-4-((1,5-dimethyl-4,5-dihydro-1H-pyrazolo[4,3-c]quinolin-6-yl)amino)-N-(methyl-d3)nicotinamide;

52: 6-(cyclopropanecarboxamido)-4-((2,5-dimethyl-4,5-dihydropyrazolo[1,5-a]quinoxalin-6-yl)amino)-N-(methyl-d3)pyridazine-3-carboxamide;

53: 6-(cyclopropanecarboxamido)-4-((2,5-dimethyl-4,5-dihydropyrazolo[1,5-a]quinoxalin-6-yl)amino)-N-(methyl-d3)nicotinamide;

54: 6-(cyclopropanecarboxamido)-N-(methyl-d3)-4-((5-methyl-2-(trifluoromethyl)-4,5-dihydropyrazolo[1,5-a]quinoxalin-6-yl)amino)pyridazine-3-carboxamide;

55: 6-(cyclopropanecarboxamido)-N-(methyl-d3)-4-((5-methyl-2-(trifluoromethyl)-4,5-dihydropyrazolo[1,5-a]quinoxalin-6-yl)amino)nicotinamide;

56: 6-(cyclopropanecarboxamido)-4-((2,5-dimethyl-4,5-dihydropyrazolo[1,5-a]quinoxalin-6-yl-4,4-d2)amino)-N-(methyl-d3)pyridazine-3-carboxamide;

57: 6-(cyclopropanecarboxamido)-4-((2,5-dimethyl-4,5-dihydropyrazolo[1,5-a]quinoxalin-6-yl-4,4-d2)amino)-N-(methyl-d3)nicotinamide;

58: 6-(cyclopropanecarboxamido)-N-(methyl-d3)-4-((5-methyl-4,5-dihydropyrazolo[1,5-a]quinoxalin-6-yl-4,4-d2)amino)pyridazine-3-carboxamide;

59: 6-(cyclopropanecarboxamido)-N-(methyl-d3)-4-((5-methyl-4,5-dihydropyrazolo[1,5-a]quinoxalin-6-yl-4,4-d2)amino)nicotinamide;

60: methyl 6-(cyclopropanecarboxamido)-4-((2,5-dimethyl-4,5-dihydro-2H-pyrazolo[4,3-c]quinolin-6-yl)amino)nicotinate;

61: 4-((2,5-dimethyl-4,5-dihydro-2H-pyrazolo[4,3-c]quinolin-6-yl)amino)-6-(3-isopropyl-2-oxoimidazolidin-1-yl)-N-(methyl-d3)nicotinamide;

62: 4-((2,5-dimethyl-4,5-dihydro-2H-pyrazolo[4,3-c][1,7]naphthyridin-6-yl-4,4-d2)amino)-N-(methyl-d3)-6-(N-methylcyclopropanecarboxamido)pyridazine-3-carboxamide;

63: 4-((2,5-dimethyl-4,5-dihydro-2H-pyrazolo[4,3-c]quinolin-6-yl-4,4-d2)amino)-6-(3-isopropyl-2-oxoimidazolidin-1-yl)-N-(methyl-d3)nicotinamide;

64: 6-(cyclopropanecarboxamido)-4-((2,5-dimethyl-4,5-dihydro-2H-pyrazolo[4,3-c][1,7]naphthyridin-6-yl)amino)-N-(methyl-d3)nicotinamide;

65: 6-(cyclopropanecarboxamido)-4-((2,5-dimethyl-4,5-dihydro-2H-pyrazolo[4,3-c][1,7]naphthyridin-6-yl)amino)-N-(methyl-d3)pyridazine-3-carboxamide;

66: 6-(cyclopropanecarboxamido)-N-(methyl-d3)-4-((2-methyl-5-(methyl-d3)-4,5-dihydro-2H-pyrazolo[4,3-c][1,7]naphthyridin-6-yl)amino)nicotinamide;

67: 6-(cyclopropanecarboxamido)-N-(methyl-d3)-4-((2-methyl-5-(methyl-d3)-4,5-dihydro-2H-pyrazolo[4,3-c][1,7]naphthyridin-6-yl)amino)pyridazine-3-carboxamide;

68: 6-(cyclopropanecarboxamido)-4-((2,5-dimethyl-4,5-dihydropyrazolo[1,5-a]pyrido[3,4-e]pyrazin-6-yl)amino)-N-(methyl-d3)pyridazine-3-carboxamide;

69: (S)-6-(cyclopropanecarboxamido)-N-(methyl-d3)-4-((2,4,5-trimethyl-4,5-dihydro-2H-pyrazolo[4,3-c][1,7]naphthyridin-6-yl)amino)pyridazine-3-carboxamide;

70: (R)-6-(cyclopropanecarboxamido)-N-(methyl-d3)-4-((2,4,5-trimethyl-4,5-dihydro-2H-pyrazolo[4,3-c][1,7]naphthyridin-6-yl)amino)pyridazine-3-carboxamide;

71: 6-(cyclopropanecarboxamido)-4-((2,5-dimethyl-4,5-dihydropyrazolo[1,5-a]pyrido[3,4-e]pyrazin-6-yl)amino)-N-(methyl-d3)nicotinamide;

72: 6-(cyclopropanecarboxamido)-4-((2,5-dimethyl-4,5-dihydro-2H-pyrazolo[4,3-c][1,7]naphthyridin-6-yl-4,4-d2)amino)-N-(methyl-d3)pyridazine-3-carboxamide;

73: 6-(cyclopropanecarboxamido)-4-((2,5-dimethyl-4,5-dihydropyrazolo[1,5-a]pyrido[3,4-e]pyrazin-6-yl-4,4-d2)amino)-N-(methyl-d3)pyridazine-3-carboxamide;

74: 4-((2,5-dimethyl-4,5-dihydro-2H-pyrazolo[4,3-c][1,7]naphthyridin-6-yl-4,4-d2)amino)-N-(methyl-d3)-6-(3-methylureido)pyridazine-3-carboxamide;

75: 4-((2,5-dimethyl-4,5-dihydro-2H-pyrazolo[4,3-c][1,7]naphthyridin-6-yl-4,4-d2)amino)-6-(3,3-dimethylureido)-N-(methyl-d3)pyridazine-3-carboxamide;

76: 6-(cyclopropanecarboxamido)-4-((2,5-dimethyl-4,5-dihydropyrazolo[1,5-a]pyrido[3,4-e]pyrazin-6-yl-4,4-d2)amino)-N-(methyl-d3)nicotinamide;

77: 6-(cyclopropanecarboxamido)-4-((2,5-dimethyl-4,5-dihydro-2H-pyrazolo[4,3-c][1,7]naphthyridin-6-yl-4,4-d2)amino)-N-(methyl-d3)nicotinamide;

78: (R)—N-(methyl-d3)-6-(3-methylureido)-4-((2,4,5-trimethyl-4,5-dihydro-2H-pyrazolo[4,3-c][1,7]naphthyridin-6-yl)amino)pyridazine-3-carboxamide;

79: 4-((2,5-dimethyl-4,5-dihydropyrazolo[1,5-a]pyrido[3,4-e]pyrazin-6-yl)amino)-N-(methyl-d3)-6-(3-methylureido)pyridazine-3-carboxamide;

80: (S)—N-(methyl-d3)-6-(3-methylureido)-4-((2,4,5-trimethyl-4,5-dihydro-2H-pyrazolo[4,3-c][1,7]naphthyridin-6-yl)amino)pyridazine-3-carboxamide;

81: (R)-6-(cyclopropanecarboxamido)-N-(methyl-d3)-4-((2,4,5-trimethyl-4,5-dihydropyrazolo[1,5-a]pyrido[3,4-e]pyrazin-6-yl)amino)pyridazine-3-carboxamide;

82: 6-(cyclopropanecarboxamido)-4-((8-fluoro-2,5-dimethyl-4,5-dihydro-2H-pyrazolo[4,3-c]quinolin-6-yl)amino)-N-(methyl-d3)nicotinamide;

83: 6-(cyclopropanecarboxamido)-4-((8-fluoro-5-methyl-2-(methyl-d3)-4,5-dihydro-2H-pyrazolo[4,3-c]quinolin-6-yl)amino)-N-(methyl-d3)nicotinamide;

84: 6-(cyclopropanecarboxamido)-N-(methyl-d3)-4-((5-methyl-2-(methyl-d3)-4,5-dihydro-2H-pyrazolo[4,3-c][1,6]naphthyridin-6-yl)amino)nicotinamide;

85: 6-(cyclopropanecarboxamido)-N-(methyl-d3)-4-((5-methyl-2-(methyl-d3)-4,5-dihydro-2H-pyrazolo[4,3-c][1,6]naphthyridin-6-yl)amino)pyridazine-3-carboxamide;

86: 6-(cyclopropanecarboxamido)-N-(methyl-d3)-4-((5-methyl-2-(methyl-d3)-4,5-dihydro-2H-pyrazolo[4,3-c][1,7]naphthyridin-6-yl)amino)nicotinamide;

87: 6-(cyclopropanecarboxamido)-N-(methyl-d3)-4-((5-methyl-2-(methyl-d3)-4,5-dihydro-2H-pyrazolo[4,3-c][1,7]naphthyridin-6-yl)amino)pyridazine-3-carboxamide; and 91: 6-(cyclopropanecarboxamido)-4-((2-isopropyl-5-methyl-4,5-dihydro-2H-pyrazolo[4,3-c]quinolin-6-yl)amino)-N-(methyl-d3)pyridazine-3-carboxamide;

or a pharmaceutically acceptable salt, tautomer, or solvate thereof.

17. A pharmaceutical composition comprising a pharmaceutically acceptable excipient and a compound of claim 1, or a pharmaceutically acceptable salt, tautomer, or solvate thereof.

18. A method for inhibiting tyrosine-protein kinase 2 (TYK2) activity in a patient in need thereof, wherein the method comprises administering to the patient a therapeutically effective amount of a compound of claim 1, or a pharmaceutically acceptable salt, tautomer, or solvate thereof.

19. The method of claim 18, wherein the patient has a condition or disease selected from the group consisting of an autoimmune condition, an autoimmune disease, an inflammatory condition, and an inflammatory disease.

20. The method of claim 19, wherein the autoimmune condition, autoimmune disease, inflammatory condition, or inflammatory disease is selected from the group consisting of alopecia, ankylosing spondylitis, atopic dermatitis, Bechet's disease, celiac disease, Crohn's disease, dry eye, hidradenitis suppurativa, idiopathic pulmonary fibrosis, intestinal bowel disease, lupus, multiple sclerosis, psoriasis, psoriatic arthritis, rheumatoid arthritis, scleroderma, Sjögren's syndrome, systemic sclerosis, type 1 diabetes, ulcerative colitis, uveitis, and vitiligo, or a combination thereof.

* * * * *